US012655442B2

(12) United States Patent
Van Der Burgt et al.

(10) Patent No.: US 12,655,442 B2
(45) Date of Patent: Jun. 16, 2026

(54) SELF-COMPATIBILITY IN CULTIVATED POTATO

(71) Applicant: Agventure B.V., Wageningen (NL)

(72) Inventors: Ate Van Der Burgt, Wageningen (NL); Ernst-Jan Eggers, Wageningen (NL); Michiel Erik De Vries, Holthees (NL); Adriaan Willem Van Heusden, Wageningen (NL); Willem Hendrik Lindhout, Wageningen (NL)

(73) Assignee: Agventure B.V., Wageningen (NL)

( * ) Notice: Subject to any disclaimer, the term of this patent is extended or adjusted under 35 U.S.C. 154(b) by 828 days.

(21) Appl. No.: 17/609,723

(22) PCT Filed: May 7, 2020

(86) PCT No.: PCT/NL2020/050295
§ 371 (c)(1),
(2) Date: Nov. 8, 2021

(87) PCT Pub. No.: WO2020/226499
PCT Pub. Date: Nov. 12, 2020

(65) Prior Publication Data

US 2022/0267386 A1 Aug. 25, 2022

(30) Foreign Application Priority Data

May 7, 2019 (EP) .................................... 19173138
Dec. 19, 2019 (EP) .................................... 19218289

(51) Int. Cl.
*C12N 15/82* (2006.01)
*A01H 5/04* (2018.01)
(Continued)

(52) U.S. Cl.
CPC ........... *C12N 15/8282* (2013.01); *A01H 5/04* (2013.01); *A01H 6/827* (2018.05); *C07K 14/415* (2013.01); *C12N 15/8287* (2013.01)

(58) Field of Classification Search
None
See application file for complete search history.

(56) References Cited

U.S. PATENT DOCUMENTS

| | | | |
|---|---|---|---|
| 9,551,007 | B2 | 1/2017 | Vossen et al. |
| 10,524,436 | B2 | 1/2020 | Lindhout et al. |

(Continued)

FOREIGN PATENT DOCUMENTS

| | | |
|---|---|---|
| CN | 109548646 | 4/2019 |
| CN | 110894539 X | 3/2020 |

(Continued)

OTHER PUBLICATIONS

Spooner, D.M., Ghislain, M., Simon, R. et al. Systematics, Diversity, Genetics, and Evolution of Wild and Cultivated Potatoes. Bot. Rev. 80, 283-383 (2014). https://doi.org/10.1007/s12229-014-9146-y (Year: 2014).*

(Continued)

*Primary Examiner* — Amjad Abraham
*Assistant Examiner* — Dequantarius Javon Speed
(74) *Attorney, Agent, or Firm* — Dentons US LLP

(57) ABSTRACT

An isolated nucleic acid molecule comprising a nucleic acid sequence encoding a protein having the amino acid sequence as depicted in SEQ ID NO:10, and sequences having at least 70% sequence identity with this amino acid sequence and conferring self-compatibility to a potato plant is provided. Also provided is a transformed plant and parts thereof that comprise the nucleic acid sequence, along with related methods for the selection and production of a plant comprising the nucleic acid sequence. Food products prepared (Continued)

from such plants are also provided. The plants provided herein may further comprise at least one allele of each of a *Phytophtera infestans* resistance gene selected from *S. avilesii* 478-2 Rpi*-avl1, *S. tarinjense* 852-5 Rpi-tar1, *S. chacoense* 543-5 Rpi-chc1, and *S. venturii* 283-1 Rpi-vnt1.

17 Claims, 53 Drawing Sheets

Specification includes a Sequence Listing.

(51) Int. Cl.
*A01H 6/82* (2018.01)
*C07K 14/415* (2006.01)

(56) References Cited

U.S. PATENT DOCUMENTS

| | | | |
|---|---|---|---|
| 11,140,841 | B2 | 10/2021 | Lindhout et al. |
| 12,433,236 | B2 | 10/2025 | Lindhout et al. |
| 2014/0115736 | A1 | 4/2014 | Lindhout et al. |
| 2020/0385819 | A1 | 12/2020 | Huang et al. |
| 2021/0029956 | A1 | 2/2021 | Lindhout et al. |
| 2021/0137041 | A1 | 5/2021 | De Vries et al. |
| 2022/0095576 | A1 | 3/2022 | Lindhout et al. |
| 2026/0013461 | A1 | 1/2026 | Lindhout et al. |

FOREIGN PATENT DOCUMENTS

| | | |
|---|---|---|
| CN | 110938120 | 3/2020 |
| WO | 2003010319 | 2/2003 |
| WO | 2011034433 A1 | 3/2011 |
| WO | 2011053135 A1 | 5/2011 |
| WO | 2018112356 A | 6/2018 |

OTHER PUBLICATIONS

Lazar et al. Transforming growth factor alpha: mutation of aspartic acid 47 and leucine 48 results in different biological activities. Mol Cell Biol. Mar. 1988;8(3):1247-52. doi: 10.1128/mcb.8.3.1247-1252. 1988. PMID: 3285178; PMCID: PMC363269. (Year: 1988).*
Nonaka et al. Truncation and pathogenic mutations facilitate the formation of intracellular aggregates of TDP-43. Hum Mol Genet. Sep. 15, 2009;18(18):3353-64. doi: 10.1093/hmg/ddp275. PMID: 19515851. (Year: 2009).*
GenPept Accession No. XP_010314855.1, dated Aug. 8, 2018.
NCBI Gene ID No. 101264806, dated May 9, 2020.
Enciso-Rodriguez, Felix et al.: "Overcoming Self-Incompatibility in Diploid Potato Using CRSPR-Cas9" Frontiers in Plant Science, vol. 10, Apr. 2, 2019, pp. 1-12.
International Search Report and Written Opinion regarding International App. No. PCT/NL2020/050295, mailed Jul. 9, 2023, 2020.
Abdalla, et al., A two-loci system of gametophytic incompatibility in Solanum phureja and S. stenotomum, Euphytica, 20:345-350, 1971.
Anithakumari, et al. A pipeline for high throughput detection and mapping of SNPs from EST databases. Mol Breeding, 26:65-75, 2010.
Bankevich, et al. SPAdes: A New Genome Assembly Algorithm and Its Applications to Single-Cell Sequencing. Journal of Computational Biology. vol. 19, No. 5, pp. 455-477, 2012.
Birhman, et al. Production of inbred progenies of diploid potatoes using an S-locus inhibitor (Sli) gene, and their characterization. Genome, vol. 43, No. 3, pp. 495-502, 2000.
Black, et al. A proposal for an international nomenclature of races of Phytophthora infestans and of genes controlling immunity in Solanum demissum derivatives. Euphytica, 2, 173-179 (1953).
Boettcher, et al. Choosing the Right Tool for the Job: RNAi, TALEN, or CRISPR. Mol. Cell, Vo. 58, Issue 4, pp. 575-585, 2015.
Brootaerts, et al. Petunia hybrida S-proteins: ribonuclease activity and the role of their glycan side chains in self-incompatibility. Sexual Plant Reprod 4, 258-266 (1991).
Deblaere, et al. Vectors for cloning in plant cell. Meth. Enzymol. 153:277-292, 1987.
Edgar. Muscle: multiple sequence alignment with high accuracy and high throughput. Nucleic Acids Research, vol. 32, Issue 5, pp. 1792-1797, 2004.
Eggers, et al. Neofunctionalisation of the Sli gene leads to self-compatibility and facilitates precision breeding in potato. Nat Commun 12, 4141, 2021.
Fernandez-Pozo, et al. The Sol Genomics Network (SGN)-from genotype to phenotype to breeding. Nucleic Acids Research, vol. 43, Issue D1, pp. D1036-D1041, 2015.
Foster, et al. Rpi-vnt1.1, a Tm-22 Homolog from Solanum venturii, Confers Resistance to Potato Late Blight. MPMI vol. 22, No. 5, pp. 589-600, 2009.
FRY. Phytophthora infestans : the plant (and R gene) destroyer. Mol. Plant Pathology. vol. 9, Issue 3, pp. 385-402, 2008.
Gaj, et al. ZFN, TALEN, and CRISPR/Cas-based methods for genome engineering. Trends in Biotechnology, vol. 31, Issue 7, pp. 397-405, 2013.
Gebhardt, et al. RFLP maps of potato and their alignment with the homoeologous tomato genome. Theoret. Appl. Genetics 83, 49-57, 1991.
Gruber, et al. Vectors for Plant Transformation. Methods in Plant Molecular Biology and Biotechnology. pp. 89-119, 1993.
Haas, et al. Genome sequence and analysis of the Irish potato famine pathogen Phytophthora infestans. Nature 461, 393-398, 2009.
Hancock, et al. The stylar 120 kDa glycoprotein is required for S-specific pollen rejection in Nicotiana. The Plant Journal, vol. 43, Issue 5, pp. 716-723, 2005.
Hanneman. Self fertility in Solanum chacoense. Am. Potato J, 62, 428-429, 1985.
Hardigan, et al. Genome Reduction Uncovers a Large Dispensable Genome and Adaptive Role for Copy Number Variation in Asexually Propagated Solanum tuberosum. The Plant Cell, vol. 28, Issue 2, pp. 388-405, 2016.
Haverkort, et al. Durable Late Blight Resistance in Potato Through Dynamic Varieties Obtained by Cisgenesis: Scientific and Societal Advances in the DuRPh Project. Potato Res. 59, 35-66, 2016.
Hawkes. Taxonomic Studies On the Tuber—Bearing Solanums. 1: Solanum Tuberosum and the Tetraploid Species Complex, Proceedings Linnean Society London, vol. 166, Issue 1-2, pp. 97-144, 1956.
Hermsen. Genetics of self-compatibility in dihaploids of *Solanum tuberosum* L. 2. Detection and identification of all possible incompatibility and compatibility genotypes in six F1'S from interdihaploid crosses. Euphytica 27, 1-11, 1978.
Higgins, et al. Fast and sensitive multiple sequence alignments on a microcomputer, Comput Appl Biosci., vol. 5, Issue 2, pp. 151-153, 1989.
Hirsch, et al. Spud DB: A Resource for Mining Sequences, Genotypes, and Phenotypes to Accelerate Potato Breeding. The Plant Genome, vol. 7, Issue 1, pp. 1-12, 2014.
Horsch, et al. A Simple and General Method for Transferring Genes into Plants. Science, vol. 227, Issue 4691, pp. 1229-1231, 1985.
Hosaka, et al. Genetics of self-compatibility in a self-incompatible wild diploid potato species *Solanum chacoense*. 1. Detection of an S locus inhibitor (Sli) gene. Euphytica 99, 191-197 (1998).
Hosaka, et al. Genetics of self-compatibility in a self-incompatible wild diploid potato species *Solanum chacoense*. 2. Localization of an S locus inhibitor (Sli) gene on the potato genome using DNA markers. Euphytica 103, 265-271 (1998).
Hutten. Basic aspects of potato breeding via the diploid level. Thesis, Wageningen University, Wageningen, ISBN 9054852925, (1994).
Jansky, et al. M6: A Diploid Potato Inbred Line for Use in Breeding and Genetics Research. J. of Plant Reg. vol. 8, Issue 2, pp. 195-199, 2014.
Karlin, et al. Methods for assessing the statistical significance of molecular sequence features by using general scoring schemes. PNAS, vol. 87, No. 6, pp. 2264-2268, 1990.

(56) References Cited

OTHER PUBLICATIONS

Karlin, et al. Applications and statistics for multiple high-scoring segments in molecular sequences. PNAS, vol. 90, No. 12, pp. 5873-5877, 1993.
Kim, et al. Genome sequence of the hot pepper provides insights into the evolution of pungency in *Capsicum* species. Nat Genet vol. 46, No. 3, 270-278 (2014).
Klein, et al. High-velocity microprojectiles for delivering nucleic acids into living cells. Nature 327, 70-73 (1987).
Li, et al. All 17 S-locus F-box proteins of the S2- and S3-haplotypes of Petunia inflata are assembled into similar SCF complexes with a specific function in self-incompatibility. The Plant Journal, vol. 87, Issue 6, pp. 606-616, 2016.
Lindhout, et al. Achieving Sustainable Cultivation of Potatoes vol. 1: Chapter 5, Hybrid potato breeding for improved varieties, 2018. United Kingdom: Burleigh Dodds Science Publishing Limited.
Mcclure, et al. Compatibility and incompatibility in S-RNase-based systems. Annals of Botany, vol. 108, Issue 4, pp. 647-658, Sep. 2011.
McDonald, et al. Pathogen Population Genetics, Evolutionary Potential, and Durable Resistance. Annual Review of Phytopathology, vol. 40:349-379, 2002.
Meijer, et al. QTL mapping in diploid potato by using selfed progenies of the cross S. tuberosum x S. chacoense. Euphytica 214, 121 (2018).
Miki, et al. 1993. Methods in Plant Molecular Biology and Biotechnology, Chapter 6, Procedures for Introducing Foreign DNA into Plants.
Miki, et al. Selectable marker genes in transgenic plants: applications, alternatives and biosafety. Journal of Biotechnology, vol. 107, Issue 3, pp. 193-232, 2004.
Myers, et al. Optimal alignments in linear space. Comput Appl Biosci. 4(1):11-17, 1988.
Nakade, et al. Cas9, Cpf1 and C2c1/2/3—What's next? Bioengineered, vol. 8, Issue 3, pp. 265-273, 2017.
Needleman, et al. A general method applicable to the search for similarities in the amino acid sequence of two proteins. J Mol Biol. 48(3):443-53, 1970.
Nettancourt, et al. Incompatibility in angiosperms. Folia geobot. phytotax. 13, 370 (1978).
Niks, et al. Breeding Crops with resistance to diseases and pests. Wageningen Academic Publishers 2011.
O'Brien, et al. Molecular analysis of the stylar-expressed Solanum chacoense small asparagine-rich protein family related to the HT modifier of gametophytic self-incompatibility in Nicotiana. The Plant Journal, vol. 32, Issue 6, pp. 985-996, 2002.
Okamura, et al. Regulation of plant gene expression: General principles. The Biochemistry of Plants 15: 1-82. 1989.
Olsder, et al. Genetics of self-compatibility in dihaploids of *Solanum tuberosum* L. I. Breeding behaviour of two self- compatible dihaploids. Euphytica 25, 597-607 (1976).
Park, et al. Characterization and high-resolution mapping of a late blight resistance locus similar to R2 in potato. Theor Appl Genet 111, 591-597 (2005).
Pearson, et al. Improved tools for biological sequence comparison. Proc Natl Acad Sci USA. 85(8):2444-8, 1988.
Pel, et al. Mapping and Cloning of Late Blight Resistance Genes from Solanum venturii Using an Interspecific Candidate Gene Approach. Mol Plant Microbe Interact. 22(5):601-15, 2009.
Phumichai, et al. Toward the development of highly homozygous diploid potato lines using the self-compatibility controlling Sli gene. Genome. 48(6): 977-984, 2005.
Phumichai, et al. Cryptic improvement for fertility by continuous selfing of diploid potatoes using Sli gene. Euphytica 149, 251-258 (2006).
Phumichai, et al. Expression of S-locus inhibitor gene (Sli) in various diploid potatoes. Euphytica 148, 227-234 (2006).
Sharma, et al. Construction of Reference Chromosome-Scale Pseudomolecules for Potato: Integrating the Potato Genome with Genetic and Physical Maps. G3 Genes|Genomes|Genetics, vol. 3, Issue 11, pp. 2031-2047, 2013.
Smith, et al. Comparison of biosequences. Adv. Appl. Math, vol. 2, pp. 482-489, 1981.
Song, et al. Gene RB cloned from Solanum bulbocastanum confers broad spectrum resistance to potato late blight. PNAS, vol. 100, No. 16, pp. 9128-9133, 2003.
Stefanowicz, et al. Plant F-box Proteins—Judges between Life and Death. Critical Reviews in Plant Sciences, vol. 34, Issue 6, pp. 523-552, 2015.
Tavazza, et al. Genetic transformation of potato (*Solanum tuberosum*): An efficient method to obtain transgenic plants. Plant Science, vol. 59, Issue 2, pp. 175-181, 1989.
Uitdewilligen, et al. A Next-Generation Sequencing Method for Genotyping-by-Sequencing of Highly Heterozygous Autotetraploid Potato. PLOS One 8(5): e62355. 2013.
Van Berloo, et al. An Online Potato Pedigree Database Resource. Potato Res. 50, 45-57 (2007).
Van Der Vossen, et al. An ancient R gene from the wild potato species *Solanum bulbocastanum* confers broad-spectrum resistance to Phytophthora infestans in cultivated potato and tomato. The Plant Journal, vol. 36, Issue 6, pp. 867-882, 2003.
Van Der Vossen, et al. The Rpi-blb2 gene from Solanum bulbocastanum is an Mi-1 gene homolog conferring broad-spectrum late blight resistance in potato. The Plant Journal, vol. 44, Issue 2, pp. 208-222, 2005.
Van Ooijen, et al. Accuracy of mapping quantitative trait loci in autogamous species. Theoret. Appl. Genetics 84, 803-811 (1992).
Verzaux, et al. High Resolution Mapping of a Novel Late Blight Resistance Gene Rpi-avl1, from the Wild Bolivian Species *Solanum avilesii*. Am. J. Pot Res 88, 511-519 (2011).
Vos, et al. Development and analysis of a 20K Snp array for potato (*Solanum tuberosum*): an insight into the breeding history. Theor Appl Genet 128, 2387-2401 (2015).
Vries, et al. The potential of hybrid potato for East-Africa. Open Agriculture, vol. 1, Issue 1, pp. 151-156, 2016.
UniProt Accession No. M1BEMO_SOLTU, dated April, 3, 2013.
Su, et al. Introgression of Genes for Resistance against Phytophtora infestans in Diploid Potato, American Journal of Potato Research 97:33-42, 2020.
Taylor, Routes to genetic gain in potato, Nature Plants 4: 631-632, 2018.
Ye et al., Generation of self-compatible diploid potato by knockout of S-RNase, Nature Plants 4:651-654, 2018.
Lindhout, et al. Towards F1 Hybrid Seed Potato Breeding, Journal of the European Association for Potato Research, 54:301-312, 2011.

* cited by examiner

Figure 1

```
                                      SEQ ID NO:
BL_17SC0100-0002_NODE_4559_lengt      14  MDYFLLLPEDCVCDILSFTSPKDVVISSAISRGFNSAAESDVIWVKFLPDDYEDINSRYV
PSC-PGSC0003DMT400043434              10  MDYFLLLPEDCVCDILSFTSPKDVVISSAISRGFNSAAESDVIWVKFLPDDYEDINSRYV
FO_D2_NODE_55467_length_4836_cov      11  MDYFLLLPEGCVCDILSFTSPKDVVISSAISRGFNSVAESDVIWVKLLPDDYEDIISRYV
FO_D8_NODE_78731_length_3613_cov      12  MDYFLLLPEGCVCDILSFTSPKDVVISSAISRGFNSAAESDVIWVKFLPDDYEDIISRYV
FO_D14_NODE_41388_length_7594_cov     13  MDYFLLLPEGCVCDILSFTSPKDVVISSAISRGFNSAAESDFIWVKFLPDDYEDIISRYV
DM-PGSC0003DMT400043434                9  MDYFLLLPEGCVCDILSFTSPKDVVISSAISRGFNSAAESDVIWVKFLPDDYEDIISRYV
                                          *********.**************************.****.****:******** ****
                                          .........|.........|.........|.........|.........|.........|
                                                  10        20        30        40        50        60

BL_17SC0100-0002_NODE_4559_lengt          SPRIYPSKKELYFSLCDFPVLMDGGKLSFSLDKKTGKKCFMISARELAITWGVDTPWYWE
PSC-PGSC0003DMT400043434                  SPRIYPSKKELYFSLCDFPVLMDGGKLSFSLDKKTGKKCFMISARELAITWGVDTPWYWE
FO_D2_NODE_55467_length_4836_cov          SPRIYPSKKELYFSLCDFPVLMDGGKLSFSLDKKTGKKCFMISARELAISWGVDTPWYWE
FO_D8_NODE_78731_length_3613_cov          SPRIYPSKRELYFSLCDFPVLMDGGKLSFSLDKKTGNKCFMISARELAISWGVDTPWYWE
FO_D14_NODE_41388_length_7594_co          SPRIYPSKKELYFSLCDFPVLMDGGKLSFSLDKKTGKKCFMISARELAISWGVDTPWYWE
DM-PGSC0003DMT400043434                   SPRIYPSKKELYFSLCDFPVLMDGGKLSFSLDKKTGKKCFMISARELAISWGVDTPWYWE
                                          ********.***************************:************:**********
                                          .........|.........|.........|.........|.........|.........|
                                                  70        80        90       100       110       120
```

Figure 1 continued

```
BL_17SC0100-0002_NODE_4559_lengt       WISHPDSRFSEVAHLKGVSWLDIRGTIGTQILSKRTKYVVYLVFKLSKNHDGLEIANAFV
PSC-PGSC0003DMT400043434               WISHPDSRFSEVAHLKGVSWLDIRGTIGTQILSKRTKYVVYLVFKLSKNHDGLEIANAFV
FO_D2_NODE_55467_length_4836_cov       WISHPDSRFSEVAHLKGVSWLDIRGTIGTQILSKRSKYVVYLVFKLAKDHDGLEIANAFV
FO_D8_NODE_78731_length_3613_cov       WISHPDSRFSEVAHLKGVSWLDIRGTIGTQILSKRTKYVVYLVFKLAKDHDGLEIANAFV
FO_D14_NODE_41388_length_7594_co       WISHPDSRFSEVAHLKGVSWLDIRGKIGTQILSKRTKYVVYLVFKLAKDHDGLEIANAFV
DM-PGSC0003DMT400043434                WISHPDSRFSEVAHLKGVSWLDIRGTIGTQILSKRTKYVVYLVFKLAKDHDGLEIANAFV
                                       *************************.*********:**********:*:***********

                                       .........|.........|.........|.........|.........|.........|
                                              130       140       150       160       170       180
BL_17SC0100-0002_NODE_4559_lengt       RFVNRVSDKEAEERASVVSLVGKRVRRRKRNVKCPRKRVDGWMEIELGNFINDTGDDGDV
PSC-PGSC0003DMT400043434               RFVNRVSDKEAEERASVVSLVGKRVRRRKRNVKCPRKRVDGWMEIELGNFINDTGDDGDV
FO_D2_NODE_55467_length_4836_cov       RFVNRVSDKEAEERASVVSLVGKRVRRRKRNVKRPRKRVDGWMEIELGNFINDTRDDGDV
FO_D8_NODE_78731_length_3613_cov       RFVNRVSDKEAEERASVVSLVGKRVRRRKRNVKRPRKRVDGWMEIELGNFINDTGDDGDV
FO_D14_NODE_41388_length_7594_co       RFVNRVSDKEAEERASVVSLVGKRVRRRKRNVKRPRKRVDGWMEIELGNFINDTGDDGDV
DM-PGSC0003DMT400043434                RFVNRVSDKDAEERASVVSLVGKRVRRRKRNVKRPRKRVDGWMEIELGNFINDTGDDGDV
                                       *********:*********************** ******************** *****

                                       .........|.........|.........|.........|.........|.........|
                                              190       200       210       220       230       240
```

Figure 1:
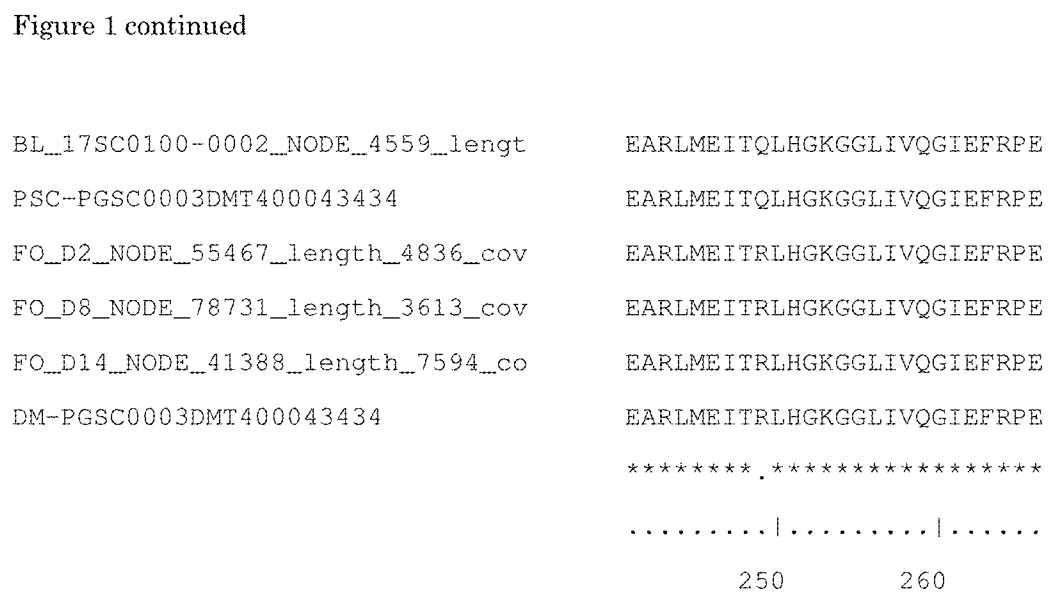

```
BL_17SC0100-0002_NODE_4559_lengt      EARLMEITQLHGKGGLIVQGIEFRPE
PSC-PGSC0003DMT400043434              EARLMEITQLHGKGGLIVQGIEFRPE
FO_D2_NODE_55467_length_4836_cov      EARLMEITRLHGKGGLIVQGIEFRPE
FO_D8_NODE_78731_length_3613_cov      EARLMEITRLHGKGGLIVQGIEFRPE
FO_D14_NODE_41388_length_7594_co      EARLMEITRLHGKGGLIVQGIEFRPE
DM-PGSC0003DMT400043434               EARLMEITRLHGKGGLIVQGIEFRPE
                                      ********.*****************
                                      .........|.........|......
                                               250       260
```

Figure 4

| | 11-0020 | 11-1007 |
|---|---|---|
| SOT12-00206188 | b | a |
| SOT12-11646765 | b | a |
| SOT12-40245065 | b | a |
| SOT12-49301746 | b | a |
| SOT12-53793483 | b | a |
| SOT12-56559959 | b | a |
| SOT12-57125022 | b | a |
| SOT12-57412546 | b | a |
| SOT12-57475688 | b | a |
| SOT12-57602201 | b | a |
| SOT12-57716039 | b | ? |
| SOT12-57817238 | b | a |
| SOT12-57902259 | b | a |
| SOT12-58127825 | b | a |
| SOT12-58205669 | b | a |
| SOT12-58470194 | b | a |
| SOT12-58517350 | b | a |
| SOT12-58601503 | b | a |
| SOT12-58772425 | a | a |
| SOT12-58820928 | a | a |
| SOT12-58960670 | a | a |
| SOT12-59068564 | a | a |
| SOT12-59118012 | a | a |
| SOT12-59230363 | a | b |
| SOT12-59631591 | a | b |
| SOT12-60102894 | a | b |
| SOT12-60390660 | a | b |
| SOT12-60708789 | a | b |
| Compatibility | SC | SC |

Figure 5

| Population | Plant | SOT12-02478572 | SOT12-50632815 | SOT12-61145775 | SOT12-57348932 | SOT12-58583551 | SOT12-58822517 | SOT12-58962004 | SOT12-58996998 | SOT12-59045637 | SOT12-59130723 | SOT12-59155059 | SOT12-59173975 | SOT12-59188763 | SOT12-59214797 | SOT12-59225998 | Classification | Total self pollinations | Total self berries | Total bulk pollinations | Total bulk berries |
|---|---|---|---|---|---|---|---|---|---|---|---|---|---|---|---|---|---|---|---|---|---|
| 18SC0011 | 0007 | b | b | b | b | b | b | b | b | b | b | b | b | b | b | b | SC | 20 | 5 | 8 | 2 |
| 18SC0011 | 0027 | a | a | a | a | b | b | b | b | b | b | b | b | b | b | b | SC | 18 | 6 | 8 | 3 |
| 18SC0011 | 0053 | a | a | a | a | b | b | b | b | b | b | b | b | b | b | b | SC | 6 | 5 | 4 | 1 |
| 18SC0011 | 0059 | a | a | a | b | b | b | b | b | b | b | b | b | b | b | b | SC | 17 | 6 | 6 | 7 |
| 18SC0011 | 0090 | a | a | a | b | b | b | b | b | b | b | b | b | b | b | b | SC | 20 | 9 | 8 | 7 |
| 18SC0011 | 0091 | a | a | a | a | b | b | b | b | b | b | b | b | b | b | b | SC | 20 | 1 | 12 | 10 |
| 18SC0011 | 0101 | b | b | b | b | b | b | b | b | b | b | b | b | b | b | b | SC | 20 | 2 | 7 | 4 |
| 18SC0011 | 0129 | a | a | a | b | b | b | b | b | b | b | b | b | b | b | b | SC | 28 | 4 | 11 | 9 |
| 18SC0011 | 0134 | a | a | a | b | b | b | b | b | b | b | b | b | b | b | b | SC | 25 | 2 | 7 | 7 |
| 18SC0011 | 0147 | a | b | b | b | b | b | b | b | b | b | b | b | b | b | b | SC | 20 | 2 | 9 | 6 |
| 18SC0011 | Ex2 | b | b | b | b | b | b | b | b | b | b | b | b | b | b | b | SC | 25 | 6 | 5 | 20 |
| 18SC0011 | Ex5 | a | b | b | b | b | b | b | b | b | b | b | b | b | b | b | SC | 9 | 8 | 6 | 0 |
| 18SC0012 | 0012 | b | a | a | a | a | a | a | b | b | b | b | b | b | b | b | SI | 20 | 0 | 10 | 5 |
| 18SC0012 | 0117 | a | b | b | b | b | b | b | b | b | a | a | a | a | a | a | SI | 23 | 0 | 8 | 6 |

Figure 6

| Genotype | SOT12-58587813 | SOT12-58960670 | SOT12-58964340 | SOT12-58977155 | SOT12-58985310 | SOT12-58990272 | SOT12-58996133 | SOT12-59003185 | SOT12-59011119 | SOT12-59016142 | SOT12-59025327 | SOT12-59030301 | SOT12-59042436 | SOT12-59043512 | SOT12-59043574 | SOT12-59045607 | SOT12-59046301 | SOT12-59047597 | SOT12-59047933 | SOT12-59060445 | SOT12-59062427 | SOT12-59065996 | SOT12-59068564 | SOT12-59068879 | SOT12-59107520 | SOT12-59118012 | SOT12-59137670 | SOT12-59230362 | Compatibility |
|---|---|---|---|---|---|---|---|---|---|---|---|---|---|---|---|---|---|---|---|---|---|---|---|---|---|---|---|---|---|
| 11-2259 | b | b | b | b | b | b | b | b | b | b | b | b | b | a | a | ? | ? | a | a | a | ? | a | a | ? | a | a | a | a | SI |
| 11-2435 | a | a | a | a | a | a | a | a | a | a | b | b | b | b | b | b | ? | b | b | b | b | b | b | ? | ? | b | b | b | SI |

Figure 7

SEQ ID NO:1

>DM4.04 chr12 ctatattttgttgttcttagtcctttcttataggattttgcattgcccccacccccaccccccttgttagtagctatatctttttccattgttttctt
cttccttgtacttacatttgttgcacttgcgttgagggtctttcgataataacatccctagcctccacaaagtactagtaagggctgcgtacactcta
ccctccttgttttcttcttccttgtacttacatttgttgcacttgagttgagggtcttttgaaaataacatctctacctccacaaggtagtgataagg
actgcgtacactctaccctccccagactccacttgtggaatttcaccggatatgttattgttattgttataaggaaaagctttggtctcgaaactctt
taaactcaatttttttcttttgcactccctcttttcttgagtacacttcactctcaattctttcttgagcacacactcttttatttgagtacacatac
aactcaaatgaccacctcaatcgaccccacttgtggaatttcaccagatatgttgttgttattgttataaggacaagcttcggtcttaaagctcgata
aactcatttttttcttttgcactccctcttttcttaagtacacttcactctcaattctttcttgagcacacactctttatttgagtaaacatacaact
caaatgatcacctctatttatcggtgttgatggaaggatctagtgaatgcaatattctagaactacaccttccacttctttctcgaattcttttagac
tttgcactctagaactctcatcctaaagttcttctttcaatacaagtcttgaatatgctagattcttctttgaaatatcttagatattaattaaggtg
gtgatgacttttaacacccctctcagcaccaacttaatttattctttgcatccattttgagtgatcctcgagacattgcaatcatcttgatgtccagt
aactttatgaatctcttcctcctttgaacttccccactcacttttctttgaatcttattcgaaggtagtagtctccttgatctagaccactctgctaa
tgttgcatcaatatacttggtgtttgggaatttcaatcatgtagacctccttagtcacggttgtggtgcttctcggacttcttcttgcaacattacag
gagtttcactttgagtctaataggaaatctctttggaccaccatgttgatgcttcatcaaataccagatttcttgacacatatatcctattagtgata
ggaaggagaaatacgaagggatataggatagacttttcgattgagccttcttgttgaatctataacaactctacaataatgtaacttgataaagtagg
tattagggctccctcgctctaacagctatagtgaccccccttagcagcagctgcgcagccctcccatggctgctacaaccactggaaagcctcctcccg
aggtagtccagcccgccccaacatggttttatctcgctcagtgaaggttcagtattagcggtaatgcaagttaaggatttgaacaaagggagagaatt
tggtagaaaagaggagcggaacatggtaatgcgcaagaaggcaacatctaatgcttctccaggttgtgagaagaggcacaatattagtaatgtttcaa
gagccctattatgttggaacaactttgatgctttattgaaggctactggaaaaaatagtaatattatggttccaacattacatatttctaatccttaa
gtagctaattaggattattcaagaaaatcaggatggcatgctactcaaatccaatccaacaatcaagccactcatggttacattgaacacctcggctc
atgaggccccttcccaatcattggagtcacttggtcaatatcaaggtgaatctggacagctactattgtcaacagggaatggtgacgatttagttact
ttagatgtgcaatcaatctttttttaattcatgcacttgtcaaaggaagtttgaggccgataactcaaccttcttaattcttggttgttatattttaac

Figure 7 cont.

attatttaagcatcctcatttgtaatatcatcagagtgtattacaaactctatggtaatcacaaaatcctagtttttctagcttttatttttcttc
atgcttgttagttagtagaggtttgttacctcattatgactggtaaggtaaggtccagctccctttacttgtacttatccctgatgaatttttttat
tatttttaatagaaagccgctaaaaaaataattttaagaaatttattttatacgtaatcaaattaaaatacgttgcataaaacatttataagaaagt
ggaatgacgtacgttgtagatcaaattaaggaaatgataagagataaacctggaatcgtggtgtttcttccattgccaagagtgtatgtcatcactcc
ccaaaatttcaagctttcttgctgctatcataaaacatttttttccactgtacttatcaataaaaaaattctgaaaggaaaaaaaaaccattaaacaa
tataaaaatgtataatattgtatttataatctaatcattaatccaaattcacaccatgtaaggaacttataattttataaagaaaagtagcatacata
atagagttattatagataaaggtaggggaaaaaaaaaggattataaagtaatgaacaaagtcaaaataagaaaataaaaatatcgtaatgacatggcc
atatcaaattgatcattacataaaatgatactttcatcgttacataatgatgaatttattgataagatacaataaaaattaaataattaacaattcaa
ataaacgttgtgtttaaaataacaatataatacaatacgataactcacaacaacccaaaggcatatagttcaatttttcgaataacctaaacttggtg
agtgaaacagaataaaacaagattcttttgatctttcttagtttcattaactatgaaaaaaataaaaaagtacaaaaaatgaaacatcaagaaagata
tagccagtgaacaatgaattgattgaaaattataagatattagattttaaattttagcaaagataaaaaattgggtggtcatttcgttctacctgctt
gagctatagaattacctggtatagtagtcgtgataaaagtttaattgaatctcctttacttgaaattacaccgatacacatggtaaaaatatattttt
aaaaaaattatatatgaattgttgaattcaaagtctagtttagcaacagaggggtacaaaggttgttttagattacgagtttaaatcctaagtgtgac
actcatttttttttaatattcttatatgaatttctaactcatcattatattgtttgatacttgtgttagtgagaggctaaaaccgatttacaagatt
aataccaatttcatatgaatcctatacttttatatatatcggaacataaatttatgtgtaaaaattcatgataaatgcaatagatatagtagatataa
atcacaactttaaagaacatcatgatttaaatgttaagtaactaaaaaattgaatccataaatcttaaattctgattttgcctctggtgataggtacc
aaatacgtacctaataaataatttaggttcacgcaaactagcacatataccaccattactaaaatataaataaaatcattgaaggtaattaatcacat
caaaatgagattttaccagtctgccgcggtcaaggagaatgggagaatcacatagactaaaaaagagctcctttttggtgttgcaaatccgaggaagc
ttagatctatcaattatttttggtaatcggaaggcaaaaatcttccccaaatttcatcagatttgcaacaaatttgaatcctgttgatgaaattgt
tgatcttactgcatctgctggagttgttcttgaaattatttcaaagatgcaaccttctggcaacatttcaaaataattcattggagctatagacttag
aaatattcatgtcaaaattcttataaaactttataatcgagaaataacctaagtttttttgttacaagctttatatatgattaaataatcaaaagata
aaaaagatttcagaggtctatacattgtcaaatatagtaataagtacatataagcatatacaattatgtttttttttcctttttgtcaatgagtaca
gataagcaaaaagtcaaacttattcaaataacaataaccattgccacaccttaatctcaaacaagtttcacgttgctttaattaagtgtaccgagact
aatattatattatataaaataaaaataacatgtacgagaagatctatttaatttggcgtgaaatgttatctaaagtctcaaataattggtattgctta
tatgaaagtaaaaaaacttccattgtgtgccatactttcgagacaactcctttgtgattttaggtctacttggtctcattttaacaccttcacactat

Figure 7 cont.

gatttcatagtgtaacaacttaattaatttttatttaatcataataaattagtacgatacagtgtaaacatcagatgtaaataagttaatattcaat
agaggtcaatttagaacatgaccaaaccgtctcatttgttttatttttattatgtgctcgatttattgttagctatttcaacatcgattccaatagta
tttagatctttcgaaaagcaaatagccataacacattattatttatatatcaagaaaacacatatgctatattatagtactattgtgcaatttcttct
TCATTCTGGTCTAAATTCAATTCCTTGAACAATAAGGCCACCTTTTCCATGAAGCCGCGTAATCTCCATCAATCGCGCTTCAACATCTCCATCATCTC
CTGTATCGTTGATAAAATTTCCCAATTCTATTTCCATCCATCCATCGACTCTTTTTCGTGGACGTTTTACGTTACGTTTGCGTCTCCTAACCCTTTTT
CCGACTAGACTCACGACACTAGCTCGTTCCTCGGCATCTTTATCGCTCACACGATTCACAAATCTAACAAATGCATTAGCAATTTCTAGTCCATCATG
ATCCTTTGCCAATTTGAACACCAAATAAACAACATATTTGGTTCTTTTCGACAATATTTGTGTTCCAATCGTGCCTCGTATGTCTAGCCAACTTACAC
CCTTGAGATGTGCCACTTCCGAAAATctacaaaataaaatgtatatatagtctcagatacatgtatttagtgagtttaagatatatatatcatcgcca
atataagtaatttttgcaccatcaaatcatcttttacctattgtaataggtaacatatttcattacatattttaacgaggctcatctatggtgacctg
attgtgttaaaaaattctttcttaccaatagtgacagaggtagaatttcaaccaagggattcaaaaaatagcatatgtagaaattcgttaaaaggcat
tgaagtataatgttttatacgtagtataatttttcgacgaacCTGGAGTCGGGATGAGAAATCCATTCCCAATACCATGGTGTATCAACTCCCCATGA
AATAGCAAGTTCTCTAGCtgatatcataaaacatttcttgcctgttttcttatcaagtgaaaagctctgttttcaaaaataaaataaaatcttagatt
cacactactagcttatagtccattcaaaaataaaataaaattgacaattgttagtataatctatttaattttgcatttttaatggtgtttgtaaccca
tttgccggaaaatcttaaaagttcagttagttgactatctgaacttctgttttactagagagagttcgattctcagtttttaacaaaaacaaaataaa
ataagaaaaattcattggctgattaattaagatttgcagcagtaagcacactagtggattttagtgcttcctatcgacatttcaactctgattaaaac
tcaaactcgagacttcaggtcaaaggttcatgacCTTTACGGTTATACAACACCAACAGCCAGGGGCGGAGCTAGAACACCCctataaattctaggaa
gtcaatagttttagttcaaactctgtatttatctttaaaaagaaaactcctctaatatgtaccaaattattaatttcgaaccaaacaactcaaaaaac
acacaaaaagaaatcccgaacccataagcttcaacgcaattatacatatattaaactaaaatgagccaaaaaaaagcttactacttcccaatttagag
ctacttacCAATTTGCCTCCATCCATTAGAACAGGGAAGTCACATAGACTAAAGTAAAGCTCCTTTTTAGACGGATAAATCCGCGGGGAGACATATCT
CGAGATAATATCTTCATAATCATCTGGTAAAAACTTTACCCAAATAACGTCGGATTCAGCAGCAGAGTTGAATCCCCGAGAGATCGCGGATGAAATCA
CGACATCTTTCGGGGAAGTAAAGGAGAGAATATCACAAACACAACCTTCTGGTAGCAATAGGAAATAGTCCATtattggaaaattgaatttgaagatt
tgtgaatttttttttgtttatataaagcaaactgagaaaagtttattgaaaagttgttacactcatgtctcaacggttaagtattgtttcgttcattt
ttacttctccagtatgaatataataagagaaaaaggtcatatgagttagaactgatatatagctcgttataaaaatgggctcatacatacctatatta
ttacacaaatagcctagatatacccttttggcctaatggaagtgaaaatatttaattttattcatttttgtttatttttcattattttatctagttct
cacatatgtacattttatttccaaaaataaataaattaaagaattgatatttgcttagatacaccaaacaaacaactcatgtggaggaagatattatt

Figure 7 cont.

ccactaacataaaacatgaaatgttttgagtttgaaactttttttttttttcctttttttggtgaagtgaaacatgaaatgtttaggaagattcatcat
tgggtattcgaaatttactggcccgactaattcaagattaatatcatctaaggtccatttatcaaggagcattcccgaccaagaatttctccattctc
tgaattcaaaccgaagacttcttgtttagttaacactggagaaatctcattcatcgcgccacatctttgatgagttgtggcagttccccaaaagcaat
attcacaaattcttacattcaccatttcatcaatttcttatagttataaaactacaataacaacatatccaatgtctccccacaaagtgaggtctagg
gagggtagagtgtacacagactttacttcaactttagagatagaaagtctttttctgatagatcctcaactcgagaaaactaatccaaagcagttcag
aattagacacaacaaaagtacaagaaacaacagatagtaacagaacagtacttcttgaatatggtactggattaggtagaaagaacataaaaaaaggc
taataacaatggaatgaatttgccactgcattttgattcaacattaacaaattactatctcttacacagaacatacacttgttcaagtggaaatctat
atacagtactttcaaaatcactctcactcgtacttgagctcgagaaaaattccttatactaactgcgtcttccccatttcacgaggagtggagagaac
gtttcacacgttgtctttactacatcttcagcaggtaacgtcttTTATCTCGTTTGGAAGTTAAATGCCTTAATAGCGAAAGCAAATGTGAAGCCAAA
AAGAACAGTGTACCCAACAATCGCGACTGCAACTATTGGAAGAAAATCATGCTTGAAGCCGAAGTAACGTCTCAAGAATTGTTCCACTGTTTCTTCAT
CAGTAAGTTTGTTCTGAAGATCTCCAAATTGTGATGCAACCAAACCATACAAGGTCCAGGCAACAGGACAACACCAGTAGTACCATCTCCACCATATG
GGAATACGctgtttttcaaaatgaaaatggaaaaaaaatacagagaatatgtcatttccgagctctaagttagttttgatgtaacaataaaatggaa
gtgtttcaagaacttacAGTTCGTGGAACGATGAATCCTGAGAAAAGATTCCATACTCCGTAGAAGAAGGAGCCGACAATTTGAGCAACACTTACATT
TGGGGTAACAGCAACGGTCATCATACCGTAGAAAGTGAAGTACAAGAGGGTGAAAAACAGGAAGAACAAGTACCAAAAGAACTTTGCTACCGTCCATT
CAAATCCGATCATAGCATACATAATTGCACCACAGAAAACAGATTGCATAAAGACATATGGGATTTCAATGGAAATctgcaagatagaaaaagttaag
taatttagacttttcacctaaattgtcgaggcacgtagtgttaagagtggataacatgtagtcacttatagtgggaaaagctcagtgatcaaatgtga
aattaacgcaagattggcttataagaaattgaactctatgttcacCTGTCCAAAGGCATAGGGCAAGGCAGAATACATTCCAGCAGCTCTTTCTCTAT
AGAATACTGTACGTTCAACGGCTACAACAGGCTGCACTGATGATGAATTTTGTGTACCGAGGAAGAGAACAGTAGCATACAAGCATCCCATCGCGTTA
AATAGATCTTGACTCTTACTCctgtaaccataaaagatcaagttttagtgttagttgagggtatttttttagtttgtgtaattgttgtttttttgcttcg
ta

Figure 7 cont.

SEQ ID NO:2

>FO_DS NODE_6145_length_29156_cov_4.538109 ctctattttgttgttcttagtcctttcttataggattttgcattgcccccacccccacccccttgttataagtaactatatctttttccattgtttt
cttcttccttgtacttacatttgttgcatttgagttgagggtctttcgaaaataacatctctacctccacgaggtagtgataaggactgcgtacactc
taccctccccagactccacttgtggaatttcaccggatatgttgttgttattgttataaggaaaagctttggtctcaaaactctttaaactcaatttt
ttttcttttgcactccctcttttcttgagtacatttcactctcaattctttcttgagcacacactcttttatttgagtacacatacaactcaaatgac
cacctcaatctatcggtgttgatggaaggatctagtgaatgcaatattctagaactacaccttccacttctttctctaattcttttagactttgcact
ctataactctcatcctaaagttcttctttcaatacaaatcttgaatattctagattcttctttgaaatatcttagatattaattaaggtggtgatgac
cttttaacacccctctcagcaccaacttaatttattctttgtatccattttgagtgatcctcgagacattgcaatcatcttgatgtccaggaacttta
tgaatctcttcctcctttgaacttccccactcacttctctttgaatcttattcgaaggtagtagtctccttgatctagaccactctgctaatgttgca
tcaatatacttggtgtttgggaatttcaatcatgtagacctagctccttagtcacggttgtggtgcttctcggacttcttcttgcaacatgacaagag
tttcacttgagtctaatagtaaatctctatagtgaccccccttagcagcagctgcgcagccctcccatggctgctacaaccactggaaagcctcctccc
gaggtagtccagcccgccccaacatggttttatctcgctcagtgaaggttcaatattagcagtaatgcaagttaacaatttgaacaaagggagagaat
ttggcagaaaagaggatcggaacatggtaatgcgcaagaaagcaacatctaatgcttctccaggttgtgagaagaggcacaatattagtaatgcttca
agagccctattatgttcgaacaactttgatgctttattgaaggctactggaaaaaatagtaatattatggctccaacattacatatttctaatcctga
agtagctaattaggattattcaagaaaatcaggatggcatgctactcaaatccaatccagcaatcaagccactcatggtcacattgaacacctaggct
catgaggtcccttcccaatctttggagtcacttggtcaatatcaaggtgaatctggacaactactattgtcaacagggaatggtgacgatttagttac
tttagatgggcaatcaatctttttttaattcatgcatttgtcaaaggaagtttgaagccgataactcaaccttcttaattcttggttgttatattttaa
cattatttaagcatcctcatttgtaatatcatcatcgtgtgtattacaaattttgtggtaatcacaaaatgctagtttttctagcttttattttctt
catacttgttagttagtaaaggtatgttacctcattatgactggtaaggtaaggttcaacttcctttgcttgtacttatccctactgagttttttatt
atttttaatagaaggctgctaaaaaaaataatttcaagaaatctattttatacgatatcaaattaaagtacgttgcataaaacatttataagaaagag
gaatgaagtacgttgtagatcaaattaaggaaatgataagagataaacctggaatcgtggtgtttcttccattgccaagagtgtatgtcatcactacc
caaaatttcaagctttcttgctgctatcataaaacatttttttcccactgtgcttatcgataaaaaaactctgaaagaaaaaaaaacattaaacaataa
aaaaatgtatagtattgtatttataatctaattattaatccaaattcacatcaattaaggaacttataattttataaagaaaagtaacatacatgata

Figure 7 cont.

gagttattatagataaaagtaggggaaaaaaataaaaaaattataaattaatgaacaaagtcaaataagaaaataaaaatattgtaatgacatggcc
atatcaaattgatcattacataaaatgatactttcatcgttacataatgatgaatttattggtaagatacaataaaaattaaataattaacaattcaa
ataaatattgtatttaaaataataatataatacaatacgatagctcacaacaacccaatatagttcaatttttgaataacttaaacttggtgagtga
aacagaataaaacatgattcttttgatctttctagtttcattaactatgaaaaaattaaaagatattagatataaaattttaataaagataaaaacac
tgggtggtcatttttctacttgcttgagctgtagagttacttggtatactagttgagataaatgacataaaaaaatttaattgaaacaccaatacaa
acaaggtgaaattatttttttaaagaaaattatatatgaatcgttgaatctaaaattctagtttagcaacagaggggtttcaaaggttgttttagagt
atgagtttaaatcctaagtgtgaaactcaatattttttttaatattcttatttgaatttctaactccaccattatattgtttaatacttgtgttagtg
agaggctaaagtagatgtagaatattaataccactttcatatgaatcctgtactttcatatatagcggaacataaatttatgtgcaaaaattcatgat
aaatgcaatagatagtagatatgaatcacaactttaaagaatataatgatttaaatgttaattaaataaaaaattgaatccataaatcttaaattctg
attttgcctctagtgataggtaccaaatacgtacctaacaaataatttaggttcacacaaactagcacatataccaccattacaaaaaataaaatgaa
acataaaaggtaattaaccacatcaaaatgagattttaccagtctgccgctatcaaggaggatgggagaatcacatagactaaaaaagagctcctttt
tggtgttgaaaatccgaggaagcttagatctatcaattatttttgataatcggaaggcaaaaatcttccccaaatttcatcagattttgcaacaaat
ttgaatcctgttgataaaattgttgatcttactgcatctgctggagttgttcttaaaattatttcaaagatgcaaccttctggcaacttttcaaaata
attcattggagctatggacttagaaatattcatgtcaaaattcttataaaaccttataaccgagaaataaccaaagtttttttgttacaagctttata
tataattaaataatcaaaagataaaaaagatttcagaggtctatacattgtcaaatatagtaataagtacaaataagcatataaaattatgttttttt
ttcctttttgtcaatgagtacagataagcaaaaagtcaaacttattcaaataacaataaccattgccacaccttaatctcaaacaagtttcacgttg
cttcaattaagtgtatcgagactaatattatattatataaaataaaaataacatgcacgagaagatctctatttaatttggcgtgaaatgttatctaa
agtctcaaataattggtattgcttatatgaaagtaaaaaaacttccattgtgtgccatactttcgagacaactccctttgtgatttaggtctacttcg
tctcattttaacaccttcacactatgatttcataatgtaacaacttaattaatttcttatttaatcatgataaattagtacgatacagtgtaaacatc
ggatgcaaataaattgttatccaatagaggttacatgaccaaaccatctcatttgttttatttttattatgtgctcgatttattgttagctatttcat
catcgattccaatagtatttagatctttcgaaaagcaaatagccataacacattattgtttatatatcaagaaaacacataagctatattatattatt
gtacaatttcttctTTATTCTGGTCTAAATTCAATTCCTTGAACAATAAGGCCACCTTTTCCATGAAGCTGCGTAATCTCCATCAATCGCGCTTCAAC
ATCTCCATCATCTCCTGTATCATTGATAAAATTTCCCAATTCTATTTCCATCCATCCATCGACTCTTTTTCGTGGACATTTCACATTACGTTTGCGTC
TCCTAACCCTTTTTCCGACTAGACTCACGACACTAGCTCGTTCCTCGGCCTCTTTGTCGCTCACACGATTCACAAACCTAACAAATGCATTAGCAATT
TCTAGTCCATCATGATTCTTTGACAATTTGAACACCAAATAAACAACATATTTGGTTCTTTTCGACAATATTTGTGTTCCAATCGTGCCTCGTATGTC

Figure 7 cont.

TAGCCAACTTACACCCTTGAGATGAGCCACTTCCGAAAATctgcaaaataaaatgtctatattgtcttagatacacgtatttagtgagtttaagttat
atataacatcgccaatataagtaatttttgcaccatcaaatcatctttacctattgtaataggtaacatatttcattacacattttagtgaggctcat
ctatatatatcttttaggtggcttgattgtgtaaaaaaaaaattctcaccaatagtggcagaggtagaatttcaaccaagggattcaaaaaataacat
atgtagaaattcgttaaaaggcaatgaagtataatttttatacgtagtacatacataaaaaaaaagaataactttttatatgtagtataatttttcg
acgaacCTGGAGTCAGGATGAGAAATCCATTCCCAATACCATGGTGTATCAACTCCCCATGTAATAGCAAGTTCTCTAGCtgatatcataaaacattt
cttgcctgttttcttatcaagtgaaaaactctgttttcaaaaataaaataaaatcttagattcacactactagcttatatatagtccattcaaaaata
aaataaaattcacacaattattattataatctatttaattttgcattttaatggtgtttgtaacccattggccagaaaatcttagaagttcatttag
ttgactatctgaacttccgttttactatagagagttggattcccagtttgtaacaaaaacaaaataaaataagaaaaattcattggctgattaattaa
gatttgcgcagccgtaagcacactagtagattttagtgcttcctattaaacacgactcaattcctaagatttcaactctgattaaaactcaaactcta
gacctcaggtcaaaggttcatgacCTTTACCGTTATACAACACCAACAGTTAGAGGCAAAGCTAGAACACCCctataaattctaggaacccaatagtt
ttagttcaaactctgtattttatctttaaaaagaaaactcctctaatttgtaccaaattattaatttcgaaccaaacaactcaaaaaacacacaaaaa
atcccgaacccataagcttcaaaacaattatacatatattcaactaatgagccaaaagaaaagcttgctacttcccaatttagagctacttacCAATT
TGCCTCCATCCATTAGAACAGGGAAGTCACATAGACTAAAGTAAAGCTCCTTTTTAGACGGATAAATCCGCGGGGAGACATATCTCGAGTTGATATCT
TCATAATCATCTGGTAAAAACTTTACCCAAATAACGTCGGATTCAGCAGCAGAGTTGAATCCCCGAGAGATCGCGGATGAAATCACGACGTCTTTCGG
GGAAGTAAAGGAGAGAATATCACAAACACAATCTTCTGGTAGCAATAGGAAATAGTCCATtattggaaaattgaatttgaagttttgtgaattttttt
tctttatataaagcaaactgagaaaagtttgttgaaaagttgttacacttcatatgtctcgacggttaagcaggggcggctcaacgtatttggaggcc
taaaacaaaatttaaattaaaggcctaaaatcttttagctgaggcaattattaaataaattgttaacattattctataagtaataagttgacaaaact
gcttataaacttctttttttatttaaaagcacataacataagtcaatctaaacaggcttgtaattcgctttatccaacacattagttttactattgat
tcatatttttgatagagctctaacttacatagagtataaaaggggtatagaaaattacaacgcgagagtaagtgaagagagtgtaagaagacaaaaca
acgtttttcttgatttcttctatttgattgaggttaaggagaataaaataatatatatatgaaaagtacatttatcttaaataattaatttttttctat
aaaaaaaattaacacataatttattgttggtaaaaatttgaggccccccctaaaattgggggcctaaggcatatgcctaattttataagcattgagcc
ggcactgcggttaaatattgttttgttcatttttacttctccagtatgaatataataagtgaaaaggtcatataatttagagctgatacatacctcgt
tataaaaatggctcatacatacctatactattacacaaatagcctagatatacccttttggcctaatggaagtgaaaatatttaattttattttattt
ttaaaaaaatcatttttgtttatttttcattatttttatctagttctcacatatgtacattttatttccaaaaaaaaaataaaattaaagaattgatat
tgcttagatacaccaaacaaacaactcatgtggaggaagatattccaataatactaaacatgaaatgttttgagtttgaaatttttttgtctttccttt

Figure 7 cont.

ttagtgaattaaaacatgaaatgtcttggaagattcgaaatttactggcccgactaatttaagattagcatcatctaaggtccatttatcaaggagcg
ttcccgaccaagaatttctccattctccgaattcaaaccaaagacttgttgtttagttaacactagagaagtctcattctcgcaccacagttgtggca
gttcccgaaaagcaatattcacaaattcttacattcatcatttcattaatttcttatagttgtaactataagaacaacataccatgtgtctcccccac
aaagtggagtatgggaagggtagagtgtaagcaaactttactcttacctcagaggtagaaagtcttcttccgatagatcctcgactcgagaaaaataa
tccaaagcagttcagaaaaagacacaacaaaagtacaagaaacaccagatagtaacagaatagtacttcaacattaacaaattactatctcttacaca
gaaaaatgaacttgaaattcataaaaaataataataataacagaacatacccttgttcaagtggtaatctatatacagtactttcaaaatcaatctct
tgctcgtacttgagctcgagaaaaattccttatactaaccgcgtcttccccatttcacgagcagtggagagaacgtttcacacgttgtctttactaca
tcttcagcaggtaatgtctttTTATCTCGTTTGGAAGTTGAATGCCTTAATAGCGAAAGCAAATGTGAAGCCAAAAAGAACAGTGTACCCAACAATCG
CGACTGCAACTATTGGAAGAAAATCATGCTTGAAGCCGAAGTAACGTCTCAAAAATTGTTCCACTGTTTCCTCATCAGTAAGTTTGTTCTGAAGATCT
CCAAATTGTGATGCAACCAAACCATACAAGGTCCAGGCAACAGGACAACACCAGTAGTACCATCTCCACCATATGGGAATACGctgtttttaaaaat
gaaaatggaaaaaaatacagagaacatgtcatttccgagctctaagtcagttttgatgtaacaataaaatggaagtgtttcaagaacttacAGTTCGT
GGAATGATGAATCCTGAGAAAAGATTCCATACTCCGTAGAAGAAGGAGCCGACAATTTGAGCAACACTTACATTTGGGGTAACAGCAACGGTCATCAT
ACCGTAGAAAGTGAAGTACAAGAGGGTGAAAAACAGGAAGAACAAGTACCAAAAGAACTTTGCTACCGTCCATTCAAATCCGATCATAGCATACATAA
TTGCACCACAGAAAACAGATTGCATAAAGACATATGGGATTTCAATGGAAATctgcaagatagaaaaagttaagtaatttagacttttcacctaaaat
tgtcgaggcacgtagtgttaagagtggataacatgtagtcacttatagtgggaaaagttcagtgatcaaatgtgaaattaactcgagattggcttata
agaaattgaactctatgttcacCTGTCCAAAGGCATAAGGTAAGGCAGAATACATTCCAGCAGCTCTTTCTCTATAGAATACTGTACGTTCAACGGCT
ACAACAGGCTGCACTGATGATGAATTTTGTGTACCGAGGAAGAGAACAGTAGCATACAAGCATCCCATCGCGTTAAATAGATCTTGACTCTTACTCct
gtaaccaaaaaagatcaagttttagtgttagttgagggtatttttagtttgtgtaattgttgtttttgcttcata

Figure 7 cont.

SEQ ID NO:3

>BL_17SC0100-0002 NODE_4559_length_28844_cov_5.188734 ctctattttgttgttcttagtcctttcttataggattttgcattgcccccacccccaccccccttgttataagtaactatatctttttccattgtttt
cttcttccttgtacttacatttgttgcatttgagttgagggtctttcgaaaataacatctctacctccacgaggtagtgataaggactgcgtacactc
taccctccccagactccacttgtggaatttcaccggatatgttgttgttattgttataaggaaaagctttggtctcaaaactctttaaactcaatttt
ttttcttttgcactccctcttttcttgagtacatttcactctcaattctttcttgagcacacactcttttatttgagtacacatacaactcaaatgac
cacctcaatctatcggtgttgatggaaggatctagtgaatgcaatattctagaactacaccttccacttctttctctaattcttttagactttgcact
ctataactctcatcctaaagttcttctttcaatacaaatcttgaatattctagattcttctttgaaatatcttagatattaattaaggtggtgatgac
cttttaacacccctctcagcaccaacttaatttattctttgtatccattttgagtgatcctcgagacattgcaatcatcttgatgtccaggaacttta
tgaatctcttcctcctttgaacttccccactcacttctctttgaatcttattcgaaggtagtagtctccttgatctagaccactctgctaatgttgca
tcaatatacttggtgtttgggaatttcaatcatgtagacctagctccttagtcacggttgtggtgcttctcggacttcttcttgcaacatgacaagag
tttcacttgagtctaatagtaaatctctatagtgacccccttagcagcagctgcgcagccctcccatggctgctacaaccactggaaagcctcctccc
gaggtagtccagcccgccccaacatggttttatctcgctcagtgaaggttcaatattagcagtaatgcaagttaacaatttgaacaaagggagagaat
ttggcagaaaagaggatcggaacatggtaatgcgcaagaaagcaacatctaatgcttctccaggttgtgagaagaggcacaatattagtaatgcttca
agagccctattatgttcgaacaactttgatgctttattgaaggctactggaaaaaatagtaatattatggctccaacattacatatttctaatcctga
agtagctaattaggattattcaagaaaatcaggatggcatgctactcaaatccaatccagcaatcaagccactcatggtcacattgaacacctaggct
catgaggtcccttcccaatctttggagtcacttggtcaatatcaaggtgaatctggacaactactattgtcaacagggaatggtgacgatttagttac
tttagatgggcaatcaatctttttaattcatgcatttgtcaaaggaagtttgaagccgataactcaaccttcttaattcttggttgttatattttaa
cattatttaagcatcctcatttgtaatatcatcatcgtgtgtattacaaattttgtggtaatcacaaaatgctagtttttctagcttttattttctt
catacttgttagttagtaaaggtatgttacctcattatgactggtaaggtaaggttcaacttcctttgcttgtacttatccctactgagtttttatt
atttttaatagaaggctgctaaaaaaaataatttcaagaaatctattttatacgatatcaaattaaagtacgttgcataaaacatttataagaaagag
gaatgaagtacgttgtagatcaaattaaggaaatgataagagataaacctggaatcgtggtgtttcttccattgccaagagtgtatgtcatcactacc
caaaatttcaagctttcttgctgctatcataaaacatttttcccactgtgcttatcgataaaaaaactctgaaagaaaaaaaacattaaacaataa
aaaaatgtatagtattgtatttataatctaattattaatccaaattcacatcaattaaggaacttataattttataaagaaaagtaacatacatgata

Figure 7 cont.

gagttattatagataaaagtaggggaaaaaaataaaaaaaattataaattaatgaacaaagtcaaataagaaaataaaaatattgtaatgacatggcc
atatcaaattgatcattacataaaatgatactttcatcgttacataatgatgaatttattggtaagatacaataaaaattaaataattaacaattcaa
ataaatattgtatttaaaataataatataatacaatacgatagctcacaacaacccaatatagttcaatttttttgaataacttaaacttggtgagtga
aacagaataaaacatgattcttttgatctttctagtttcattaactatgaaaaaattaaaagatattagatataaaattttaataaagataaaaacac
tgggtggtcatttttttctacttgcttgagctgtagagttacttggtatactagttgagataaatgacataaaaaaatttaattgaaacaccaatacaa
acaaggtgaaattattttttttaaagaaaattatatatgaatcgttgaatctaaaattctagtttagcaacagaggggtttcaaaggttgttttagagt
atgagtttaaatcctaagtgtgaaactcaatattttttttaatattcttatttgaatttctaactccaccattatattgtttaatacttgtgttagtg
agaggctaaagtagatgtagaatattaataccactttcatatgaatcctgtactttcatatatagcggaacataaatttatgtgcaaaaattcatgat
aaatgcaatagatagtagatatgaatcacaactttaaagaatataatgatttaaatgttaattaaataaaaaattgaatccataaatcttaaattctg
attttgcctctagtgataggtaccaaatacgtacctaacaaataatttaggttcacacaaactagcacatataccaccattacaaaaaataaaatgaa
acataaaaggtaattaaccacatcaaaatgagattttaccagtctgccgctatcaaggaggatgggagaatcacatagactaaaaaagagctcctttt
tggtgttgaaaatccgaggaagcttagatctatcaattatttttttgataatcggaaggcaaaaatcttccccaaatttcatcagattttgcaacaaat
ttgaatcctgttgataaaattgttgatcttactgcatctgctggagttgttcttaaaattatttcaaagatgcaaccttctggcaacttttcaaaata
attcattggagctatggacttagaaatattcatgtcaaaattcttataaaccttataaccgagaaataaccaaagtttttttgttacaagctttata
tataattaaataatcaaaagataaaaaagatttcagaggtctatacattgtcaaatatagtaataagtacaaataagcatataaaattatgttttttt
ttcctttttgtcaatgagtacagataagcaaaaagtcaaacttattcaaataacaataaccattgccacaccttaatctcaaacaagtttcacgttg
cttcaattaagtgtatcgagactaatattatattatataaaataaaaataacatgcacgagaagatctctatttaatttggcgtgaaatgttatctaa
agtctcaaataattggtattgcttatatgaaagtaaaaaaacttccattgtgtgccatactttcgagacaactcctttgtgattttaggtctacttcg
tctcattttaacaccttcacactatgatttcataatgtaacaacttaattaatttcttatttaatcatgataaattagtacgatacagtgtaaacatc
ggatgcaaataaattgttatccaatagaggttacatgaccaaaccatctcatttgttttatttttattatgtgctcgatttattgttagctatttcat
catcgattccaatagtatttagatctttcgaaaagcaaatagccataacacattattgtttatatatcaagaaaacacataagctatattatattatt
gtacaatttcttctTTATTCTGGTCTAAATTCAATTCCTTGAACAATAAGGCCACCTTTTCCATGAAGCTGCGTAATCTCCATCAATCGCGCTTCAAC
ATCTCCATCATCTCCTGTATCATTGATAAAATTTCCCAATTCTATTTCCATCCATCCATCGACTCTTTTTCGTGGACATTTCACATTACGTTTGCGTC
TCCTAACCCTTTTTCCGACTAGACTCACGACACTAGCTCGTTCCTCGGCCTCTTTGTCGCTCACACGATTCACAAACCTAACAAATGCATTAGCAATT
TCTAGTCCATCATGATTCTTTGACAATTTGAACACCAAATAAACAACATATTTGGTTCTTTTCGACAATATTTGTGTTCCAATCGTGCCTCGTATGTC

Figure 7 cont.

TAGCCAACTTACACCCTTGAGATGAGCCACTTCCGAAAATctgcaaaataaaatgtctatattgtcttagatacacgtatttagtgagtttaagttat
atataacatcgccaatataagtaattttgcaccatcaaatcatctttacctattgtaataggtaacatatttcattacacattttagtgaggctcat
ctatatatatcttttaggtggcttgattgtgtaaaaaaaaaattctcaccaatagtggcagaggtagaatttcaaccaagggattcaaaaaataacat
atgtagaaattcgttaaaaggcaatgaagtataatttttatacgtagtacatacataaaaaaaaagaataacttttatatgtagtataatttttcg
acgaacCTGGAGTCAGGATGAGAAATCCATTCCCAATACCATGGTGTATCAACTCCCCATGTAATAGCAAGTTCTCTAGCtgatatcataaaacattt
cttgcctgttttcttatcaagtgaaaaactctgttttcaaaaataaaataaaatcttagattcacactactagcttatatatagtccattcaaaaata
aaataaaattcacacaattattattataatctatttaattttgcatttttaatggtgtttgtaacccattggccagaaaatcttagaagttcatttag
ttgactatctgaacttccgttttactatagagagttggattcccagtttgtaacaaaaacaaaataaaataagaaaaattcattggctgattaattaa
gatttgcgcagccgtaagcacactagtagattttagtgcttcctattaaacacgactcaattcctaagatttcaactctgattaaaactcaaactcta
gacctcaggtcaaaggttcatgacCTTTACCGTTATACAACACCAACAGTTAGAGGCAAAGCTAGAACACCCctataaattctaggaacccaatagtt
ttagttcaaactctgtattttatctttaaaaagaaaactcctctaatttgtaccaaattattaatttcgaaccaaacaactcaaaaaacacacaaaaa
atcccgaacccataagcttcaaaacaattatacatatattcaactaatgagccaaaagaaaagcttgctacttcccaatttagagctacttacCAATT
TGCCTCCATCCATTAGAACAGGGAAGTCACATAGACTAAAGTAAAGCTCCTTTTTAGACGGATAAATCCGCGGGGAGACATATCTCGAGTTGATATCT
TCATAATCATCTGGTAAAAACTTTACCCAAATAACGTCGGATTCAGCAGCAGAGTTGAATCCCCGAGAGATCGCGGATGAAATCACGACGTCTTTCGG
GGAAGTAAAGGAGAGAATATCACAAACACAATCTTCTGGTAGCAATAGGAAATAGTCCATtattggaaaattgaatttgaagttttgtgaattttttt
tctttatataaagcaaactgagaaaagtttgttgaaaagttgttacacttcatatgtctcgacggttaagcaggggcggctcaacgtatttggaggcc
taaaacaaaatttaaattaaaggcctaaaatcttttagctgaggcaattattaaataaattgttaacattattctataagtaataagttgacaaaact
gcttataaacttctttttttatttaaaagcacataacataagtcaatctaaacaggcttgtaattcgctttatccaacacattagttttactattgat
tcatatttttgatagagctctaacttacatagagtataaaaggggtatagaaaattacaacgcgagagtaagtgaagagagtgtaagaagacaaaaca
acgtttttcttgatttcttctatttgattgaggttaaggagaataaaataatatatatatgaaaagtacatttatcttaaataattaatttttctat
aaaaaaaattaacacataatttattgttggtaaaaatttgaggccccctaaaattgggggcctaaggcatatgcctaatttttataagcattgagcc
ggcactgcggttaaatattgttttgttcatttttacttctccagtatgaatataataagtgaaaaggtcatataatttagagctgatacatacctcgt
tataaaaatggctcatacatacctatactattacacaaatagcctagatatacccttttggcctaatggaagtgaaaatatttaattttattttattt
ttaaaaaaatcatttttgtttatttttcattatttttatctagttctcacatatgtacattttatttccaaaaaaaaataaaattaaagaattgatat
tgcttagatacaccaaacaaacaactcatgtggaggaagatattccaataatactaaacatgaaatgttttgagtttgaaatttttttgtctttccttt

Figure 7 cont.

ttagtgaattaaaacatgaaatgtcttggaagattcgaaatttactggcccgactaatttaagattagcatcatctaaggtccatttatcaaggagcg
ttcccgaccaagaatttctccattctccgaattcaaaccaaagacttgttgtttagttaacactagagaagtctcattctcgcaccacagttgtggca
gttcccgaaaagcaatattcacaaattcttacattcatcatttcattaatttcttatagttgtaactataagaacaacataccatgtgtctcccccac
aaagtggagtatgggaagggtagagtgtaagcaaactttactcttacctcagaggtagaaagtcttcttccgatagatcctcgactcgagaaaaataa
tccaaagcagttcagaaaaagacacaacaaaagtacaagaaacaccagatagtaacagaatagtacttcaacattaacaaattactatctcttacaca
gaaaaatgaacttgaaattcataaaaaataataataataacagaacataccccttgttcaagtggtaatctatatacagtactttcaaaatcaatctct
tgctcgtacttgagctcgagaaaaattccttatactaaccgcgtcttccccatttcacgagcagtggagagaacgtttcacacgttgtctttactaca
tcttcagcaggtaatgtcttttTATCTCGTTTGGAAGTTGAATGCCTTAATAGCGAAAGCAAATGTGAAGCCAAAAAGAACAGTGTACCCAACAATCG
CGACTGCAACTATTGGAAGAAAATCATGCTTGAAGCCGAAGTAACGTCTCAAAAATTGTTCCACTGTTTCCTCATCAGTAAGTTTGTTCTGAAGATCT
CCAAATTGTGATGCAACCAAACCATACAAGGTCCAGGCAACAGGACAACACCAGTAGTACCATCTCCACCATATGGGAATACGctgtttttaaaaat
gaaaatggaaaaaaatacagagaacatgtcatttccgagctctaagtcagttttgatgtaacaataaaatggaagtgtttcaagaacttacAGTTCGT
GGAATGATGAATCCTGAGAAAAGATTCCATACTCCGTAGAAGAAGGAGCCGACAATTTGAGCAACACTTACATTTGGGGTAACAGCAACGGTCATCAT
ACCGTAGAAAGTGAAGTACAAGAGGGTGAAAAACAGGAAGAACAAGTACCAAAAGAACTTTGCTACCGTCCATTCAAATCCGATCATAGCATACATAA
TTGCACCACAGAAAACAGATTGCATAAAGACATATGGGATTTCAATGGAAATctgcaagatagaaaaagttaagtaatttagacttttcacctaaaat
tgtcgaggcacgtagtgttaagagtggataacatgtagtcacttatagtgggaaaagttcagtgatcaaatgtgaaattaactcgagattggcttata
agaaattgaactctatgttcacCTGTCCAAAGGCATAAGGTAAGGCAGAATACATTCCAGCAGCTCTTTCTCTATAGAATACTGTACGTTCAACGGCT
ACAACAGGCTGCACTGATGATGAATTTTGTGTACCGAGGAAGAGAACAGTAGCATACAAGCATCCCATCGCGTTAAATAGATCTTGACTCTTACTCct
gtaaccaaaaaagatcaagttttagtgttagttgagggtatttttagtttgtgtaattgttgtttttttgcttcata

Figure 7 cont.

SEQ ID NO:4

>BL_17SC0100-0018 NODE_4276_length_28842_cov_5.003099 ctctattttgttgttcttagtcctttcttataggattttgcattgcccccacccccacccccccttgttataagtaactatatctttttccattgtttt cttcttccttgtacttacatttgttgcatttgagttgagggtctttcgaaaataacatctctacctccacgaggtagtgataaggactgcgtacactc taccctccccagactccacttgtggaatttcaccggatatgttgttgttattgttataaggaaaagctttggtctcaaaactctttaaactcaatttt ttttcttttgcactccctcttttcttgagtacatttcactctcaattctttcttgagcacacactcttttatttgagtacacatacaactcaaatgac cacctcaatctatcggtgttgatggaaggatctagtgaatgcaatattctagaactacaccttccacttctttctctaattcttttagactttgcact ctataactctcatcctaaagttcttctttcaatacaaatcttgaatattctagattcttctttgaaatatcttagatattaattaaggtggtgatgac cttttaacacccctctcagcaccaacttaatttattctttgtatccattttgagtgatcctcgagacattgcaatcatcttgatgtccaggaacttta tgaatctcttcctcctttgaacttccccactcacttctctttgaatcttattcgaaggtagtagtctccttgatctagaccactctgctaatgttgca tcaatatacttggtgtttgggaatttcaatcatgtagacctagctccttagtcacggttgtggtgcttctcggacttcttcttgcaacatgacaagag tttcacttgagtctaatagtaaatctctatagtgaccccttagcagcagctgcgcagccctcccatggctgctacaaccactggaaagcctcctccc gaggtagtccagcccgccccaacatggttttatctcgctcagtgaaggttcaatattagcagtaatgcaagttaacaatttgaacaaagggagagaat ttggcagaaaagaggatcggaacatggtaatgcgcaagaaagcaacatctaatgcttctccaggttgtgagaagaggcacaatattagtaatgcttca agagccctattatgttcgaacaactttgatgctttattgaaggctactggaaaaatagtaatattatggctccaacattacatatttctaatcctga agtagctaattaggattattcaagaaaatcaggatggcatgctactcaaatccaatccagcaatcaagccactcatggtcacattgaacacctaggct catgaggtcccttcccaatctttggagtcacttggtcaatatcaaggtgaatctggacaactactattgtcaacagggaatggtgacgatttagttac tttagatgggcaatcaatctttttaattcatgcatttgtcaaaggaagtttgaagccgataactcaaccttcttaattcttggttgttatattttaa cattatttaagcatcctcatttgtaatatcatcatcgtgtgtattacaattttgtggtaatcacaaaatgctagtttttctagcttttattttctt catacttgttagttagtaaaggtatgttacctcattatgactggtaaggtaaggttcaacttcctttgcttgtacttatccctactgagtttttatt atttttaatagaaggctgctaaaaaaaataatttcaagaaatctattttatacgatatcaaattaaagtacgttgcataaaacatttataagaaagag gaatgaagtacgttgtagatcaaattaaggaaatgataagagataaacctggaatcgtggtgtttcttccattgccaagagtgtatgtcatcactacc caaaatttcaagctttcttgctgctatcataaaacatttttcccactgtgcttatcgataaaaaaactctgaaagaaaaaaaaacattaaacaataa aaaaatgtatagtattgtatttataatctaattattaatccaaattcacatcaattaaggaacttataattttataaagaaaagtaacatacatgata

Figure 7 cont.

gagttattatagataaaagtaggggaaaaaaataaaaaaaattataaattaatgaacaaagtcaaataagaaaataaaaatattgtaatgacatggcc
atatcaaattgatcattacataaaatgatactttcatcgttacataatgatgaatttattggtaagatacaataaaaattaaataattaacaattcaa
ataaatattgtatttaaaataataatataatacaatacgatagctcacaacaacccaatatagttcaatttttttgaataacttaaacttggtgagtga
aacagaataaaacatgattcttttgatctttctagtttcattaactatgaaaaaattaaaagatattagatataaaattttaataaagataaaaacac
tgggtggtcatttttttctacttgcttgagctgtagagttacttggtatactagttgagataaatgacataaaaaaatttaattgaaacaccaatacaa
acaaggtgaaattatttttttaaagaaaattatatatgaatcgttgaatctaaaattctagtttagcaacagaggggtttcaaaggttgttttagagt
atgagtttaaatcctaagtgtgaaactcaatattttttttaatattcttatttgaatttctaactccaccattatattgtttaatacttgtgttagtg
agaggctaaagtagatgtagaatattaataccactttcatatgaatcctgtactttcatatatagcggaacataaatttatgtgcaaaaattcatgat
aaatgcaatagatagtagatatgaatcacaactttaaagaatataatgatttaaatgttaattaaataaaaaattgaatccataaatcttaaattctg
attttgcctctagtgataggtaccaaatacgtacctaacaaataatttaggttcacacaaactagcacatataccaccattacaaaaataaaatgaa
acataaaaggtaattaaccacatcaaaatgagattttaccagtctgccgctatcaaggaggatgggagaatcacatagactaaaaaagagctcctttt
tggtgttgaaaatccgaggaagcttagatctatcaattatttttttgataatcggaaggcaaaaatcttccccaaatttcatcagattttgcaacaaat
ttgaatcctgttgataaaattgttgatcttactgcatctgctggagttgttcttaaaattatttcaaagatgcaaccttctggcaacttttcaaaata
attcattggagctatggacttagaaatattcatgtcaaaattcttataaaaccttataaccgagaaataaccaaagtttttttgttacaagctttata
tataattaaataatcaaaagataaaaaagatttcagaggtctatacattgtcaaatatagtaataagtacaaataagcatataaaattatgttttttt
ttcctttttttgtcaatgagtacagataagcaaaaagtcaaacttattcaaataacaataaccattgccacaccttaatctcaaacaagtttcacgttg
cttcaattaagtgtatcgagactaatattatattatataaaataaaaataacatgcacgagaagatctctatttaatttggcgtgaaatgttatctaa
agtctcaaataattggtattgcttatatgaaagtaaaaaaacttccattgtgtgccatactttcgagacaactcctttgtgattttaggtctacttcg
tctcattttaacaccttcacactatgatttcataatgtaacaacttaattaatttcttatttaatcatgataaattagtacgatacagtgtaaacatc
ggatgcaaataaattgttatccaatagaggttacatgaccaaaccatctcatttgttttatttttattatgtgctcgatttattgttagctatttcat
catcgattccaatagtatttagatctttcgaaaagcaaatagccataacacattattgtttatatatcaagaaaacacataagctatattatattatt
gtacaatttcttctTTATTCTGGTCTAAATTCAATTCCTTGAACAATAAGGCCACCTTTTCCATGAAGCTGCGTAATCTCCATCAATCGCGCTTCAAC
ATCTCCATCATCTCCTGTATCATTGATAAAATTTCCCAATTCTATTTCCATCCATCCATCGACTCTTTTTCGTGGACATTTCACATTACGTTTGCGTC
TCCTAACCCTTTTTCCGACTAGACTCACGACACTAGCTCGTTCCTCGGCCTCTTTGTCGCTCACACGATTCACAAACCTAACAAATGCATTAGCAATT
TCTAGTCCATCATGATTCTTTGACAATTTGAACACCAAATAAACAACATATTTGGTTCTTTTCGACAATATTTGTGTTCCAATCGTGCCTCGTATGTC

Figure 7 cont.

TAGCCAACTTACACCCTTGAGATGAGCCACTTCCGAAAATctgcaaaataaaatgtctatattgtcttagatacacgtatttagtgagtttaagttat
atataacatcgccaatataagtaattttttgcaccatcaaatcatctttacctattgtaataggtaacatatttcattacacattttagtgaggctcat
ctatatatatcttttaggtggcttgattgtgtaaaaaaaaaattctcaccaatagtggcagaggtagaatttcaaccaagggattcaaaaaataacat
atgtagaaattcgttaaaaggcaatgaagtataatttttatacgtagtacatacataaaaaaaaagaataactttttatatgtagtataatttttcg
acgaacCTGGAGTCAGGATGAGAAATCCATTCCCAATACCATGGTGTATCAACTCCCCATGTAATAGCAAGTTCTCTAGCtgatatcataaaacattt
cttgcctgttttcttatcaagtgaaaaactctgttttcaaaaataaaataaaatcttagattcacactactagcttatatatagtccattcaaaaata
aaataaaattcacacaattattattataatctatttaattttgcatttttaatggtgtttgtaacccattggccagaaaatcttagaagttcatttag
ttgactatctgaacttccgttttactatagagagttggattcccagtttgtaacaaaaacaaaataaaataagaaaaattcattggctgattaattaa
gatttgcgcagccgtaagcacactagtagattttagtgcttcctattaaacacgactcaattcctaagatttcaactctgattaaaactcaaactcta
gacctcaggtcaaaggttcatgacCTTTACCGTTATACAACACCAACAGTTAGAGGCAAAGCTAGAACACCCctataaattctaggaacccaatagtt
ttagttcaaactctgtattttatctttaaaaagaaaactcctctaatttgtaccaaattattaatttcgaaccaaacaactcaaaaaacacacaaaaa
atcccgaacccataagcttcaaaacaattatacatatattcaactaatgagccaaaagaaaagcttgctacttcccaatttagagctacttacCAATT
TGCCTCCATCCATTAGAACAGGGAAGTCACATAGACTAAAGTAAAGCTCCTTTTTAGACGGATAAATCCGCGGGGAGACATATCTCGAGTTGATATCT
TCATAATCATCTGGTAAAAACTTTACCCAAATAACGTCGGATTCAGCAGCAGAGTTGAATCCCCGAGAGATCGCGGATGAAATCACGACGTCTTTCGG
GGAAGTAAAGGAGAGAATATCACAAACACAATCTTCTGGTAGCAATAGGAAATAGTCCATtattggaaaattgaatttgaagttttgtgaattttttt
tctttatataaagcaaactgagaaaagtttgttgaaaagttgttacacttcatatgtctcgacggttaagcaggggcggctcaacgtatttggaggcc
taaaacaaaatttaaattaaaggcctaaaatcttttagctgaggcaattattaaataaattgttaacattattctataagtaataagttgacaaaact
gcttataaacttctttttttatttaaaagcacataacataagtcaatctaaacaggcttgtaattcgctttatccaacacattagttttactattgat
tcatatttttgatagagctctaacttacatagagtataaaaggggtatagaaaattacaacgcgagagtaagtgaagagagtgtaagaagacaaaaca
acgtttttcttgatttcttctatttgattgaggttaaggagaataaaataatatatatatgaaaagtacatttatcttaaataattaatttttttctat
aaaaaaaattaacacataatttattgttggtaaaaatttgaggccccccctaaaattgggggcctaaggcatatgcctaatttttataagcattgagcc
ggcactgcggttaaatattgttttgttcatttttacttctccagtatgaatataataagtgaaaaggtcatataatttagagctgatacatacctcgt
tataaaaatggctcatacatacctatactattacacaaatagcctagatatacccttttggcctaatggaagtgaaaatatttaattttattttattt
ttaaaaaaatcatttttgtttatttttcattatttttatctagttctcacatatgtacattttatttccaaaaaaaaaataaaattaaagaattgatat
tgcttagatacaccaaacaaacaactcatgtggaggaagatattccaataatactaaacatgaaatgttttgagtttgaaatttttttgtctttccttt

Figure 7 cont.

ttagtgaattaaaacatgaaatgtcttggaagattcgaaatttactggcccgactaatttaagattagcatcatctaaggtccatttatcaaggagcg
ttcccgaccaagaatttctccattctccgaattcaaaccaaagacttgttgtttagttaacactagagaagtctcattctcgcaccacagttgtggca
gttcccgaaaagcaatattcacaaattcttacattcatcatttcattaatttcttatagttgtaactataagaacaacataccatgtgtctcccccac
aaagtggagtatgggaagggtagagtgtaagcaaactttactcttacctcagaggtagaaagtcttcttccgatagatcctcgactcgagaaaaataa
tccaaagcagttcagaaaaagacacaacaaaagtacaagaaacaccagatagtaacagaatagtacttcaacattaacaaattactatctcttacaca
gaaaaatgaacttgaaattcataaaaaataataataataacagaacatacccttgttcaagtggtaatctatatacagtactttcaaaatcaatctct
tgctcgtacttgagctcgagaaaaattccttatactaaccgcgtcttccccatttcacgagcagtggagagaacgtttcacacgttgtctttactaca
tcttcagcaggtaatgtcttttTATCTCGTTTGGAAGTTGAATGCCTTAATAGCGAAAGCAAATGTGAAGCCAAAAAGAACAGTGTACCCAACAATCG
CGACTGCAACTATTGGAAGAAAATCATGCTTGAAGCCGAAGTAACGTCTCAAAAATTGTTCCACTGTTTCCTCATCAGTAAGTTTGTTCTGAAGATCT
CCAAATTGTGATGCAACCAAACCATACAAGGTCCAGGCAACAGGACAACACCAGTAGTACCATCTCCACCATATGGGAATACGctgtttttaaaaat
gaaaatggaaaaaaatacagagaacatgtcatttccgagctctaagtcagttttgatgtaacaataaaatggaagtgtttcaagaacttacAGTTCGT
GGAATGATGAATCCTGAGAAAAGATTCCATACTCCGTAGAAGAAGGAGCCGACAATTTGAGCAACACTTACATTTGGGGTAACAGCAACGGTCATCAT
ACCGTAGAAAGTGAAGTACAAGAGGGTGAAAAACAGGAAGAACAAGTACCAAAAGAACTTTGCTACCGTCCATTCAAATCCGATCATAGCATACATAA
TTGCACCACAGAAAACAGATTGCATAAAGACATATGGGATTTCAATGGAAATctgcaagatagaaaaagttaagtaatttagacttttcacctaaaat
tgtcgaggcacgtagtgttaagagtggataacatgtagtcacttatagtgggaaaagttcagtgatcaaatgtgaaattaactcgagattggcttata
agaaattgaactctatgttcacCTGTCCAAAGGCATAAGGTAAGGCAGAATACATTCCAGCAGCTCTTTCTCTATAGAATACTGTACGTTCAACGGCT
ACAACAGGCTGCACTGATGATGAATTTTGTGTACCGAGGAAGAGAACAGTAGCATACAAGCATCCCATCGCGTTAAATAGATCTTGACTCTTACTCct
gtaaccaaaaaagatcaagttttagtgttagttgagggtatttttagtttgtgtaattgttgtttttgcttcata

Figure 7 cont.

SEQ ID NO:5

>DM4.04 chr12 ctatattttgttgttcttagtcctttcttataggattttgcattgcccccacccccacccccccttgttagtagctatatctttttccattgttttctt
cttccttgtacttacatttgttgcacttgcgttgagggtctttcgataataacatccctagcctccacaaagtactagtaagggctgcgtacactcta
ccctccttgttttcttcttccttgtacttacatttgttgcacttgagttgagggtcttttgaaaataacatctctacctccacaaggtagtgataagg
actgcgtacactctaccctccccagactccacttgtggaatttcaccggatatgttattgttattgttataaggaaaagctttggtctcgaaactctt
taaactcaatttttttcttttgcactccctcttttcttgagtacacttcactctcaattctttcttgagcacacactcttttatttgagtacacatac
aactcaaatgaccacctcaatcgaccccacttgtggaatttcaccagatatgttgttgttattgttataaggacaagcttcggtcttaaagctcgata
aactcatttttttcttttgcactccctcttttcttaagtacacttcactctcaattctttcttgagcacacactctttatttgagtaaacatacaact
caaatgatcacctctatttatcggtgttgatggaaggatctagtgaatgcaatattctagaactacaccttccacttctttctcgaattcttttagac
tttgcactctagaactctcatcctaaagttcttctttcaatacaagtcttgaatatgctagattcttctttgaaatatcttagatattaattaaggtg
gtgatgacttttaacacccctctcagcaccaacttaatttattctttgcatccattttgagtgatcctcgagacattgcaatcatcttgatgtccagt
aactttatgaatctcttcctcctttgaacttccccactcacttttctttgaatcttattcgaaggtagtagtctccttgatctagaccactctgctaa
tgttgcatcaatatacttggtgtttgggaatttcaatcatgtagacctccttagtcacggttgtggtgcttctcggacttcttcttgcaacattacag
gagtttcactttgagtctaataggaaatctctttggaccaccatgttgatgcttcatcaaataccagatttcttgacacatatatcctattagtgata
ggaaggagaaatacgaagggatataggatagacttttcgattgagccttcttgttgaatctataacaactctacaataatgtaacttgataaagtagg
tattagggctccctcgctctaacagctatagtgaccccttagcagcagctgcgcagccctcccatggctgctacaaccactggaaagcctcctcccg
aggtagtccagcccgccccaacatggttttatctcgctcagtgaaggttcagtattagcggtaatgcaagttaaggatttgaacaaagggagagaatt
tggtagaaaagaggagcggaacatggtaatgcgcaagaaggcaacatctaatgcttctccaggttgtgagaagaggcacaatattagtaatgtttcaa
gagccctattatgttggaacaactttgatgctttattgaaggctactggaaaaaatagtaatattatggttccaacattacatatttctaatccttaa
gtagctaattaggattattcaagaaaatcaggatggcatgctactcaaatccaatccaacaatcaagccactcatggttacattgaacacctcggctc
atgaggccccttcccaatcattggagtcacttggtcaatatcaaggtgaatctggacagctactattgtcaacagggaatggtgacgatttagttact
ttagatgtgcaatcaatctttttaattcatgcacttgtcaaaggaagtttgaggccgataactcaaccttcttaattcttggttgttatattttaac
attatttaagcatcctcatttgtaatatcatcagagtgtattacaaactctatggtaatcacaaaatcctagtttttctagcttttatttttttcttc

Figure 7 cont.

atgcttgttagttagtagaggtttgttacctcattatgactggtaaggtaaggtccagctccctttacttgtacttatccctgatgaattttttttat
tatttttaatagaaagccgctaaaaaaataattttaagaaatttattttatacgtaatcaaattaaaatacgttgcataaaacatttataagaaagt
ggaatgacgtacgttgtagatcaaattaaggaaatgataagagataaacctggaatcgtggtgtttcttccattgccaagagtgtatgtcatcactcc
ccaaaatttcaagctttcttgctgctatcataaaacatttttttccactgtacttatcaataaaaaaattctgaaaggaaaaaaaaaccattaaacaa
tataaaaatgtataatattgtatttataatctaatcattaatccaaattcacaccatgtaaggaacttataattttataaagaaaagtagcatacata
atagagttattatagataaaggtaggggaaaaaaaaaggattataaagtaatgaacaaagtcaaaataagaaaataaaaatatcgtaatgacatggcc
atatcaaattgatcattacataaaatgatactttcatcgttacataatgatgaatttattgataagatacaataaaaattaaataattaacaattcaa
ataaacgttgtgtttaaaataacaatataatacaatacgataactcacaacaacccaaaggcatatagttcaatttttcgaataacctaaacttggtg
agtgaaacagaataaaacaagattcttttgatctttcttagtttcattaactatgaaaaaaataaaaaagtacaaaaaatgaaacatcaagaaagata
tagccagtgaacaatgaattgattgaaaattataagatattagattttaaattttagcaaagataaaaaattgggtggtcatttcgttctacctgctt
gagctatagaattacctggtatagtagtcgtgataaaagtttaattgaatctcctttacttgaaattacaccgatacacatggtaaaaatatattttt
aaaaaaattatatatgaattgttgaattcaaagtctagtttagcaacagaggggtacaaaggttgttttagattacgagtttaaatcctaagtgtgac
actcatttttttttaatattcttatatgaatttctaactcatcattatattgtttgatacttgtgttagtgagaggctaaaaccgatttacaagatt
aataccaatttcatatgaatcctatacttttatatatatcggaacataaatttatgtgtaaaaattcatgataaatgcaatagatatagtagatataa
atcacaactttaaagaacatcatgatttaaatgttaagtaactaaaaaattgaatccataaatcttaaattctgattttgcctctggtgataggtacc
aaatacgtacctaataaataatttaggttcacgcaaactagcacatataccaccattactaaaatataaataaaatcattgaaggtaattaatcacat
caaaatgagattttaccagtctgccgcggtcaaggagaatgggagaatcacatagactaaaaaagagctcctttttggtgttgcaaatccgaggaagc
ttagatctatcaattatttttttggtaatcggaaggcaaaaatcttccccaaatttcatcagattttgcaacaaatttgaatcctgttgatgaaattgt
tgatcttactgcatctgctggagttgttcttgaaattatttcaaagatgcaaccttctggcaacatttcaaaataattcattggagctatagacttag
aaatattcatgtcaaaattcttataaaactttataatcgagaaataacctaagtttttttgttacaagctttatatatgattaaataatcaaaagata
aaaaagatttcagaggtctatacattgtcaaatatagtaataagtacatataagcatatacaattatgtttttttttcctttttttgtcaatgagtaca
gataagcaaaaagtcaaacttattcaaataacaataaccattgccacaccttaatctcaaacaagtttcacgttgctttaattaagtgtaccgagact
aatattatattatataaaataaaaataacatgtacgagaagatctatttaatttggcgtgaaatgttatctaaagtctcaaataattggtattgctta
tatgaaagtaaaaaaacttccattgtgtgccatactttcgagacaactcctttgtgattttaggtctacttggtctcattttaacaccttcacactat
gatttcatagtgtaacaacttaattaatttttatttaatcataataaattagtacgatacagtgtaaacatcagatgtaaataagttaatattcaat

Figure 7 cont.

agaggtcaatttagaacatgaccaaaccgtctcatttgttttatttttattatgtgctcgatttattgttagctatttcaacatcgattccaatagta
tttagatctttcgaaaagcaaatagccataacacattattatttatatatcaagaaaacacatatgctatattatagtactattgtgcaatttcttct
TCATTCTGGTCTAAATTCAATTCCTTGAACAATAAGGCCACCTTTTCCATGAAGCCGCGTAATCTCCATCAATCGCGCTTCAACATCTCCATCATCTC
CTGTATCGTTGATAAAATTTCCCAATTCTATTTCCATCCATCCATCGACTCTTTTTCGTGGACGTTTTACGTTACGTTTGCGTCTCCTAACCCTTTTT
CCGACTAGACTCACGACACTAGCTCGTTCCTCGGCATCTTTATCGCTCACACGATTCACAAATCTAACAAATGCATTAGCAATTTCTAGTCCATCATG
ATCCTTTGCCAATTTGAACACCAAATAAACAACATATTTGGTTCTTTTCGACAATATTTGTGTTCCAATCGTGCCTCGTATGTCTAGCCAACTTACAC
CCTTGAGATGTGCCACTTCCGAAAATctacaaaataaaatgtatatatagtctcagatacatgtatttagtgagtttaagatatatatatcatcgcca
atataagtaatttttgcaccatcaaatcatcttttacctattgtaataggtaacatatttcattacatattttaacgaggctcatctatggtgacctg
attgtgttaaaaaattctttcttaccaatagtgacagaggtagaatttcaaccaagggattcaaaaaatagcatatgtagaaattcgttaaaaggcat
tgaagtataatgttttatacgtagtataatttttcgacgaacCTGGAGTCGGGATGAGAAATCCATTCCCAATACCATGGTGTATCAACTCCCCATGA
AATAGCAAGTTCTCTAGCTGATATCATAAAACATTTCTTGCCTGTTTTCTTATCAAGTGAAAAGCTctgttttcaaaaataaaataaaatcttagatt
cacactactagcttatagtccattcaaaaataaaataaaattgacaattgttagtataatctatttaattttgcatttttaatggtgtttgtaaccca
tttgccggaaaatcttaaaagttcagttagttgactatctgaacttctgttttactagagagagttcgattctcagtttttaacaaaaacaaaataaa
ataagaaaaattcattggctgattaattaagatttgcagcagtaagcacactagtggattttagtgcttcctatcgacatttcaactctgattaaaac
tcaaactcgagacttcaggtcaaaggttcatgacctttacggttatacaacaccaacagccaggggcggagctagaacacccctataaattctaggaa
gtcaatagttttagttcaaactctgtatttatctttaaaaagaaaactcctctaatatgtaccaaattattaatttcgaaccaaacaactcaaaaaac
acacaaaaagaaatcccgaacccataagcttcaacgcaattatacatatattaaactaaaatgagccaaaaaaaagcttactacttcccaatttagag
ctacttacCAATTTGCCTCCATCCATTAGAACAGGGAAGTCACATAGACTAAAGTAAAGCTCCTTTTTAGACGGATAAATCCGCGGGGAGACATATCT
CGAGATAATATCTTCATAATCATCTGGTAAAAACTTTACCCAAATAACGTCGGATTCAGCAGCAGAGTTGAATCCCCGAGAGATCGCGGATGAAATCA
CGACATCTTTCGGGGAAGTAAAGGAGAGAATATCACAAACACAACCTTCTGGTAGCAATAGGAAATAGTCCATtattggaaaattgaatttgaagatt
tgtgaattttttttttgtttatataaagcaaactgagaaaagtttattgaaaagttgttacactcatgtctcaacggttaagtattgtttcgttcattt
ttacttctccagtatgaatataataagagaaaaaggtcatatgagttagaactgatatatagctcgttataaaaatgggctcatacatacctatatta
ttacacaaatagcctagatatacccttttggcctaatggaagtgaaaatatttaattttattcatttttgtttatttttcattattttatctagttct
cacatatgtacattttatttccaaaaataaataaattaaagaattgatatttgcttagatacaccaaacaaacaactcatgtggaggaagatattatt
ccactaacataaaacatgaaatgttttgagtttgaactttttttttttttcctttttttggtgaagtgaaacatgaaatgtttaggaagattcatcat

Figure 7 cont.

tgggtattcgaaatttactggcccgactaattcaagattaatatcatctaaggtccatttatcaaggagcattcccgaccaagaatttctccattctc tgaattcaaaccgaagacttcttgtttagttaacactggagaaatctcattcatcgcgccacatctttgatgagttgtggcagttccccaaaagcaat attcacaaattcttacattcaccatttcatcaatttcttatagttataaaactacaataacaacatatccaatgtctccccacaaagtgaggtctagg gagggtagagtgtacacagactttacttcaactttagagatagaaagtctttttctgatagatcctcaactcgagaaaactaatccaaagcagttcag aattagacacaacaaaagtacaagaaacaacagatagtaacagaacagtacttcttgaatatggtactggattaggtagaaagaacataaaaaaaggc taataacaatggaatgaatttgccactgcattttgattcaacattaacaaattactatctcttacacagaacatacacttgttcaagtggaaatctat atacagtactttcaaaatcactctcactcgtacttgagctcgagaaaaattccttatactaactgcgtcttccccatttcacgaggagtggagagaac gtttcacacgttgtctttactacatcttcagcaggtaacgtctt

Figure 7 cont.

SEQ ID NO:6

>FO_DS NODE_6145_length_29156_cov_4.538109 ctctattttgttgttcttagtcctttcttataggattttgcattgcccccacccccacccccccttgttataagtaactatatctttttccattgtttt
cttcttccttgtacttacatttgttgcatttgagttgagggtctttcgaaaataacatctctacctccacgaggtagtgataaggactgcgtacactc
taccctccccagactccacttgtggaatttcaccggatatgttgttgttattgttataaggaaaagctttggtctcaaaactctttaaactcaatttt
ttttcttttgcactccctcttttcttgagtacatttcactctcaattctttcttgagcacacactcttttatttgagtacacatacaactcaaatgac
cacctcaatctatcggtgttgatggaaggatctagtgaatgcaatattctagaactacaccttccacttctttctctaattcttttagactttgcact
ctataactctcatcctaaagttcttctttcaatacaaatcttgaatattctagattcttctttgaaatatcttagatattaattaaggtggtgatgac
cttttaacacccctctcagcaccaacttaatttattctttgtatccattttgagtgatcctcgagacattgcaatcatcttgatgtccaggaacttta
tgaatctcttcctcctttgaacttccccactcacttctctttgaatcttattcgaaggtagtagtctccttgatctagaccactctgctaatgttgca
tcaatatacttggtgtttgggaatttcaatcatgtagacctagctccttagtcacggttgtggtgcttctcggacttcttcttgcaacatgacaagag
tttcacttgagtctaatagtaaatctctatagtgaccccccttagcagcagctgcgcagccctcccatggctgctacaaccactggaaagcctcctccc
gaggtagtccagcccgccccaacatggttttatctcgctcagtgaaggttcaatattagcagtaatgcaagttaacaatttgaacaaagggagagaat
ttggcagaaaagaggatcggaacatggtaatgcgcaagaaagcaacatctaatgcttctccaggttgtgagaagaggcacaatattagtaatgcttca
agagccctattatgttcgaacaactttgatgctttattgaaggctactggaaaaaatagtaatattatggctccaacattacatatttctaatcctga
agtagctaattaggattattcaagaaaatcaggatggcatgctactcaaatccaatccagcaatcaagccactcatggtcacattgaacacctaggct
catgaggtcccttcccaatctttggagtcacttggtcaatatcaaggtgaatctggacaactactattgtcaacagggaatggtgacgatttagttac
tttagatgggcaatcaatctttttttaattcatgcatttgtcaaaggaagtttgaagccgataactcaaccttcttaattcttggttgttatattttaa
cattatttaagcatcctcatttgtaatatcatcatcgtgtgtattacaaattttgtggtaatcacaaaatgctagtttttttctagcttttattttctt
catacttgttagttagtaaaggtatgttacctcattatgactggtaaggtaaggttcaacttcctttgcttgtacttatccctactgagtttttttatt
atttttaatagaaggctgctaaaaaaaataatttcaagaaatctattttatacgatatcaaattaaagtacgttgcataaaacatttataagaaagag
gaatgaagtacgttgtagatcaaattaaggaaatgataagagataaacctggaatcgtggtgtttcttccattgccaagagtgtatgtcatcactacc
caaaatttcaagctttcttgctgctatcataaaacatttttttcccactgtgcttatcgataaaaaaactctgaaagaaaaaaaaacattaaacaataa
aaaaatgtatagtattgtatttataatctaattattaatccaaattcacatcaattaaggaacttataattttataaagaaaagtaacatacatgata

Figure 7 cont.

gagttattatagataaaagtaggggaaaaaaataaaaaaaattataaattaatgaacaaagtcaaataagaaaataaaaatattgtaatgacatggcc
atatcaaattgatcattacataaaatgatactttcatcgttacataatgatgaatttattggtaagatacaataaaaattaaataattaacaattcaa
ataaatattgtatttaaaataataatataatacaatacgatagctcacaacaacccaatatagttcaatttttttgaataacttaaacttggtgagtga
aacagaataaaacatgattcttttgatctttctagtttcattaactatgaaaaaattaaaagatattagatataaaattttaataaagataaaaacac
tgggtggtcatttttttctacttgcttgagctgtagagttacttggtatactagttgagataaatgacataaaaaaatttaattgaaacaccaatacaa
acaaggtgaaattatttttttaaagaaaattatatatgaatcgttgaatctaaaattctagtttagcaacagaggggtttcaaaggttgttttagagt
atgagtttaaatcctaagtgtgaaactcaatatttttttaatattcttatttgaatttctaactccaccattatattgtttaatacttgtgttagtg
agaggctaaagtagatgtagaatattaataccactttcatatgaatcctgtactttcatatatagcggaacataaatttatgtgcaaaaattcatgat
aaatgcaatagatagtagatatgaatcacaactttaaagaatataatgatttaaatgttaattaaataaaaaattgaatccataaatcttaaattctg
attttgcctctagtgataggtaccaaatacgtacctaacaaataatttaggttcacacaaactagcacatataccaccattacaaaaaataaaatgaa
acataaaaggtaattaaccacatcaaaatgagattttaccagtctgccgctatcaaggaggatgggagaatcacatagactaaaaaagagctcctttt
tggtgttgaaaatccgaggaagcttagatctatcaattatttttgataatcggaaggcaaaaatcttccccaaatttcatcagattttgcaacaaat
ttgaatcctgttgataaaattgttgatcttactgcatctgctggagttgttcttaaaattatttcaaagatgcaaccttctggcaacttttcaaaata
attcattggagctatggacttagaaatattcatgtcaaaattcttataaaaccttataaccgagaaataaccaaagtttttttgttacaagctttata
tataattaaataatcaaaagataaaaaagatttcagaggtctatacattgtcaaatatagtaataagtacaaataagcatataaaattatgttttttt
ttcctttttgtcaatgagtacagataagcaaaaagtcaaacttattcaaataacaataaccattgccacaccttaatctcaaacaagtttcacgttg
cttcaattaagtgtatcgagactaatattatattatataaaataaaaataacatgcacgagaagatctctatttaatttggcgtgaaatgttatctaa
agtctcaaataattggtattgcttatatgaaagtaaaaaaacttccattgtgtgccatactttcgagacaactcctttgtgattttaggtctacttcg
tctcattttaacaccttcacactatgatttcataatgtaacaacttaattaatttcttatttaatcatgataaattagtacgatacagtgtaaacatc
ggatgcaaataaattgttatccaatagaggttacatgaccaaaccatctcatttgttttatttttattatgtgctcgatttattgttagctatttcat
catcgattccaatagtatttagatctttcgaaaagcaaatagccataacacattattgtttatatatcaagaaaacacataagctatattatattatt
gtacaatttcttctTTATTCTGGTCTAAATTCAATTCCTTGAACAATAAGGCCACCTTTTCCATGAAGCTGCGTAATCTCCATCAATCGCGCTTCAAC
ATCTCCATCATCTCCTGTATCATTGATAAAATTTCCCAATTCTATTTCCATCCATCCATCGACTCTTTTTCGTGGACATTTCACATTACGTTTGCGTC
TCCTAACCCTTTTTCCGACTAGACTCACGACACTAGCTCGTTCCTCGGCCTCTTTGTCGCTCACACGATTCACAAACCTAACAAATGCATTAGCAATT
TCTAGTCCATCATGATTCTTTGACAATTTGAACACCAAATAAACAACATATTTGGTTCTTTTCGACAATATTTGTGTTCCAATCGTGCCTCGTATGTC

Figure 7 cont.

TAGCCAACTTACACCCTTGAGATGAGCCACTTCCGAAAATctgcaaaataaaatgtctatattgtcttagatacacgtatttagtgagtttaagttat
atataacatcgccaatataagtaattttgcaccatcaaatcatctttacctattgtaataggtaacatatttcattacacattttagtgaggctcat
ctatatatatcttttaggtggcttgattgtgtaaaaaaaaattctcaccaatagtggcagaggtagaatttcaaccaagggattcaaaaaataacat
atgtagaaattcgttaaaaggcaatgaagtataatttttttatacgtagtacatacataaaaaaaaagaataactttttatatgtagtataatttttcg
acgaacCTGGAGTCAGGATGAGAAATCCATTCCCAATACCATGGTGTATCAACTCCCCATGTAATAGCAAGTTCTCTAGCTGATATCATAAAACATTT
CTTGCCTGTTTTCTTATCAAGTGAAAAACTctgttttcaaaaataaaataaaatcttagattcacactactagcttatatatagtccattcaaaaata
aaataaaattcacacaattattattataatctatttaattttgcattttttaatggtgtttgtaacccattggccagaaaatcttagaagttcatttag
ttgactatctgaacttccgttttactatagagagttggattcccagtttgtaacaaaaacaaaataaaataagaaaaattcattggctgattaattaa
gatttgcgcagccgtaagcacactagtagattttagtgcttcctattaaacacgactcaattcctaagatttcaactctgattaaaactcaaactcta
gacctcaggtcaaaggttcatgacctttaccgttatacaacaccaacagttagaggcaaagctagaacacccctataaattctaggaacccaatagtt
ttagttcaaactctgtattttatctttaaaaagaaaactcctctaatttgtaccaaattattaatttcgaaccaaacaactcaaaaaacacacaaaaa
atcccgaacccataagcttcaaaacaattatacatatattcaactaatgagccaaaagaaaagcttgctacttcccaatttagagctacttacCAATT
TGCCTCCATCCATTAGAACAGGGAAGTCACATAGACTAAAGTAAAGCTCCTTTTTAGACGGATAAATCCGCGGGGAGACATATCTCGAGTTGATATCT
TCATAATCATCTGGTAAAAACTTTACCCAAATAACGTCGGATTCAGCAGCAGAGTTGAATCCCCGAGAGATCGCGGATGAAATCACGACGTCTTTCGG
GGAAGTAAAGGAGAGAATATCACAAACACAATCTTCTGGTAGCAATAGGAAATAGTCCATtattggaaaattgaatttgaagttttgtgaattttttt
tctttatataaagcaaactgagaaaagtttgttgaaaagttgttacacttcatatgtctcgacggttaagcaggggcggctcaacgtatttggaggcc
taaaacaaaatttaaattaaaggcctaaaatcttttagctgaggcaattattaaataaattgttaacattattctataagtaataagttgacaaaact
gcttataaacttctttttttatttaaaagcacataacataagtcaatctaaacaggcttgtaattcgctttatccaacacattagttttactattgat
tcatatttttgatagagctctaacttacatagagtataaaaggggtatagaaaattacaacgcgagagtaagtgaagagagtgtaagaagacaaaaca
acgtttttcttgatttcttctatttgattgaggttaaggagaataaaataatatatatatgaaaagtacatttatcttaaataattaatttttttctat
aaaaaaaattaacacataatttattgttggtaaaaatttgaggccccccctaaaattgggggcctaaggcatatgcctaatttttataagcattgagcc
ggcactgcggttaaatattgttttgttcatttttacttctccagtatgaatataataagtgaaaaggtcatataatttagagctgatacatacctcgt
tataaaaatggctcatacatacctatactattacacaaatagcctagatataccctttttggcctaatggaagtgaaaatatttaattttattttattt
ttaaaaaaatcatttttgtttatttttcattatttttatctagttctcacatatgtacattttatttccaaaaaaaaataaaattaaagaattgatat
tgcttagatacaccaaacaaacaactcatgtggaggaagatattccaataatactaaacatgaaatgttttgagtttgaaatttttttgtctttccttt

Figure 7 cont.

ttagtgaattaaaacatgaaatgtcttggaagattcgaaatttactggcccgactaatttaagattagcatcatctaaggtccatttatcaaggagcg
ttcccgaccaagaatttctccattctccgaattcaaaccaaagacttgttgtttagttaacactagagaagtctcattctcgcaccacagttgtggca
gttcccgaaaagcaatattcacaaattcttacattcatcatttcattaatttcttatagttgtaactataagaacaacataccatgtgtctcccccac
aaagtggagtatgggaagggtagagtgtaagcaaactttactcttacctcagaggtagaaagtcttcttccgatagatcctcgactcgagaaaaataa
tccaaagcagttcagaaaaagacacaacaaaagtacaagaaacaccagatagtaacagaatagtacttcaacattaacaaattactatctcttacaca
gaaaaatgaacttgaaattcataaaaaataataataataacagaacatacccttgttcaagtggtaatctatatacagtactttcaaaatcaatctct
tgctcgtacttgagctcgagaaaaattccttatactaaccgcgtcttccccatttcacgagcagtggagagaacgtttcacacgttgtctttactaca
tcttcagcaggtaatgtcttt

Figure 7 cont.

SEQ ID NO:7

>BL_17SC0100-0002 NODE_4559_length_28844_cov_5.188734 ctctattttgttgttcttagtcctttcttataggattttgcattgcccccacccccaccccccttgttataagtaactatatctttttccattgtttt
cttcttccttgtacttacatttgttgcatttgagttgagggtctttcgaaaataacatctctacctccacgaggtagtgataaggactgcgtacactc
taccctccccagactccacttgtggaatttcaccggatatgttgttgttattgttataaggaaaagctttggtctcaaaactctttaaactcaatttt
ttttcttttgcactccctcttttcttgagtacatttcactctcaattctttcttgagcacacactcttttatttgagtacacatacaactcaaatgac
cacctcaatctatcggtgttgatggaaggatctagtgaatgcaatattctagaactacaccttccacttctttctctaattcttttagactttgcact
ctataactctcatcctaaagttcttctttcaatacaaatcttgaatattctagattcttctttgaaatatcttagatattaattaaggtggtgatgac
cttttaacacccctctcagcaccaacttaatttattctttgtatccattttgagtgatcctcgagacattgcaatcatcttgatgtccaggaacttta
tgaatctcttcctcctttgaacttccccactcacttctctttgaatcttattcgaaggtagtagtctccttgatctagaccactctgctaatgttgca
tcaatatacttggtgtttgggaatttcaatcatgtagacctagctccttagtcacggttgtggtgcttctcggacttcttcttgcaacatgacaagag
tttcacttgagtctaatagtaaatctctatagtgaccccttagcagcagctgcgcagccctcccatggctgctacaaccactggaaagcctcctccc
gaggtagtccagcccgccccaacatggttttatctcgctcagtgaaggttcaatattagcagtaatgcaagttaacaatttgaacaaagggagagaat
ttggcagaaaagaggatcggaacatggtaatgcgcaagaaagcaacatctaatgcttctccaggttgtgagaagaggcacaatattagtaatgcttca
agagccctattatgttcgaacaactttgatgctttattgaaggctactggaaaaatagtaatattatggctccaacattacatatttctaatcctga
agtagctaattaggattattcaagaaaatcaggatggcatgctactcaaatccaatccagcaatcaagccactcatggtcacattgaacacctaggct
catgaggtcccttcccaatctttggagtcacttggtcaatatcaaggtgaatctggacaactactattgtcaacagggaatggtgacgatttagttac
tttagatgggcaatcaatctttttaattcatgcatttgtcaaaggaagtttgaagccgataactcaaccttcttaattcttggttgttatattttaa
cattatttaagcatcctcatttgtaatatcatcatcgtgtgtattacaaattttgtggtaatcacaaaatgctagtttttctagcttttattttctt
catacttgttagttagtaaaggtatgttacctcattatgactggtaaggtaaggttcaacttcctttgcttgtacttatccctactgagtttttatt
atttttaatagaaggctgctaaaaaaaataatttcaagaaatctattttatacgatatcaaattaaagtacgttgcataaaacatttataagaaagag
gaatgaagtacgttgtagatcaaattaaggaaatgataagagataaacctggaatcgtggtgtttcttccattgccaagagtgtatgtcatcactacc
caaaatttcaagctttcttgctgctatcataaaacatttttcccactgtgcttatcgataaaaaaactctgaaagaaaaaaaaacattaaacaataa
aaaaatgtatagtattgtatttataatctaattattaatccaaattcacatcaattaaggaacttataattttataaagaaaagtaacatacatgata

Figure 7 cont.

gagttattatagataaaagtaggggaaaaaaataaaaaaaattataaattaatgaacaaagtcaaataagaaaataaaaatattgtaatgacatggcc
atatcaaattgatcattacataaaatgatactttcatcgttacataatgatgaatttattggtaagatacaataaaaattaaataattaacaattcaa
ataaatattgtatttaaaataataatataatacaatacgatagctcacaacaacccaatatagttcaatttttgaataacttaaacttggtgagtga
aacagaataaaacatgattcttttgatctttctagtttcattaactatgaaaaaattaaaagatattagatataaattttaataaagataaaaacac
tgggtggtcatttttctacttgcttgagctgtagagttacttggtatactagttgagataaatgacataaaaaaatttaattgaaacaccaatacaa
acaaggtgaaattatttttttaaagaaaattatatatgaatcgttgaatctaaaattctagtttagcaacagaggggtttcaaaggttgttttagagt
atgagtttaaatcctaagtgtgaaactcaatattttttttaatattcttatttgaatttctaactccaccattatattgtttaatacttgtgttagtg
agaggctaaagtagatgtagaatattaataccactttcatatgaatcctgtactttcatatatagcggaacataaatttatgtgcaaaaattcatgat
aaatgcaatagatagtagatatgaatcacaactttaaagaatataatgatttaaatgttaattaaataaaaaattgaatccataaatcttaaattctg
attttgcctctagtgataggtaccaaatacgtacctaacaaataatttaggttcacacaaactagcacatataccaccattacaaaaaataaaatgaa
acataaaaggtaattaaccacatcaaaatgagattttaccagtctgccgctatcaaggaggatgggagaatcacatagactaaaaaagagctcctttt
tggtgttgaaaatccgaggaagcttagatctatcaattatttttgataatcggaaggcaaaaatcttccccaaatttcatcagattttgcaacaaat
ttgaatcctgttgataaaattgttgatcttactgcatctgctggagttgttcttaaaattatttcaaagatgcaaccttctggcaacttttcaaaata
attcattggagctatggacttagaaatattcatgtcaaaattcttataaaaccttataaccgagaaataaccaaagtttttttgttacaagctttata
tataattaaataatcaaaagataaaaaagatttcagaggtctatacattgtcaaatatagtaataagtacaaataagcatataaaattatgttttttt
ttcctttttgtcaatgagtacagataagcaaaaagtcaaacttattcaaataacaataaccattgccacaccttaatctcaaacaagtttcacgttg
cttcaattaagtgtatcgagactaatattatattatataaaataaaaataacatgcacgagaagatctctatttaatttggcgtgaaatgttatctaa
agtctcaaataattggtattgcttatatgaaagtaaaaaaacttccattgtgtgccatactttcgagacaactcctttgtgattttaggtctacttcg
tctcattttaacaccttcacactatgatttcataatgtaacaacttaattaatttcttatttaatcatgataaattagtacgatacagtgtaaacatc
ggatgcaaataaattgttatccaatagaggttacatgaccaaaccatctcatttgttttatttttattatgtgctcgatttattgttagctatttcat
catcgattccaatagtatttagatctttcgaaaagcaaatagccataacacattattgtttatatatcaagaaaacacataagctatattatattatt
gtacaatttcttctTTATTCTGGTCTAAATTCAATTCCTTGAACAATAAGGCCACCTTTTCCATGAAGCTGCGTAATCTCCATCAATCGCGCTTCAAC
ATCTCCATCATCTCCTGTATCATTGATAAAATTTCCCAATTCTATTTCCATCCATCCATCGACTCTTTTTCGTGGACATTTCACATTACGTTTGCGTC
TCCTAACCCTTTTTCCGACTAGACTCACGACACTAGCTCGTTCCTCGGCCTCTTTGTCGCTCACACGATTCACAAACCTAACAAATGCATTAGCAATT
TCTAGTCCATCATGATTCTTTGACAATTTGAACACCAAATAAACAACATATTTGGTTCTTTTCGACAATATTTGTGTTCCAATCGTGCCTCGTATGTC

Figure 7 cont.

TAGCCAACTTACACCCTTGAGATGAGCCACTTCCGAAAATctgcaaaataaaatgtctatattgtcttagatacacgtatttagtgagtttaagttat
atataacatcgccaatataagtaattttgcaccatcaaatcatctttacctattgtaataggtaacatatttcattacacattttagtgaggctcat
ctatatatatcttttaggtggcttgattgtgtaaaaaaaaaattctcaccaatagtggcagaggtagaatttcaaccaagggattcaaaaaataacat
atgtagaaattcgttaaaaggcaatgaagtataatttttatacgtagtacatacataaaaaaaaagaataactttttatatgtagtataatttttcg
acgaacCTGGAGTCAGGATGAGAAATCCATTCCCAATACCATGGTGTATCAACTCCCCATGTAATAGCAAGTTCTCTAGCTGATATCATAAAACATTT
CTTGCCTGTTTTCTTATCAAGTGAAAAACTctgttttcaaaaataaaataaaatcttagattcacactactagcttatatatagtccattcaaaaata
aaataaaattcacacaattattattataatctatttaattttgcatttttaatggtgtttgtaacccattggccagaaaatcttagaagttcatttag
ttgactatctgaacttccgttttactatagagagttggattcccagtttgtaacaaaaacaaaataaaataagaaaaattcattggctgattaattaa
gatttgcgcagccgtaagcacactagtagattttagtgcttcctattaaacacgactcaattcctaagatttcaactctgattaaaactcaaactcta
gacctcaggtcaaaggttcatgacctttaccgttatacaacaccaacagttagaggcaaagctagaacacccctataaattctaggaacccaatagtt
ttagttcaaactctgtattttatctttaaaaagaaaactcctctaatttgtaccaaattattaatttcgaaccaaacaactcaaaaaacacacaaaaa
atcccgaacccataagcttcaaaacaattatacatatattcaactaatgagccaaaagaaaagcttgctacttcccaatttagagctacttacCAATT
TGCCTCCATCCATTAGAACAGGGAAGTCACATAGACTAAAGTAAAGCTCCTTTTTAGACGGATAAATCCGCGGGGAGACATATCTCGAGTTGATATCT
TCATAATCATCTGGTAAAAACTTTACCCAAATAACGTCGGATTCAGCAGCAGAGTTGAATCCCCGAGAGATCGCGGATGAAATCACGACGTCTTTCGG
GGAAGTAAAGGAGAGAATATCACAAACACAATCTTCTGGTAGCAATAGGAAATAGTCCATtattggaaaattgaatttgaagttttgtgaatttttt
tctttatataaagcaaactgagaaaagtttgttgaaaagttgttacacttcatatgtctcgacggttaagcaggggcggctcaacgtatttggaggcc
taaaacaaaatttaaattaaaggcctaaaatcttttagctgaggcaattattaaataaattgttaacattattctataagtaataagttgacaaaact
gcttataaacttcttttttatttaaaagcacataacataagtcaatctaaacaggcttgtaattcgctttatccaacacattagttttactattgat
tcatatttttgatagagctctaacttacatagagtataaaaggggtatagaaaattacaacgcgagagtaagtgaagagagtgtaagaagacaaaaca
acgtttttcttgatttcttctatttgattgaggttaaggagaataaaataatatatatatgaaaagtacatttatcttaaataattaatttttctat
aaaaaaaattaacacataatttattgttggtaaaaatttgaggccccccctaaaattgggggcctaaggcatatgcctaatttttataagcattgagcc
ggcactgcggttaaatattgttttgttcatttttacttctccagtatgaatataataagtgaaaaggtcatataatttagagctgatacatacctcgt
tataaaaatggctcatacatacctatactattacacaaatagcctagatataccctttggcctaatggaagtgaaaatatttaattttattttattt
ttaaaaaaatcatttttgtttatttttcattatttttatctagttctcacatatgtacattttatttccaaaaaaaaaataaaattaaagaattgatat
tgcttagatacaccaaacaaacaactcatgtggaggaagatattccaataatactaaacatgaaatgttttgagtttgaaatttttttgtctttccttt

Figure 7 cont.

ttagtgaattaaaacatgaaatgtcttggaagattcgaaatttactggcccgactaatttaagattagcatcatctaaggtccatttatcaaggagcg ttcccgaccaagaatttctccattctccgaattcaaaccaaagacttgttgtttagttaacactagagaagtctcattctcgcaccacagttgtggca gttcccgaaaagcaatattcacaaattcttacattcatcatttcattaatttcttatagttgtaactataagaacaacataccatgtgtctcccccac aaagtggagtatgggaagggtagagtgtaagcaaactttactcttacctcagaggtagaaagtcttcttccgatagatcctcgactcgagaaaaataa tccaaagcagttcagaaaaagacacaacaaaagtacaagaaacaccagatagtaacagaatagtacttcaacattaacaaattactatctcttacaca gaaaaatgaacttgaaattcataaaaaataataataacagaacatacccttgttcaagtggtaatctatatacagtactttcaaaatcaatctct tgctcgtacttgagctcgagaaaaattccttatactaaccgcgtcttccccatttcacgagcagtggagagaacgtttcacacgttgtctttactaca tcttcagcaggtaatgtcttt

Figure 7 cont.

SEQ ID NO:8

>BL_17SC0100-0018 NODE_4276_length_28842_cov_5.003099 ctctattttgttgttcttagtcctttcttataggattttgcattgcccccacccccacccccccttgttataagtaactatatctttttccattgtttt cttcttccttgtacttacatttgttgcatttgagttgagggtctttcgaaaataacatctctacctccacgaggtagtgataaggactgcgtacactc taccctccccagactccacttgtggaatttcaccggatatgttgttgttattgttataaggaaaagctttggtctcaaaactctttaaactcaatttt ttttcttttgcactccctcttttcttgagtacatttcactctcaattctttcttgagcacacactcttttatttgagtacacatacaactcaaatgac cacctcaatctatcggtgttgatggaaggatctagtgaatgcaatattctagaactacaccttccacttctttctctaattcttttagactttgcact ctataactctcatcctaaagttcttctttcaatacaaatcttgaatattctagattcttctttgaaatatcttagatattaattaaggtggtgatgac cttttaacacccctctcagcaccaacttaatttattctttgtatccattttgagtgatcctcgagacattgcaatcatcttgatgtccaggaacttta tgaatctcttcctcctttgaacttccccactcacttctctttgaatcttattcgaaggtagtagtctccttgatctagaccactctgctaatgttgca tcaatatacttggtgtttgggaatttcaatcatgtagacctagctccttagtcacggttgtggtgcttctcggacttcttcttgcaacatgacaagag tttcacttgagtctaatagtaaatctctatagtgaccccttagcagcagctgcgcagccctcccatggctgctacaaccactggaaagcctcctccc gaggtagtccagcccgccccaacatggttttatctcgctcagtgaaggttcaatattagcagtaatgcaagttaacaatttgaacaaagggagagaat ttggcagaaaagaggatcggaacatggtaatgcgcaagaaagcaacatctaatgcttctccaggttgtgagaagaggcacaatattagtaatgcttca agagccctattatgttcgaacaactttgatgctttattgaaggctactggaaaaaatagtaatattatggctccaacattacatatttctaatcctga agtagctaattaggattattcaagaaaatcaggatggcatgctactcaaatccaatccagcaatcaagccactcatggtcacattgaacacctaggct catgaggtcccttcccaatctttggagtcacttggtcaatatcaaggtgaatctggacaactactattgtcaacagggaatggtgacgatttagttac tttagatgggcaatcaatctttttaattcatgcatttgtcaaaggaagtttgaagccgataactcaaccttcttaattcttggttgttatattttaa cattatttaagcatcctcatttgtaatatcatcatcgtgtgtattacaaattttgtggtaatcacaaaatgctagtttttctagctttattttctt catacttgttagttagtaaaggtatgttacctcattatgactggtaaggtaaggttcaacttcctttgcttgtacttatccctactgagtttttatt atttttaatagaaggctgctaaaaaaataatttcaagaaatctattttatacgatatcaaattaaagtacgttgcataaaacatttataagaaagag gaatgaagtacgttgtagatcaaattaaggaaatgataagagataaacctggaatcgtggtgtttcttccattgccaagagtgtatgtcatcactacc caaaatttcaagctttcttgctgctatcataaaacatttttcccactgtgcttatcgataaaaaaactctgaaagaaaaaaaaacattaaacaataa aaaaatgtatagtattgtatttataatctaattattaatccaaattcacatcaattaaggaacttataattttataaagaaaagtaacatacatgata

Figure 7 cont.

gagttattatagataaaagtaggggaaaaaaataaaaaaaattataaattaatgaacaaagtcaaataagaaaataaaaatattgtaatgacatggcc atatcaaattgatcattacataaaatgatactttcatcgttacataatgatgaatttattggtaagatacaataaaaattaaataattaacaattcaa ataaatattgtatttaaaataataatataatacaatacgatagctcacaacaacccaatatagttcaatttttgaataacttaaacttggtgagtga aacagaataaaacatgattcttttgatctttctagtttcattaactatgaaaaaattaaaagatattagatataaaattttaataaagataaaaacac tgggtggtcatttttctacttgcttgagctgtagagttacttggtatactagttgagataaatgacataaaaaaatttaattgaaacaccaatacaa acaaggtgaaattatttttttaaagaaaattatatatgaatcgttgaatctaaaattctagtttagcaacagaggggtttcaaaggttgttttagagt atgagtttaaatcctaagtgtgaaactcaatatttttttaatattcttatttgaatttctaactccaccattatattgtttaatacttgtgttagtg agaggctaaagtagatgtagaatattaataccactttcatatgaatcctgtactttcatatatagcggaacataaatttatgtgcaaaaattcatgat aaatgcaatagatagtagatatgaatcacaactttaaagaatataatgatttaaatgttaattaaataaaaaattgaatccataaatcttaaattctg attttgcctctagtgataggtaccaaatacgtacctaacaaataatttaggttcacacaaactagcacatataccaccattacaaaaataaaatgaa acataaaaggtaattaaccacatcaaaatgagattttaccagtctgccgctatcaaggaggatgggagaatcacatagactaaaaaagagctcctttt tggtgttgaaaatccgaggaagcttagatctatcaattatttttgataatcggaaggcaaaaatcttccccaaatttcatcagattttgcaacaaat ttgaatcctgttgataaaattgttgatcttactgcatctgctggagttgttcttaaaattatttcaaagatgcaaccttctggcaacttttcaaaata attcattggagctatggacttagaaatattcatgtcaaaattcttataaaaccttataaccgagaaataaccaaagtttttttgttacaagctttata tataattaaataatcaaaagataaaaaagatttcagaggtctatacattgtcaaatatagtaataagtacaaataagcatataaaattatgttttttt ttcctttttgtcaatgagtacagataagcaaaaagtcaaacttattcaaataacaataaccattgccacaccttaatctcaaacaagtttcacgttg cttcaattaagtgtatcgagactaatattatattatataaaataaaaataacatgcacgagaagatctctatttaatttggcgtgaaatgttatctaa agtctcaaataattggtattgcttatatgaaagtaaaaaaacttccattgtgtgccatactttcgagacaactcctttgtgattttaggtctacttcg tctcattttaacaccttcacactatgatttcataatgtaacaacttaattaatttcttatttaatcatgataaattagtacgatacagtgtaaacatc ggatgcaaataaattgttatccaatagaggttacatgaccaaaccatctcatttgttttatttttattatgtgctcgatttattgttagctatttcat catcgattccaatagtatttagatctttcgaaaagcaaatagccataacacattattgtttatatatcaagaaaacacataagctatattatattatt gtacaatttcttctTTATTCTGGTCTAAATTCAATTCCTTGAACAATAAGGCCACCTTTTCCATGAAGCTGCGTAATCTCCATCAATCGCGCTTCAAC ATCTCCATCATCTCCTGTATCATTGATAAAATTTCCCAATTCTATTTCCATCCATCCATCGACTCTTTTTCGTGGACATTTCACATTACGTTTGCGTC TCCTAACCCTTTTTCCGACTAGACTCACGACACTAGCTCGTTCCTCGGCCTCTTTGTCGCTCACACGATTCACAAACCTAACAAATGCATTAGCAATT TCTAGTCCATCATGATTCTTTGACAATTTGAACACCAAATAAACAACATATTTGGTTCTTTTCGACAATATTTGTGTTCCAATCGTGCCTCGTATGTC

Figure 7 cont.

TAGCCAACTTACACCCTTGAGATGAGCCACTTCCGAAAATctgcaaaataaaatgtctatattgtcttagatacacgtatttagtgagtttaagttat
atataacatcgccaatataagtaattttgcaccatcaaatcatctttacctattgtaataggtaacatatttcattacacattttagtgaggctcat
ctatatatatcttttaggtggcttgattgtgtaaaaaaaaaattctcaccaatagtggcagaggtagaatttcaaccaagggattcaaaaaataacat
atgtagaaattcgttaaaaggcaatgaagtataatttttatacgtagtacatacataaaaaaaaagaataactttttatatgtagtataatttttcg
acgaacCTGGAGTCAGGATGAGAAATCCATTCCCAATACCATGGTGTATCAACTCCCCATGTAATAGCAAGTTCTCTAGCTGATATCATAAAACATTT
CTTGCCTGTTTTCTTATCAAGTGAAAAACTctgttttcaaaaataaaataaaatcttagattcacactactagcttatatatagtccattcaaaaata
aaataaaattcacacaattattattataatctatttaattttgcatttttaatggtgtttgtaacccattggccagaaaatcttagaagttcatttag
ttgactatctgaacttccgttttactatagagagttggattcccagtttgtaacaaaaacaaaataaaataagaaaaattcattggctgattaattaa
gatttgcgcagccgtaagcacactagtagattttagtgcttcctattaaacacgactcaattcctaagatttcaactctgattaaaactcaaactcta
gacctcaggtcaaaggttcatgacctttaccgttatacaacaccaacagttagaggcaaagctagaacacccctataaattctaggaacccaatagtt
ttagttcaaactctgtattttatctttaaaaagaaaactcctctaatttgtaccaaattattaatttcgaaccaaacaactcaaaaaacacacaaaaa
atcccgaacccataagcttcaaaacaattatacatatattcaactaatgagccaaaagaaaagcttgctacttcccaatttagagctacttacCAATT
TGCCTCCATCCATTAGAACAGGGAAGTCACATAGACTAAAGTAAAGCTCCTTTTTAGACGGATAAATCCGCGGGGAGACATATCTCGAGTTGATATCT
TCATAATCATCTGGTAAAAACTTTACCCAAATAACGTCGGATTCAGCAGCAGAGTTGAATCCCCGAGAGATCGCGGATGAAATCACGACGTCTTTCGG
GGAAGTAAAGGAGAGAATATCACAAACACAATCTTCTGGTAGCAATAGGAAATAGTCCATtattggaaaattgaatttgaagttttgtgaatttttt
tctttatataaagcaaactgagaaaagtttgttgaaaagttgttacacttcatatgtctcgacggttaagcaggggcggctcaacgtatttggaggcc
taaaacaaaatttaaattaaaggcctaaaatcttttagctgaggcaattattaaataaattgttaacattattctataagtaataagttgacaaaact
gcttataaacttctttttttatttaaaagcacataacataagtcaatctaaacaggcttgtaattcgctttatccaacacattagttttactattgat
tcatatttttgatagagctctaacttacatagagtataaaaggggtatagaaaattacaacgcgagagtaagtgaagagagtgtaagaagacaaaaca
acgtttttcttgatttcttctatttgattgaggttaaggagaataaaataatatatatatgaaaagtacatttatcttaaataattaatttttctat
aaaaaaaattaacacataatttattgttggtaaaaatttgaggccccctaaaattgggggcctaaggcatatgcctaatttttataagcattgagcc
ggcactgcggttaaatattgttttgttcatttttacttctccagtatgaatataataagtgaaaaggtcatataatttagagctgatacatacctcgt
tataaaaatggctcatacatacctatactattacacaaatagcctagatataccctttttggcctaatggaagtgaaaatatttaattttattttattt
ttaaaaaaatcatttttgtttatttttcattatttttatctagttctcacatatgtacattttatttccaaaaaaaaaataaaattaaagaattgatat
tgcttagatacaccaaacaaacaactcatgtggaggaagatattccaataatactaaacatgaaatgttttgagtttgaatttttttgtctttccttt

Figure 7 cont.

ttagtgaattaaaacatgaaatgtcttggaagattcgaaatttactggcccgactaatttaagattagcatcatctaaggtccatttatcaaggagcg ttcccgaccaagaatttctccattctccgaattcaaaccaaagacttgttgtttagttaacactagagaagtctcattctcgcaccacagttgtggca gttcccgaaaagcaatattcacaaattcttacattcatcatttcattaatttcttatagttgtaactataagaacaacataccatgtgtctcccccac aaagtggagtatgggaagggtagagtgtaagcaaactttactcttacctcagaggtagaaagtcttcttccgatagatcctcgactcgagaaaaataa tccaaagcagttcagaaaaagacacaacaaaagtacaagaaacaccagatagtaacagaatagtacttcaacattaacaaattactatctcttacaca gaaaaatgaacttgaaattcataaaaaataataataataacagaacatacccttgttcaagtggtaatctatatacagtactttcaaaatcaatctct tgctcgtacttgagctcgagaaaaattccttatactaaccgcgtcttccccatttcacgagcagtggagagaacgtttcacacgttgtctttactaca tcttcagcaggtaatgtcttt

A B C D

A

B

| Genotype | SOT12-59016142 | SOT12-59016842 | SOT12-59019869 | SOT12-59019907 | SOT12-59024580 | SOT12-59025293 | SOT12-59025327 | SOT12-59030123 | SOT12-59030301 | SOT12-59030880 | SOT12-59042250 | SOT12-59042436 | SOT12-59043512 | SOT12-59043614 | phenotype |
|---|---|---|---|---|---|---|---|---|---|---|---|---|---|---|---|
| 4016 | a | a | a | a | a | a | a | a | a | a | a | a | b | b | SC |
| 4017 | a | a | a | a | a | a | a | a | a | a | a | a | b | b | SC |
| 4024 | a | a | a | a | a | a | a | a | a | a | b | b | b | b | SI |
| 4028 | a | a | a | a | a | a | a | a | a | a | b | b | b | b | SI |

Figure 13

| genotype | SOT12-59016142 | SOT12-59016842 | SOT12-59019869 | SOT12-59019907 | SOT12-59024580 | SOT12-59025293 | SOT12-59025327 | SOT12-59030880 | SOT12-59042250 | SOT12-59042436 | SOT12-59043512 | SOT12-59043614 | Phenotype |
|---|---|---|---|---|---|---|---|---|---|---|---|---|---|
| 4016 | a | a | a | a | a | a | a | a | a | a | b | b | SC |
| 4017 | a | a | a | a | a | a | a | a | a | a | b | b | SC |
| 4024 | a | a | a | a | a | a | a | a | b | b | b | b | SI |
| 4028 | a | a | a | a | a | a | a | a | b | b | b | b | SI |
| 4040 | b | b | b | b | b | b | b | b | b | b | a | a | SI |
| 4053 | a | a | a | a | a | a | a | a | b | b | b | b | SI |

SEQ ID NO:17

>FO_DS Reversed: NODE_6145_length_29156_cov_4.538109
caagggtatgttctgttattattattatttttatgaatttcaagttcatttttctgtgtaagagatagtaatttgttaatgttgaagtact
attctgttactatctggtgtttcttgtacttttgttgtgtctttttctgaactgctttggattatttttctcgagtcgaggatctatcggaag
aagactttctacctctgaggtaagagtaaagtttgcttacactctacccttcccatactccactttgtgggggagacacatggtatgttg
ttcttatagttacaactataagaaattaatgaaatgatgaatgtaagaatttgtgaatattgcttttcgggaactgccacaactgtgg
tgcgagaatgagacttctctagtgttaactaaacaacaagtctttggtttgaattcggagaatggagaaattcttggtcgggaacgct
ccttgataaatggaccttagatgatgctaatcttaaattagtcgggccagtaaatttcgaatcttccaagacatttcatgttttaattca
ctaaaaaggaaagacaaaaaatttcaaactcaaaacatttcatgtttagtattattggaatatcttcctccacatgagttgtttgtttg
gtgtatctaagcaatatcaattctttaattttatttttttttggaaataaaatgtacatatgtgagaactagataaaaataatgaaaa
ataaacaaaaatgattttttaaaaataaaataaaattaaatattttcacttccattaggccaaaagggtatatctaggctatttgtg
taatagtataggtatgtatgagccatttttataacgaggtatgtatcagctctaaattatatgaccttttcacttattatattcatactg
gagaagtaaaaatgaacaaaacaatatttaaccgcagtgccggctcaatgcttataaaaattaggcatatgccttaggcccccaatt
ttagggggcctcaaatttttaccaacaataaattatgtgttaattttttttatagaaaaaattaattatttaagataaatgtacttttc
atatatatattattttattctccttaacctcaatcaaatagaagaaatcaagaaaaacgttgttttgtcttcttacactctcttcacttac
tctcgcgttgtaattttctataccccttttatactctatgtaagttagagctctatcaaaaatatgaatcaatagtaaaactaatgtgtt
ggataaagcgaattacaagcctgtttagattgacttatgttatgtgcttttaaataaaaaaagaagtttataagcagttttgtcaact
tattacttatagaataatgttaacaatttatttaataattgcctcagctaaaagattttaggcctttaatttaaattttgttttaggcctc
caaatacgttgagccgcccctgcttaaccgtcgagacatatgaagtgtaacaacttttcaacaaacttttctcagtttgctttatataa
agaaaaaaaattcacaaaacttcaaattcaattttccaataATGGACTATTTCCTATTGCTACCAGAAGATT
GTGTTTGTGATATTCTCTCCTTTACTTCCCCGAAAGACGTCGTGATTTCATCCGCGATCT
CTCGGGGATTCAACTCTGCTGCTGAATCCGACGTTATTTGGGTAAAGTTTTTACCAGAT
GATTATGAAGATATCAACTCGAGATATGTCTCCCCGCGGATTTATCCGTCTAAAAAGGA
GCTTTACTTTAGTCTATGTGACTTCCCTGTTCTAATGGATGGAGGCAAATTGAGTTTTTC
ACTTGATAAGAAAACAGGCAAGAAATGTTTTATGATATCAGCTAGAGAACTTGCTATTA
CATGGGGAGTTGATACACCATGGTATTGGGAATGGATTTCTCATCCTGACTCCAGATTT
TCGGAAGTGGCTCATCTCAAGGGTGTAAGTTGGCTAGACATACGAGGCACGATTGGAA
CACAAATATTGTCGAAAAGAACCAAATATGTTGTTTATTTGGTGTTCAAATTGTCAAAG
AATCATGATGGACTAGAAATTGCTAATGCATTTGTTAGGTTTGTGAATCGTGTGAGCGA
CAAAGAGGCCGAGGAACGAGCTAGTGTCGTGAGTCTAGTCGGAAAAAGGGTTAGGAGA
CGCAAACGTAATGTGAAATGTCCACGAAAAAGAGTCGATGGATGGATGGAAATAGAAT
TGGGAAATTTTATCAATGATACAGGAGATGATGGAGATGTTGAAGCGCGATTGATGGA
GATTACGCAGCTTCATGGAAAAGGTGGCCTTATTGTTCAAGGAATTGAATTTAGACCAG
AATAAagaagaaattgtacaataatataatatagcttatgtgttttcttgatatataaacaataatgtgttatggctatttgctttt
cgaaagatctaaatactattggaatcgatgatgaaatagctaacaataaatcgagcacataataaaaataaaacaaatgagatg
gtttggtcatgtaacctctattggataacaatttatttgcatccgatgtttacactgtatcgtactaatttatcatgattaaataagaaa
ttaattaagttgttacattatgaaatcatagtgtgaaggtgttaaaatgagacgaagtagacctaaaatcacaaaggagttgtctcg
aaagtatggcacacaatggaagtttttttactttcatataagcaataccaattatttgagactttagataacatttcacgccaaattaa
atagagatcttctcgtgcatgttatttttattttatataatataatattagtctcgatacacttaattgaagcaacgtgaaacttgtttg
agattaaggtgtggcaatggttattgttatttgaataagtttgactttttgcttatctgtactcattgacaaaaaaggaaaaaaaaac
ataattttatatgcttatttgtacttattactatatttgacaatgtatagacctctgaaatctttttttatcttttgattatttaattatatat
aaagcttgtaacaaaaaaactttggttatttctcggt<

Figure 19

SEQ ID NO:18 caagggtatgttctgttattattattattttttatgaatttcaagttcatttttctgtgtaagagatagtaatttgttaatgttgaagtact
attctgttactatctggtgtttcttgtacttttgttgtgtctttttctgaactgctttggattatttttctcgagtcgaggatctatcggaag
aagactttctacctctgaggtaagagtaaagtttgcttacactctacccttcccatactccactttgtgggggagacacatggtatgttg
ttcttatagttacaactataagaaattaatgaaatgatgaatgtaagaatttgtgaatattgcttttcgggaactgccacaactgtgg
tgcgagaatgagacttctctagtgttaactaaacaacaagtctttggtttgaattcggagaatggagaaattcttggtcgggaacgct
ccttgataaatggaccttagatgatgctaatcttaaattagtcgggccagtaaatttcgaatcttccaagacatttcatgttttaattca
ctaaaaaggaaagacaaaaaatttcaaactcaaaacatttcatgtttagtattattggaatatcttcctccacatgagttgtttgtttg
gtgtatctaagcaatatcaattctttaattttattttttttggaaataaaatgtacatatgtgagaactagataaaaataatgaaaa
ataaacaaaaatgatttttttaaaaataaaataaaattaaatattttcacttccattaggccaaaagggtatatctaggctatttgtg
taatagtataggtatgtatgagccatttttataacgaggtatgtatcagctctaaattatatgaccttttcacttattatattcatactg
gagaagtaaaaatgaacaaaacaatatttaaccgcagtgccggctcaatgcttataaaaattaggcatatgccttaggcccccaatt
ttagggggggcctcaaatttttaccaacaataaattatgtgttaattttttttatagaaaaaattaattatttaagataaatgtacttttc
atatatatattattttattctccttaacctcaatcaaatagaagaaatcaagaaaaacgttgttttgtcttcttacactctcttcacttac
tctcgcgttgtaattttctataccccttttatactctatgtaagttagagctctatcaaaaatatgaatcaatagtaaaactaatgtgtt
ggataaagcgaattacaagcctgtttagattgacttatgttatgtgcttttaaataaaaaaagaagtttataagcagttttgtcaact
tattacttatagaataatgttaacaatttatttaataattgcctcagctaaaagattttaggcctttaatttaaattttgttttaggcctc
caaatacgttgagccgcccctgcttaaccgtcgagacatatgaagtgtaacaacttttcaacaaacttttctcagtttgctttatataa
agaaaaaaaattcacaaaacttcaaattcaattttccaata

Figure 20

SEQ ID NO:19

ATGGACTATTTCCTATTGCTACCAGAAGATTGTGTTTGTGATATTCTCTCCTTTACTTCC
CCGAAAGACGTCGTGATTTCATCCGCGATCTCTCGGGGATTCAACTCTGCTGCTGAATC
CGACGTTATTTGGGTAAAGTTTTTACCAGATGATTATGAAGATATCAACTCGAGATATG
TCTCCCCGCGGATTTATCCGTCTAAAAAGGAGCTTTACTTTAGTCTATGTGACTTCCCT
GTTCTAATGGATGGAGGCAAATTGAGTTTTTCACTTGATAAGAAAACAGGCAAGAAATG
TTTTATGATATCAGCTAGAGAACTTGCTATTACATGGGGAGTTGATACACCATGGTATT
GGGAATGGATTTCTCATCCTGACTCCAGATTTTCGGAAGTGGCTCATCTCAAGGGTGTA
AGTTGGCTAGACATACGAGGCACGATTGGAACACAAATATTGTCGAAAAGAACCAAATA
TGTTGTTTATTTGGTGTTCAAATTGTCAAAGAATCATGATGGACTAGAAATTGCTAATG
CATTTGTTAGGTTTGTGAATCGTGTGAGCGACAAAGAGGCCGAGGAACGAGCTAGTGT
CGTGAGTCTAGTCGGAAAAAGGGTTAGGAGACGCAAACGTAATGTGAAATGTCCACGA
AAAAGAGTCGATGGATGGATGGAAATAGAATTGGGAAATTTTATCAATGATACAGGAG
ATGATGGAGATGTTGAAGCGCGATTGATGGAGATTACGCAGCTTCATGGAAAAGGTGG
CCTTATTGTTCAAGGAATTGAATTTAGACCAGAATAA

Figure 21

SEQ ID NO:20 tgtacttttcatatatatattattttattctccttaacctcaatcaaatagaagaaatcaagaaaaacgttgttttgtcttcttacactct
cttcacttactctcgcgttgtaattttctataccccttttatactctatgtaagttagagctctatcaaaaatatgaatcaatagtaaaac
taatgtgttggataaagcgaattacaagcctgtttagattgacttatgttatgtgcttttaaataaaaaaagaagtttataagcagtt
ttgtcaacttattacttatagaataatgttaacaatttatttaataattgcctcagctaaaagattttaggcctttaatttaaattttgtt
ttaggcctccaaatacgttgagccgcccctgcttaaccgtcgagacatatgaagtgtaacaacttttcaacaaacttttctcagtttgct
ttatataaagaaaaaaaattcacaaaacttcaaattcaattttccaata

SELF-COMPATIBILITY IN CULTIVATED POTATO

INCORPORATION OF SEQUENCE LISTING

The sequence listing that is contained in the file named "VONL025US_ST25.txt", is 198 KB (as measured in Microsoft Windows®), was created on Nov. 8, 2021, and is filed herewith by electronic submission and incorporated by reference herein.

CROSS-REFERENCE TO RELATED APPLICATIONS

This application is a 371 National Stage application of International Application No. PCT/NL2020/050295, filed May 7, 2020, which claims the benefit of, and priority to European Application No. 19173138.9, entitled "SELF-COMPATIBILITY IN CULTIVATED POTATO" filed May 7, 2019, and European Application No. 19218289.7, entitled "SELF-COMPATIBILITY IN CULTIVATED POTATO" filed Dec. 19, 2019, the entire contents each of which are hereby incorporated by reference in their entireties.

FIELD OF THE INVENTION

The present invention relates to a novel gene that gametophytically controls self-incompatibility (SI) in plants, in particular in potato plants, and methods for controlling gametophytic self-incompatibility in plants using the gene. More specifically, the present invention relates to a novel gene that inhibits gametophytic self-incompatibility of plants and methods for creating self-compatible plants using the gene. The invention further relates to the self-compatibility allele of a Potato Self-Compatible gene (PSC) cloned from potato along with its native promoter and regulatory regions, a construct containing the gene and a constitutive promoter, a vector containing the construct, a method of transforming a plant utilizing the construct and vector, and plants transformed with the gene construct. The invention further relates to methods for selecting a plant comprising a novel self-compatibility allele that gametophytically controls self-compatibility (PSC) and to plants produced by marker-assisted selection using molecular markers linked to or inside the novel gene or to the self-compatible or self-incompatible phenotype.

BACKGROUND OF THE INVENTION

Classic tetraploid potato breeding is cumbersome. Already for 50 years the possibilities of a transition of the conventional tetraploid breeding to diploid hybrid breeding have been investigated (Hawkes, 1956). Yet, no vigorous and fertile homozygous diploid potato genotypes were developed for decades.

Production of diploid homozygotes in potato is hampered by two phenomena: i) self-incompatibility, i.e. a genetic system that prevents self-fertilization through rejection of self pollen, and ii) inbreeding depression, i.e. the gradual reduction in fertility and vigour upon continued self-fertilization.

Most diploid (2n=2x=24) potato species are in principle self-incompatible (SI). The self-incompatibility system is thought to be controlled by a single, gametophytically inherited, multiallelic locus, the S-locus (Abdalla & Hermsen, 1971, *Euphytica* 20:345-350). Yet, self-compatible (SC) variants have exceptionally been discovered. The genetic basis of the unexpected self-compatibility of two dihaploid clones of *S. tuberosum* (G254 and B16) was investigated in detail through complete diallels and reciprocal crosses of self-compatible and self-incompatible F1 plants resulting from the intercross between the two clones (Olsder & Hermsen, 1976, *Euphytica* 25:597-607). Based, inter alia, on the lack of segregation of the trait in the various selfing and reciprocal backcrossing schemes of the first inbred generation, it was concluded that self-compatibility is caused by the presence of an S-allele bearing fragment that is present as a translocation which is not linked to the S-locus (i.e. an S-bearing translocation), on the assumption that translocation homozygotes are lethal and the S-allele on the translocation is active in the pollen only (Olsder & Hermsen, 1978, *Euphytica* 27:1-11). An alternative possibility, that self-compatibility was caused by a dominant inhibitor gene "I" which is independent of the S-locus and inactivates S-alleles (i.e. a dominant inhibitor), was discarded as a hypothesis.

In another instance, a self-compatible (SC) variant of the wild diploid potato species *Solanum chacoense* was discovered (Hanneman, 1985, *Am Potato J* 62:428-429), and a highly inbred line (chc 525-3) was produced through selfing (Hosaka and Hanneman, 1998, *Euphytica* 99:191-197). Detailed investigation of the nature and genetics of the self-compatibility in this inbred line (chc 525-3) was carried out, for which it was crossed as a female with SI cultivated diploid *S. phureja* (Hosaka and Hanneman 1998, *Euphytica* 99: 191-197). Based, inter alia, on F2 segregation ratios it was concluded that self-compatibility was caused by a single dominant gene ('Sli') with sporophytic action which inhibits S gene expression in the pollen. Plants having a Sli-gene produce pollen which is compatible to its own parent and to plants with similar S genes. So the Sli-gene is dominant over the S-alleles dependent incompatibility and is therefore designated as a locus conferring self-compatibility. As the Sli-gene was maintained in a heterozygous condition through eight selfing generations (S8), and no homozygotes were ever identified, it was concluded that dominant homozygotes might be associated with lethality. It is noteworthy that this hypothetical mechanism for self-compatibility was specifically discarded in the studies on SC dihaploid *S. tuberosum* clones described above in the study of Olsder & Hermsen, 1976, 1978.

The presumed S-locus inhibitor gene (Sli) of *S. chacoense* chc 525-3 has since been studied in more detail (Hosaka & Hanneman, 1998, *Euphytica* 103:265-271. Birhman and Hosaka, 2000, *Genome* 43:495-602; Phumichai et al., 2005, *Genome* 48:977-984; Phumichai et al., 2006, *Euphytica* 148:227-234; Phunmichai & Hosaka, 2006, *Euphytica* 149: 251-258), and the self-compatibility from this source has eventually led to the successful development of diploid inbred *S. tuberosum* lines with high levels of homozygosity, fertility and vigour (Lindhout et al. 2011, Potato Res. 54:301-312; Jansky et al., 2014, J. Plant Reg. 8:195-199). Such homozygous diploid potato inbred lines are instrumental in the generation of diploid commercial varieties, and development of hybrids by marker assisted backcrossing that are, inter alia, resistant to *Phytophthora infestans*, preferably by stacking of different *Phytophthora* resistance genes. This hybrid breeding approach relies on self-compatible homozygous inbred lines.

At present, detailed understanding of the genetic basis of self-compatibility in potato is still largely lacking. It is postulated in the art that the SC system in diploid *S. chacoense* chc 525-3 differs from that in dihaploid *S. tuberosum* clones G254 and B16, and this suggests that different systems are thus available for inbreeding in potato. Although the trait of self-compatibility is now successfully used in the generation of inbred diploid *S. tuberosum* lines, the suggested Sli-gene has not been identified yet, and heritability of the trait cannot entirely be predicted by the current genetic models, which models predict that the gene is sporophytically inherited.

For this reason, there is a need for definitive mapping and sequencing of the proposed 'Sli'-gene.

There is also a need for being able to detect Sli-gene based self-compatibility in potato plants, in order to detect self-compatible offspring plants in breeding programs at an early stage. Such detection is preferably based on genetic markers.

There is also a need for methods of producing self-compatible potato plants more easily and more predictable, such that targeted breeding can be achieved, stacking of resistance and other agronomically beneficial traits becomes possible, and linkage drag can be minimized.

SUMMARY OF THE INVENTION

The inventors have now successfully mapped the SC trait from *S. chacoense*. They discovered that this self-compatibility is not inherited sporophytically, but gametophytically, and that this incorrect qualification has greatly hampered the mapping of the gene. Initial genetic analysis in F2 populations and the observed segregation of the trait in these populations did at first not appear to be in conflict with sporophytic inheritance, but it neither could support gametophytic inheritance. Yet, mapping of this supposed monogenic trait was unsuccessful. The inventors subsequently discovered that instead of using an F2 population, the use of an F1 population with two F1s as parents, which were pre-selected from being reproducibly self-(in)compatible, resulted in a breakthrough, and provided conclusive evidence that the self-compatibility gene is inherited gametophytically. Mapping of a gametophytically inherited trait is not possible in an F2, because each F2 plant will inherit at least one copy of the dominant self-compatible Sli allele. This explains the failure of mapping studies in the past.

Without wishing to be bound by any theory, the present inventors consider that the observed segregation of the trait in F2 is due to inbreeding depression, which causes a severe reduction or even loss of fertility in a large proportion of the offspring population. Such phenotype may therefore mistakenly have been scored as self-incompatible. The inventors noted that the segregating populations contain many plants that are not fertile. Only by very detailed phenotyping, including monitoring of the actual growth of the pollen tubes into the style by using UV microscopy, were the inventors able to clearly discern self-compatible plants from self-incompatible plants. In fact, removal from the analysis of approximately ⅓ of all plants from the offspring population, based on lack of unambiguous phenotypic scorings, was needed to successfully map the trait. Previous attempts to map the gene may thus also have suffered from inaccurate phenotyping.

The gametophytic inheritance of this gene, which differs from the alleged sporophytic inheritance of Sli, prompted us to name the newly identified gene Potato Self Compatibility gene or PSC. Similar to Sli, PSC was mapped to the distal end of Chromosome 12. It is possible that the alleged sporophytic inheritance of Sli is not correct, in which case Sli and PSC may be identical.

The present inventors consider that a functional homolog of the *S. chacoense* self-compatibility allele of the PSC gene may occur in *S. tuberosum*, and in other self-compatible plant species.

In accordance with this discovery, it is an object of the invention to provide an isolated nucleic acid molecule comprising a nucleic acid sequence encoding a protein having the amino acid sequence as depicted in SEQ ID NO:10, and sequences having at least 70%, preferably at least 80%, 90% or even at least 95%, sequence identity with said amino acid sequence and conferring self-compatibility to a potato plant.

In a preferred embodiment of this aspect, said sequences having at least 70%, preferably at least 80%, 90% or even at least 95%, sequence identity with said amino acid sequence confer self-compatibility to a potato plant when expressed in pollen of said plant.

In another preferred embodiment of this aspect, said isolated nucleic acid molecule further comprises a promoter operably linked to nucleic acid sequence encoding said protein, wherein said promoter initiates transcription of said nucleic acid sequence encoding said protein in a plant cell, preferably in pollen.

In yet another a preferred embodiment of this aspect, said promoter comprises a truncated or non-truncated promoter region of the native PSC gene which gene is located at coordinates 53954293 to 53532708 of the Solyntus 1.0 genome assembly, preferably wherein said promoter at least comprises the nucleic acid sequence as depicted in SEQ ID NO:18 or SEQ ID NO:20.

It is another object of the invention to provide a promoter nucleic acid sequence comprising or consisting of the nucleic acid sequence indicated in SEQ ID NO:18 or SEQ ID NO:20, and sequences having at least 80% sequence identity with SEQ ID NO:18 or SEQ ID NO:20, and having promoter activity for expressing a gene in plant pollen, preferably the PSC gene as defined herein.

It is another object of the invention to provide an isolated nucleic acid molecule conferring self-compatibility to a potato plant, said isolated nucleic acid molecule consisting of a sequence selected from SEQ ID NO:2, SEQ ID NO:3, SEQ ID NO:4, SEQ ID NO:6, SEQ ID NO:7 and SEQ ID NO:8, and sequences having at least 70%, preferably at least 80%, 90% or even at least 95%, sequence identity therewith and conferring self-compatibility to a potato plant.

In another aspect, the present invention further provides an isolated nucleic acid molecule encoding PSC, wherein said nucleic acid molecule is selected from the group consisting of:

(a) a nucleic acid molecule comprising a sequence of a mutant allele of a gene, said gene having a wild-type nucleotide sequence of SEQ ID NO:1 or 5, said mutant allele encoding a gene product that inhibits self-incompatibility in plants;

(b) a nucleic acid molecule encoding a naturally occurring allelic variant of the nucleic acid molecule under a) and encoding a gene product gametophytically inhibiting self-incompatibility in plants. Exemplary alleles that provide self-compatibility are provided SEQ ID NOs: 2, 3 and 4, and exemplary coding gene sequences of the PSC-gene are provided in SEQ ID NOs: 6, 7 and 8.

It is also an object of the invention to provide an isolated nucleic acid molecule comprising a self-compatibility allele of a Potato Self Compatibility (PSC) gene that is a mutant sequence of a wildtype *S. tuberosum* allele of gene A indicated by SEQ ID NO:1 or 5 that encodes a product that confers gametophytic self-incompatibility in plants, said mutant sequence having at least 70%, preferably at least 80%, 90% or even at least 95%, sequence identity with SEQ ID NO:1 or 5 and wherein said mutant sequence encodes a product that inhibits gametophytic self-incompatibility in plants. Exemplary self-compatibility alleles are provided SEQ ID NOs: 2, 3 and 4, and exemplary coding gene sequences of these self-compatibility alleles are provided in SEQ ID NOs: 6, 7 and 8.

SEQ ID NOs: 5-8 provide the gene-region sequences (including promoter & terminator region) of the PSC gene. The coding sequences therein are indicated in uppercase. Underlined in SEQ ID NOs: 5-8 (but not in SEQ ID NOs: 1-4) are the structural differences between the ITAG and PGSC gene models (underlined lowercase=misinterpreted as CDS, underlined uppercase=misinterpreted as intronic sequence). The difference between SEQ ID NOs: 1-4 and SEQ ID Nos: 5-8 (i.e., between 1/5, 2/6, 3/7, 4/8) is that SEQ ID NOs: 1-4 also contains the coding exons of the adjacent gene model (Sotub12g029970).

A preferred nucleic acid molecule according to the invention encodes a mutant protein of a (WT) protein as depicted in SEQ ID NO:9.

The present invention also provides a protein that inhibits gametophytic self-incompatibility in plants, said protein comprising an amino acid sequence as depicted in SEQ ID NO:10.

The present invention also provides a protein that does not inhibit gametophytic self-incompatibility in plants, said protein comprising an amino acid sequence as depicted in SEQ ID NO:9.

Preferred altered amino acid residues in the mutant (SC) protein relative to the wildtype (SI) protein are selected from the group consisting of G10D, V37A, F42V, L47F, I56N, R69K, N97K, S110T, K146T, S156T, A167S, D169N, D190E, R214C, R235G and R249Q and combinations thereof based on the numbering of FIG. 1. More preferably, the altered amino acid residues in the mutant protein relative to the wildtype protein (e.g. SEQ ID NO:9) are selected from the group consisting of G10D, I56N, S110T, A167S, D169N, R214C and R249Q. A preferred nucleic acid molecule encodes a mutant protein comprising at least 1, 2, 3, 4, 5, 6, 7, 8, 9, 10, 11, 12, 13, 14, 15 or at least 16 of the alterations mentioned above.

A preferred nucleic acid molecule comprises a nucleic acid sequence encoding a mutant protein as depicted in SEQ ID NO:10.

It is yet another object of the invention to provide an isolated nucleic acid molecule hybridizing under stringent conditions to the nucleic acid molecule of this invention or a complementary sequence thereof.

It is yet another object of the invention to provide a recombinant nucleic acid construct comprising a nucleic acid molecule in accordance with this invention operably linked to a promoter functional in plants, preferably functional in pollen.

It is yet another object of the invention to provide a vector comprising the recombinant nucleic acid construct of this invention.

It is yet another object of the invention to provide a plant protoplast, cell (e.g. pollen), or callus transformed with the recombinant nucleic acid construct of this invention or the vector of this invention, preferably said plant being a potato plant more preferably a *S. tuberosum* Group *Tuberosum* plant.

It is yet another object of the invention to provide a transformed plant regenerated from the protoplast, cell (e.g. pollen), or callus of this invention.

It is yet another object of the invention to provide a progeny plant or clone of the transformed plant of this invention.

It is yet another object of the invention to provide a part of the transformed plant of this invention, wherein said part is an isolated cell, a propagation material, or an isolated organ, preferably a tuber or seed.

It is yet another object of the invention to provide a food product prepared from at least one of the cell, the propagation material, and the organ of this invention.

It is yet another object of the invention to provide a method for selecting a plant comprising in its genome at least one copy of the self-compatibility allele of PSC, the product of which inhibits gametophytic self-incompatibility in plants, comprising screening the genome of said plant for the presence of a mutant allele of a gene having a wild-type nucleotide sequence of SEQ ID NO: 1 or 5, or a naturally occurring allelic variant thereof wherein said mutant allele or the naturally occurring allelic variant thereof encodes a gene product that inhibits gametophytic self-incompatibility in said plant.

It is yet another object of the invention to provide a method for the production of a plant comprising in its genome at least one copy of the self-compatibility allele of PSC, the product of which inhibits gametophytic self-incompatibility in plants, said method comprising the steps of:

a) selecting a plant by performing the method of this invention, and crossing said selected plant with itself or another plant to produce seed, and optionally growing said seed into a plant.
b) crossing said selected plant with another plant or with itself to produce seed;
c) optionally growing said seed into plants to produce offspring plants;
d) further optionally repeating the crossing and growing steps of steps b) and c), and
e) optionally selecting from amongst the offspring plants a plant wherein said allele is present in homozygous or heterozygous form.

In a preferred embodiment of a method for the production of a plant in accordance with this invention, said selection in steps a) and/or e) is performed by marker assisted selection using DNA markers that are diagnostic for the mutant allele.

In another preferred embodiment of a method for the production of a plant in accordance with this invention, said plant is a potato plant, more preferably a plant of the species *Solanum tuberosum.*

It is yet another object of the invention to provide a plant obtainable by the method for the production of a plant in accordance with this invention. In a preferred embodiment of this object of the invention a plant thus obtainable in accordance with methods of this invention, further comprises at least one allele of a resistance gene, such as one or more of the *Phytophthora infestans* resistance genes:

*S. avilesii* 478-2 Rpi*-avl1, Chr11 (position ~1.8 Mb);
*S. tarinjense* 852-5 Rpi-tar1, Chr10 (position ~53 Mb);
*S. chacoense* 543-5 Rpi-chc1, Chr10 (position ~53 Mb), and
*S. venturii* 283-1 Rpi-vnt1, Chr9 (position ~51 Mb)

It is yet another object of the invention to provide a plant part of the plant of this invention, preferably a tuber or seed.

It is yet another object of the invention to provide a food product prepared from the plant part of this invention.

It is yet another object of the invention to provide a protein encoded by the nucleic acid molecule of this invention, or having the amino acid sequence of SEQ ID NO:10.

It is yet another object of the invention to provide the use of a protein according to the present invention as noted above as an antigen.

It is yet another object of the invention to provide an antibody that binds to the antigen protein of this invention. Such an antibody may be a polyclonal or a monoclonal antibody. Such antibodies are useful for in assays for detecting SC phenotypes in plants. Such assays may comprise ELISA assays or Western blotting assays, both of which are well known to one of skill in the art.

It is yet another aspect of the present invention to provide a promoter for expressing a gene in plant pollen, wherein the promoter is the native promoter of a PSC gene. In a preferred aspects, the promoter comprises or consists of the nucleic acid sequence indicated in SEQ ID NO:18 or 20, and sequences having at least 80% sequence identity, preferably at least 90%, more preferably at least 95 or 98% sequence identity with SEQ ID NO:18 Or 20, and having promoter activity for expressing a gene in plant pollen.

In aspects of this invention, the nucleic acids described herein may take the form of a cDNA sequence. The term "cDNA", as used herein, refers to single-stranded or double-stranded complementary DNA that is reverse transcribed from RNA, preferably mRNA. A cDNA of the present invention may comprise both introns and exons, e.g. the introns and exons as described herein, but preferably comprises only exons.

In aspects of this invention, plants may be transgenic or non-transgenic, transformed or non-transformed, recombinant or non-recombinant, Aspects of this invention can also be performed and also relate to other crops than potato.

Other objects and advantages of this invention will become readily apparent from the ensuing description.

BRIEF DESCRIPTION OF THE DRAWINGS

FIG. 1. Comparison of F-box PP2-B10 protein sequences numbered amino acid acids 1-266 from SC plants (BL_17SC0100-0002_NODE_4559_lengt [SEQ ID NO:14] and PSC-PGSC0003DMT400043434 [SEQ ID NO:10]) and self-incompatible plants (FO_D2_NODE_55467_length_4836_cov [SEQ ID NO:11], FO_D8_NODE_78731_length_3613_cov [SEQ ID NO:12], FO_D14_NODE_41388_length_7594_cov [SEQ ID NO:13], and DM-PGSC0003DMT400043434 [SEQ ID NO:9]). BL_17SC0100-0002_NODE_4559_lengt and PSC-PGSC0003DMT400043434 are sequences from different self-compatible potato plants, which sequences are identical (SEQ ID NO:10). "PSC" in PSC-PGSC0003DMT400043434 refers to the fact that the sequence is a projection of the sequence of the self-compatible plant on the gene model of DM-PGSC0003DMT400043434, the self-incompatible wildtype gene in *S. tuberosum* Group Phureja DM1-3 (SEQ ID NO:1).

FIG. 4. Two genotypes show recombination around the PSC gene, defining the interval in which it must be located. The letter a indicates the parental haplotype that is linked to the self-compatibility allele of PSC, whereas the letter b indicates the haplotype that is not linked to the self-compatibility allele of PSC. Arrows indicate the markers defining the 629 kb interval.

FIG. 5. Twelve plants from population 18SC0011 show pseudo self-compatibility. The letter a indicates the parental haplotype that is linked to the self-compatibility allele of PSC, whereas the letter b indicates the haplotype that is not linked to the self-compatibility allele of PSC. Two genotypes from population 18SC0012 show recombination around the PSC gene, defining the interval in which it must be located. Arrows indicate the markers defining the 169 kb interval.

FIG. 6. Genotypes of two important recombinants. The letter "a" indicates the parental haplotype that is linked to the self-compatibility allele of PSC, whereas the letter "b" indicates the haplotype that is not linked to the self-compatibility allele of PSC. The arrows indicate the markers that define the new interval. The interval is indicated by DM coordinates.

FIG. 7. Genomic sequences of a wildtype *S. tuberosum* allele of gene A (SEQ ID NO:1), from potato reference genome sequence DM4.04; a corresponding genomic sequence from self-compatible potato line DS comprising the self-compatibility allele of PSC (SEQ ID NO:2); self-compatible line BL_17SC0100-0002 (SEQ ID NO:3) and self-compatible line BL_17C0100-0018 (SEQ ID NO:4). Regulatory sequence, intronic and non-coding exonic sequences are indicated in lowercase, coding sequences are indicated in uppercase. SEQ ID NO: 1-4 also show exons of the adjacent gene in capital letters. Also, one exon (no 2) appears too small and there is one extra exon in capital letters (this is the ITAG gene model). This has been corrected in SEQ ID NO: 5-8.

FIG. 13 shows the result of a fine mapping experiment indicating the genotypes of recombinants found. The letter "a" indicates the parental haplotype that is linked to the self-compatibility allele of PSC, whereas the letter "b" indicates the haplotype that is not linked to the self-compatibility allele of PSC. The arrows indicate the markers that define the interval. The interval is indicated by DM coordinates.

FIG. 14 shows the result of an extended fine mapping experiment as depicted in FIG. 13, indicating the genotypes of still further recombinants found. The letter "a" indicates the parental haplotype that is linked to the self-compatibility allele of PSC, whereas the letter "b" indicates the haplotype that is not linked to the self-compatibility allele of PSC. The arrows indicate the markers that define the interval. The interval is indicated by DM coordinates.

FIG. 17 shows the sequence of the synthesized PSC gene as cloned into pBINPLUS vector as described in Example 8 (SEQ ID NO: 17).

FIG. 19 shows the nucleotide sequence of the native promoter of the PSC gene of donor plant DS (SEQ ID NO:18).

FIG. 20 shows the nucleotide sequence of the coding sequence (CDS) of the PSC gene of donor plant DS (SEQ ID NO:19).

FIG. 21 shows the nucleotide sequence of a truncated promoter of the PSC gene of donor plant DS (SEQ ID NO:20).

DETAILED DESCRIPTION OF THE INVENTION

Figure 2:
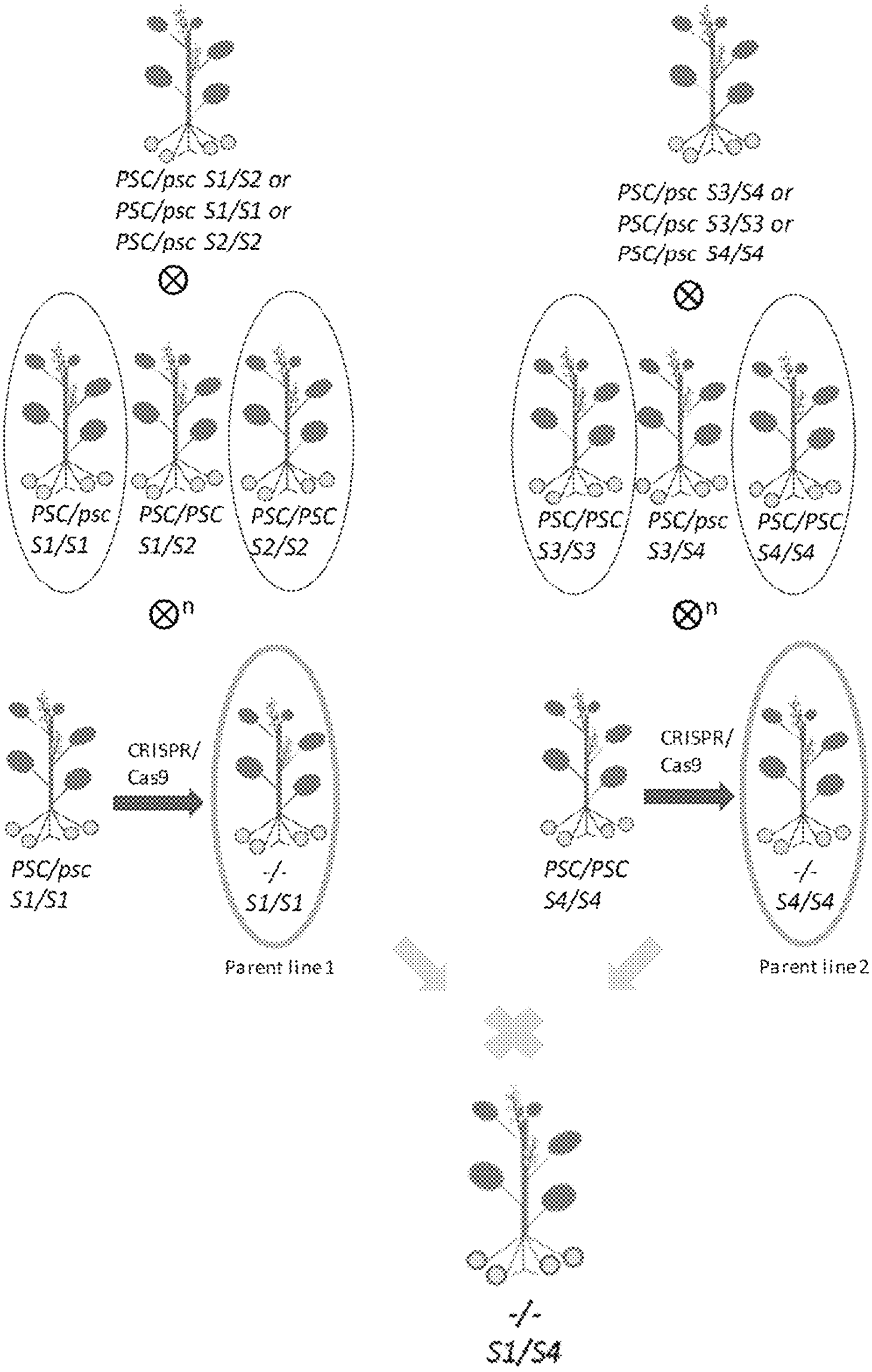
FIG. 2. A breeding scheme for producing F1 hybrid involving inactivation of the self-compatibility allele of PSC.

This invention concerns the identification and isolation of the self-compatibility allele of a Potato Self Compatibility (PSC) gene, a self-compatibility-conferring gene in potato, the cloning and functional analysis of the self-compatibility allele of PSC in potato, and the transformation of self-incompatible lines of potato with the nucleic acid encoding the self-compatibility allele of PSC-gene product. Using the compositions and methods of the invention, plant cells are genetically manipulated resulting in plants carrying the self-compatibility gene of the present invention. The nucleic acid molecules, constructs and vectors of the invention and the methods of using them can be utilized to produce plant comprising the self-compatibility gene, and select self-compatible potato plants.

Definitions

As used herein, the term "potato" refers to a tuber bearing *Solanum* species. A preferred potato species is *S. tuberosum*. A plant of the species *S. tuberosum* may include introgression segments of other tuber bearing *Solanum* species such as *Solanum chacoense, Solanum phureja, Solanum andigena, Solanum demissum*, and/or of a non tuber bearing *Solanum* species that is crossable with *S. tuberosum* such as *S. palustre, S. fernandezianum* and *S. tuberosum*, due to the history of said *S. tuberosum* plant, as is known to a person skilled in the art.

The term "self-incompatible", as is used herein, refers to a genetic mechanism that prevents self-fertilization and thus forces outcrossing and allogamy. Self-incompatibility in Solanaceae, including *S. tuberosum*, is the result of mechanism involving an S-gene encoding a pollen determinant and a S-RNase gene encoding a pistil determinant. S-RNases interact with pollen S-allele products to inhibit the growth of self-pollen tubes in the style.

The term "self-compatible", as is used herein, refers to a mechanism that has overcome the prevention of self-fertilization.

A preferred potato plant is a *Solanum tuberosum* plant, preferably a diploid, vigorous and essential homozygous *S. tuberosum* potato plant as described (WO2011/053135).

The terms "homozygous" and "essential homozygous" plant, as are used herein, indicate that more than 50% of the genomic loci in said plant, preferably more than 60% of the genomic loci, preferably more than 70% of the genomic loci, preferably more than 80% of the genomic loci, preferably more than 90% of the genomic loci, preferably more than 95% of the genomic loci, are homozygous.

As used herein, the terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like. A polynucleotide may be a polymer of RNA or DNA that is single- or double-stranded and that optionally contains synthetic, non-natural or altered nucleotide bases. A polynucleotide in the form of a polymer of DNA may be comprised of one or more segments of cDNA, genomic DNA, synthetic DNA, or mixtures thereof.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Preferably, the isolated polynucleotide is also substantially free from other substances naturally occurring within a cell, such as proteins and lipids.

Conventional nucleic acid purification methods known to skilled artisans may be used to obtain isolated polynucleotides. The term also embraces recombinant polynucleotides and chemically synthesized polynucleotides.

As used herein, "recombinant" refers to a nucleic acid molecule which has been obtained by manipulation of genetic material using restriction enzymes, ligases, and similar genetic engineering techniques as described by, for example, Sambrook et al. 1989. Molecular Cloning: A Laboratory Manual, Second Edition, Cold Spring Harbor Laboratory Press, Cold Spring Harbor, NY or DNA Cloning: A Practical Approach, Vol. I and II (Ed. D. N. Glover), IRL Press, Oxford, 1985. The term "recombinant," as used herein, does not refer to naturally occurring genetic recombinations.

As used herein, the term "express" or "expression" is defined to mean transcription, and, preferably, also translation. The regulatory elements are operably linked to the coding sequence of the PSC gene such that the regulatory element is capable of controlling expression of PSC gene. "Altered levels" or "altered expression" refers to the production of gene product(s) in transgenic organisms in amounts or proportions that differ from that of normal or non-transformed organisms.

The phrase "driving expression of", as used herein in relation to promotor activity, can be used interchangeably with the phrase "initiating transcription of".

As used herein, the term "PSC gene" refers to genes encoding a PSC protein, i.e. an F-box protein PP2-B10. The gene is defined as occurring in two allelic forms: PSC and pec. PSC is the dominant allele of the PGSC0003DMG400016861 gene that is responsible for self-compatibility in genotype DS (IVP007-1001/4). In one embodiment the PSC allele sequence is as provided in SEQ-ID NO:2. In contrast, psc is any allele of the PGSC0003DMG400016861 gene that is different from the PSC allele. In one embodiment the psc allele sequence is as provided in SEQ-ID NO:1. The psc allele is unable to confer self-compatibility.

The term "gene," as used herein, refers to a polynucleotide comprising a protein-coding or RNA-coding sequence, in an expressible form, e.g. operably linked to an expression control sequence and may also comprise a termination region. The "coding sequence" of the gene generally does not include expression control sequences, unless they are embedded within the coding sequence. Optionally, the term "coding sequence" (CDS) refers to the exons of a gene, but may include reference to the both exons and introns, The term "allele' as used herein is any one of a number of alternative forms a given locus (position) on a chromosome. An allele may be used to indicate one form of a polymorphism, for example, a biallelic SNP may have possible alleles A and B. An allele may also be used to indicate a particular combination of alleles of two or more SNPs in a given gene or chromosomal segment. The frequency of an allele in a population is the number of times that specific allele appears divided by the total number of alleles of that locus. The terms "allele" and "gene" may be used interchangeably in the context of this invention.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated or transcribed regions of the nucleic acid or may lack such intervening non-translated sequences (e.g., as in cDNA).

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The terms "regulatory elements" or "regulatory sequences", which terms can be used interchangeably herein, refer to nucleotide sequences located upstream (non-coding sequences), within, or downstream (non-coding sequences) of a coding sequence, and which influence the transcription, RNA processing or stability, or translation of the associated coding sequence. Regulatory sequences may include promoters, translation leader sequences (5' untranslated regions (UTRs)), introns, polyadenylation recognition sequences and trailer sequence (3' UTRs).

In addition to regulatory elements, the construct of the invention may comprise a promoter. The term "promoter" refers to a nucleotide sequence capable of controlling the expression of a coding sequence or functional RNA. In general, a coding sequence is located downstream to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, as for example, the promoter disclosed here which specifically induces the PSC gene expression in pollen, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. The tissue-specificity of a promoter, for example, is exemplified by the promoter sequence (described above) which specifically induces the PSC gene expression in pollen. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg. 1989. Biochemistry of Plants 15:1-82. It is further recognized that since in most cases the exact boundaries of regulatory sequences have not been completely defined, nucleic acid fragments of different lengths may have identical promoter activity.

In addition to regulatory elements, a construct of the invention may comprise a translation leader sequence. The term "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency.

A gene product in accordance with this invention may comprise an RNA transcript. The term "RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from posttranscriptional processing of the primary transcript and is referred to as the mature RNA.

"Messenger RNA (mRNA)" refers to the RNA that is without introns and that can be translated into polypeptides by the cell. "cDNA" refers to a DNA that is complementary to and derived from an mRNA template. The cDNA can be single-stranded or converted to double stranded form using, for example, the Klenow fragment of DNA polymerase I.

"Sense" RNA refers to an RNA transcript that includes the mRNA and so can be translated into a polypeptide by the cell. "Antisense", when used in the context of a particular nucleotide sequence, refers to the complementary strand of the reference transcription product.

"Antisense RNA" refers to an RNA transcript that is complementary to all or part of a target primary transcript or mRNA and that blocks the expression of a target gene. The complementarity of an antisense RNA may be with any part of the specific nucleotide sequence, i.e., at the 5' non-coding sequence, 3' non-coding sequence, introns, or the coding sequence.

"Functional RNA" refers to sense RNA, antisense RNA, ribozyme RNA, or other RNA that may not be translated but yet has an effect on cellular processes.

As used herein, the terms "introgression", "introgressed" and "introgressing" refer to both a natural and artificial process, and the resulting events, whereby genes of one species, variety or cultivar are moved into the genome of another species, variety or cultivar, by crossing those species. The process may optionally be completed by backcrossing to the recurrent parent.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. 1987. Meth. Enzymol. 143:277) and particle-accelerated or "gene gun" transformation technology (Klein et al. 1987. Nature (London) 327:70-73; U.S. Pat. No. 4,945,050, incorporated herein by reference). Additional transformation methods are disclosed below. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. The term "vector" as used herein refers to a DNA molecule that carries a specific gene into a host cell and uses the cell's protein synthesis machinery to produce the protein encoded by the gene. The term is equivalent to the term "expression vector". A number of vectors suitable for stable transfection of plant cells or for the establishment of transgenic plants have been described in, e.g., Pouwels et al. 1985. Supp. 1987. Cloning Vectors: A Laboratory Manual; Weissbach and Weissbach. 1989. Methods for Plant Molecular Biology, Academic Press, New York; and Flevin et al. 1990. Plant Molecular Biology Manual, Kluwer Academic Publishers, Boston. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

A "protein" or "polypeptide" is a chain of amino acids arranged in a specific order determined by the coding sequence in a polynucleotide encoding the polypeptide. Each protein or polypeptide has a unique function.

The invention includes functional PSC polypeptides and functional fragments thereof, as well as mutants and variants having the same biological function or activity. As used herein, the terms "functional fragment", "mutant" and "variant" refers to a polypeptide which possesses biological function or activity identified through a defined functional assay and associated with a particular biologic, morphologic, or phenotypic alteration in the cell. The term "functional fragments of PSC polypeptide", refers to all fragments of PSC that retain PSC activity and function as defined herein. Functional fragments, for example, can vary in size from a polypeptide fragment as small as an epitope capable of binding an antibody molecule, to a large polypeptide capable of participating in the characteristic induction or programming of phenotypic changes within a cell. Furthermore, the function or activity of PSC can be utilized in bioassays to identify functional fragments of PSC polypeptide or related polypeptides. Thus, two orthologs of PSC may have a certain percentage of nucleotide sequence identity between them and similarity at the amino acid level to the self-compatibility allele of the PSC gene have been found in other lines, and the gene encoding these polypeptides is preferentially expressed in the pollen of plants, indicating that these orthologs harbor a portion of the PSC polypeptide that indeed has PSC biological activity.

Modifications of the self-compatibility allele of PSC primary amino acid sequence may result in further mutant or variant proteins having substantially equivalent activity to the PSC polypeptides described herein. Such modifications may be deliberate, as by site-directed mutagenesis, or may occur by spontaneous changes in amino acid sequences where these changes produce modified polypeptides having substantially equivalent activity to the PSC polypeptides. Any polypeptides produced by minor modifications of the PSC primary amino acid sequence are included herein as long as the biological activity of PSC is present; e.g., having a role in pathways leading to self-compatibility in plants.

Genes encoding a PSC protein can be cloned using a variety of techniques according to the invention. The simplest procedure for the cloning of PSC genes requires the cloning of genomic DNA from an organism identified as producing a PSC protein, and the transfer of the cloned DNA on a suitable plasmid or vector to a host organism which does not produce the PSC protein, followed by the identification of transformed hosts to which the ability to produce the PSC protein has been conferred. The transforming PSC-conferring DNA can be cleaved into smaller fragments and the smallest which maintains the PSC-conferring ability can be further characterized. Techniques suitable for cloning by homology include standard library screening by DNA hybridization or polymerase chain reaction (PCR) amplification using primers derived from conserved sequences. As defined herein, two DNA sequences are substantially homologous or identical when at least 80% (preferably at least 85% and most preferably 90%) of the nucleotides match over a defined length of the sequences, preferably the complete length of the sequences, using algorithms such as CLUSTAL or PILEUP. Sequences that are substantially homologous can be identified in a Southern hybridization experiment under stringent conditions as is known in the art. See, for example, Sambrook et al., supra. Sambrook et al. describe highly stringent conditions as a hybridization temperature 5-10° C. below the Tm of a perfectly matched target and probe; thus, sequences that are "substantially homologous" would hybridize under such conditions.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof.

Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Each of the proposed modifications is well within the routine skill in the art, as is determination of retention of biological activity of the encoded products. A method of selecting an isolated polynucleotide that affects the level of expression of a polypeptide in a virus or in a host cell (eukaryotic, such as plant, yeast, fungi, or algae; prokaryotic, such as bacteria) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize, especially under stringent conditions. Estimates of such homology are provided by either DNA-DNA or DNA-RNA hybridization under conditions of stringency as is well understood by those skilled in the art (Nucleic Acid Hybridization, 1985. Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms.

Thus, isolated nucleic acid sequences that encode a PSC polypeptide and which hybridize under stringent conditions to the PSC nucleic acid sequences disclosed herein, or to fragments thereof are encompassed by the present invention.

Substantially similar nucleic acid fragments of the instant invention may also be characterized by the percent identity of the amino acid sequences that they encode to the amino acid sequences disclosed herein, as determined by algorithms commonly employed by those skilled in this art.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (Myers and Miller, 1988. CABIOS 4:11-17), the local homology algorithm of Smith et al. (1981. Adv. Appl. Math, 2:482); the homology alignment algorithm of Needleman and Wunsch (1970. J. MoI. Biol. 48:443-453); the search-for-similarity-method of Pearson and Lipman (1988. Proc. Natl. Acad. Sci 85:2444-2448; the algorithm of Karlin and Altschul (1990. Proc. Natl. Acad. ScL USA 87:2264), modified as in Karlin and Altschul (1993. Proc. Natl. Acad. ScL USA 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Unless otherwise indicated, sequence alignments and percent identity calculations were performed using the Megalign program of the LASERGENE bioinformatics computing suite (DNASTAR Inc., Madison, Wis.), or any equivalent program. Multiple alignment of the sequences can be performed using the Clustal W method of alignment (Higgins and Sharp (1989. CABIOS 5:151-153) with the default parameters (GAP PENALTY=IO, GAP LENGTH PENALTY=I.0), while default parameters for pairwise alignments using the Clustal W method were GAP PENALTY=IO, GAP LENGTH PENALTY=LO, Slow-Accurate unless otherwise indicated. Protein alignments can also be performed using the muscle (Edgar, 2004. Nucleic Acids Res 32: 1792-7) parameter "-clw" to generate output format in the ClustalW format.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window (preferably over the full length of the sequence), wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence", may refer to a defined sequence used as a basis for sequence comparison for the purpose of determining sequence similarity. The reference sequence may be a subset or the entirety of a specified sequence; for example, as a segment of a full-length cDNA or gene sequence, or the complete cDNA or gene sequence. The term "reference sequence" is also used herein in the context of determining the position of a gene in a reference genome sequence. The position of a gene is indicated by the corresponding coordinates of the reference genome sequence. All coordinates herein are those based on DM4.03 and DM 4.04. A reference sequence for the mutant allele according to the present invention is the wild-type sequence, preferably the DM4.04 sequence. The DM4.04 sequence, as referred to herein, is the sequence of the doubled monoploid *S. tuberosum* Group Phureja clone DM1-3 (DM) based on the v4.04 pseudomolecules (Hardigan et al., 2016, Plant Cell, doi:10.1105/tpc.15.00538).

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. J. Mol. Biol. 48:443).

Another indication that nucleotide sequences are substantially identical is if two molecules hybridize to each other under stringent conditions. Generally, stringent conditions are selected to be about 5C lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise a particular plant protein. The skilled artisan, having the benefit of the sequences as reported herein, may now use all or a substantial portion of the disclosed sequences for purposes known to those skilled in this art. Thus, such a portion represents a "substantial portion" and can be used to establish "substantial identity", i.e., sequence identity of at least 80%, compared to the reference sequence, sorghum. Accordingly, the instant invention comprises the complete sequences as reported in the accompanying Sequence Listing, as well as substantial portions at those sequences as defined above.

Fragments and variants of the disclosed nucleotide sequences and proteins encoded thereby are also encompassed by the present invention. By "fragment" a portion of the nucleotide sequence or a portion of the amino acid sequence and hence protein encoded thereby is intended. Fragments of a nucleotide sequence may encode protein fragments that retain the biological activity of the native protein and hence have PSC-like activity. Alternatively, fragments of a nucleotide sequence that are useful as hybridization probes may not encode fragment proteins retaining biological activity.

By "variants" substantially similar sequences are intended. For nucleotide sequences, conservative variants include those sequences that, because of the degeneracy of the genetic code, encode the amino acid sequence of one of the PSC polypeptides of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they continue to possess the desired biological activity of the native protein, that is, PSC-like activity as described herein. Such variants may result from, for example, genetic polymorphism or from human manipulation. Biologically active variants of a native PSC protein of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even one amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms.

Likewise, the proteins of the invention encompass naturally occurring proteins as well as variations and modified forms thereof. Such variants will continue to possess the desired PSC activity. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of PSC protein can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

It is to be understood that as used herein the term "transgenic" includes any cell, cell line, callus, tissue, plant part, or plant the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

The term "guide RNA (gRNA) molecule, or single gRNA molecule (sgRNA)", as is used herein, refers to a specific single RNA sequence that recognizes the target DNA region of interest and directs an associated nuclease there for editing. Said gRNA preferably comprises a 17-20 nucleotide sequence complementary to the target DNA, and a binding scaffold for the associated nuclease.

The term "CRISPR associated endonuclease" (Cas), as is used herein, refers to an endonuclease that is guided by gRNA or CRISPR to a target DNA. Said target DNA is subsequently cut by the endonuclease. Said CRISPR associated endonuclease may be a Cas9, for example isolated from *Streptococcus pyogenes*, a Cpf1, for example isolated from *Francisella novicida*, C2c1, C2c2 and C2c3, or variants thereof (Nakade et al., 2017. Bioengineered 8: 265-273).

As used herein, the term "plant" includes reference to whole plants, plant organs (e.g., leaves, stems, roots, etc.), seeds, plant cells (including pollen), and progeny of same. Parts of transgenic plants are to be understood within the scope of the invention to comprise, for example, plant cells (including pollen), protoplasts, tissues, callus, embryos as well as flowers, stems, fruits, tubers, leaves, roots originating in transgenic plants or their progeny previously transformed with a DNA molecule of the invention and therefore consisting at least in part of transgenic cells, are also an object of the present invention.

As used herein, the term "plant cell" includes, without limitation, seeds suspension cultures, embryos, meristematic regions, callus tissue, leaves, roots, shoots, gametophytes, sporophytes, pollen, and microspores. The class of plants that can be used in the methods of the invention is generally as broad as the class of higher plants amenable to transformation techniques, including both monocotyledonous and dicotyledonous plants.

The successful cloning of PSC is a major step in our understanding of the regulatory mechanisms underlying self-compatibility in plants. Deciphering the mechanism by which this system functions to result in plants that can be inbred without inbreeding depression will aid in improving plant breeding in potato and many other plant species from for instance the Solanaceae, Rosaceae Plantaginaceae and Zea.

Nucleic Acid Constructs

In a first embodiment, the invention provides an isolated nucleic acid molecule comprising a self-compatibility allele of a Potato Self Compatibility (PSC) gene, wherein said nucleic acid molecule is a nucleic acid molecule comprising a mutant sequence of a wildtype *S. tuberosum* allele of gene A, indicated by SEQ ID NO:1 as provided in FIG. 7, said mutant sequence having at least 70%, preferably at least 80%, 90% or even at least 95%, sequence identity with SEQ ID NO:1, whereby the indicated wildtype gene A encodes a product that confers gametophytic self-incompatibility in plants, and wherein said mutant sequence encodes a product that inhibits gametophytic self-incompatibility in plants.

SEQ ID NO:1 depicts a reference sequence from potato reference genome sequence DM4.04. The Potato Self Compatibility (PSC) gene is located on Chromosome 12, between nucleotides 59034522 and 59042307. The Potato *Genome* Sequencing Consortium (PGSC) annotation of a transcript from this genomic region is PGSC0003DMT400043434, while the gene is name is PGSC0003DMG400016861. The ITAG annotation of this gene is Sotub12g029960.1.1. Known RefSeq sequences are protein sequence RefSeq XP_015165222.1 and mRNA sequence RefSeq XM_015309736.1 (an F-box gene).

Mapping experiments, as described in Example 3 below, narrowed the location of the gene to a 12.6 kb interval (FIG. 13 and FIG. 14), between nucleotides 59030880 and 590424386 on Chromosome 12. Two genes are located in this 12.6 kb interval, PGSC0003DMG400016861 (having as an alternative gene model the ITAG annotation Sotub12g029960.1.1.) and PGSC0003DMG400016860 (having as an alternative gene model the ITAG annotation Sotub12g029970). For the gene PGSC0003DMG400016860, the ITAG annotation Sotub12g029970 is considered to represent to truest model, as the PGSC annotation is considered to be truncated, evidenced by the fact that the ITAG annotation refers to a larger sequence, in which additional exons could be present. However, more detailed mapping, variation analysis (Example 4), and RNA-seq expression analysis (Example 6) showed that Sotub12g029970 could be excluded as the PSC gene. In the case of gene model PGSC0003DMG400016861, the corresponding ITAG annotation Sotub12g029960.1.1 contained one additional (incorrect) exon, whereas the second exon was predicted as being too small. Hence, the ITAG model Sotub12g029960.1.1. for the PSC gene was dismissed. In contrast, the PGSC annotation PGSC0003DMG400016861 showed to be fully supported by RNA-seq data (Example 6). PGSC0003DMG400016861 is therefore disclosed herein as a correct gene model. The invention thus provides the sequence of PGSC0003DMG400016861 as the PSC gene. This region is located on the negative strand, and starts at the last coding sequence of Sotub12g029970 (nt:59042307), and includes a promoter region, a coding sequence and a region including a terminator (ending at nt:59034522), whereby numbering is based on the DM v4.03/v4.04 genome assemblies (See FIG. 16), and is in the order of the higher coordinate towards the lower coordinate.

A corresponding genomic sequence from a self-compatible potato line encoding a self-compatibility allele of PSC is provided in SEQ ID NO:2, SEQ ID NO:3 and SEQ ID NO:4 as provided in FIG. 7, of which the putative coding gene sequence are narrowed to the respective sequences SEQ ID NO:6, SEQ ID NO:7 and SEQ ID NO:8 as provided in FIG. 7. Alterations between the self-incompatible genomic sequence of SEQ ID NO:1 (and the narrowed gene sequence SEQ ID NO:5, which excludes adjacent gene sequences still present in SEQ ID NO:1), and the "Self Compatible" (SC) genomic sequence of SEQ ID NO:2, SEQ ID NO:3 and SEQ ID NO:4 are depicted in Table 1.

One of skill will understand that an alteration in the gene sequence of SEQ ID NO:1 or SEQ ID NO:5 may occur in the coding gene sequence, but may also occur in a promotor or terminator (or any other regulatory) region. Preferably, an alteration in the gene sequence of SEQ ID NO:1 or SEQ ID NO:5 occurs in the promotor, which is known to be critical for regulation or tissue specific expression of the gene. More preferably, the promoter region is indicated by SEQ ID NO:18, or promoter regions having at least 70%, 80%, 90%, or more preferably 95% sequence identity therewith and drives expression of the PSC gene in pollen.

In some preferred embodiments of aspects of this invention, the self-compatibility allele of PSC is provided in SEQ ID NO:6, SEQ ID NO:7 and/or SEQ ID NO:8 as provided in FIG. 7, more broadly as an alteration in gene sequence SEQ ID NO:5.

A preferred isolated nucleic acid molecule that encodes a self-compatibility allele of Potato Self Compatibility (PSC) gene, or a functional part thereof, preferably comprises one or more of the alterations depicted in Table 1, preferably at least two of said alterations, preferably at least ten of said alterations, preferably at least twenty of said alterations, more preferably all of said alterations.

Figure 16:
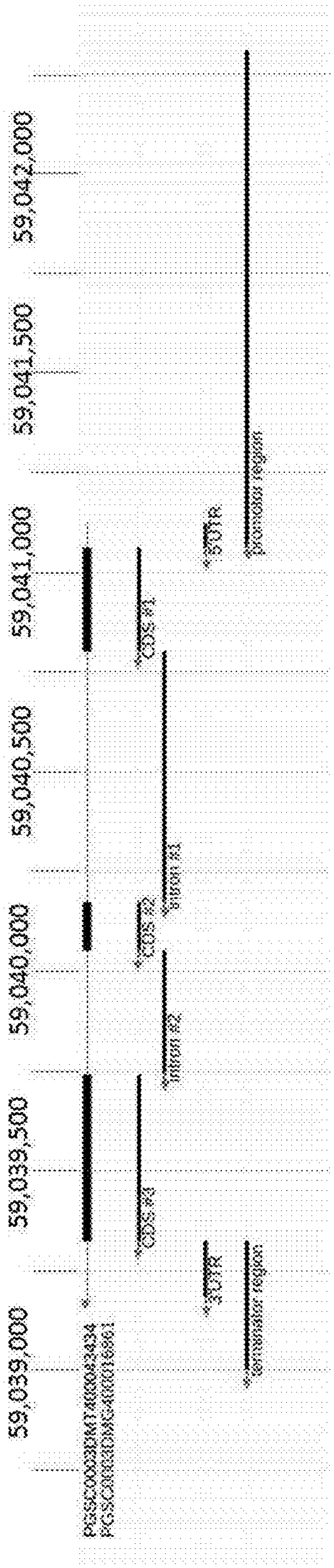
FIG. 16 shows a graphic representation of the PSC locus comprising the intron-exon structures of gene PGSC0003DMG400016861 displayed on chromosome 12 of DM (version 4.04), and indicates from left to right, the terminator region (740 bp downstream), the 3' UTR, exon (coding sequence, CDS) #3, intron #2, CDS #2, intron #1, CDS #1, 3' UTR, and promoter region (1563 bp upstream).

The invention also provides an isolated nucleic acid molecule (encoding a protein) conferring self-compatibility to a potato plant, said isolated nucleic acid molecule comprising a nucleic acid sequence selected from SEQ ID NO:2, SEQ ID NO:3, SEQ ID NO:4, SEQ ID NO:6, SEQ ID NO:7 and SEQ ID NO:8, and sequences having at least 70%, at least 80%, at least 90% or at 95% sequence identity therewith and (encoding a protein) conferring self-compatibility to a potato plant. Preferably, said isolated nucleic acid molecule comprises an operably linked promotor that is functional (allows for expression) in plants, preferably is functional (allows for expression) in pollen of a potato plant. Preferably, said promotor comprises a nucleic acid sequence that has at least 100, 200, 300, 400, 500, 600, 700, 800, 1000, 1200, 1500, 2000, 2500, 3000, 3500, 4000, 5000 or at least 6000 consecutive nucleotide residues of the consecutive nucleotide residues as present in the nucleic acid sequence region indicated by nt:59042307-nt:59034522 of the DM4.04 reference sequence, except that said promotor comprises one or more of the alterations mentioned in Table 1, preferably at least 2, 3, 4, 5, 6, 7, 8, 9 or at least 10 of said alterations, preferably at least 15, 20, 50, 100 or at least 200 of said alterations, more preferably all of said alterations (wherein the alteration(s) of Table 1 are at a corresponding position in said promotor). More preferably, said one or more alterations in said promotor (region) are selected from one or more of the alterations last mentioned in Table 1 (i.e. the alteration at position 59042302, which is the alteration positioned most upstream of the coding region) up to and including the (3106) alteration at position 59036043 in Table 1 (when counting from below to above in said Table 1). All alterations in between said last mentioned alteration in Table 1 (i.e. the alteration at position 59042302) and said $310^{th}$ alteration at position 59036043 in Table 1 (i.e. when counting from below to above) are expressly included in said group of one or more alterations. In the same manner, said one or more alterations in said promotor (region) are selected from one or more of the alterations last mentioned in Table 1 (i.e. the alteration at position 59042302) up to and including the ($91^{th}$) alteration at position 59040009 in Table 1 (when counting from below to above. All alterations in between said last mentioned alteration in Table 1 (i.e. the alteration at position 59042302) and 91th alteration at position 59040009 in Table 1 (when counting from below to above) are expressly included in said group of one or more alterations. Preferably, the promoter region is as indicated in FIG. 16, more preferably the promoter is SEQ ID NO:18.

Further preferred alterations comprise one or more alterations that are present in the coding parts of PGSC0003DMG400016861, preferably at least two of said alterations that are present in the coding parts of PGSC0003DMG400016861, preferably at least ten of said alterations, preferably at least twenty of said alterations, more preferably all of the alterations that are present in the coding parts of PGSC0003DMG400016861.

The gene with reference 107061040 encodes a protein with UniProt reference M1BEM0 (M1BEM0_SOLTU). M1BEM0 encodes a putative F-box protein PP2-B10-like. A reference sequence of M1BEM0 is provided herein as SEQ ID NO:9.

F-box proteins are involved in the Skp1-Cullin-F-box (SCF) complex that functions in the proteasomal degradation pathway by recognizing proteins and tagging them with ubiquitin for degradation. The F-box domain of F-box protein PP2-B10 is involved in interactions with the other proteins in the SCF complex, whereas the PP2 domain is involved in recognition of sugar moieties (Stefanowicz et al., 2015. Critical Rev Plant Sci 34: 523-552). A total of six non-synonymous mutations were identified in this F-box protein that are specific for self-compatible plants (see SEQ ID NO:10). One of these mutations, R249Q is uncommon among similar F-box proteins and might lead to altered specificity of the recognition domain. Furthermore, a variety of small and large insertions and deletions was found, as well as many substitutions in the promoter region of this gene. Most noticeably, a 533 nt PSC-specific insertion was found at position −108 from the ATG (when compared to DM), whereas this position is absent in other SI-plants because of a 193 nt deletion (−85 to −278 nt). The −50 nt to −150 nt region upstream of the start codon is known to contain elements crucial to initiate coordinated transcription. Without wishing to be bound by any theory, it is considered that this, and other variations in the promoter region, has eventually lead to the altered expression pattern as shown in example 6. In the solanaceous self-incompatibility system, F-box proteins are involved in the detoxification of style secreted S-RNases in pollen tubes during compatible pollinations (Li et al., 2016. Plant J 87: 606-616). Moreover, S-RNases are known to be glycosylated (Broothaerts et al., 1991. Sexual Plant Reprod 4: 258-266). It is therefore not surprising that altered expression of an F-box PP2-B10 protein with a possibly altered recognition specificity leads to self-compatibility. It is likely that expression of this gene in self-pollen tubes leads to recognition and degradation of self S-RNases, thus allowing self-fertilization.

A comparison of F-box PP2-B10 protein sequences from SC plants and self-incompatible plants is provided in FIG. 1.

An isolated nucleic acid molecule comprising a PSC allele of gene A preferably encodes a protein that comprises at least one of the altered (substituted) amino acid residues in the SC sequences (BL_17SC0100-0002_NODE_4559_lengt and PSC-PGSC0003DMT400043434) relative to any of the SI sequences (FO_D2_NODE_55467_length4836_cov, F)_D8_NODE_78731_length_3613_cov, FO_D14_NODE_41388_length_7594_cov and DM-PGSC0003DMT400048434) as indicated in FIG. 1, more preferred at least two of the altered amino acid residues as depicted in FIG. 1, more preferred at least three, four, five, six or seven of the altered amino acid residues as depicted in FIG. 1, more preferred all altered amino acid residues as depicted in FIG. 1. Said isolated nucleic acid molecule comprising a self-compatibility allele of PSC preferably encodes a protein in which at least an isoleucine amino acid residue at position 56 is replaced for a asparagine, resulting in I56N. Said isolated nucleic acid molecule comprising a PSC allele preferably encodes a protein in which at least an arginine amino acid residue at position 249 is replaced for a glutamine, resulting in R249Q.

A recombinant nucleic acid construct comprising an nucleic acid molecule according to the invention preferably is operably linked to a promoter that is functional in plants, preferably functional in a growing pollen tube.

A preferred recombinant nucleic acid construct is present in a vector. The invention therefore also provides a vector comprising the recombinant nucleic acid construct of the invention. More particularly, the invention provides a vector comprising an isolated, synthetic or recombinant nucleic acid sequence encoding a protein that comprises at least one of the altered amino acid sequences as depicted in FIG. 1, or a functional fragment or a functional highly homologous sequence thereof. Examples of a suitable vector are Bacterial Artificial Chromosome (BAC) vectors such as BeloBACII, pBINplus, pKGW-MG, or any other commercially available cloning vector.

As will be outlined below there are multiple ways in which a nucleic acid of the invention can be transferred to a plant. One suitable means of transfer is mediated by *Agrobacterium* in which the nucleic acid to be transferred is part of a binary vector and hence it is preferred that the above described vector is a binary vector. Another suitable means is by crossing a plant which expresses a protein that comprises at least one of the altered amino acid sequences as depicted in FIG. 1, or a functional fragment or a functional highly homologous sequence thereof to a plant that does not contain the gene (i.e. the PSC allele of the PSC genes) and to identify those progeny of the cross that have inherited the gene encoding a protein that comprises at least one of the altered amino acid sequences as depicted in FIG. 1, or a functional fragment or a functional highly homologous sequence thereof.

The invention further provides a host cell comprising a nucleic acid as described herein or a vector as described herein. Examples of a preferred host cell are an *E. coli* cell suitable for BAC clones (e.g. DH10B) or an *Agrobacterium* cell. In another embodiment, said host cell comprises a plant cell. A preferred plant cell is a cell derived from a member of the Solanaceae family and even more preferred said plant cell comprises a cell from *S. tuberosum*, preferably a diploid, vigorous and essential homozygous *S. tuberosum* potato plant as described (WO2011/053135). From such a cell, a transgenic or genetically modified plant can be obtained by methods known by the skilled person including, for example, regeneration protocols.

Methods

The invention further provides a method for selecting a *S. tuberosum* plant, comprising screening the genome of said *S. tuberosum* plant for the presence of a mutant sequence as defined in claim 1. Said mutant sequence preferably comprises one or more of the alterations depicted in Table 1, preferably at least two of said alterations, preferably at least ten of said alterations, preferably at least twenty of said alterations, more preferably all of said alterations.

Further preferred alterations comprise one or more alterations that are present in the coding parts of PGSC0003DMG400016861, preferably at least two of said alterations that are present in the coding parts of PGSC0003DMG400016861, preferably at least ten of said alterations, preferably at least twenty of said alterations, more preferably all of the alterations that are present in the coding parts of PGSC0003DMG400016861.

The invention further provides a method for the production of a plant comprising in its genome at least one copy of the self-compatibility allele of a Potato Self Compatibility (PSC) gene, the product of which inhibits gametophytic self-incompatibility in plants, said method comprising the steps of a) selecting a plant by performing the method selecting according to the invention and crossing said selected plant with itself or another plant to produce seed, and optionally growing said seed into a plant; b) crossing said selected plant with another plant or with itself to produce seed; c) optionally growing said seed into plants to produce offspring plants; d) further optionally repeating the crossing and growing steps of steps b) and c), and e) optionally selecting from amongst the offspring plants a plant wherein said allele is present in homozygous or heterozygous form.

Said selection in steps a) and/or e) is preferably performed by marker assisted selection using polymorphic markers for the mutant allele. Suitable markers are provided in Table 1.

In a preferred embodiment of such a method, said plant is a member of the Solanaceae family and even more preferred said plant is a potato plant, more preferably a plant of the species *S. tuberosum*, preferably a diploid, vigorous and essential homozygous *S. tuberosum* potato plant as described (WO2011/053135).

The introgression of a nucleic acid molecule comprising a self-compatibility allele of PSC as described herein may suitably be accomplished by using traditional breeding techniques. The gene is preferably introgressed into potato lines by using marker-assisted selection (MAS) or marker-assisted breeding (MAB). MAS and MAB involves the use of one or more of the molecular markers for the identification and selection of those offspring plants that contain one or more of the genes that encode for the desired trait. In the present instance, such identification and selection is based on selection of the gene of the present invention or markers associated therewith. MAS can also be used to develop near-isogenic lines (NIL) harboring the gene of interest, or the generation of gene isogenic recombinants (QIRs), allowing a more detailed study of each gene effect and is also an effective method for development of backcross inbred line (BIL) populations. Potato plants developed according to this embodiment can advantageously derive a majority of their traits from the recipient plant, and derive a self-compatibility allele of PSC from the donor plant.

The now available markers allow introgression of only part of the telomeric region of Chromosome 12 of a self-compatible potato plant. Said region encompasses the mutant gene as defined in Claim 1, but preferably does not comprise genomic sequences from the self-compatible donor plant that are centromeric to SOT12-58962004, preferably SOT12-59016142, and/or telomeric to SOT12-59130723, preferably SOT12-59043512.

Based on the herein described nucleic acid sequences, the invention also provides probes and primer, i.e. oligonucleotide sequences complementary to the DNA strand as described herein, or complementary to the complementing strand. Said primers and probes are for example useful in PCR analysis. Primers based on the herein described nucleic acid sequences are very useful to assist plant breeders active in the field of classical breeding and/or breeding by genetic modification of the nucleic acid content of a plant and in selecting a plant that is capable of expressing PSC or a functional fragment or functional highly homologous sequence thereof.

Preferably, the nucleic acid of a plant to be tested is isolated from said plant and the obtained isolated nucleic acid is brought in contact with one or more of the primers and/or probes. One can for example use a PCR analysis to test plants for the presence or absence of a self-compatibility allele of PSC in the plant genome. Such a method would be especially preferable in marker-free transformation protocols, such as described in WO 03/010319.

Plants

The invention further provides a plant protoplast, cell, or callus transformed with a recombinant nucleic acid molecule according to the invention, preferably a recombinant nucleic acid construct according to the invention or a vector according to the invention. Said plant preferably is a potato plant, more preferably a *S. tuberosum* Group *Tuberosum* plant, even more preferred a diploid, vigorous and essential homozygous *S. tuberosum* potato plant as described in WO2011/053135.

A nucleic acid molecule that comprises a self-compatibility allele of PSC gene, or a PSC-conferring part thereof may be transferred to a suitable recipient plant by any method available. For instance, said nucleic acid molecule may be transferred by crossing a plant comprising a self-compatibility allele of PSC with a selected breeding line i.e. by introgression, by transformation, by protoplast fusion, by a doubled haploid technique or by embryo rescue or by any other nucleic acid transfer system, optionally followed by selection of offspring plants comprising the self-compatibility allele of PSC, as assessed by markers, and/or exhibiting self-compatibility.

For transgenic methods of transfer a nucleic acid molecule comprising PSC may be isolated from a donor plant by using methods known in the art and the thus isolated nucleic acid molecule may be transferred to a recipient plant by transgenic methods, for instance by means of a vector, in a gamete, or in any other suitable transfer element, such as a bombardment with a particle coated with said nucleic acid sequence.

Said nucleic acid molecule preferably comprises an isolated nucleic acid molecule as defined in claim 1, encoding PSC. Said nucleic acid molecule preferably comprises a recombinant nucleic acid construct that encodes a protein having an amino acid sequence of SEQ ID NO:10. Said nucleic acid molecule preferably comprises a recombinant nucleic acid construct having SEQ ID NO:2, 3, and/or 4, or SEQ ID NO:6, 7, and/or 8 or a combination or part thereof.

Plant transformation generally involves the construction of a vector with an expression cassette that will function in plant cells. In the present invention, such a vector consists of a nucleic acid sequence that comprises a self-compatibility allele of PSC, which gene may be under control of or is operably linked to a regulatory element, such as a promoter. The expression vector may contain one or more such operably linked gene/regulatory element combinations, provided that at least one of the genes contained in the combinations confers self-compatibility. The vector(s) may be in the form of a plasmid, and can be used, alone or in combination with other plasmids, to provide transgenic plants that exhibit self-compatibility, using transformation methods known in the art, such as the *Agrobacterium* transformation system.

Expression vectors can include at least one marker gene, operably linked to a regulatory element (such as a promoter) that allows transformed cells containing the marker to be either recovered by negative selection (by inhibiting the growth of cells that do not contain the selectable marker gene), or by positive selection (by screening for the product encoded by the marker gene). Many commonly used selectable marker genes for plant transformation are known in the art, and include, for example, genes that code for enzymes that metabolically detoxify a selective chemical agent which may be an antibiotic or a herbicide, or genes that encode an altered target which is insensitive to the inhibitor. Several positive selection methods are known in the art, such as mannose selection. Alternatively, marker-less transformation can be used to obtain plants without mentioned marker genes, the techniques for which are known in the art. Suitable marker genes are described in Miki and McHugh, 2004 (Miki and McHugh, 2004. J Biotech 107: 193-232).

One method for introducing an expression vector into a plant is based on the natural transformation system of *Agrobacterium* (See e.g. Horsch et al., 1985. Science 227: 1229-1231). *A. tumefaciens* and *A. rhizogenes* are plant pathogenic bacteria that genetically transform plant cells. The Ti and Ri plasmids of *A. tumefaciens* and *A. rhizogenes*, respectively, carry genes responsible for genetic transformation of the plant. Methods of introducing expression vectors into plant tissue include the direct infection or co-cultivation of plant cells with *Agrobacterium tumefaciens*. Descriptions of *Agrobacterium* vectors systems and methods for *Agrobacterium*-mediated gene transfer are provided in U.S. Pat. No. 5,591,616. General descriptions of plant expression vectors and reporter genes and transformation protocols and descriptions of *Agrobacterium* vector systems and methods for *Agrobacterium*-mediated gene transfer can be found in Gruber and Crosby, 1993. (Gruber and Crosby, 1993, Vectors for plant transformation, in Methods in Plant Molecular Biology and Biotechnology (Glick, B. R. and Thompson, J. E., eds.), CRC, Boca Raton, FL). General methods of culturing plant tissues are provided for example by Miki et al., 1993 (Miki et al., 1993. In: B. R. Glick and J. E. Thompson, eds. Techniques in plant molecular biology and biotechnology. CRC Press Inc.), and by Tavazza et al., 1989 (Tavazza et al., 1989. Plant Science 59: 175-181). A proper reference handbook for molecular cloning techniques and suitable expression vectors is Sambrook and Russell, 2001 (Sambrook J and Russell D W (2001) Molecular cloning: a laboratory manual. 3rd ed. Cold Spring Harbor Laboratory Press, Cold Spring Harbor, New York).

Another method for introducing an expression vector into a plant is based on microprojectile-mediated transformation (particle bombardment) wherein DNA is carried on the surface of microprojectiles. The expression vector is introduced into plant tissues with a biolistic device that accelerates the microprojectiles to speeds of 300 to 600 m/s which is sufficient to penetrate plant cell walls and membranes.

Another method for introducing DNA to plants is via sonication of target cells. Alternatively, liposome or spheroplast fusion has been used to introduce expression vectors into plants. Direct uptake of DNA into protoplasts using $CaCl_2$) precipitation, polyvinyl alcohol or poly-L-ornithine has also been reported. Electroporation of protoplasts and whole cells and tissues has also been described.

Other well-known techniques such as the use of BACs, wherein parts of the potato genome are introduced into bacterial artificial Chromosomes (BACs), i.e. vectors used to clone DNA fragments (100- to 300-kb insert size; average, 150 kb) in *Escherichia coli* cells, based on naturally occurring F-factor plasmid found in the bacterium *E. coli* may for instance be employed in combination with the BIBAC system to produce transgenic plants.

Following transformation of potato target tissues, expression of the above described selectable marker genes allows for preferential selection of transformed cells, tissues and/or plants, using regeneration and selection methods now well known in the art.

In an alternative embodiment for producing a potato plant exhibiting self-compatibility, protoplast fusion can be used for the transfer of nucleic acids from a donor plant to a recipient plant. Protoplast fusion is an induced or spontaneous union, such as a somatic hybridization, between two or more protoplasts (cells of which the cell walls are removed by enzymatic treatment) to produce a single bi- or multi-nucleate cell. The fused cell, that may even be obtained with plant species that cannot be interbred in nature, is tissue cultured into a hybrid plant exhibiting the desirable combination of traits. More specifically, a first protoplast can be obtained from a self-compatible potato plant. A second protoplast can be obtained from a second potato plant, preferably a potato line that comprises commercially valuable characteristics, such as, but not limited to disease resistance, insect resistance, valuable tuber characteristics, etc. The protoplasts are then fused using traditional protoplast fusion procedures, which are known in the art.

Alternatively, embryo rescue may be employed in the transfer of a nucleic acid comprising a self-compatibility allele of PSC as described herein from a donor plant to a recipient plant. Embryo rescue can be used as a procedure to isolate embryo's from crosses wherein plants fail to produce viable seed. In this process, the fertilized ovary or immature seed of a plant is tissue cultured to create new plants.

The invention further provides a transformed plant regenerated from the protoplast, cell, or callus according to the invention. Said transformed plant, comprising the recombinant nucleic acid molecule of the invention, preferably the recombinant nucleic acid construct of claim 10 or the vector of claim 11, is present, preferably in the form of a homologous recombination replacing the endogenous genomic sequences of the *S. tuberosum* plant.

The invention further provides a part of the transformed plant, wherein said part preferably is an isolated cell, a propagation material, or an isolated organ, preferably a tuber or seed.

The invention further provides a plant that is obtainable or obtained by the method for production of a plant comprising in its genome at least one copy of a self-compatibility allele of Potato Self Compatibility (PSC) according to the invention.

The methods of the invention allow the introgression of a single mutant allele, or of only a limited number of mutant alleles from a self-compatible plant. Said plant comprises the mutant gene as defined in claim 1, but said plant preferably does not comprise one or more of the alleles that are present in the genomic region between genomic markers SOT12-58962004, preferably SOT12-59017500, and SOT12-59130723, preferably SOT12-59041500, and that are associated with the mutant gene as defined in Claim 1.

Said genomic region comprises at least four genes, including Sotub12g029930.1.1, Sotub12g029940.1.1, Sotub12g029950.1.1 and PGSC0003DMG400016861 (PSC). A plant of the invention preferably comprises the mutant gene as defined in claim 1, and/or mutant alleles of Sotub12g029930.1.1, Sotub12g029940.1.1, Sotub12g029950.1.1, but does not comprise non-*S. tuberosum* genomic sequences centromeric to SOT12-58962004, preferably centromeric to SOT12-59016142, and/or telomeric to SOT12-59130723, preferably telomeric to SOT12-59043512.

In a further embodiment, the invention provides a *S. tuberosum* potato plant wherein a self-compatibility allele of PSC, a mutant sequence of a wildtype *S. tuberosum* allele of gene A, indicated by SEQ ID NO:1, is functionally inactivated, preferably by using any one of CRISPR-CAS, TALEN, and CRE-LOX. Inactivation of the self-compatibility allele of PSC renders the resulting plants self-incompatible.

Self-incompatibility may be advantageous, for example when generating hybrid seed of potatoes that is obtained from two independent parental diploid and essentially homozygous lines. Transformants that are homozygous for the self-compatibility allele of PSC knock-out are self-incompatible. Even without emasculation, a PSC knock-out parent line used as mother will produce insignificant amounts of self-seed.

For self-compatible plants, the two parental lines may be cultivated in the same field or greenhouse, and manually crossings are made after emasculation of the flowers of the female parent, thus generating 100% F1 hybrid seed. Alternatively, flowers of the female plants can be genetically made male sterile by using male sterility genes or S-gene derived self-incompatibility systems.

Modification of the self-compatibility allele of PSC such that expression is reduced or eliminated, allows intercrossing two inbred potato lines in which the S alleles are fixed in homozygous state. As the individual plants within a population will be the products of self-fertilization, and selected to be homozygous and comprise identical S alleles, crossing will not occur within the population, in contrast to mating with individuals from the other inbred population. This outcome will result in production of 100% hybrid seed by each plant. An example of a suitable breeding scheme for producing F1 hybrid, involving inactivation of the self-compatibility allele of PSC, is provided in FIG. 2.

Inactivation of the self-compatibility allele of PSC may be accomplished by homologous recombination, for example by introduction of a frameshift mutation in the coding region of the self-compatibility allele of PSC, by deletion of a genomic region, for example a regulatory sequence, a part of an exon, or one or more exons, and/or by insertion of one or more nucleic acid residues in a genomic region, for example a regulatory sequence, a part of an exon, or one or more exons, by a DNA recognition site-specific recombinase, as is known to a person skilled in the art. Said insertion may include specific sequences that activate, or inactivate, the self-compatibility allele of PSC.

Said DNA recognition site-specific recombinase preferably is selected from a Zinc finger nuclease, a transcription activator-like effector nuclease (TALEN), a topoisomerase I like recombinase such as Cre recombinase from the P1 bacteriophage, a *Saccharomyces cerevisiae*-derived flippase (Flp recombinase), a lambda integrase, a gamma-delta resolvase, Tn3 resolvase, φC31 integrase and/or a clustered regularly interspaced short palindromic repeats (CRISPR)-guided nuclease. Preferred site-specific recombinases are a Zinc finger nuclease, a transcription activator-like effector nuclease (TALEN) and/or a clustered regularly interspaced short palindromic repeats (CRISPR)-guided nuclease.

TALEN, Zinc finger nuclease or CRISPR-CAS mediated disruption of the self-compatibility allele of PSC is mediated by targeting a nuclease to at least one specific position on the self-compatibility allele of PSC, preferably at least two specific positions. Said targeting is mediated by the TALE-DNA binding domains, or by the CRISPR single chimeric guide RNA sequences. The nuclease, a FOK1 nuclease in the case of a TALEN, and a CAS protein, preferably a CAS9 protein, for CRISPR, mediates double stranded breaks in the genomic DNA of the PSC gene. The introduction of DNA double stranded breaks increases the efficiency of gene editing via homologous recombination, in the presence of suitable donor DNA to delete a part or all of the PSC gene (Gaj et al., 2013. Trends Biotechnol 31: 397-405).

Zinc finger proteins are DNA-binding motifs and consist of modular zinc finger domains that are coupled to a nuclease. Each domain can be engineered to recognize a specific DNA triplet in the PSC gene. A combination of three or more domains results in the recognition of a PSC-specific sequence. Expressing said coupled zinc finger protein-nuclease in a relevant plant cell will result in restriction of the self-compatibility allele of PSC and thus silencing of the self-compatibility allele of PSC.

Similarly, synthetic transcription factor DNA binding domains (DBDs) can be programmed to recognize specific DNA motifs. Such transcription activator-like effector (TALE) DNA binding domains (DBD) preferably contain a number, from 7 to 34, highly homologous direct repeats, each consisting of 33-35 amino acids. Specificity is contained in the two amino acid residues in positions 12 and 13 of each repeat. Since the DNA:protein binding code of said two amino acid residues has been deciphered, it is possible to design TALEs that bind any desired target DNA sequence by engineering an appropriate DBD. Typically, the TALEs are designed to recognize 15 to 20 DNA base-pairs, balancing specificity with potential off targeting (Boettcher and McManus, 2015. Mol Cell 58: 575-585). A PSC-specific TALE is then coupled to a nuclease, for example Cas9. Expressing said coupled TALE-nuclease in a relevant plant cell will result in restriction of the self-compatibility allele of PSC and thus silencing of the self-compatibility allele of PSC.

A preferred site-specific recombinase is CRISPR associated protein 9 (Cas 9). Cas9 is a RNA-guided DNA endonuclease enzyme that can cleave any sequence that is complementary to the nucleotide sequence in a CRISPR-comprising guide RNA. The target specificity of this system originates from the gRNA:DNA complementarity, and is not dependent on modifications to the protein itself, like in TALE and Zinc-finger proteins.

As an alternative, the invention provides a *S. tuberosum* potato plant wherein the wildtype *S. tuberosum* allele of gene A, as defined in claim 1 and depicted in SEQ ID NO:1, is functionally restored, preferably by using any one of CRISPR-CAS, TALEN, and CRE-LOX Restoration of the wildtype *S. tuberosum* allele of gene A renders the plant self-incompatible, thus efficiently allowing the generation of F1 hybrid seed.

As is indicated herein above, DNA recognition site-specific recombinases can be used to perform targeted genome editing in cells. Targeted gene deletion and replacement employing targeting modules at two positions within the self-compatibility allele of PSC will effectively generate targeted deletions of varied length. In the presence of a homology repair donor, this system can guide precise gene replacement by exchanging the self-compatibility allele of PSC or a relevant part thereof for the corresponding part of a self-incompatible gene, for example as provided in SEQ ID NO:1.

The invention further provides a plant part, including leaf, tuber, fruit or seed or part or progeny of a modified plant as described herein. A preferred plant part of the plant is a tuber or seed.

Preferred Resistance Genes

Despite some popularity of low carb foods, potatoes become worldwide more and more popular. Potato is relatively cheap to grow and tubers are available all year long. Many potential, health beneficial effects of consuming potatoes have been described. There are more than 4000 potato cultivars worldwide but still there is room for more diversification of potato cultivars for the thousands of different potato markets. Over 70% of the wild tuber bearing relatives of potato are diploids; the cultivated potato however is an allogamous, auto-tetraploid with four sets of Chromosomes (2n=4x=48). This makes targeted breeding for specific traits extremely complicated, if not impossible. Breeding programs require starting populations of over 100,000 plants with still a small chance on a new cultivar that is significantly better than all existing ones. As an example, the yield of potato cultivars, which have been released in US in the 20th century, did not improve. In the last decades, new sequence-based breeding technology like marker assisted selection and whole background selection were developed to support breeding. Still, this did not result in accelerated production of improved varieties. It remains difficult to breed for cultivars with a combination of specific traits, like resistances to biotic and abiotic stresses or presence of health-related components.

*Phytophthora infestans* is the most important pathogen threatening potato and is the causal agent of late blight. Late blight destroys leaves and stems what results in lower economic tuber yield. Nowadays, the damage of late blight infection is limited due to frequent applications with fungicides (up to 20 times per season). In the Netherlands, about 50% of all crop protection chemicals in agriculture is used to control *Phytophthora* in potato fields. An efficient integrated pest management (IPM) is operational and based on information about the disease epidemiology and results in application advices. The results of IPM can be improved with potato cultivars with a certain level of resistance. The development of new cultivars with enhanced levels of resistance to *P. infestans*, after interspecific hybridization, started already in the beginning of the $20^{th}$ century with *Solanum demissum* as donor. In the 1950s and 1960s the first cultivars were introduced into the market. However, the efficient reproduction of the oomycete *Phytophthora infestans* in both asexual as sexual forms, in combination with fast-evolving effector R genes, which are necessary for a successful infection (Haas et al. 2009), make it a rapidly evolving pathogen, that easily generates new virulent races. Even a combination of several resistance genes from *S. demissum* in a single cultivar did not result in durable resistance (Fry, 2008. Mol Plant Pathol 9: 385-402). The rapid adaption of *P. infestans* makes it very difficult to breed durable resistant potato varieties (Black et al., 1953. Euphytica 2: 173-179; Fry, 2008. Mol Plant Pathol 9: 385-402; McDonald and Linde, 2002. Annu Rev Phytopathol 40: 349-379). Pyramiding differently acting *P. infestans* resistance genes for specific regions and isolates might be a solution to increase both durability and level of resistance. Many resistance genes to *P. infestans* have been identified and in mapping studies their position on the potato genome has been determined and often the R-genes have been cloned (e.g. van der Vossen et al., 2005. Plant J. 44:208-222; van der Vossen et al., 2003. Plant J 36: 867-882; Pel et al., 2009. Mol Plant-Microbe Interactions 22: 601-615; Song et al., 2003. Proc Natl Acad Sci U.S.A. 100: 9128-9133; Park et al., 2005. Theor Appl. Genet 111: 591-597). In conventional potato breeding, it is impossible to stack different resistance genes from different sources in a commercial cultivar without disrupting its genetic composition. Therefore, genetic modification was used to stack *Phytophthora*-resistance genes in the commercial cultivar Desirée (Haverkort et al., 2016. Pot Res 59: 35-66). In this DuRPh (Durable Resistance to *Phytophthora*) program only resistance genes were used that originated from crossable wild species of potato (cis-genesis). This was a successful approach and the presence of several combinations of resistance genes caused that the multi-stack cultivars remained unaffected after inoculation. However, legislation prevents the production and consumption of genetic modified potatoes and successful application is beyond the realistic horizon in EU. In the US one of the genetically modified Innate potato plants, with tolerance to late blight, was approved by the USDA in 2014.

An alternative approach to stack different resistance genes into potato has recently become available as more and more homozygous diploid potato inbred lines have been developed (Lindhout et al., 2011. Potato Res 54: 301-312; Lindhout et al., 2018. "Hybrid potato breeding for improved varieties". In: Achieving sustainable cultivation of potatoes Vol. 1 Breeding improved varieties. Edt. Burleigh Dodds, Science Publishing, Cambridge, UK. ISBN: 9781 78676 100 2). These inbred lines are instrumental to generate double stack resistant hybrids by marker assisted backcrossing according to the following procedure: (1) crosses of elite, homozygous diploid lines with diploid donors carrying *Phytophthora* resistance genes; (2) repeated backcrosses to the elite parent in combination with marker assisted selection; (3) selfings to obtain homozygous diploid lines harbouring one resistance gene; (4) crosses of parent lines with different resistance genes to generate F1 hybrid seeds; (5) confirmation of durable resistance by field testing hybrids with stacked resistance genes. This hybrid approach relies on self-compatible and vigorous potato inbred lines (Lindhout et al., 2011. Potato Res 54: 301-312; Lindhout et al., 2018. "Hybrid potato breeding for improved varieties". In: Achieving sustainable cultivation of potatoes Vol. 1 Breeding improved varieties. Edt. Burleigh Dodds, Science Publishing, Cambridge, UK ISBN: 978 178676 100 2). Though initially, the first inbred lines were very weak, gradually they were considerably improved by consistent breeding, resulting in the first acceptable hybrid cultivars (Lindhout et al., 2018. "Hybrid potato breeding for improved varieties". In: Achieving sustainable cultivation of potatoes Vol. 1 Breeding improved varieties. Edt. Burleigh Dodds, Science Publishing, Cambridge, UK. ISBN: 9781 78676 100 2; De Vries et al., 2016. Open Agriculture 1: 151-156). Already for 50 years the possibilities of a transition of the conventional tetraploid breeding to diploid hybrid breeding have been investigated (Hawkes 1956), however, no acceptable homozygous diploid potato clones were developed. This is likely due to a high level of alleles with negative effects in tetraploids and more and more of these alleles becoming homozygous during the repeated selfings resulting in inbreeding depression (Lindhout et al., 2018. "Hybrid potato breeding for improved varieties". In: Achieving sustainable cultivation of potatoes Vol. 1 Breeding improved varieties. Edt. Burleigh Dodds, Science Publishing, Cambridge, UK. ISBN: 9781 78676 100 2). For a good domestication of diploid potatoes, it is important to find the most efficient method for removal of deleterious alleles. While most diploid potatoes are self-incompatible, self-compatible exceptions have been found occasionally. Some of the diploid founder lines of the Solynta breeding program were partly self-compatible, furthermore an additional source of self-compatibility was a diploid, inbred *Solanum chacoense* genotype (designated as DS) (Hosaka and Hanneman, 1998. Euphytica 103: 265-271). The self-compatibility makes it possible to develop diploid lines with high levels of homozygosity.

The invention therefore provides a plant comprising the self-compatibility allele of PSC according to the invention, further comprising at least one allele of a resistance gene such as a Phytophtora infestans resistance gene selected from: *S. avilesii* 478-2 Rpi*-avl1, Chr11 (position ~1.8 Mb); *S. tarinjense* 862-5 Rpi-tar1, Chr10 (position ~53 Mb); *S. chacoense* 543-5 Rpi-chc1, Chr10 (position ~53 Mb), and *S. venturii* 283-1 Rpi-vnt1, Chr9 (position ~51 Mb).

The Phytophtora infestans resistance gene *S. avilesii* 478-2 Rpi*avl1, Chr11 (position ~1.8 Mb) is a commonly known resistance gene and is for instance described in Verzaux et al., *Am. J. Pot. Res.,* 88:511-519 (2011), the contents of which are incorporated herein by reference, specifically with regard to the description of *S. avilesii* 478-2 Rpi*-avl1.

The Phytophtora infestans resistance gene *S. tarinjense* 852-5 Rpi-tar1, Chr10 (position ~53 Mb) and *S. chacoense* 543-5 Rpi-chc1, Chr10 (position ~53 Mb) are generally known resistance genes and are for instance described in WO 2011034483 A1, the contents of which are incorporated herein by reference, specifically with regard to the description of *S. tarinjense* 862-5 Rpi-tar1 and *S. chacoense* 543-5 Rpi-chc1.

The Phytophtora infestans resistance gene *S. venturii* 283-1 Rpi-vnt1, Chr9 (position ~51 Mb) is a commonly known resistance gene and is for instance described in Foster et al., Mol. Plant Microbe Interact, 22:589-600 (2009) and Pel et al., Molecular Plant-Microbe Interactions, 22:601-615 (2009), the contents of which are incorporated herein by reference, specifically with regard to the description of *S. venturii* 283-1 Rpi-vnt1.

Food Products

The invention further provides a food product prepared from a plant part of a plant according to the invention, preferably a genetically modified plant according to the invention. Said plant part is at least one of the cell, the propagation material, and the organ of the invention.

Suitable food products include ajiaco, aligot, aloo gobi, batates, aloo gosht, aloo posto, aloo tikki, baeckeoffe, batata harra, batata vada, bauernfr-hstdck, bengal potatoes, bonda, boxty, bruendende keerlighed, bryndzovd haluiky, bubble and squeak, canarian wrinkly potatoes, carne asada fries, cepelinai, chapalele, cheese fries, chips, chorrillana, chufio, clapshot, coddle, colcannon, corned beef pie, crocchd, croquette, dabeli, duchess potatoes, dum aloo, far far, fish pie, french fries, fritter, funeral potatoes, gamja ongsimi, gamjajeon, gamjatang, german fries, gnocchi, gratin, hachis parmentier, halal snack pack, hash browns, hasselbackspotatis, home fries, hot hamburger plate, hutspot, janssons frestelse, kapsalon, knish, knödel, kouign patatez, kroppkaka, kugel, kugelis, kyselo, lefse, llapingacho, lyonnaise potatoes, mashed potato, massaman curry, meat and potato pie, munini-imo, olivier salad, panackelty, papa a la huancaina, papa rellena, papas chorreadas, pasty Cornish, patatas bravas, patatnik, patd aux pommes de terre, pattie, pola, pickert, pitepalt, pommes anna, pommes dauphine, pommes sarladaise, pommes souffides, potato babka, potato bread, potato cake, potato chip, potato doughnut, potato filling, potato pancake, potato salad, potato scone, potato skins, potato waffle, potato wedges, potatoes o'brien, potatonik, poutine original, raclette, rappie pie, raspeball, rewena bread, rösti, rumbledethumps, salchipapas, salt potatoes, samosa, scotch pie, silesian dumplings, skomakarlåda, spanish omelette, spice bag, stargazy pie, steak frites, stegt flsk, stoemp, stovies, sweetened potato casserole, sweetened potato chips, szalot, tartiflette, tater tots, tombet, trinxat, truffade, batata vada, woolton pie and xogoi momo.

Said food products also include food products that comprise potato starch or a derivative thereof. Said potato starch or a derivative thereof may be present as a water binder, a thickener, an anti caking ingredient, a bulking ingredient and/or a gluing agent. Potato starch and potato starch derivatives are used in many recipes, for example in noodles, wine gums, cocktail nuts, potato chips, hot dog sausages, bakery cream and instant soups and sauces, in gluten-free recipes, in kosher foods for Passover and in Asian cuisine.

Remnants of plant or plant part according to the invention will be present in said food product, such as traces of the genomic recombination process. Said remnants can be visualized, for example by amplification of the genomic region comprising the self-compatibility allele of PSC, as is known to a person skilled in the art.

Having now generally described this invention, the same will be better understood by reference to certain specific examples, which are included herein only to further illustrate the invention and are not intended to limit the scope of the invention as defined by the claims.

EXAMPLES

Example 1 Bioinformatics Approach for Finding Suitable Markers

Being successful in the process of fine-mapping a phenotypic trait to a single gene of interest (GOI) depends on many aspects. Two of the most crucial skills concern the correct determination of phenotype and genotype with an as high specificity and lowest error rate as possible. For the genotyping part, the development of highly specific markers seems a trivial task when having access to next-generation sequencing (NGS) data of (parental) plants. However, at least for potato, it is far from that. In large, complex, repetitive, polyploid and heterozygous genomes such as potato genomes, development of markers is very challenging. As an extra complication, the singular available potato reference genome sequence (DM4.04) is far from representative enough to faultless interpret re-sequencing data at the level of single nucleotide polymorphisms (SNPs), which are the typical targets for molecular genotyping.

In order to overcome these hurdles, a marker development platform was developed based on re-sequencing data (NGS short-reads) that highly contributed to the fast, accurate and successful fine-mapping of a Potato Self Compatibility gene (PSC), as described herein below.

The applied stringent strategy drills down to:

a) taking the cumulative and exhaustive variation of all ancestral genotypes into account, so that marker assays have a high chance to successfully amplify in all Solynta germplasm lines;
b) avoiding any genomic area where the interpretation of re-sequencing data of any of ancestral genotypes to the reference genome is or could be ambiguous. These include, for example, low-complexity sequences, repetitive sequences, and sites that underwent copy-number variation;
c) discarding any SNP for which any of the parental genotypes has flanking variation; and
d) scoring all remaining SNPs with a suite of properties known to (anti)correlate with the chance of yielding a successful molecular assay.

This approach was flexible enough to be compatible with distinct marker-platforms, where thresholds applied in (c) and (d) would depend on the assay type/marker platform. Because the cumulative variation was taken into account in (a), markers are specific to any descendant genotype (i.e. permutation of the given sets of ancestral genotypes). Although mostly based on criterion (b) and, depending on assay type, criterion (c), the vast majority of biological relevant SNPs was excluded. The remaining SNPs will have, combined with the prioritization implied by (d), extremely high success rates when applied on a segregating population consisting of many individuals.

The final result of this approach was a highly customized prioritizable panel of genotypic markers, that was tailor-made to represent the (sub)set of (ancestral) genotypes that is taken into account. Results were stored and accessible through in-house developed database and web-interfaces, empowering the genetic researchers to successfully manage marker development for their own experiments, without the interference of bioinformatician(s).

Resulting markers that were used in the mapping experiments provided in Examples 2-4, as provided in Table 10.

Example 2 Development of Populations for Mapping of the PSC Gene

To develop mapping populations for the PSC gene, we had to survey our materials for suitable contrasting parents. The parents that we identified were used to create the mapping populations that resulted in the localization of the PSC gene. We define PSC as the dominant allele of the PGSC0003DMG400016861 gene that is responsible for self-compatibility (SEQ-ID NO:6). In contrast, psc is any allele of the PGSC0003DMG400016861 gene that is different from the PSC allele.

Materials and Methods

Plant Materials

DS (IVP07-1001/4) is an inbred line derived from the cross [*S. stenotomum* x *S. phureja*] x [*S. chacoense* x *S. phureja*]. DS show moderate to good flowering and is self-fertile. The self-compatibility of DS was derived from a *S. chacoense* accession that was used to localize a Sli gene by Hosaka and Hanneman 1998. (Hosaka and Hanneman 1998. *Euphytica* 103: 265-271). DS is homozygous for an S-locus inhibitor gene (Sli). DS is homozygous for the PSC gene.

D2 (IVPAA-096-18) is one of the diploid *Solanum tuberosum* founding genotypes of Solynta's breeding program (see WO2011/053135). It produces abundant flowers that produce many fertile pollen and set cross-berries regularly but are self-incompatible. D2 (RH88-025-50) is a diploid resulting from a cross between diploid breeding line DB-207 (mother) and SH_76-128-1865 (father). The father line is a descendant of dihaploids generated from the original tetraploid cultivars "Chippewa", "Fennema", "Maritta", "Minn-20-20-34" "Merrimack", "Grata", "Primura", "Sirtema", and wild relative "*S. andigena*".

D14 (IVP06-155-9) is a diploid *S. tuberosum, S. tarijense* hybrid and a founding genotype of Solynta's breeding program (see WO2011/053135). D14 flowers abundantly, produces many fertile pollen, never sets self-berries, but also sets cross berries only occasionally. D14 is a diploid clone generated from a cross between diploid mother IVP92-057 (offspring of mother CE 1062 and father SUH 4567, a.k.a. SH 70-104-1353) and diploid father *S. tarijense* 852-2 (TAR862-5, deriving from CGN22729, see U.S. Pat. No. 9,551,007B2). Dihaploid germplasm of IVP92-057 is rooted in tetraploids MPI 44.1016/10, H 50FRD, *S. vernei* EBS 1984, MPI 49.540/2, Chippewa, Katahdin, Primura, Fennema, Merrimack, and Grata.

D16 (IVPAA-134-16) is another diploid *S. tuberosum* founding genotype of the Solynta breeding program (see WO2011/053135). It produces abundant flowers that produce many fertile pollen and set cross-berries regularly but is self-incompatible. D16 is a diploid clone generated from a cross between diploid mother BE (offspring of mother USW 5295-7 and father VPH4 77.2102.37) and diploid father SH 76-128. Dihaploid germplasm of BE is rooted in tetraploids H 50FRD, MPI 44.1016/10, MPI 49.540/2, *S. vernei* EBS 1984, and Katahdin, while dihaploid germplasm of SH 76-128 is rooted in tetraploids as described for D2.

Diploid potato lines D2, D14 and D16 are heterozygous lines of a diploid potato breeding program at the Department of Plant Breeding, Wageningen University, the Netherlands. This program spans a period of over 50 years, and was initiated using a wide range of dihaploids generated from tetraploid potato cultivars in the 1960's. Pedigree information is available from the public Potato Pedigree Database (Van Berloo et al., 2007. Potato research 50, 45-57).

16HP0001-0066 (HP66) is a diploid *S. tuberosum* genotype obtained in Solynta's breeding program. It grows vigorously, flowers abundantly, produces many fertile pollen and readily sets both self and cross berries. HP66 is heterozygous for a Potato Self Compatibility gene (PSC).

16BL5033-2702 is a diploid *S. tuberosum* F3 genotype obtained in Solynta's breeding program. It was detected on a selection field where it produced more than 300 berries on a single plant. It grew vigorously, flowered abundantly, produced many fertile pollen and readily set both self and cross berries. Whilst this plant no longer exists, self- and cross seed are available. 16BL5033-2702 is homozygous for the self-compatibility allele of PSC.

17SC0025-0008 is a diploid *S. tuberosum* F1 genotype derived from the cross 16BL5033-2702 x D14. It grows vigorously, flowers abundantly, produces many fertile pollen and readily sets both self and cross berries. 17SC0025-0008 is heterozygous for PSC.

17SC0011-0021 is a diploid *S. tuberosum* F1 plant derived from the cross HP66 x D16. It grows vigorously, flowers abundantly, produces many pollen and readily sets cross-berries, but is self-incompatible.

17SC0011-0027 is a diploid *S. tuberosum* F1 plant derived from the cross HP66 x D16. It grows vigorously, flowers abundantly, produces many pollen and readily sets cross-berries. 17SC0011-0027 does not contain the self-compatibility allele of PSC, but it does occasionally set self-berries containing small amounts of seed, indicating that this plant is pseudo self-compatible.

Figure 3:
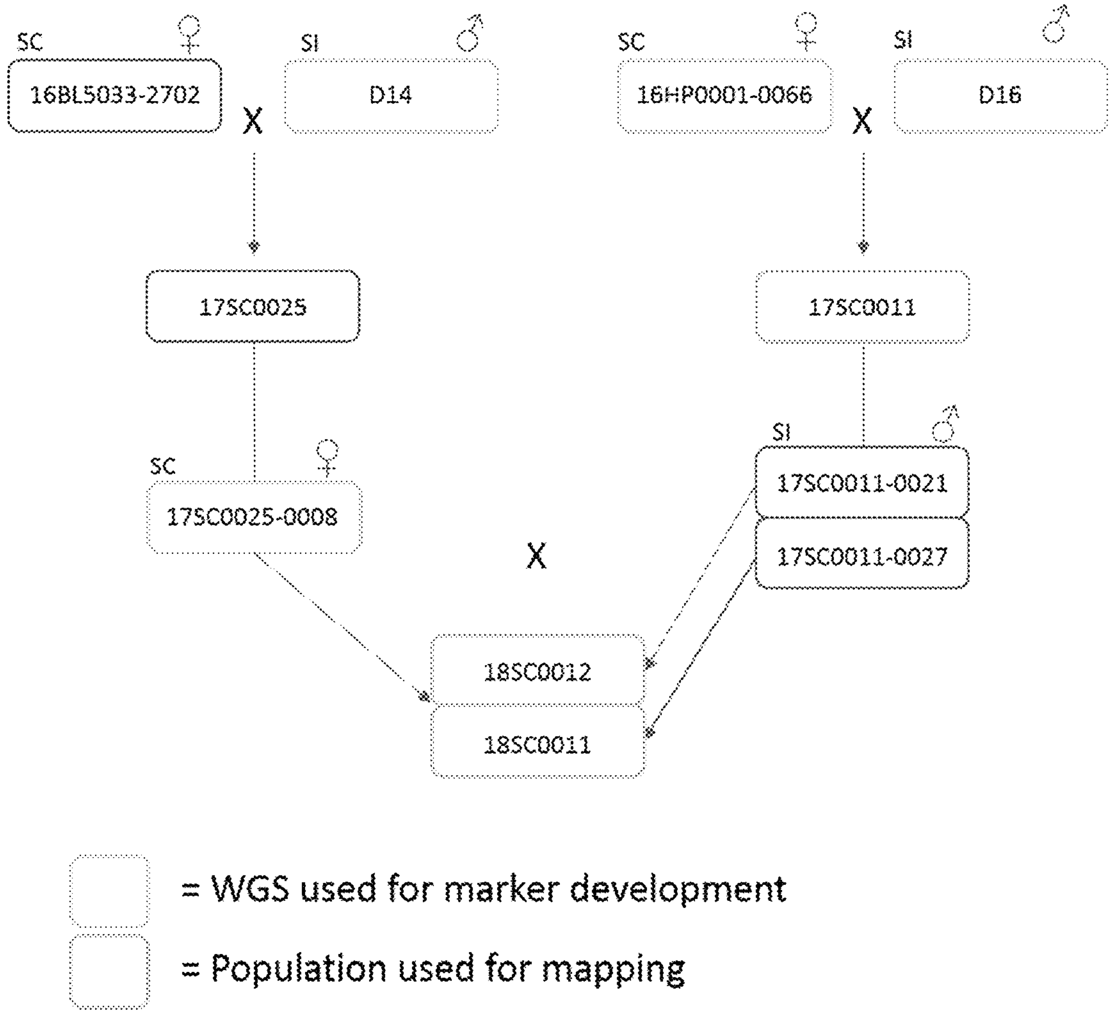
FIG. 3. Crossing scheme as used for the development of the mapping populations.

A crossing scheme that was used to map and clone PSC is provided in FIG. 3. A suitable crossing scheme to identify PSC, may start by crossing any self-compatible potato plant with a self-incompatible potato plant. Said potato plant preferably is a diploid, essential homozygous *S. tuberosum* plant. Suitable starting plants are provided by the self-compatible potato lines NCIMB accession number 41663, NCIMB accession number 41664, NCIMB accession number 41665, or NCIMB accession number 41765, representative seeds of said lines having been deposited with the NCIMB, Aberdeen, Scotland under breeders reference AGVD1, AGVD2, AGVD3, and AGVD17 respectively.

Greenhouse Conditions

All plants were grown in a greenhouse in The Netherlands. The greenhouse compartment was heated when the temperature dropped below 14° C. and cooled by opening the windows when temperature increased above 19° C. Artificial lighting supplemented the natural light when the light intensity dropped below 85 W/M2. Plants were grown in a special potato substrate mix from Lentse Potgrond (Lentse Potgrond B.V, Katwijk, the Netherlands). The substrate mix used is composed out of a peat-mixture for balanced water uptake, basic slow release fertilizer and lime to ensure the required pH level. The substrate mix was fertilized using a 20:20:20 Nitrogen:Phosphorus:Potassium solution with an electrical conductivity (EC) of 1.5.

Evaluation of Self-Compatibility

Flowers and buds were counted once a week and vigour was scored once per month on a scale from 1-9 with 1 being an extremely non-vigorous plant, and a 9 being an extremely vigorous plant. Pollen from multiple flowers from one plant was collected in an Eppendorf tube and used immediately for self-pollination on the same flowers with a maximum of 10 flowers per plant per week. Plants that set more than two self-berries containing at least 35 seed per self-berry were classified as self-compatible. To determine female fertility, plants were pollinated with bulked pollen from at least three unrelated genotypes from the potato breeding program. Plants that did not set self-berries after at least 15 self-pollinations, but did set at least one bulk berry and showed fertile pollen in microscopic analysis of self-pollinated styles were classified as self-incompatible. Self-pollen and bulk-pollen tube growth were visualized in plants that did not produce enough flowers to complete the phenotyping protocol, and plants that produced self-berries containing fewer than 35 seed per berry, to classify those plants as self-compatible or self-incompatible.

Style Imaging

To visualize pollen tube growth, pollinated styles were removed 24 hours after pollination and then fixed in 3:1 ethanol:acetic acid for at least 24 hours. The styles were then macerated in 8 M NaOH for 10 minutes at 65° C. and rinsed twice with demi water. Styles were placed on microscopy slides and stained for 2-5 minutes using 0.1% Aniline blue (Carl Roth GmbH) in 0.1 M K4P207 (pH=7), then squashed in glycerol using a cover slip and observed using a Zeiss Axiolab fluorescence microscope using filter set 01 (BP 365/12, FT 395 and LP 397). All styles were observed and scored using two parameters: 1) deepest penetration into the style, as expressed in percentage of maximal penetration, 2) % of pollen tubes reaching the deepest penetration.

DNA Extraction

Leaf samples were sent to VHLgenetics (Wageningen, The Netherlands) for DNA extraction using sbeadextm kits (LGC genomics GmbH, Berlin, Germany) according to the protocol supplied by the manufacturer.

KASP Analysis

Kompetitive allele specific PCR (KASP™) analysis was performed by VHLgenetics (Wageningen, The Netherlands) using KASP assays designed to be specific for SNPs that segregate in our material. KASP assays were conducted according to the protocol supplied by the manufacturer (LGC Genomics GmbH, Berlin, Germany). The results from the KASP assays were visualized using SNPviewer (available at lgcgroup.com/products/genotyping-software/snpviewer) to confirm correct segregation and genotype calling.

Linkage Analysis

Haplotypes of self-compatible female parents were reconstructed from the genotype data by analyzing recombination rates between different SNPs. This data was used to convert the SNP calls into an "axb" format, wherein the "a" haplotype is linked to the self-compatible allele of PSC, while the "b" haplotype is linked to a self-incompatible allele of PSC. Linkage maps were created using Joinmap 4.1 with population type DH and default settings (van Ooijen, 2006.

JoinMap® 4. Software for the calculation of genetic linkage maps in experimental populations. Kyazma BV, Wageningen. 38(10.1371).

QTL Mapping

The phenotype data was converted to a numerical trait by assigning 1 to each self-compatible genotype, 0 to each self-incompatible genotype and * to genotypes for which compatibility could not be determined. QTL mapping was performed using interval mapping in MapQTL 6 (van Ooijen, 1992. Theor Appl Genet 84: 803-811; van Ooijen, 2006. JoinMap® 4. Software for the calculation of genetic linkage maps in experimental populations. Kyazma BV, Wageningen. 33(10.1371).

Results

Self Incompatible Parent

Most of present day Solynta's germplasm is self-compatible (SC), requiring us to go back to the founder genotypes of our breeding program to find a self-incompatible (SI) parent. Among the 17 founder genotypes, three stand out for their abundant flowering and self-incompatibility: D2 (IVPAA-096-18 a.k.a. RH88-025-50), D14 (IVP06-145-2) and D16 (IVP06-149-12; see WO2011/053135 Table 6), all available from Dr. Ronald Hutten, Laboratory for Plant Breeding, Wageningen University.

D2 was used as SI parent in an F2 mapping population based on the cross DSxD2. The results revealed a QTL, that increased self-compatibility of moderate LOD score on Chromosome 2 (see herein below). Next, D14 was used to create several mapping populations that upon examination showed high rates of pollinated flower abortion, leading us to suspect that the genetics of D14 were unfavorable for berry set. Initially, D16 was not considered a good candidate because it occasionally set self-berries that contained small amounts of seeds. However, when we tested an F1 population (17SC0011), resulting from a cross between D16 as father and HP66 as mother, we found that this population showed 1:1 segregation and performed well. From this F1 population, we obtained two SI genotypes that we thereafter used as SI parents for new mapping populations.

SC Parent

We tried several SC genotypes to use as parents for mapping populations. One genotype, 16HP0001-0066 (HP66) showed abundant flowering, good pollen production and high berry set rates. After analyzing several inbred populations derived from HP66 we decided to cross it to D16 to generate a mapping population. This population segregated for self-compatibility, indicating that HP66 is heterozygous for a self-compatibility gene. A second SC genotype, 16BL5033-2702 was identified on a field where it showed tremendous berry set. When we analyzed a mapping population from 16BL5033-2702, we found that all offspring plants were self-compatible suggesting that 16BL5033-2702 is homozygous for the self-compatibility allele of PSC.

Mapping Populations

To localize a self-compatibility gene, we tested several populations for segregation of self-compatibility. Hosaka and Hanneman had indicated that a single dominant S-locus inhibitor gene (Sli) with sporophytic action resides on Chromosome 12 (Hosaka and Hanneman, 1998. *Euphytica* 99: 191-197).

To map the Sli gene, an F2 population derived from the cross DSxD2 was analyzed for self-compatibility. Here, we found a QTL with a moderate significance that could be responsible for a self-compatibility gene on Chromosome 2. The fact that this QTL segregated in an F2 population, suggested that this QTL on Chromosome 2 acts sporophytically.

At that time we hypothesized that the lack of a highly significant QTL on Chromosome 12 might be due to genetic background noise as a result of the heterozygosity of the D2 parent.

When HP66 was first identified, we analyzed a selfed population from it that appeared to segregate for self-compatibility. A genetic analysis was performed in which Chromosomes 1, 2 and 12 were targeted, because there was theoretical evidence related to self-compatibility for these Chromosomes: Chromosome 1 containing the S-locus (Gebhardt et al., 1991. Theor Applied Genet 83: 49-57); Chromosome 2 containing a potato homolog of the *Nicotiana alata* 120K gene (Hancock et al., 2005. Plant J 43: 716-723); and Chromosome 12 containing the HT-B gene (O'Brien et al., 2002. Plant J 32: 985-996). Both 120K and HT-B have been shown to be required for self-incompatibility (O'Brien et al., 2002. Plant J 32: 985-996). However, this targeted genetic analysis did not reveal any significant QTL with sporophytic self-compatibility activity.

Inbreeding was continued with several lines derived from HP66 with the idea that a self-compatibility gene may be identified if genetic background noise could be reduced. However, this ultimately proved futile.

Surprisingly, QTL analysis on an F1 derived from HP66xD16 revealed a highly significant QTL with a LOD score >60 on Chromosome 12 having gametophytic activity. This very high LOD score indicates that genetic background noise, that may be present in HP66, does not pose a problem for mapping. As this gene acted gametophytically, this gene might differ from Sli, and was tentatively termed Potato Self Compatible (PSC) gene. The locus on Chromosome 12 could be mapped to an ~600 KB interval in which PSC must be located. All available data supported presence of a single dominant gene with gametophytic action on Chromosome 12.

By crossing 175C0025-0008 to two new SI genotypes, 17SC0011-0021 and 17SC0011-0027 that were identified in population 17SC0011, two large segregating F1 populations were grown that were used to confirm the location of PSC on Chromosome 12, and which also allowed us to reduce the interval where PSC is located to ~170 KB (see Example 4).

Phenotyping of the Mapping Populations

When the F2 population from the cross DSxD2 was analyzed, both self-compatible (SC) and self-incompatible (SI) plants were identified. However, since we now know that all F2 plants should already have the self-compatibility allele of PSC due to the gametophytic action of this gene, we wondered why SI plants were identified in this population. We hypothesized that the SI phenotypes of those plants were due to other fertility problems such as pollen quality or berry set. For this reason, we composed a new phenotyping protocol that included a strong emphasis on measuring not only self-compatibility but also other fertility related traits. Using this protocol, we determined flowering, pollen quality, in vivo pollen tube growth and bulk berry set. In this way we could exclude confounding infertility characteristics from the SI classification by assigning all plants with fertility issues a'Not Determined' (ND) classification as the self-compatibility scoring could not be assessed accurately due to lack of fertility. Unfortunately, this significantly reduced the effective size of the mapping populations, implying that more individuals are required to obtain the same resolution. For instance, population 175C0011 consisted of 252 plants of which 86 were SC, 78 were SI and 88 were ND, reducing the effective mapping population size from 252 to 164 plants.

Example 8. Fine Mapping and Analysis of Genomic DNA

To identify the self-compatibility allele of PSC we genotyped and phenotyped three mapping populations, 175C0011, 18SC0011 and 18SC0012 and performed a QTL analysis for self-compatibility. This allowed us to define a 169 kb interval on Chromosome 12 in which PSC must be located. We then screened a further 1374 seedlings from population 175C0011 for recombinants in this interval, allowing us to reduce the interval to 27.4 kb.

Material and Methods

Plant Materials

D14, D16, 16HP0001-0066, 16BL5033-2702, 17SC0025-0008, 17SC0011-0021 and 17SC0011-0027 are described in Example 2.

Mapping Populations

175C0011 is an F1 population derived from the cross HP66 x D16. In total, 252 plants were grown for the mapping study, out of which 86 were self-compatible, 78 were self-incompatible and 88 were ambiguous (not determined).

18SC0011 is an F1 population derived from the cross 17SC0025-0008 x 17SC0011-0027. In total, 161 plants were grown for the mapping study, out of which 95 were self-compatible, 40 were self-incompatible and 26 were not determined. This population shows significantly deviation from 1:1 segregation for self-compatible to self-incompatible plants. This is likely due to pseudo self-compatibility originating from parent 17SC0011-0027

18SC0012 is an F1 population derived from the cross 17SC0025-0008 x 17SC0011-0021. In total, 250 plants were grown for the mapping study, out of which 97 were self-compatible, 85 were self-incompatible and 68 were ambiguous (not determined).

Other Methods

Greenhouse conditions, evaluation of self-compatibility, style imaging, DNA extraction, KASP analysis, Linkage analysis and QTL mapping were performed as described in Example 2.

Results

QTL for Self-Compatibility on Chromosome 12

In earlier studies, a QTL for self-compatibility with sporophytic action was identified on Chromosome 2 in an F2 population from the cross DS×D2 (see example 2). However, other research pointed to a gene for sporophytic self-compatibility on Chromosome 12 (Hosaka and Hanneman, 1998. Euphytica 103: 265-271). Therefore, we selected 18 SNPs on Chromosome 2 and 6 SNPs on Chromosome 12 that were heterozygous in parent HP66 and homozygous in parent D16. Out of 18 SNPs that we selected on Chromosome 2, 14 segregated 1:1 as expected, 2 segregated 1:2:1 and 2 did not segregate at all. Out of 6 SNPs selected on Chromosome 12, five segregated 1:1 as expected and one segregated 1:2:1. All SNPs that did not segregate as expected were not used for further analysis. Using the genotype data, maps of Chromosomes 2 and 12 were constructed of 70.5 and 69.7 cM, respectively. QTL mapping revealed a highly significant QTL on Chromosome 12 but not on Chromosome 2. We therefore selected 25 more SNPs on Chromosome 12 from our marker database as described in Example 1, out of which 23 segregated as expected. Using these data we were able to determine a 629 kb interval in which PSC is located, between markers SOT12-58601503 and SOT12-59230363 (see FIG. 4).

Genetic Mapping in Populations 18SC0011 and 18SC0012 Confirmed the Location of PSC on Chromosome 12

To confirm the presence of a gene for self-compatibility in population 17SC0011, genetic analyses were performed in populations 18SC0011 and 18SC0012. 15 markers were selected on Chromosome 12 that were heterozygous in a self-compatible mother 17SC0025-0008 and homozygous in both paternal grandparents HP66 and D16. All markers showed the expected 1:1 segregation, and genetic analyses confirmed the location of PSC in both populations. Interestingly, the LOD score of population 18SC0011 was much lower than that of population 18SC0012, likely due to pseudo self-compatibility being present in parent 17SC0011-0027. Indeed, manual inspection of a subset of plants with contradictions between the genotypic and phenotypic data revealed 12 plants that did not have the self-compatibility allele of PSC but were nevertheless scored as self-compatible because they did set self-berries. It is possible that plants without the self-compatibility allele of PSC that did set self-berries have a less efficient self-incompatibility systems based on S-alleles, for instance due to naturally lower levels of S-RNase expression, allowing them to set self-berries occasionally. Two plants of population 188C0012 showed recombination around PSC that reduced the interval to 169 kb (see FIG. 5).

Reduction of Interval for PSC Gene to 27 kb

To further narrow down the location of PSC, 1374 seedlings from population 17SC0011 were sampled and genotyped with four markers around the 629 kb interval (Interval I, 629 kb, FIG. 4). Unfortunately, one marker that produced good results in the genetic mapping of population 17SC0011, yielded poor results in the recombinant screening, allowing to select 81 recombinants between the two outer markers. When the recombinant genotypes reached sufficient length, two cuttings from each genotype were generated to increase the accuracy of phenotyping. All 81 recombinants were then genotyped with 28 markers in the 169 kb interval (Interval II, 169 kb, FIG. 5), 24 of which segregated as expected. Two plants with clear SI phenotypes showed recombination that allowed us to reduce the interval from 169 to 27 kb (FIG. 6), in which at least four candidate genes remained.

Reduction of Interval for PSC Gene to 12.6 kb

In order to determine which of the candidate genes is the PSC gene, we screened another 10.165 seedlings with four markers (SOT12-59003185; SOT12-59016142; SOT12-59043512; SOT12-59043574) surrounding the 27 kb interval (Interval III, 27 kb, FIG. 6). We identified 53 plants with apparent recombinations in the 27 kb interval. We then genotyped the 53 recombinants with 16 markers (Table 11) including the inner markers that we used for the initial screen of the 10.165 seedlings. Two markers (SOT12-59022612 and SOT12-59030235) did not segregate and were not used for further analysis. With the remaining markers we identified 14 true recombinants. The other 39 genotypes were included due to genotyping errors in the initial screen. Nonetheless, we phenotyped all 53 plants identified in the initial screen, and found six plants that define a new interval of 12.6 kb (Interval IV, 12.6 kb, FIG. 13). Two plants with an SC phenotype and one with an SI phenotype confirm the distal border of the previous 27 kb interval, whereas three other plants with an SI phenotype define a new proximal border at 59.030.880 bp, resulting in a new interval of 12.6 kb (FIG. 13). Two genes are located in this 12.6 kb interval, PGSC0003DMG400016861 and Sotub12g029970 (for the latter ITAG annotation is used as the present inventors consider that the PGSC annotation may be truncated. This is evidenced by the fact that the ITAG annotation refers to a larger sequence, in which additional exons are supported by RNA-seq data. The corresponding PGSC model is PGSC0003DMG400016860.

Example 4. Identification of the Self-Compatibility Allele of PSC

Materials and Methods

Plant Materials

Genotypes DS, D16, 16HP0001-0066 and 17SC0025-0008 are described in Examples 2 and 3.

Genotype 17SC0100-0018 is an diploid F4 potato genotype derived from 16HP0001-0066. It is homozygous for the self-compatibility allele of PSC, because when crossed to 17SC0011-0021 all progeny were either SC or Not Determined. The genome of 17SC0100-0018 was sequenced.

Genotype 17SC0100-0002 is a diploid F4 potato genotype derived from 16HP0001-0066. It is homozygous for the self-compatibility allele of PSC, because when crossed to 17SC0011-0021 all progeny plants were either SC or Not Determined. The genome of 17SC0100-0002 was sequenced.

Bioinformatic Analysis of Candidate Genes

To identify correct gene models in the initial 27 kb interval referred to herein (Interval III and which could later be reduced to 12.6 kb (Interval IV) as explained in Example 3), we investigated two separate gene annotations for the DM 4.04 reference genome, the PGSC annotation and the ITAG annotation. See also Hirsch et al., 2014. Plant Genome 7:1-12. To confirm the correctness of the annotations, we performed blastp searches with the predicted protein sequences from both annotations. By comparing the best hits in the blastp search to our query, we determined whether all annotated exons and domains in the predicted protein sequence were supported by similar proteins in potato and other plant species. Furthermore, publicly available RNA-seq libraries on SPUD DB (available at solanaceae.plantbiology.msu.edu/cgi-bin/gbrowse/potato/) and NCBI genome data viewer ncbi.nlm.nih.gov/genome/gdv/browser/) were used to determine whether putative exons had expression evidence. Together, these two approaches allowed us to validate the intron-exon structures of the gene models in both annotations, resulting in an informed choice for one or more isoforms of gene models to represent the gene in question. Based on these approaches, candidate gene PGSC0003DMG400016862 was recognized as likely partial and insignificantly expressed and discarded from further analyses. The gene model Sotub12g029970 was deemed correct, while its PGSC counterpart PGSC0003DMG400016860 is likely truncated. Because it is located largely outside the designated interval, and no relevant amino acid substitutions between SC and SI plants could be identified, this gene was discarded from further analyses.

Variation Analysis

To identify mutations in the 27 kb interval (see Example 3) that are specific for self-compatible genotypes, all high confidence SNPs (see Example 1) were determined that were (1) homozygous in DS, 17SC0100-0018 and 17SC0100-0002 (because all three are homozygous for the SC allele of PSC (PSC/PSC)), (2) homozygous different in D16 (because homozygous for the SI allele of PSC (psc/psc)), and (3) heterozygous in both 16HP0001-0066 and 17SC0025-0008 (because both are heterozygous for SC allele PSC (PSC/psc)). Allelic sequence were obtained by de novo assembly using SPAdes version 3.11.1 (Bankevich et al., 2012. J Comput Biol 19: 455-477) of 150 nt paired-end Illumina data of the above listed plants (of approximately 25-30x sequencing depth). Resulting contigs were aligned to the DM reference (using minimap2 version 2.1), and filtered for those reliably aligning to the 27 kb. From these aligned contigs, variation relative to DM was quantified straightforward (using the subroutines mpileup and call from bcftools, version 1.9) and listed in the Variant Call Format (VCF).

Amino Acid Change Analysis

From this list of SC specific mutations, all non-synonymous SNPs were identified by overlapping with the designated coding exons. The amino acid changes relative to either DM or SI sequence were listed. Unique amino acid changes were identified by performing blastp searches using the protein sequence and performing multiple sequence alignment using the top 100 blastp hits.

Variation in Promoter and Terminator Regions

The promoter region was chosen to be the sequence upstream of the start codon until the coding sequence of the upstream gene with a maximum of 1500 nt. Dramatic variation in promotor regions was found within the 27 kb interval, of which most striking were several larger deletions and insertions of tens to hundreds of nucleotides of length. All variation in the PSC interval, relative to DM, was obtained, including that of the promotor/upstream region as well as the terminator/downstream region.

Results

PGSC0003DMG400016861 is the wildtype sequence of gene A.

PGSC0003DMG400016861 (PGSC annotation) is a gene located on Chromosome 12 from nt 59039183 to nt 59041123 (- strand). It is annotated as a gene, and contains an F-Box domain and a PP2 lectin domain. The PGSC and ITAG annotations show two different gene models, with the ITAG annotation having an additional exon. This additional exon was not supported by any similar proteins, and there was no evidence that this exon is expressed in the RNA-seq datasets available on SPUD DB and NCBI genome data viewer. We therefore rejected the ITAG gene model in favor of the PGSC gene model (as later confirmed in Example 6).

F-box proteins are involved in the SCF (Skp1-Cullin-F-box) complex that functions in the proteasomal degradation pathway by recognizing proteins and tagging them with ubiquitin for degradation. The F-box domain of F-box protein PP2-B10 is involved in interactions with the other proteins in the SCF complex, whereas the PP2 domain is involved in recognition of sugar moieties (Stefanowicz et al., 2015. Critical Rev Plant Sci 34: 523-552). In self-compatible plants, we found six non-synonymous mutations in this gene that are specific for self-compatible plants, one of which, R249Q is uncommon among similar F-box proteins and might lead to altered specificity of the recognition domain. Furthermore, a variety of small and large insertions and deletions was found, as well as many substitutions in the promoter region of this gene. Most noticeably, a 533 nt PSC-specific insertion was found at position −108 from the ATG (when compared to DM), whereas this position is absent in other SI-plants because of a 193 nt deletion of the region from −85 to −278 nt. The −50 to −150 nt region upstream of the start codon is known to contain elements crucial to initiate coordinated transcription. This, and other variations in the promoter region are likely to eventually lead to altered expression patterns. In the Solanaceous self-incompatibility system, F-box proteins are involved in the detoxification of style secreted S-RNases in pollen tubes during compatible pollinations (Li et al., 2016. Plant J 87: 606-616). Moreover, S-RNases are known to be glycosylated (Broothaerts et al., 1991. Sexual Plant Reprod 4: 258-266). The present inventors conclude that F-box proteins, notably F-box PP2-B10 protein encoded by SEQ ID NOs: 2-4 and 6-8, should exhibit timely regulated expression in pollen. It is therefore not surprising that altered expression of an F-box PP2-B10 protein with a possibly altered recognition specificity leads to self-compatibility. It is postulated that expression of this gene in self-pollen tubes leads to recognition and degradation of self S-RNases, thus allowing self-fertilization.

Example 5. Stacking of Resistance Genes in a Single Variety Using Self-Compatible Material

Materials and Methods

Greenhouse

Plants were grown in Solynta's greenhouses (minimum temperature 16-18° C., 16 hours light) in the Netherlands. After germination and growing in small plugs (0.2 liter) the seedlings were transplanted to bigger pots (4 liter). Emasculation, crosses and subsequently berry collection were done in the greenhouse. After vibrating ripe anthers, pollen were collected in Eppendorf tubes and, if needed, stored in the refrigerator, and subsequently used for crosses. Seed collection and cleaning were done after the berries ripened (about six weeks after pollination).

Plant Material

Figure 8:
FIG. 8. Four different sources of *Phytophthora* resistance genes (RPi=resistance gene to *Phytophthora infestans*). Sources are *S. avilesii* 478-2 Rpi*-avl1 (A); *S. tarinjense* 852-5 Rpi-tar1(B); *S. chacoense* 543-5 Rpi-chc1 (C); and *S. venturii* 283-1 Rpi-vnt1 (D).

Four different wild relatives with known resistance genes against 15 *Phytophthora infestans* were used. These accessions belonged to *S. avilesii* (Rpi-avl1, Verzaux et al., 2011. Am. J. Pot. Res. 88:511-519); *S. tarijensi* (Rpi-tar1, Vossen et al., 2009; WO 2011034433); *S. chacoense* (Rpi-chc1, Vossen et al., 2009; WO 2011034433) and *S. venturii* (Rpi-vnt1, Foster et al., 2009. MPMI 22: 589-600; Pel et al., 2009. Mol Plant-Microbe Interactions 22: 601-615). The different sources of resistance genes are shown in FIG. 8. The Solynta lines were obtained after crosses and repeated selfings of original donor lines (the D-numbers) and the Sli-gene donor "DS" (Lindhout et al. 2011).

Genotyping

The KASP genotyping system is a PCR method based on two specific forward primers which are each specific for one of the two alleles of the SNP and a common reverse primer (available at lgcgroup.com). The amplified fragment is between 50-100 base pairs. KASP genotyping was outsourced to van Haeringen Laboratories, Wageningen (see vhlgenetics.com). Different sources of sequence information were used to find suitable SNPs (Anithakumari et al., 2010. Mol Breeding, 26:65-75; Uitdewilligen et al., 2013. PLoS One 8:e62355; Vos et al., 2015. Theor. Appl. Genet. 128, 2387-2401) and the SolCAP array (available at solcap.msu.edu/potato_infnium.shtml) was used to find additional markers. The SolCap experiments were outsourced to Trait-Genetics, Germany (see traitgenetics.com)

Field Trials

*Phytophthora* resistance was screened for in three separate field trials. The main location was in clay soil (Wageningen, The Netherlands). The two other locations for confirmation and back-up were at sandy soils. One of the trials on sandy soil was done under supervision of HLB (Wijster, The Netherlands). The field growing season was from June till September 2017. *Phytophthora* infection was spontaneous on the two sandy soils, and one of these regions is known for the occurrence of virulent *Phytophthora* strains. Although the first spontaneous signs of *Phytophthora* infections were already visible on the experimental field at soil, an extra artificial inoculation was done with *Phytophthora* strain IPO-C on 20 Jul. 2017 to be sure of a uniform disease pressure in the field. This strain was grown on artificial medium (1 g agar, 12 g rye grains and 3 g sucrose per 100 ml water) and transferred to detached leaves and collected after an incubation period of seven days. The final concentration was $5\times10^4$ spores/ml and 10 liters were sprayed over the plants growing in the field. The demonstration field consisted of 44 blocks of 10-12 plants. The blocks consisted of BC1xBC2 or BC2xBC2 hybrids with 0, 1 or 2 different RPi genes in a background of one of the three parental lines (P1, P2, P3) No hybrids with the combination of the allelic chc1 and tar1 resistance genes were made. The overall disease scores of the individual blocks were visually determined on a scale from 0 (all plants dead) to 10 (all plants completely healthy).

Results

Parental Lines

Figure 9:
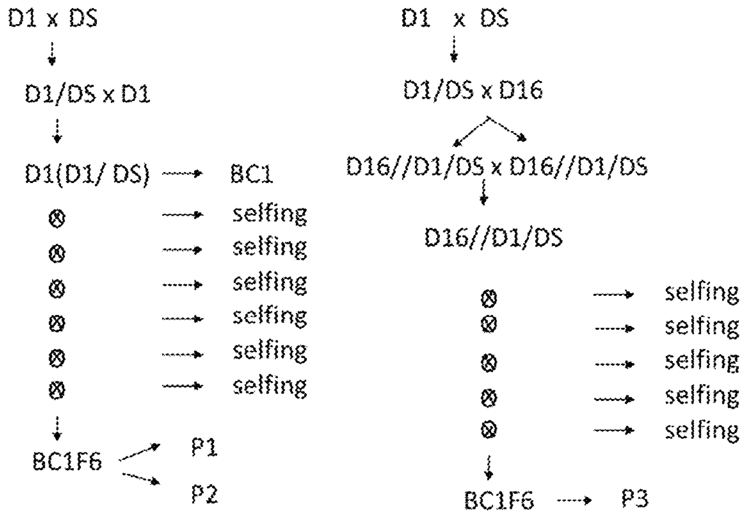
FIG. 9. Pedigree of three parental lines. The homozygosity levels of P1, P2 and P3 were calculated based on 67 markers covering the whole genome as much as possible. (DS), donor Sli-gene, fertility, inbreeding tolerance (Hosaka and Hanneman, 1998. *Euphytica* 103: 265-271). D1 (yellow flesh, good cooking quality) and D16 (early, round, yellow) are diploid potato selections from the diploid breeding program from Wageningen University (Hutten et al., 1994. Thesis, Wageningen University, Wageningen, ISBN 9054852925; Lindhout et al., 2011. Potato Res. 54, 301-312).

From Solynta's breeding program three different parent lines were chosen: P1, P2 and P3. The pedigrees of these lines trace back to crosses with two to three different diploid founders ("D-numbers") (FIG. 9). These plants were predominantly developed based on field performance and the capability to produce enough flowers, berries and seeds. This made it possible to perform several rounds of selfings. During the last two selfings the best performing progeny plants were screened for homozygosity. This was done with a set of informative molecular markers (single nucleotide polymorphisms, SNP) equally distributed over the twelve potato Chromosomes. The development of the three lines is shown in FIG. 9, the final homozygosity scores were 88%, 88%, and 79% for P1, P2 and P3 resp. These percentages are lower than expected, which is probable due to the relative preference to select more heterozygous plants in the selfed populations.

Molecular Marker Development

Based on the screening with the SolCap array specific resistance gene linked SNP markers were chosen (Table 8), these markers were used to select backcross plants with the resistance gene for further breeding and to screen before the field trials BC1xBC2 resp. BC2xBC2 offspring populations to determine the number of Rpi genes in the individual plants. A total of sixty-seven other SNPs were used for determining the percentage recurrent parent in the BC1 and BC2 plants, these SNPs were selected because they were polymorphic between the group of four donor plants and the group of three parental lines (Table 9). They were spread over the whole genome (data not shown). The time needed for finding the right markers for selection of the avl1 Rpi-gene caused a delay in making BC2 crosses including avl1. To include hybrids with avl1-genes in the field-trial we used the best BC1 plant with the avl1 R-gene. These BC1 plants contain consequently more DNA of the wild relatives which make the BC1xBC2 populations less uniform compared to the BC2xBC2 hybrids.

Development of Material

Figure 10:
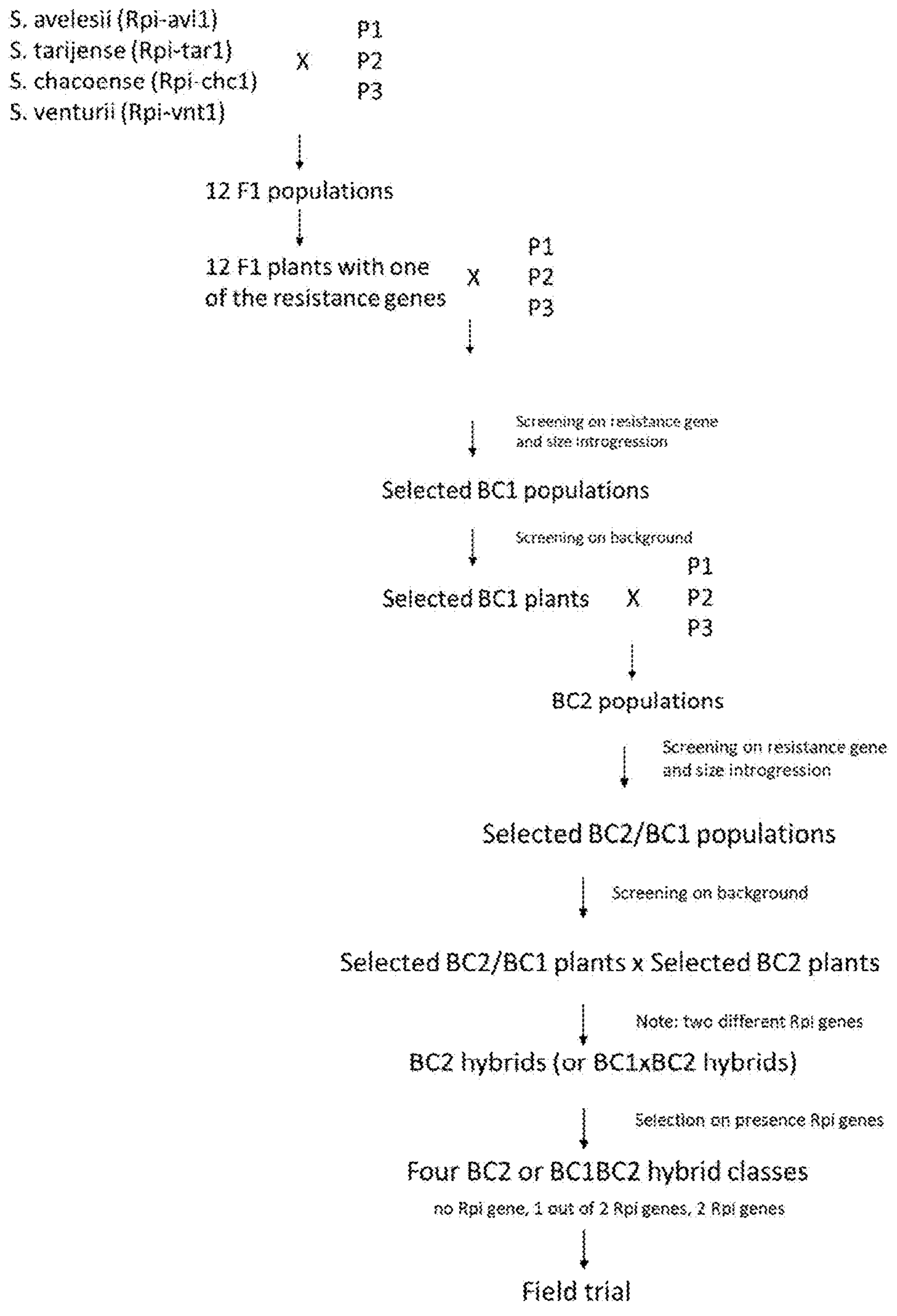
FIG. 10. Development of a series of diploid potato hybrids without, with one or with two different Rpi genes (A). Results from a field trial are depicted in (B).
Figure 10:
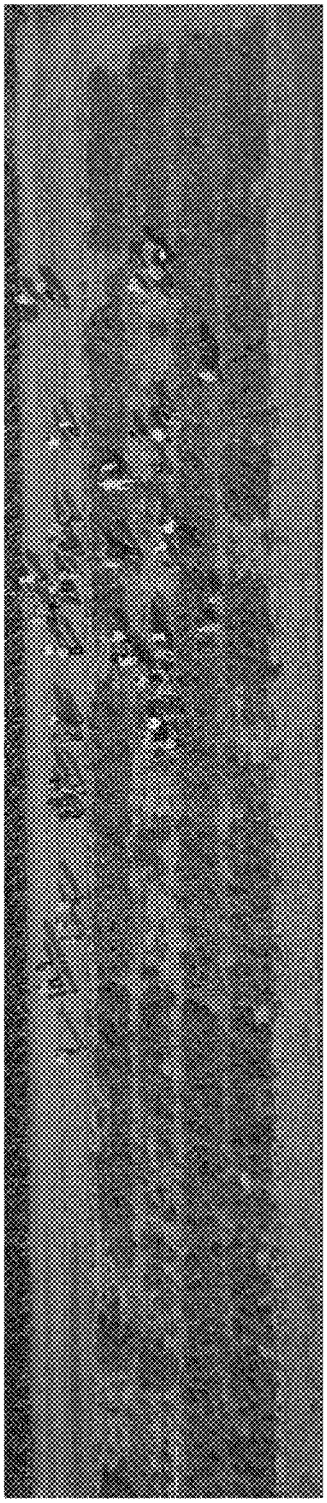
Figure 11:
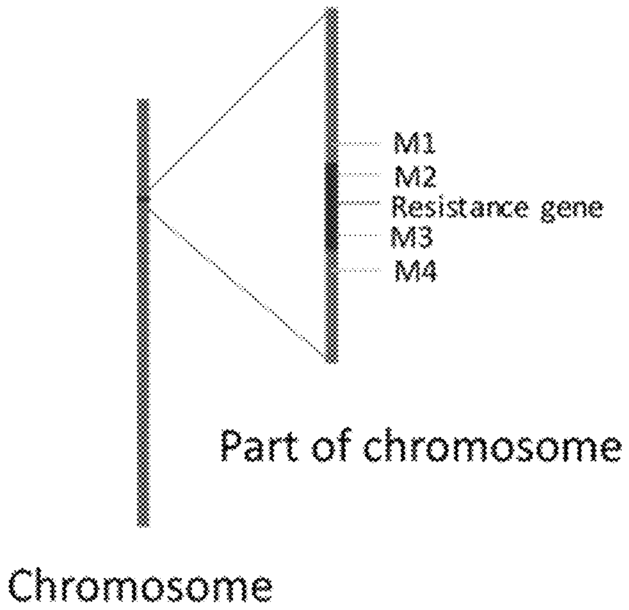
FIG. 11. Example of the selection procedure for making parental lines with a small introgression. The flanking markers M2 and M3 were used to confirm the presence of the RPi gene. M1 and M4 were used to know the maximum size of the introgression.
Figure 12:
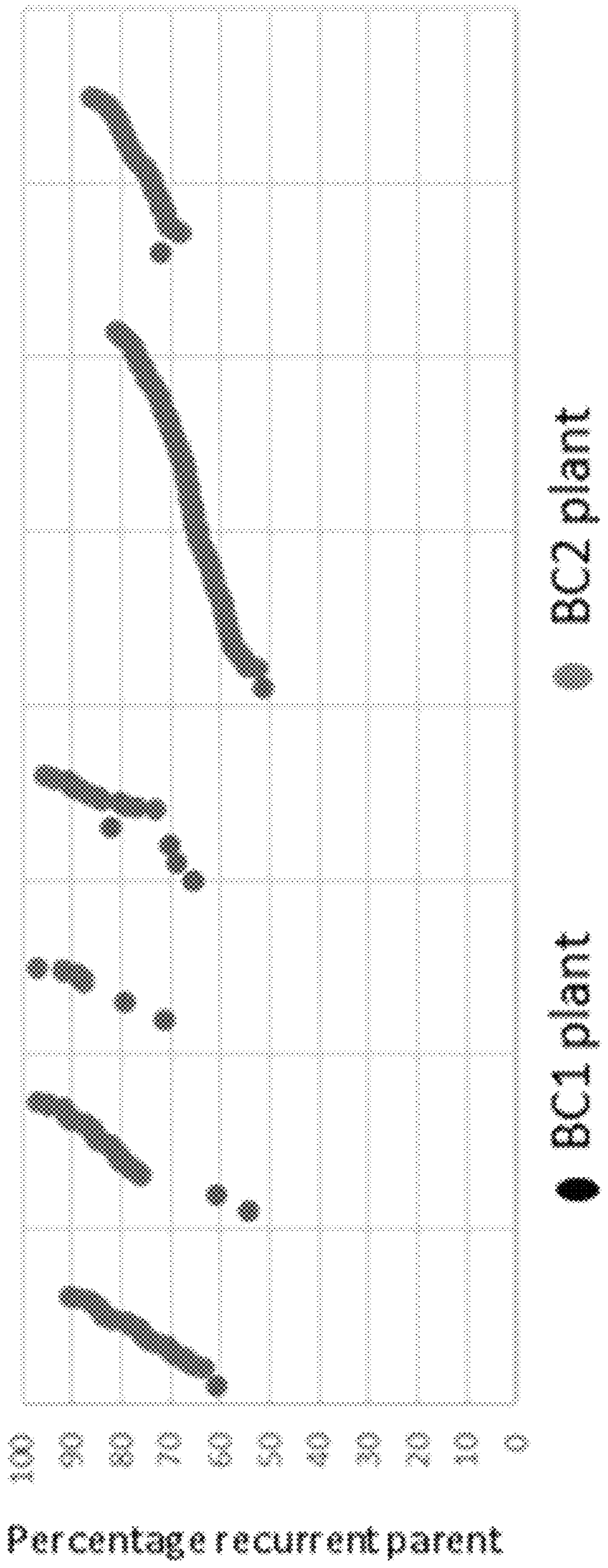
FIG. 12. Examples are shown of the percentage recurrent parent of 1 to 4 BC1 plants (black dots) of the six BC2 populations and the percentages recurrent parent in these BC2 plants (blue dots).

The overall procedure of making our hybrids, with double stacked resistance genes, is shown in FIG. 10. The four wild relatives (*S. avilesii, S. tarinjense, S. chacoense* and *S. venturii*) were crossable with the three potato parental lines (FIG. 8) and a sufficient number of F1 seeds was obtained (the different steps are shown in Tables 2 and 3). The best growing and flowering resistant F1 plants were backcrossed with the parental lines (reciprocal). Two thousand plants of the six best BC1 populations were screened with four markers based on the principle as shown in FIG. 11 These markers made it possible to select 45-70 plants in the first backcross population with a recombination close to the resistance gene and a relatively small introgression up or downstream of the genes. The maximum size of the introgression depended on the location of good markers (localization of markers M1 and M4). The 45-70 BC1 offspring plants were all genotyped for the overall percentage recurrent parent genome. The best flowering and vigorous BC1 plants were used for backcrossing to the recurrent parent. In choosing the best BC2 plants the same procedure was followed (but now for the other side of the resistance gene). This resulted in a few selected BC2 plants which were used for making hybrids. The resistance gene avl1 is located at the top of Chromosome 11 (1.8 Mb) and therefore only selection for a recombination is needed at the proximal side of the resistance gene. The whole background selection was very successful as most of the genome of the donor wild species parent was not present anymore after two BC generations. Without marker screenings this could not have been accomplished. The percentages of recurrent parent in the BC1 and BC2 plants varied substantially (FIG. 12).

For example, in the first BC2 population the variation was normally distributed and ranged between 60 and 90% (BC1 value 60%), in the second population the variation varied between 75 and 97% (BC1 values 52 and 60%) and similar results were obtained for the other populations. The main criterion for selecting parental plants was the high level of recurrent parent genome. After BC2 and marker selection a selfing is needed to make parents with the resistance allele homozygous, this selfing step can also be an extra step in removing any remaining unwanted introgressions. For instance, when two introgressions are left in the selfing, it is expected that one out of 16 offspring plants is homozygous for the region of the Rpi-gene without any other introgression. A cross of two homozygous lines with different Rpi-genes lines will automatically give isogenic hybrids with both resistance genes. In the present study, we made the cross between two BC2 plants (or in the case of the Rpi of *S. avilesii* a cross between a BC1 and a BC2 plant). Therefore it was needed to perform a marker assisted selection for the presence of the Rpi-genes (Table 3). Because the hybrids were made by crossing two parents with resistance gene heterozygous, molecular marker analyses were done to divide the offspring plants in four classes (plants with two Rpi-genes, one Rpi-gene, the other Rpi-gene and plants without Rpi-genes). The segregation ratios are given in Table 4. Since the Rpi-gene of *S. tarinjense* 852-5 is allelic to the Rpi-gene of *S. chacoense* 543-5, it is possible that these two resistances have the same mode of action, therefore increasing the risk that a combination of these genes does not have added value and therefore hybrids with the combination of these two genes were not made.

In Table 5 it is shown that hybrids with all four expected combinations of resistance genes were generated. In general, however there is a preference towards plants with no Rpi genes compared to the number of plants with two Rpi genes (759 vs 427). The preference can be an indication that introgressions from the wild source influence viability of the hybrids resulting in less hybrids with two introgressions. This is not be a problem in practice, there the parents of the hybrids are homozygous for the Rpi genes and 100% of the hybrids will be heterozygous for both resistance genes Disease Evaluations After transplanting the plants to the main field (clay) on 16 Jun. 2017 the first disease score was done on 20 Aug. 2017. The border lines of the experimental field consisting of hybrids between the original three parental lines (without introgressions) were heavily diseased or already dead. Most of the hybrid offspring plants without Rpi-genes were also heavily diseased but occasionally one or two of the plants did not show severe symptoms and grew surprisingly quite well. The reason for this field resistance is still unknown. Recombination between marker and resistance gene or unknown genomic parts of the wild species donor might result in plants without obvious symptoms. The spontaneous infection gave the most serious damage, this spontaneous infection must be due to a very virulent *Phytophthora* strain or to Genotype x Environment interactions. In August, all plants with one or two Rpi genes did not show symptoms at all three sites (Table 6). Sometimes small leaf damages were visible, but these might have been caused by other pathogens. The results were relatively similar on all three locations, and the plants looked quite uniform per block showing that the level of heterozygosity in the BC2 (vnt1, chc1, tar1) and the BC1 (avl1) parental parents was relatively low. In the August score the disease symptoms of the combined gene combinations vnt1+chc1; tar1+vnt1; avl1+tar1; avl1+chc1; avl1+vnt1 were in general higher than the disease scores in plants with a single resistance gene (Table 6). Unexpectedly, the combined score of the plants with only vnt1 was higher (9.2) than the plants containing vnt1 and chc1. This small difference is probably due to the relatively small number of plants (10-12) in the different groups. Since the results were similar on the three locations (Table 6) we focused on the results of one of the sites and did an additional scoring on 20 Sep. 2017. Most combinations of resistance genes were present. Table 6 shows that the resistance due to avl1 was declining the fastest (score 4.7 on 20 September) but also the resistance of the other plants with only a single Rpi gene declined (7.6, 7.9 and 6.0). The resistance in the hybrids with two Rpi-genes was still high (8.3, 8.0, 7.0, 8.3 and 8.0). The combination avl1/chc1 was still resistant (score 8.3) despite the low scores of the individual parents (scores 4.7 resp. 6.0).

Discussion

To prevent a rapid breakdown of resistances which have been introduced in plant varieties in a long and laborious way a change in the breeding approach is needed. This new approach must lead to a faster development of new varieties, varieties that have not only one resistance gene but a combination of differently acting resistance genes (stacking resistance genes in a single variety). Successful varieties that are only different in their R-gene composition, will make it possible to grow an agronomically identical variety in a monoculture without enhancing the chance on a fast adaption of *Phytophthora*. The introduction of two or more R-genes in a single successful tetraploid variety is possible with genetic modification (Haverkort et al., 2016. Pot Res 59: 35-66). However, in many countries it is still not accepted as a new tool in plant breeding. CRIPR-Cas9 and similar techniques might also be successful to change non-functional resistance genes into functional ones.

Solynta has chosen another approach to make varieties with different sets of resistance genes (Lindhout et al., 2011. Potato Res 54: 301-312; Lindhout et al., 2018. "Hybrid potato breeding for improved varieties". In: Achieving sustainable cultivation of potatoes Vol. 1 Breeding improved varieties. Edt. Burleigh Dodds, Science Publishing, Cambridge, UK. ISBN: 978 178676 100 2; Meijer et al., 2018. Euphytica 214: 121; doi.org/10.1007/s10681-018-2191-6;

Niks et al., Breeding Crops with resistance to diseases and pests. Wageningen Academic Publishers, The Netherlands, 2011). The Solynta approach of potato breeding has many advantages, but for allowing backcross breeding programs the moot important changes are: (a) the transition of tetraploid to diploid commercial varieties; (b) to breed for homozygous diploid lines; (c) to make hybrids; (d) to produce true seeds. The transition to diploids and the introduction of self-compatibility makes it possible to select for homozygous lines that perform well. Then lines can be used in a backcross program. In this study the aim was to introduce known resistance genes to *P. infestans* in existing genotypes via a backcross program. As the development of inbred lines in diploid potato started recently, complete homozygous and fertile diploids lines were not yet available at the start of this research in 2015. Our three backcross parents were 88% homozygous (P1 and P2) and 79% homozygous (P3). Them three lines showed the optimal combination of fertility, self-compatibility and plant vigour, while tuber traits were not taken into account. Other more homozygous plants were less vigorous or not flowering/seed setting and were therefore not chosen. Our studies aimed at generating double stack hybrids as soon as possible. Therefore, we included whole background screening. The percentage recurrent parent in the BC2-individuals of a single BC1 plant (60% homozygous recurrent parent) may vary from 60-90% (FIG. 12). By choosing good growing plants with a high percentage recurrent parent and a relatively small introgression it is possible to obtain highly homozygous BC2 plants with a specific R-gene. One round of selfing of a BC2 plant will give BC281-plants with R-gene homozygous, and eventually rare genomic fragments of the donor parents can still be selected away. By crossing two plants of the same inbred line, each with a different R-gene, double stack hybrids can be made. Eventually hybrids with four or more different R-genes will be feasible.

Two months after planting the presence of all four resistance genes resulted in plants with high levels of resistance (between 8.6 and 10), one month later (20 Sep. 2017) all plants with a combination of resistance genes varied in resistance level between 8 and 9. The only exception was the avl1+vnt1 combination where the resistance level was equal or even lower as the resistance level of vnt1 alone. This indicates that the avl1 doesn't contribute anymore in the resistance level in the combination avl1+vnt1 and avl1 doesn't appear to contribute to durability. The resistance score of the chc1+avl1 combination remained high (8.3) although the values of the individual parents declined (6.0 resp. 4.7). This shows that in this combination avl1 still contributes in making the chc1+avl1 plants more durable resistant.

In this research we showed that in a relatively short period of two to three years it is possible to introgress and to combine different resistance genes to *Phytophthora infestans* in elite, diploid potato lines. This might even be faster if conditions can be optimized in climate rooms to get more generations in a single year. The combination of different resistance genes in a hybrid showed higher levels of resistance than if only a single resistance gene was present. The differences become more pronounced in time and suggest a more durable effect. We showed that in a very directed and fast way it is possible to introgress valuable genes such as resistance genes in diploid potatoes and that these genes can be stacked through hybrid seed production.

Example 6. Expression Analysis of PSC in Germinated Pollen of Diploid SC and SI Potato Plants In order to gain more insight into the genetic basis of the SC and SI phenotypes observed, gene expression (RNA-seq) analysis was performed on pollen of established populations of SC and SI plants, and the RNA-seq reads observed were compared to public data on RNA expression to confirm the gene model (Table 13). Expression was measured in FPKM (Fragments per Kilobase Million). It was established that the observed expression products fully supported the PSC gene model consistent with PGSC0003DMG400016861 as disclosed herein.

Material and Methods

Plant Materials

Genotypes 17SC0011-1096, 18SC0012-0076 and 18SC0012-0180 are self-incompatible diploid F1 progeny belonging to populations 17SC0011 & 18SC0012 and are homozygous for the SI allele of PSC (psc/psc). As noted herein above, there are multiple psc alleles all of which confer a phenotype of self-incompatibility. Genotypes 18SC0012-0151 and 17SC0011-1157 are self-compatible diploid F1 progeny belonging to populations 17SC0011 & 18SC0012 and are heterozygous for the SC allele of PSC (PSC/psc). Populations 17SC0011 & 18SC0012 are described in Example 3.

Climate Chamber Conditions

All plants were grown from in-vitro plantlets in 41 pots containing substrate mix in a climate chamber. The plants were grown under long days, with 18 hours of light produced by fluorescent tubes producing 300 μM $m^{-2}$ $s^{-1}$ of light and 6 hours of darkness. The temperature was set to 20° C. during the day and 18° C. during the night, and the relative humidity was constant at 70%.

Pollen Acquisition and Germination

Pollen from plants 17SC0011-1096, 18SC0012-0076, 18SC0012-0180, 18SC0012-0151 and 17SC0011-1157 was obtained using the methodology described in example 2. After acquisition, the pollen was dried by storing the open Eppendorf tubes with pollen in an air-sealed box containing silica gel for 24 hours at room temperature. Afterwards, the pollen was stored at −20° C. until further use.

The pollen was germinated by suspending 2.5 mg of dried pollen in 5 ml of liquid medium (9% (w/v) sucrose, 50 mg/L Boric acid, 73.5 mg/L $CaCl_2 \cdot 2H_2O$, 118 mg/L $Ca(NO_3)_2 \cdot 4H_2O$, 123 mg/L $MgSO_4 \cdot 7H_2O$) in 3.5 cm diameter petri-dishes sealed with parafilm. The pollen was left to germinate in the petri-dishes for 24 hours in the dark in a shaking incubator at room temperature and shaking at 125 RPM. The liquid medium containing the germinated pollen was then carefully pipetted into 2 ml Eppendorf tubes using pipette tips that were modified to increase the aperture size so as not to damage the pollen tubes. The Eppendorf tubes were then centrifuged at 2500 rpm for one minute and the medium was carefully removed by pipetting. The pellet and some remaining medium was then immediately frozen in liquid nitrogen, two stainless steel beads (2 mm diameter) were added and the samples were grinded using a TissueLyser H (Qiagen GmbH, Hilden, Germany) at 20 Hz for 1 minute.

RNA Extraction

Buffer RLT (Qiagen GmbH) was added to the grinded pollen samples while making sure that the samples remained frozen. RNA extraction was then performed using the RNeasy mini kit according to the manufacturers protocol (Qiagen GmbH, Hilden, Germany). The 250-300 bp insert-size cDNA libraries were sequenced as 150 nt paired-end reads, yielding 30-42 million read-pairs per sample.

Other RNA-Seq Datasets

To create an overview of (tissue-specific) expression levels, all paired-end sequenced RNA-seq datasets tagged as ORGANISM '*Solanum tuberosum*' were downloaded from the public domain (NCBI-SRA, date 2018/17/13), totaling to 441 paired fastq datasets. From these 441 public datasets, 3 were generated from style tissue (SRR7402817-SRR7402819) and all others from various non-pollen tissues, developmental stages and accessions of plants.

Solyntus Reference Assembly

For expression analyses, the recently acquired draft assembly of homozygous reference line Solyntus (version 1.0; plantbreeding.wur.nl/Solyntus/) was used as reference genome. Solyntus is an essentially homozygous variety generated as part of the program of Solynta. This unique genotype is the first potato (*Solanum tuberosum*) genotype, that is highly homozygous, relatively vigorous and self-compatible. The mapping intervals in this study were inferred from the DM v4.03 genome assembly (Sharma et al., 2013, G3: Genes Genomes Genetics 3 (11): 2031-2047) to the Solyntus 1.0 genome assembly by basic similarity searches (using blastn and bedtools) to be located at (Solyntus 1.0 genome assembly coordinates) 53532708-53954293 (Interval I, 421.6 kb←628.9 kb), 53683239-53867377 (Interval II, 184.1 kb←168.7 kb), 53731620-53763003 (Interval III, 31.4 kb←27.4 kb) and 53753977-53763003 (Interval IV, 9.0 kb←12.6 kb), respectively. In between brackets are the consecutive mapping interval number [Solyntus 1.0 coordinates], size in Solyntus-1.0 and size in DM-4.03/4.04, respectively. All intervals are located on chromosome ST4.03ch12_RaGOO (being chromosome 12) and do not contain a single gap in the Solyntus 1.0 assembly. Interval size variation is caused by a multitude of gaps (N's) in the corresponding DM sequence and extensive variation between both genomes. Corresponding intervals on DM genome (DM-4.03/4.04): Interval I: chr12: 58601503-59230363, Interval II: chr12: 58962004-59130723; Interval III: 59016142-59043512; Interval IV: chr12: 59030880-59043512 (Example 3).

Gene annotation on Solyntus 1.0 were inferred from three distinct gene catalogues (potato DM4.03 [above], ITAG4.0 Tomato Genome Annotation Release of Sep. 6, 2019 [Fernandez-Pozo et al., 2015 Nucleic Acids Res. 43: D1036-D1041], and Pepper-v. 1.55 [Kim et al., 2014. Nat Genet 46, 270-278]), which were mapped onto the Solytus assembly by using GeMoMa (v1.6.1). This was done to compensate for imperfections in individual gene catalogues and maximize our awareness of existence of possible genes and/or expressed loci.

RNA-Seq Read-Mapping and Transcript Abundance Quantification

All 5 SC, 3 SI and all 441 public RNA-seq datasets were mapped to the Solyntus reference genome using hisat2 (version 2.1.0). The hybrid gene catalogue obtained using GeMoMa was used for transcript-guided abundance estimation using StringTie (version 2.1.1) with settings -t -c 5 -f 0.05 -G and a GeMoMa concatenated Solyntus1.0 gf file. All observed expression in a 500 kb interval surrounding the PSC locus as a center was evaluated, in which interval a total of 90 (inferred) gene loci are located. We confirmed absence of any noticeable expression in SC samples outside of any of these gene loci. In the 500 kb interval, we indicated the subsequently smaller number of candidates genes when intersecting with our mapping intervals I to IV as defined above.

Confirmation of Haplotype-Specific Expression

From 90 expressed loci in the 500 kb interval, only 8 were expressed above a selected threshold of 20 FPKM in all of the SC/SI samples. We used these sites to measure haplotype-specific (PSC or psc) expression level difference. The expression threshold selected enabled sufficient read depth to eventually and reliably phase the expression into (at most) 2 haplotypes. Together with the PSC locus itself (which lacks expression in SI-plants), these 8+1 loci were haplotyped in each of the 8 samples (SAMtools phase version 1.7, default settings). The resulting haplotyped (paired) fastq files were de novo assembled using SPAdes (version 3.11.1). The resulting contigs were filtered for ample abundance and presumed full-length mRNAs, corresponding to the main (haplotyped) expressed isoform. In some cases, this removed alternatively spliced isoforms, none of which were supported by ample reads to be of any obvious biologically importance. The variation in these haplotyped mRNA sequences was used to (dis)confirm if one or both haplotypes were expressed in each of the corresponding loci/samples.

Results

RNA-seq analyses was conducted on several SC and SI genotypes, and was compared to an elaborate expression catalogue of a multitude of tissues as described above. Apart from three (public) samples from styles tissue, no pollen-related tissue types were among the 400+ public RNA-seq dataset samples. When comparing expression in pollen to this broad expression catalogue, it shows that in the complete 500 kb interval in which PSC is located, expression is remarkably regulated, since expression is different in pollen when compared to any (other) tissue. Many genes being on average expressed in many conditions are fully silent in both SC and SI pollen, and some genes exhibit pollen (and/or styles) specific expression. When comparing expression levels in SC to SI pollen in an interval even subtly larger as our initial mapping interval, only two candidate genes have significant expression difference of 7-fold (PGSC0003DMG400016861, which is psc) and 5-fold (PGSC0003DMG400008625). Fold changes lower than 2 were considered insignificant and thus irrelevant. In both cases, the gene exhibits biologically relevant expression levels in SC pollen only. The 2nd gene (PGSC0003DMG400008625) can be rejected as a candidate for PSC in the second mapping interval (II). Both consecutive recombinant screenings reduced the interval size even further. In the most discrete interval, PSC is the single expressed gene. The results of the RNA-seq studies are summarized in Table 13 and show that PSC expression can be annotated to gene model PGSC0003DMG400016861.

The observation that gene PGSC0003DMG400016861 is PSC, is further strengthened when observing haplotype-specific expression. In none of the SC samples (being PSC/psc) was any heterozygous variant in the RNA observed, as if the plants were homozygous PSC/PSC plants. By restriction analyses (Example 7) we were able to confirm that this was not caused by an (incidental) deletion of psc in these genotypes, showing that the DNA of these plants contains psc (and thus are truly PSC/psc). This finding was further supported by the observation of haplotype-specific expression of adjacent genes. Adjacent genes with sufficient expression were checked, and all (that contain specific variants in any of the exons of the mRNAs) clearly correspond to a mixture of both the PSC and the psc haplotype. From this, we conclude that the many differences between the PSC and psc promotor as listed in Table 1, and discussed in example 1, indeed change the regulation of the PSC protein. The PSC promotor, but not its psc counterpart, enables pollen-specific upregulation, allowing the PSC protein to be expressed in pollen and resulting in the self-compatible phenotype of plants containing the PSC-gene.

Unexpectedly, some PSC haplotype specific expression was detected in two from three SI pollen samples. This was less than 1% of the PSC haplotype specific expression of pollen from SC genotypes. Since all gene expression was from the PSC allele, that is absent in SI genotypes, it was considered that this background expression was due to impurity introduced during the technological process of gene expression studies. We confirmed via the same haplotype specific restriction site analyses (See Example 7) that all these three SI genotypes are psc/psc and thus lack PSC, thereby confirming the consideration that this low level of PSC expression was due to impurity.

Example 7 Haplotype Specific Restriction Site Analyses Using a Novel CAPS Marker

Methods

DNA Extraction, PCR Conditions, Digestion and Gel Electrophoresis.

DNA extraction and PCR was performed using the Phire Plant Direct PCR kit (Thermo Fisher Scientific, Bremen, Germany) according to the manufacturers protocol. PCR amplicons were digested for 2 hours at 37° C. PCR amplicons and restriction fragments were visualized on a 2% agarose gel. Fragment size was determined by comparing to the Generuler™ 1 kb plus DNA ladder (Thermo Fisher Scientific, Bremen, Germany).

Results

To determine the presence of the SC allele of the PSC gene in potato, we developed a CAPS marker in the coding sequence of PSC that can distinguish the SC allele from SI alleles. First, we identified all variation in the PSC locus present in our whole genome sequenced genotypes. Then, we determined which variants are only present in our SC genotypes (Example 4). Based on these results we identified several SNPs that are exclusively present in our SC genotypes (Table 1). We developed a CAPS marker on the SNP 59040898 (a>g, DM>DS). This CAPS marker consists of a primer pair on exon 1 of PSC (Table 14) and the restriction enzyme Eco32I. The primers amplify a 186 bp long amplicon. In the SC PSC allele, an Eco32I restriction site is present that allows digestion of the amplicon into a 92 and a 94 bp long fragment.

Figure 15:
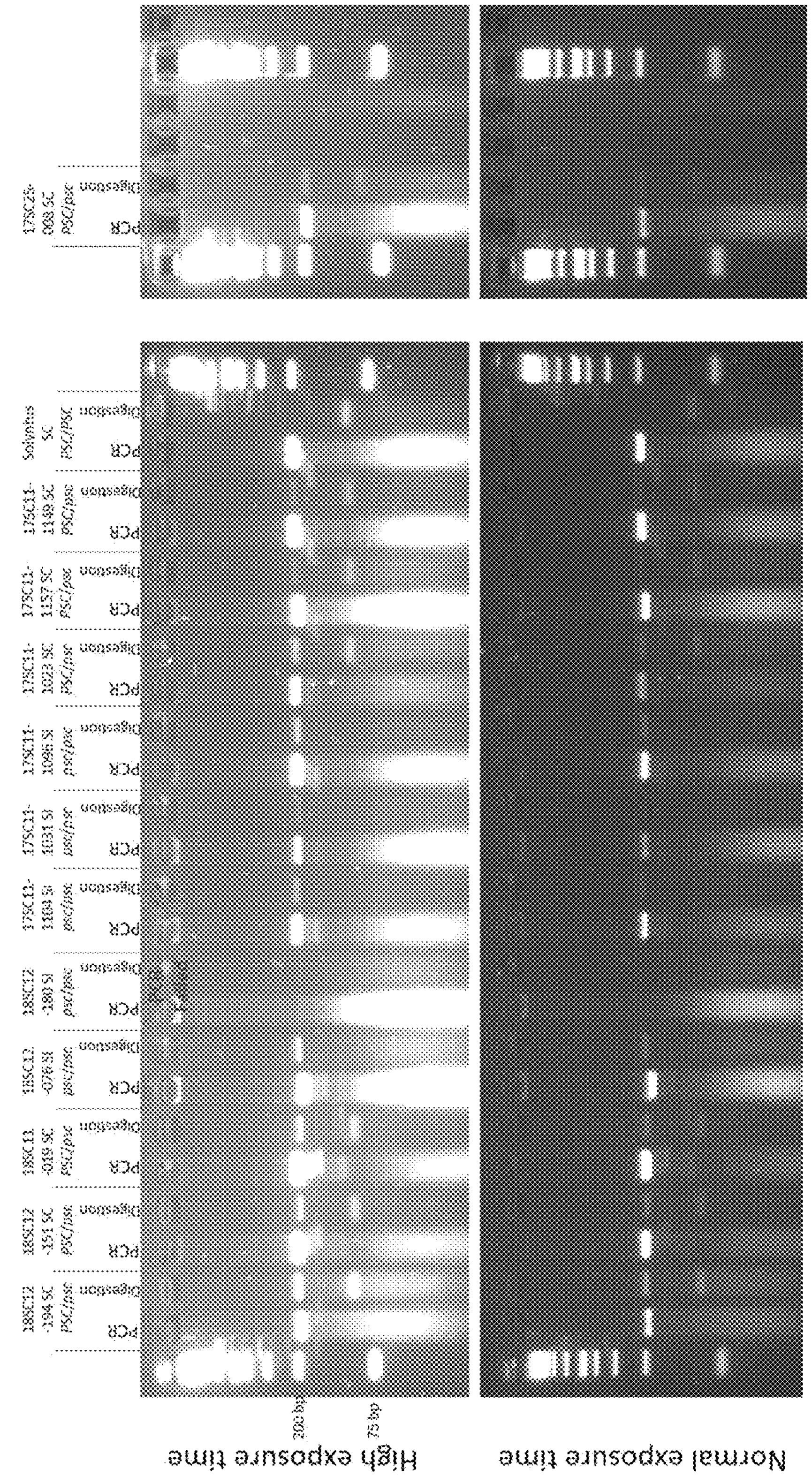
FIG. 15 shows a photograph of an agarose gel representing the result of the CAPS marker experiment as described in Example 7.

We tested this marker on five SI genotypes (psc/psc), seven SC genotypes heterozygous for PSC (PSC/psc) and on one genotype homozygous for PSC (PSC/PSC) (FIG. 15).

While the PCR reaction failed on one SI genotype (18SC12-180), all other genotypes show expected results: PSC heterozygotes show presence of both the original 186 bp amplicon as well as the digestion products (18SC12-194, 18SC12-151, 18SC12-019, 17SC11-1023, 17SC11-1157, 17SC11-1149 & 17SC25-008), psc homozygotes show presence of only the original 186 amplicon (18SC12-076, 18SC11-1104, 17SC11-1031 & 17SC11-1096) and the PSC homozygote shows presence of only the digestion products.

Example 8. Generation of PSC Transgenic Plants

To confirm that SEQ ID NO: 6 is the SC allele of the PSC gene we designed a vector that enables transgenic expression of the SC allele in SI genotypes.

Materials and Methods

Plant Materials

Genotypes 18SC0012-076 and 18SC0012-180 are SI F1 plants from population 18SC0012. Genotype 17SC0011-1104 is an SI F1 plant from population 17SC0011. Populations 18SC0012 and 17SC0011 are described in Example 3.

Design of Expression Construct

We used the sequence of the PSC donor plant DS (Example 2, SEQ ID NO:6) to design the PSC expression cassette. To allow native expression of PSC, we constructed a nucleic acid sequence comprising the native promoter (1563 bp upstream of start codon), the three exons and the native terminator (740 bp downstream of stop codon) (SEQ ID NO: 17). Thus, both introns were removed from the PSC gene of donor plant DS. This sequence was synthesized and cloned into pBINPLUS by Genscript (Genscript Biotech, Leiden, the Netherlands). We refer to the vector containing the PSC insert as pBINPLUS-PSC.

Transformation of pBRNPLUS-PSC into *Agrobacterium tumefaciens*

We transformed the pBINPLUS-PSC plasmid into *A. tumefaciens* strain AGL0 using an electroporation protocol. We took 40 μl of competent AGL0 cells and added 110 μl of ice cold milliQ water. We pipetted 50 μl of this mixture into pre-cooled Eppendorf tubes on ice and added 1 μl of plasmid. We left the cells on ice for 15 minutes and transferred the cells to pre-cooled electroporation cuvettes. We electroporated the mixtures with a Micropulser™ (Bio-Rad Laboratories, Veenendaal, the Netherlands) using the program Ec1 (1.8 kV, 0.1 cm cuvette). We added 1 ml of LB and incubated the cells for 3 hours on a shaker at 28° C. and 200 RPM. Afterwards, we inoculated LB agar plates containing Rifampicin (100 μg/ml) and Kanamycin (50 μg/ml) with the transformation culture. We picked eight colonies from the LB plates and screened for the presence of the construct using M13 primers and insert specific primers. All picked colonies were confirmed to contain the correct vector.

Transformation of SI Potato Genotypes

We transformed genotypes 18SC0012-076, 188C0012-180 and 17SC0011-1104 with pBINPLUS-PSC using the stem explant method described by Visser (Visser, 1991, Plant tissue culture manual. Springer, Dordrecht, pp: 301-309). After regeneration, the shoots were grown on MS20 media containing cefotaxime (200 μg/ml), vancomycin (200 μg/ml) and kanamycin (100 μg/ml). When the shoots reached sufficient length, cuttings were made and grown in MS20 without antibiotics. After two weeks of growing on MS20 without antibiotics, the plants were planted in the climate chamber.

Climate Chamber Conditions

The transgenic plants and non-transformed controls were grown in a climate chamber under the same conditions as described in Example 6.

Microscopy of Self-Pollinated Styles

Pollen tube growth was visualized using the same method as described in Example 2.

Ploidy Analysis

The ploidy of transgenic plants as well as the non-transformed controls was determined using flow cytometry by Plant Cytometry Services (Didam, the Netherlands)

Results

We obtained 34 transformed regenerants from genotype 18SC0012-076, 7 from genotype 18SC0012-180 and 23 from genotype 17SC0011-1104. We made a selection based on shoot size to transfer to the climate chamber. This selection consisted of 5 independently transformed plants derived from 18SC0012-076, 9 independently transformed plants derived from 17SC0011-1104 and 3 independently transformed plants derived from 18SC0012-180. We also planted no *A. tumefaciens* controls from 18SC0012-076 and 17SC0011-1104 that had gone through all steps of the transformation protocol except *A. tumefaciens* inoculation and were grown on MS-20 media without kanamycin. Furthermore, we planted non-transformed controls from all three genotypes that had not undergone the transformation protocol at all. From each independently transformed genotype as well as the controls we planted either 1, 2 or 3 clones.

After growing in the climate chamber for two weeks, we noticed differences in the morphology of the transgenic plants compared to the non-transformed controls. Notably, some transgenic plants displayed enlarged leaves and flowers, leading us to suspect that these plants had become tetraploid. Since tetraploid potato is known to be self-compatible due to the heteroallelic pollen effect, these transgenics cannot be used to confirm the function of PSC (de Nettancourt, 1977, Incompatibility in Angiosperms. Springer-Verlag, Berlin; McClure et al, 2011, Annals of botany 108.4: 647-658).

To determine whether our suspicions were correct, we obtained leaf samples from all plants and had the ploidy level analyzed. While many of the transgenic genotypes were indeed tetraploid (11 out of 17), several were diploid (6 out of 17). Out of the non-transgenic controls only one of the no *A. tumefaciens* control genotype was tetraploid, all others were diploid (Table 15).

Pollen Tube Growth

Figure 18:
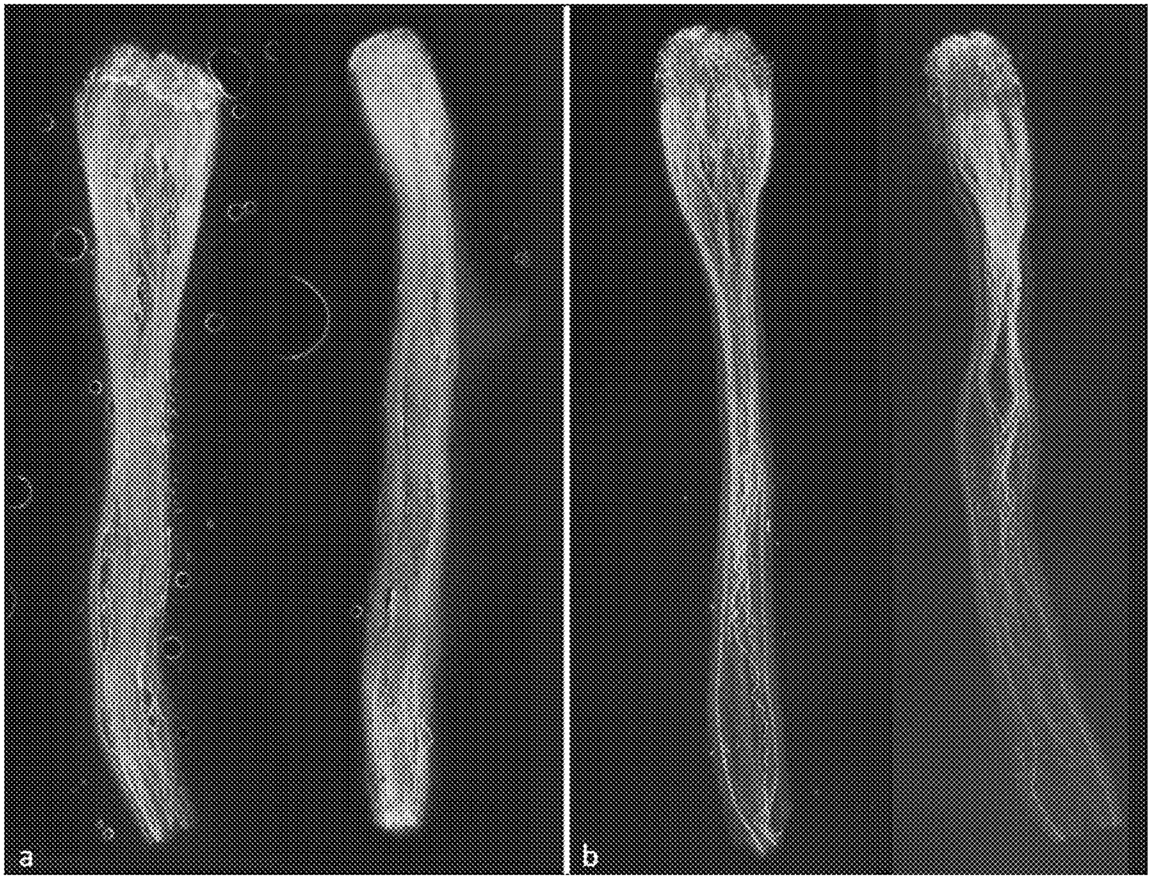
FIG. 18 shows UV microscopic images of styles of potato plants visualizing pollen tube growth in transgenic and non-transgenic potato plants as described in Example 8. A: style of a PSC transgenic derived from genotype 18SC0012-180. B: Style of a plant of the same genotype but non-transformed.

Styles of transgenic and non-transformed 18SC0012-180 were studied by UV microscopy using the method as described in Example 2. In the PSC-transgenic plants (FIG. 18*a*), many pollen tubes penetrated deeply into the styles, whereas in the non-transformed control plants (FIG. 18*b*), pollen tube growth into the styles was severely impaired, as was expected in self-incompatible plants.

We conclude that the PSC-gene is expressed in PSC-transgenic 188C0012-180, and that these plants are successfully transformed into a self-compatible phenotype.

```
                                                    SEQ ID NO: 9
>DM-PGSC0003DMT400043434
        10         20         30         40         50
MDYFLLLPEG CVCDILSFTS PKDVVISSAI SRGFNSAAES DVIWVKFLPD

        60         70         80         90        100
DYEDIISRYV SPRIYPSKKE LYFSLCDFPV LMDGGKLSFS LDKKTGKKCF

       110        120        130        140        150
MISARELAIS WGVDTPWYWE WISHPDSRFS EVAHLKGVSW LDIRGTIGTQ

       160        170        180        190        200
ILSKRTKYVV YLVFKLAKDH DGLEIANAFV RFVNRVSDKD AEERASVVSL

       210        220        230        240        250
VGKRVRRRKR NVKRPRKRVD GWMEIELGNF INDTGDDGDV EARLMEITRL

       260
HGKGGLIVQG IEFRPE*

                                                   SEQ ID NO: 10
>PSC-PGSC0003DMT400043434
        10         20         30         40         50
MDYFLLLPED CVCDILSFTS PKDVVISSAI SRGFNSAAES DVIWVKFLPD

        60         70         80         90        100
DYEDINSRYV SPRIYPSKKE LYFSLCDFPV LMDGGKLSFS LDKKTGKKCF

       110        120        130        140        150
MISARELAIT WGVDTPWYWE WISHPDSRFS EVAHLKGVSW LDIRGTIGTQ

       160        170        180        190        200
ILSKRTKYVV YLVFKLSKNH DGLEIANAFV RFVNRVSDKE AEERASVVSL

       210        220        230        240        250
VGKRVRRRKR NVKCPRKRVD GWMEIELGNF INDTGDDGDV EARLMEITQL

       260
HGKGGLIVQG IEFRPE*
```

TABLE 1

Alterations in PSC region on Chromosome 12 when comparing DM4.04 reference sequence to the PSC sequence (simplified output based on VCF output).

| Position | Reference sequence | PSC sequence |
|---|---|---|
| 59034524 | A | C |
| 59034589 | TA | TATAA |
| 59034594 | G | A |
| 59034609 | ATTGTTTTCTTCTTCCTT<br>GTACTTACATTTGTTGCA<br>CTTGCGTTGAGGGTCTT<br>TCGATAATAACATCCCTA<br>GCCTCCACAAAGTACTA<br>GTAAGGGCTGCGTACAC<br>TCTACCCTCCTTGTTTTC<br>TTCTTCCTTGTACTTACA<br>TTTGTTGCACTTGAGTTG<br>AGGGTCTTT | ATTGTTTTCTTCTTCCTTGTACTTACATTT<br>GTTGCACTTGAGTTGAGGGTCTTT |
| 59034759 | C | T |
| 59034777 | T | C |
| 59034801 | A | G |
| 59034872 | A | G |
| 59034905 | G | A |
| 59034922 | ATTTTTTT | ATTTTTTTT |
| 59034959 | C | T |
| 59035033 | CGACCCCACTTGTGGAA<br>TTTCACCAGATATGTTGT<br>TGTTATTGTTATAAGGAC<br>AAGCTTCGGTCTTAAAG<br>CTCGATAAACTCATTTT<br>TTCTTTTGCACTCCCTCT<br>TTTCTTAAGTACACTTCA<br>CTCTCAATTCTTTCTTGA<br>GCACACACTCTTTATTTG<br>AGTAAACATACAACTCAA<br>ATGATCACCTCTATT | C |
| 59035292 | G | T |
| 59035317 | G | T |
| 59035351 | G | A |
| 59035362 | G | T |
| 59035410 | AC | ACC |
| 59035452 | C | T |
| 59035501 | T | G |
| 59035545 | T | C |
| 59035645 | CCT | CCTAGCT |
| 59035693 | T | G |
| 59035697 | G | A |
| 59035706 | CTT | CTT |
| 59035721 | G | T |
| 59035727 | TCTTTGGACCACCATGTTC<br>ATCAAATACCAGATTTCTT<br>ATATCCTATTAGTGATAGG<br>AATACGAAGGGATATAGGA | TCT |

TABLE 1-continued

Alterations in PSC region on Chromosome 12 when comparing DM4.04 reference sequence to the PSC sequence (simplified output based on VCF output).

| Position | Reference sequence | PSC sequence |
|---|---|---|
| | TTTCGATTGAGCCTTCTTG TATAACAACTCTACAATAA TGATAAAGTAGGTATTAGC TCGCTCTAACAGCT | |
| 59036043 | G | A |
| 59036051 | G | A |
| 59036066 | G | C |
| 59036067 | G | A |
| 59036093 | T | C |
| 59036105 | G | T |
| 59036129 | G | A |
| 59036182 | T | C |
| 59036203 | G | C |
| 59036257 | T | C |
| 59036283 | T | G |
| 59036344 | A | G |
| 59036364 | T | C |
| 59036378 | C | A |
| 59036390 | C | T |
| 59036403 | A | T |
| 59036442 | G | A |
| 59036489 | T | G |
| 59036516 | C | T |
| 59036535 | G | A |
| 59036612 | A | ATC |
| 59036614 | A | T |
| 59036627 | C | T |
| 59036629 | C | T |
| 59036631 | A | G |
| 59036647 | C | G |
| 59036667 | ATTTTTT | ATTTT |
| 59036680 | G | A |
| 59036695 | G | A |
| 59036700 | T | A |
| 59036732 | C | T |
| 59036735 | G | A |
| 59036738 | C | T |
| 59036744 | A | G |

TABLE 1-continued

Alterations in PSC region on Chromosome 12 when comparing DM4.04 reference sequence to the PSC sequence (simplified output based on VCF output).

| Position | Reference sequence | PSC sequence |
|---|---|---|
| 59036760 | G | A |
| 59036761 | A | C |
| 59036764 | AAT | A |
| 59036767 | T | G |
| 59036790 | A | G |
| 59036793 | C | T |
| 59036811 | T | C |
| 59036819 | T | C |
| 59036831 | T | A |
| 59036832 | A | T |
| 59036844 | A | G |
| 59036873 | T | A |
| 59036881 | C | A |
| 59036970 | C | A |
| 59037015 | T | C |
| 59037023 | A | G |
| 59037030 | A | G |
| 59037040 | T | C |
| 59037047 | AGG | AG |
| 59037058 | ACC | AC |
| 59037072 | T | A |
| 59037084 | A | G |
| 59037105 | C | T |
| 59037123 | C | T |
| 59037126 | T | A |
| 59037127 | G | T |
| 59037159 | G | A |
| 59037167 | A | G |
| 59037188 | G | A |
| 59037199 | AAAA | AAAATAAA |
| 59037205 | G | A |
| 59037206 | G | A |
| 59037215 | G | T |
| 59037229 | CAAAA | CAAA |
| 59037251 | C | T |
| 59037327 | A | G |
| 59037369 | C | T |

TABLE 1-continued

Alterations in PSC region on Chromosome 12 when comparing DM4.04 reference sequence to the PSC sequence (simplified output based on VCF output).

| Position | Reference sequence | PSC sequence |
|---|---|---|
| 59037370 | G | A |
| 59037375 | G | A |
| 59037386 | C | T |
| 59037406 | A | G |
| 59037420 | AAAGGCA | AA |
| 59037442 | C | T |
| 59037450 | C | T |
| 59037481 | A | T |
| 59037498 | CTT | CT |
| 59037518 | AAAAAATAAAAAAGTACA AAAAATGAAACATCAAG AAAGATATAGCCAGTGA ACAATGAATTGATTGAAA A | AAAAA |
| 59037592 | T | A |
| 59037605 | T | A |
| 59037607 | T | A |
| 59037616 | G | A |
| 59037617 | C | T |
| 59037628 | A | AC |
| 59037630 | T | C |
| 59037643 | TC | T |
| 59037645 | G | T |
| 59037652 | C | T |
| 59037663 | A | G |
| 59037668 | A | G |
| 59037673 | C | T |
| 59037681 | G | C |
| 59037686 | C | T |
| 59037688 | T | A |
| 59037694 | A | ATGAC |
| 59037695 | AGTT | A |
| 59037702 | T | A |
| 59037703 | T | A |
| 59037704 | G | A |
| 59037706 | ATCTCCT | AT |
| 59037716 | C | A |
| 59037721 | AATTA | AA |

TABLE 1-continued

Alterations in PSC region on Chromosome 12 when comparing DM4.04 reference sequence to the PSC sequence (simplified output based on VCF output).

| Position | Reference sequence | PSC sequence |
|---|---|---|
| 59037730 | G | A |
| 59037734 | CA | CAAA |
| 59037738 | T | A |
| 59037742 | A | G |
| 59037746 | A | T |
| 59037750 | A | T |
| 59037758 | A | AG |
| 59037775 | T | C |
| 59037782 | T | TC |
| 59037784 | C | A |
| 59037788 | G | T |
| 59037809 | GT | GTT |
| 59037811 | A | T |
| 59037828 | T | G |
| 59037831 | C | T |
| 59037853 | C | A |
| 59037857 | CA | CAA |
| 59037860 | T | A |
| 59037880 | A | T |
| 59037893 | TC | TCC |
| 59037896 | T | C |
| 59037910 | G | A |
| 59037935 | A | AGT |
| 59037936 | ACC | A |
| 59037942 | T | G |
| 59037945 | C | G |
| 59037948 | G | T |
| 59037959 | A | C |
| 59037975 | A | G |
| 59037982 | T | C |
| 59037990 | T | G |
| 59038010 | T | C |
| 59038034 | GATATA | GATA |
| 59038048 | A | G |
| 59038067 | C | T |
| 59038070 | C | A |
| 59038087 | G | T |

TABLE 1-continued

Alterations in PSC region on Chromosome 12 when comparing DM4.04 reference sequence to the PSC sequence (simplified output based on VCF output).

| Position | Reference sequence | PSC sequence |
|---|---|---|
| 59038091 | C | A |
| 59038135 | G | A |
| 59038162 | T | C |
| 59038180 | G | A |
| 59038206 | C | CA |
| 59038207 | T | A |
| 59038213 | AT | A |
| 59038219 | A | G |
| 59038222 | AT | A |
| 59038227 | T | A |
| 59038228 | G | A |
| 59038240 | T | C |
| 59038273 | G | T |
| 59038274 | G | A |
| 59038283 | A | G |
| 59038329 | C | A |
| 59038367 | G | A |
| 59038434 | G | A |
| 59038473 | G | A |
| 59038506 | A | T |
| 59038532 | A | G |
| 59038569 | T | C |
| 59038576 | T | C |
| 59038589 | T | A |
| 59038618 | G | A |
| 59038686 | T | A |
| 59038698 | C | A |
| 59038814 | T | C |
| 59038826 | C | T |
| 59038866 | T | C |
| 59038875 | ATCT | ATCTCT |
| 59039003 | G | C |
| 59039039 | G | A |
| 59039060 | T | C |
| 59039073 | A | G |
| 59039103 | A | G |

TABLE 1-continued

Alterations in PSC region on Chromosome 12 when comparing DM4.04 reference sequence to the PSC sequence (simplified output based on VCF output).

| Position | Reference sequence | PSC sequence |
|---|---|---|
| 59039108 | T | C |
| 59039115 | G | A |
| 59039118 | A | G |
| 59039119 | A | T |
| 59039123 | T | C |
| 59039132 | GTCAATT | GT |
| 59039139 | TAGAA | TA |
| 59039156 | G | A |
| 59039208 | A | T |
| 59039266 | A | G |
| 59039290 | T | A |
| 59039301 | AG | A |
| 59039303 | TAC | T |
| 59039312 | G | A |
| 59039325 | C | T |
| 59039379 | C | T |
| 59039429 | G | A |
| 59039485 | G | A |
| 59039489 | T | C |
| 59039492 | G | A |
| 59039555 | A | C |
| 59039561 | A | G |
| 59039582 | T | C |
| 59039620 | C | T |
| 59039626 | C | A |
| 59039726 | T | A |
| 59039744 | A | G |
| 59039758 | A | C |
| 59039764 | A | T |
| 59039769 | C | T |
| 59039777 | T | C |
| 59039796 | A | T |
| 59039805 | T | A |
| 59039844 | CTTTT | CTTT |
| 59039881 | T | C |
| 59039888 | A | G |
| 59039889 | C | T |

TABLE 1-continued

Alterations in PSC region on Chromosome 12 when comparing DM4.04 reference sequence to the PSC sequence (simplified output based on VCF output).

| Position | Reference sequence | PSC sequence |
|---|---|---|
| 59039902 | T | TATATATCTTTTA |
| 59039907 | A | G |
| 59039909 | C | T |
| 59039945 | A | G |
| 59040009 | T | A |
| 59040029 | CGTAGTA | CGTAGTACATACATAAAAAAAAAGAATAA CTTTTTATATGTAGTA |
| 59040060 | G | A |
| 59040107 | A | T |
| 59040171 | G | A |
| 59040218 | TTATA | TTATATATA |
| 59040247 | T | TCA |
| 59040248 | G | C |
| 59040255 | G | A |
| 59040259 | G | T |
| 59040310 | G | A |
| 59040329 | G | T |
| 59040351 | T | C |
| 59040361 | G | T |
| 59040370 | C | G |
| 59040383 | T | G |
| 59040457 | G | A |
| 59040475 | T | TTAAACA |
| 59040479 | C | CTCAATTCCTAAG |
| 59040508 | G | T |
| 59040560 | C | T |
| 59040563 | G | A |
| 59040567 | G | A |
| 59040568 | G | A |
| 59040624 | ATT | ATTTT |
| 59040654 | A | T |
| 59040702 | AAAGAA | AAA |
| 59040730 | C | A |
| 59040731 | G | A |
| 59040748 | A | C |
| 59040752 | TAAAA | TAA |
| 59040766 | A | AG |

TABLE 1-continued

Alterations in PSC region on Chromosome 12 when comparing DM4.04 reference sequence to the PSC sequence (simplified output based on VCF output).

| Position | Reference sequence | PSC sequence |
|---|---|---|
| 59040775 | A | G |
| 59040896 | A | T |
| 59040898 | A | G |
| 59041034 | C | T |
| 59041085 | A | T |
| 59041093 | ATTTTTTTTT | ATTTTTTTT |
| 59041103 | G | C |
| 59041149 | CT | CTT |
| 59041151 | CAT | CATAT |
| 59041159 | A | G |
| 59041168 | G | GCAGGGGCGGCTCAACGTATTTGGAGG CCTAAAACAAAATTTAAATTAAAGGCCTA AAATCTTTTAGCTGAGGCAATTATTAAAT AAATTGTTAACATTATTCTATAAGTAATA AGTTGACAAAACTGCTTATAAACTTCTTT TTTTATTTAAAAGCACATAACATAAGTCA ATCTAAACAGGCTTGTAATTCGCTTTATC CAACACATTAGTTTTACTATTGATTCATA TTTTTGATAGAGCTCTAACTTACATAGAG TATAAAAGGGGTATAGAAAATTACAACG CGAGAGTAAGTGAAGAGAGTGTAAGAA GACAAAACAACGTTTTTCTTGATTTCTTC TATTTGATTGAGGTTAAGGAGAATAAAAT AATATATATATGAAAAGTACATTTATCTT AAATAATTAATTTTTTCTATAAAAAAAATT AACACATAATTTATTGTTGGTAAAAATTT GAGGCCCCCCTAAAATTGGGGGCCTAA GGCATATGCCTAATTTTTATAAGCATTGA GCCGGCACTGCGGTTAAA |
| 59041177 | C | T |
| 59041213 | A | T |
| 59041214 | GAAAAA | GAAAA |
| 59041228 | G | A |
| 59041230 | G | T |
| 59041236 | A | G |
| 59041243 | T | C |
| 59041247 | G | C |
| 59041261 | TG GG | TGG |
| 59041281 | T | C |
| 59041344 | TT | TTTTATTTTTAAAAAAAT |
| 59041409 | T | A |
| 59041413 | TAAA | TAAAA |
| 59041430 | ATTT | ATT |
| 59041472 | ATATTATT | ATATT |
| 59041483 | C | A |

TABLE 1-continued

Alterations in PSC region on Chromosome 12 when comparing DM4.04 reference sequence to the PSC sequence (simplified output based on VCF output).

| Position | Reference sequence | PSC sequence |
|---|---|---|
| 59041485 | AACA | AA |
| 59041490 | A | ACT |
| 59041516 | AC | A |
| 59041524 | T | G |
| 59041526 | T | C |
| 59041531 | CTTTTTTT | CTTTTT |
| 59041539 | G | A |
| 59041545 | G | T |
| 59041547 | G | A |
| 59041561 | T | C |
| 59041563 | A | T |
| 59041568 | GATTCATCATTGGGTATTC | GATTC |
| 59041610 | C | T |
| 59041696 | C | G |
| 59041719 | A | G |
| 59041727 | CA | C |
| 59041737 | CATCTTTGATGA | CA |
| 59041819 | A | G |
| 59041820 | TAAAA | TAA |
| 59041831 | T | G |
| 59041861 | TG | TGG |
| 59041872 | GA | GAA |
| 59041886 | C | A |
| 59041923 | T | C |
| 59041999 | A | C |
| 59042015 | C | T |
| 59042132 | CACAGAA | CACAGAAAAATGAACTTGAAATTCATAAAAAATAATAATAATAACAGAA |
| 59042144 | A | C |
| 59042158 | A | T |
| 59042190 | C | T |
| 59042191 | A | G |
| 59042302 | C | T |

TABLE 2

Development of BC1 plants (last column) with one of four Rpi genes with a recombination event close to the Rpi gene and a high level of recurrent parent. These BC1 plants have been chosen to make BC2 plants.

| | Number of F1 seeds | Number of F1 plants with Rpi-gene | No. of chosen BC1 plants | No. of BC1 plants used for making BC2 |
|---|---|---|---|---|
| SOL015-0047 × *S. avilesii* 478-2 (avl1) | 461 | 80 out of 184 | 31 | 7 |
| SOL015-0047 × *S. tarinjense* 852-5 (tar1) | 370 | 35 out of 79 | 67 | 5 |
| SOL015-0047 × *S. chacoense* 543-5 (chc1) | 185 | 5 out of 13 | 0 | — |
| SOL015-0047 × *S. venturii* 283-1 (vnt1) | 2 | 0 out of 1 | — | — |
| SOL015-0044 × *S. avilesii* 478-2 (avl1) | 0 | — | — | — |
| SOL015-0044 × *S. tarinjense* 852-5 (tar1) | 218 | 14 out of 30 | 0 | — |
| SOL015-0044 × *S. chacoense* 543-5 (chc1) | 0 | — | — | — |
| SOL015-0044 × *S. venturii* 283-1 (vnt1) | 44 | 14 out of 24 | 30 | 4 |
| SOL015-0097 × *S. avilesii* 478-2 (avl1) | 27 | 0 out of 15 | — | — |
| SOL015-0097 × *S. tarinjense* 852-5 (tar1) | 446 | 127 out of 333 | 58 | 5 |

TABLE 2-continued

Development of BC1 plants (last column) with one of four Rpi genes with a recombination event close to the Rpi gene and a high level of recurrent parent. These BC1 plants have been chosen to make BC2 plants.

| | Number of F1 seeds | Number of F1 plants with Rpi-gene | No. of chosen BC1 plants | No. of BC1 plants used for making BC2 |
|---|---|---|---|---|
| SOL015-0097 × *S. chacoense* 543-5 (chc1) | 63 | 7 out of 19 | 67 | 5 |
| SOL015-0097 × *S. venturii* 283-1 (vnt1) | 27 | 6 out of 13 | 63 | 5 |

TABLE 3

Development of BC2 plants (last column) with a Rpi gene, a small introgression and a high level of recurrent parent. These BC2 plants have been used to make hybrids.

| | No. of BC2 plants with small introgression | No. of plants with additionally a high % recurrent parent |
|---|---|---|
| SOL015-0047 × *S. tarinjense* 852-5 | 43 | 12 |
| SOL015-0097 × *S. tarinjense* 852-5 | 20 | 11 |
| SOL015-0097 × *S. chacoense* 543-5 | 46 | 21 |
| SOL015-0097 × *S. venturii* 283-1 | 16 | 11 |

TABLE 4

Eleven different hybrids based on BC1 × BC2 and BC2 × BC2 crosses. The germination rate and the segregation ratios in the offspring of the different gene combinations are shown.

| | Parental plants of hybrids | Hybrids sown | Germination | No Rpi gene | Avl1 | Tar1 | Chc1 | Vnt1 | Tar1 + Vnt1 | Avl1 + Chc1 | Avl1 + Tar1 | Avl1 + Vnt1 |
|---|---|---|---|---|---|---|---|---|---|---|---|---|
| 1 | SOL015-0097 + chc1 (BC2) × SOL015-0047 + avl1 (BC1) | 416 | 50% | 74 | 45 | | 58 | | | 31 | | |
| 2 | SOL015-0097 + avl1 (BC1) × SOL0097 + vnt1 (BC2) | 416 | 77% | 98 | 71 | | 89 | | | 61 | | |
| 3 | SOL015-0097 − tar1 (BC2) × SOL015-0047 + avl1 (BC1) | 416 | 59% | 94 | 34 | | 70 | | | 48 | | |
| 4 | SOL015-0047 + avl1 (BC1) × SOL015-0097 − tar1 (BC2) | 283 | 72% | 87 | 35 | 37 | | | | | 44 | |
| 5 | SOL015-0047 + avl1 (BC1) × SOL015-0097 − tar1 (BC2) | 133 | 28% | 18 | 5 | 6 | | | | | 8 | |
| 6 | SOL015-0097 − tar1 (BC2) × SOL015-0047 + avl1 (BC1) | 416 | 94% | 139 | 87 | 103 | | | | | 64 | |
| 7 | SOL0097 + vnt1 (BC2) × SOL015-0047 + avl1 (BC1) | 416 | 81% | 123 | 75 | | | 65 | | | | 69 |
| 8 | SOL015-0047 + avl1 (BC1) × SOL0097 + vnt1 (BC2) | 121 | 78% | 36 | 22 | | | 23 | | | | 13 |
| 9 | SOL015-0047 + avl1 (BC1) × SOL0097 + vnt1 (BC2) | 295 | 56% | 50 | 34 | | | 47 | | | | 34 |
| 10 | SOL015-0047 − tar1 (BC2) × SOL0097 + vnt1 (BC2) | 59 | 20% | 3 | | 3 | | 5 | 1 | | | |
| 11 | SOL015-0047 − tar1 (BC2) × SOL0097 + vnt1 (BC2) | 357 | 55% | 37 | | 42 | | 62 | 55 | | | |

TABLE 5

Segregation ratio's in eleven different hybrids coming from BC1 × BC2 and BC2 × BC2 crosses. The expected segregation ratio is 1:1:1:1.

| Hybrids/Rpi genes | None | avl | chc, tar or vnt | Combination of two Rpi genes |
|---|---|---|---|---|
| avl and chc combination (Hybrid 1) | 266 | 150 | 217 | 140 |
| avl and tar combination (Hybrids 3, 4, 5, 6) | 244 | 127 | 146 | 116 |
| avl and vnt combination (Hybrids 2, 7, 8, 9) | 209 | 131 | 135 | 116 |
| | | tar | vnt | |
| tar and vnt combination (Hybrids 10, 11) | 40 | 45 | 67 | 55 |

TABLE 6

Average scores on a scale of 0 (dead) to 10 (completely resistant) per plot with different combinations of Rpi genes.

| Rpi composition | Wijster 20 Aug. | Hoge Born 21 Aug. | Haarweg 22 Aug. | Haarweg 20 Sept. |
|---|---|---|---|---|
| — | 1.8 | 5.0 | 5.3 | 2.7 |
| avl1 | 8.7 | 8.9 | 9.7 | 4.7 |
| avl1 + chc1 | 9.7 | 9.8 | 10.0 | 8.3 |
| avl1 + tar1 | 10.0 | 10.0 | 9.7 | 8.0 |
| avl1 + vnt1 | 9.5 | 9.8 | 10.0 | 7.0 |
| tar1 | 9.0 | 9.1 | 9.2 | 7.6 |
| tar1 + vnt1 | 9.6 | 9.6 | 10.0 | 8.3 |

TABLE 6-continued

Average scores on a scale of 0 (dead) to 10 (completely resistant) per plot with different combinations of Rpi genes.

| Rpi composition | Wijster 20 Aug. | Hoge Born 21 Aug. | Haarweg 22 Aug. | Haarweg 20 Sept. |
|---|---|---|---|---|
| vnt1 | 9.2 | 8.6 | 9.6 | 7.9 |
| vnt1 + chc1 | 9.0 | 9.5 | 10.0 | 8.0 |
| chc1 | 9.0 | 7.3 | 9.5 | 6.0 |

TABLE 7

Original diploid parents of breeding lines DS (Hosaka and Hanneman, 1998. Euphytica 103: 265-271), D1 and D16 (Hutten et al., 1994. Thesis, Wageningen University, Wageningen, ISBN 9054852925). Homozygosity levels were calculated based on assays with the 20k potato array of Vos et al., 2015. 2015. Theor Appl Genet 128: 2387-2401).

| Abbreviation | Plant Code | Pedigree | Short description |
|---|---|---|---|
| DS | IVP07-1004-2 | 5H130-5 (S7) Selfings | Sli-gene, fertility, inbreeding tolerance, homozygosity level: 99% |
| D1 | IVP97-079-9 | IVP92-053-1 × IVP92-027-9 | yellow flesh, Qcook (Quality cooking), homozygosity level: 78% |
| D16 | IVPAA134-16 | BE 1042 × SH 76-128-1857 | Early, round, yellow, homozygosity level: 79% |

TABLE 8

SNP markers used for screening for presence of the different Rpi-genes and for introgression size. SNP marker names were based on the Chromosome's number and position on the PGSC *S. tuberosum* group Phureja DM1-3 Pseudomolecules (v4.03).

| SNP | Flanking sequence | SNP | Re-current parent | R-gene haplo-type |
|---|---|---|---|---|
| SOT09-46180085 | GCCTGCAGGAATTGAAGCTAAGTATATTATGCGGACTCCACGAGACTGGGACAGGTTCATGAG ATTTATGGAGCG[A/G]TATGCTAATTCAAATGGCTTGCAATTTGTTAAAAGTTGAGATTATA TTGTATGTTTTCTTTTGCCTCGCCAATTT | [A/G] | G | A |
| SOT09_49453657 | GCTAAGACGACGCCAGCTAAGGTTGCAAAGACAGCTACCAGAACGACTCCAAGTCGGAAAGCT GCACCAAAGGCA[A/G]CACCTGCCAAAAAGGAGCCGGCTAAGAAGGCACCTGCGAAGAACGT GAAGTCGCCGGTGAAGAAGGCTACCCCAA | [A/G] | A | G |
| SOT09-50367159 | TTTCTTATCTCCTGTTTTACAACCATAACCACAAGAACCACAATAATGATTCTCTGAAGAATT TCTTGGTATTTT[A/C]TCAACCTTCAAACCAAGATTTTCACACCCTTTTCGTATTACTTGAT TCTGAAGTCCTTCCTCAGAGCAATTCTCT | [A/C] | C | A |
| SOT09_50367228 | TGCAGTACATCCAGTCAAGATAACGGCGCCTGCATTAACAGCATCGACAAGCCAAGTGGAATC AGTCCCTTTCTT[A/G]TCTCCTGTTTTACAACCATAACCACAAGAACCACAATAATGATTCT CTGAAGAATTTCTTGGTATTTTATCAACC | [A/G] | G | A |
| unt1 | | | | |
| SOT09-52799014 | AAGTACTGTCTCCGGCTTACCGGAAGCAAAACCCTTGCGCACAAAAGGCCCAACATCTTCACC GTTGCAGATGGC[A/G]GCGGATAAGAGGACTTGGTCAAATTTGTCGGCGGAGTCTCCGTTTT CTACCGCCGGAACAACTTTCCGGCGCATC | [A/G] | A | G |
| SOT9-54060817 | ACCTTTTCAAAATTTGCTCAACCAAACACTCTGAAACAACAAATCTGCTTTTATTCAATGCAT CCACAACAGCAT[T/C]GGGTGATTTGAAATTAAACCTCAGTACTTTGCTGATCTTATCAACA TCGTTTTCCGTCAAATCACTTGCCAAACT | [T/C] | T | C |
| SOT09_54548387 | AGAGGATCTAGCAAAGTCTTGTTCTAGCTCGGACCTTGACAAGAAACAATCTGAATCTCGTAT CCTGAAACTTCT[T/C]GTTTCTATTTATCGTTGGTGTACTGAGAAGGATCCAAACGACCGTC CCACAGCAGAGAACCTCTACAACCTCTTA | [T/C] | C | T |
| SOT10-46118085 | CCTCTCATTAAAACTCGAATAACTATAGTTAAATCTGCCTCTATATAGTGATTTATAGTTTCA ACAGGAAGTAGT[A/G]ACAAAAGTTGGCCTAAGGAAAAAAGGAGGATCCCAAGCATAAGAGA AGTTGACAGTATTCTTTCCTGGTATGATA | [A/G] | G | A |

TABLE 8-continued

SNP markers used for screening for presence of the different Rpi-genes and for introgression size. SNP marker names were based on the Chromosome's number and position on the PGSC *S. tuberosum* group Phureja DM1-3 Pseudomolecules (v4.03).

| SNP | Flanking sequence | SNP | Re-current parent | R-gene haplo-type |
|---|---|---|---|---|
| SOT10-47116772 | AGTTCTCCCTGCAATATACTATCTAACAATGATGCTCGAACCAATGAAGGATCAGCACTGGAA CTTGTTGAAGAA[T/C]TGGTTTTCATAGACTTGGAAATTGAACTCCCAGACCCACTCGACCT CTCAGGTTGGTTGTCTGCCCTCTGGTATG | [T/C] | T | C |
| SOT10-50782097 | AATAATATTATTATTATTATGATCTCTTCCTATCTGATGATTTTGTGGTTCAAATCCATCACC AAACATGAATCC[G/C]TCGTTATTTGCATCGATACCAAAACGTCGTGCTGCATTTCTGGGGA AAGACTCCGATGATAAACCCCCAATTCCA | [G/C] | G | C |
| SOT10-52167709 | AAGGGAGGTCAGAGTTCAGCTGATACCGGGCAAATGCCTTGGTAATTTCTCCTCCAGCAATAC TGGCACTTCGAA[T/C]GGACATTTGATCATTTTTGAGTTCCTTCTCTGACATGCTTTGGGTT TCCCAAGGTTTAGCACCCATCCATCGATC | [T/C] | C | T |

tar1 and chc1
_____

| SNP | Flanking sequence | SNP | Re-current parent | R-gene haplo-type |
|---|---|---|---|---|
| SOT10-54199691 | ACTGAGATCTTCCTGTGGATTTTCTCATGATGCAAAAGATTATAGGAAAGAAGTTACAAGTGC TTCAAACAAAAC[T/C]GGTCCTCCTTTGAATTGTAGCAACATCAACCATAAATCAAATGTTA TTGGTTCTAGTCCTGGCCAACACCGACAT | [T/C] | C | T |
| SOT10-55698400 | TGAATCTGGTTTTCTTCGATCAGAAAGACTATTACAAGATGAAAGCATTTCAGGAGGTCTCCA CAAGCTGTCTCA[T/C]AACCCCCATGAACGGTATGTTAAGTCAGCAAACCATAGTCCCCGCT CTTCTCCACGATTTTCCATTAAGCCATTC | [T/C] | C | T |
| SOT10-56448463 | GGCTTTGCGTGTTCGTGACAAGGACTCACAAACTCTAATGCCCGGAACAGCTAAATCTGGTGC AGAGTACTTCGC[A/C]ACTAGGTCATATCACGGCCTTGACATTCATCCTGAAAATAATTTCT CCGAGCCGTTTTTGATTGGTAAAAGTGGG | [A/C] | A | C |
| SOT10_58620886 | ATACTCCCATGATTGGACTGAATGTCCATTTGTCCATCCAGGTGAAAATGCTCGAAGAAGAGA TCCAAGAAAGTA[T/C]CACTACAGCTGTGTACCTTGCCCTGAGTTCCGCAAGGGAGCTTGCA GACGAGGGGACATGTGTGAATATGCTCAT | [T/C] | T | C |
| SOT11-00597066 | CTAATACATCGACGACTTATTGTAGGTTCAAAATGCAAAGCTTGAGATCATCTATTCTGAAGT ATGTGCGGGTTA[G/A]GGTCCCATTGCAAGTATCATTATCTCAAGCTGAAGGCCGGAGTGCG TTAAATATACTCAATTTGCAAATACGCAC | [A/G] | G | A |
| SOT11-00761409 | ATGTGGCAACTGGGAACACTCAAATTTGGACAAAAATGCTCCACCAAACTTTGTCAAATCAGT GAATGGCATCTC[A/G]GCGTGAACAGCAATAGTGTTGCCAGGAATGCTCCTTTCATCTGGAC CAGACTGAGCCAAAAATAACTGTAAGGCA | [A/G] | G | A |

av11
_____

| SNP | Flanking sequence | SNP | Re-current parent | R-gene haplo-type |
|---|---|---|---|---|
| SOT11-01776687 | GAAAAGCTTTTCAACTACATCGTTCCAGTTAGTTCTTGCATCGGTGGAATGGCTTGTACTTGT GGATGCATCTTC[G/T]ATAAGAGAAGCCGTCTCTGTTACTCCTCGCGCTGATTCTTCCTCTT TATGTACTGATAGTTCCTCATCTGTGTCT | [G/T] | G | T |
| SOT11-01859231 | TCGGGTGAAAAGTGGAGTTGGAATTACCTATGAGTTTACTGAAGACGAACTGGATAATATGGC GTTATCAGAGCG[A/G]ATGCAGCTATACTCTAAGAGAAGGGCTCCTTCATTCAAGATAGGTA GAGTTGTAGAGTGCTCAAGCAAAATAGCT | [A/G] | G | A |
| SOT11-02259927 | TGTCGACGAGTACGAGACCGGTGTTAACGTCGCCGGAGAGAAGCAGCGATTCATCTTCCTCCA CCGGAATCTCAC[T/C]CTTCAGTAAGTCAATCGCCGCCTCTTGCGCCACCGTTCCCATCACT GATTTTTTTATTTGTCTTCTCCTTCTTTC | [T/C] | T | C |
| SOT11-03155246 | TTAATCTTCTTTCCCATGTTTTACTTGTCCGCCTTTTAAGAATCTCATGAACCAGTAAGCAGA AGATTTCAGATG[T/C]CGGGTTAGCCCATTCTTGAAGTCCACATATGTCAGACCGAAGCGTT TTGTATAACCAAGATTCCATTCAAAGTTA | [T/C] | T | C |

TABLE 9

SNP markers used for calculating percentage recurrent parent in the BC1 and BC2 plants. SNP marker names were based on the Chromosome's number and position on the PGSC *S. tuberosum* group Phureja DM1-3 Pseudomolecules (v4.03).

| SNP | Flanking sequence |
|---|---|
| SOT01-02505120 | AGCATAATGAAGTTTCGCCAAATGCATACACGCCATTGAATACGCATCTCTCCATATAGG[T/C] ACAACCGAATGCCATGGACCTGAATGTAACTGTTCCCACGCCATCTCCTTCGCCGCCTCC |

TABLE 9-continued

SNP markers used for calculating percentage recurrent parent in the BC1 and BC2 plants. SNP marker names were based on the Chromosome's number and position on the PGSC *S. tuberosum* group Phureja DM1-3 Pseudomolecules (v4.03).

| SNP | Flanking sequence |
|---|---|
| SOT01-10559698 | GGGGTGGTCCTTTCTTTTTCACTGTTCTCATAATTTCAAGCAGCATAACTTTCAATGTGT[A/G]TAAGTTTGAGACTGAGGCATGGAATTCTTCAATTAGCTTGAAGGACTTCAAGATTATATT |
| SOT01-23932807 | TGTCACAAAGGCGTGTATCACATTGCTGAACCCTCGAGCCCACGAAGGGACATTTGAGTC[A/G]ACGGGCATCCTCATCCTCAAACTGGTTGTCTTGTTCTTGCTCCTTGCAGTTCTTATGAAC |
| SOT01-46271058 | TCCCTGAATTCTCTCACTAAGTCAATGATGACCGATCTTGCTCGAATTTTCAAGTCTCTG[A/G]ACGCAGATGATTCGGTTCGGGTCATTATACTCACCGGATCGGGTCGATCGTTCTGCTCCG |
| SOT01-61269756 | GCTTGCAGACAAAGTTGCAGCAGCTGGCTTCTATGTAGTAGTCCCTGATTTCCTTCGTGG[A/C]GATCCCCGTATACCTAATGATGAGAAGCCTTTAGAAGTATGGATAATAGATCATGGACCG |
| SOT01-80162442 | ACCTGGCAGTTCTGATGGACCTTCAGAATCATCATCTGGGAAGGGACCTGATGGAGATGA[T/C]GTAATTGATGCTGATTTCACCGACAGCAAGTGAACATAGAGGAGCAATTTTGAGGCTATA |
| SOT1-84986138 | ATTTCTCCGTGCCATAAGTAAAGAAAAATTCCAGTAATTGTCAAGAAACCCAATTCTTTA[A/G]ATCAAGAATCACATACATGCTTAAATATTTCAAGAAACGCATAAATCCACGCTAAGAATT |
| SOT2-05170759 | CCTATATCTTAAATTACTTAGATTGGGTACATGAATCATCTAAAATCTAAATCTAATGCT[T/C]AATAATTTGTATTTTAATGTAAATTAAAAGTTTCCTGAAGTCTGGGGGCTCCTTTAAAAG |
| SOT02-17760016 | GATGAGGCATCATCTACACAGTGTCTGAAGTTGTTTGGTAAAACCGTATTAGTCACTGAT[A/G]CTTATATGCCTTCTTCAACTTCTGGCCAAATATCACTGACAGATGAGAATGATGAGCCAG |
| SOT02-24387762 | TTGGATGACACGAAGCAAGGAAAACTAAATAGTAGCAAACAAGAGAAGTTTACCTGAAGA[A/G]GTGGAATAACACTGCAGGGAAACTGAAGAAAATATATGGGACTAGAAGTCCAGTCAGCAT |
| SOT02-31350493 | GGAGCTTACAACTTCTGAGGTTGACAGCCTCAAGGCTCGTCCTCGCATTGACTTCTCCTC[T/C]ATTTTCGGCACTGTGAGTTAACAATGCTTCTTGAACTAATTTCTTATTTTTTTTTCCCTT |
| SOT02-41359775 | TGGCTTTGGCCTTGACCGAATTTGAGGCCTTGTGTGGCTTCATAAGTCTTGAGGTACTTC[A/G]TAAGTTGTGCTAGATTTCAAGAAATTCCAATAGAGTTAAGCAACTTGTTTTACTGGATCA |
| SOT02-44565469 | AACAAATCAGGAAATGAAAATGCCGTGCTGGTAGGCAGTGCATTGACTTCAAGTACGCCC[A/G]TGCTTACTGAATTGAATGATGTCTTCAAAGGCGAGTCACAACTTGGTTATGAATTTGACG |
| SOT02-45091129 | GATTTGTTAAATTCTCTGCTTTGTTGTATATGTAAAAAGAGTTCTTCCTTGTAGACCACG[T/C]TGCAGTCAATACGTACAATTTTTCTCAGGAAGAAGTAAAGAAACAGATCCTCCAGTGTGA |
| SOT02-45105742 | TAATTCCAAAATGTATAGCATTAAGTAGCAAGAACATTTAAAGATTGAACCCATCAAACT[T/C]AAATTCTAAATTCTCTTGATTCCACTTTCCAGGAACCCTTTATGGTCCTCCAGCTGTCGA |
| SOT02-46731334 | TGGTATAACAGCAAGCAAATTGTCCCATCCTCCACGAACACCACCACAGTGCCTCTCTAT[T/C]AGCTCCTTCAATGAAATACTCATTTCCTCTTCAACTGTGCAGGGCTTGTTAACATGGCCT |
| SOT02-46774414 | AGCGTCACGTTCAGCTTTGTTGAAAGGAGTGGAGGAGACGAGGACGGAGGCGTCGCAGCC[A/G]CCGACGAAGCAGTCGTGGAAGAAGAGGCGGAGGGTGGCGGCGGCGGTAGTAGGTGAAGTG |
| SOT03-50790774 | CGCCCTCTCTCTCCTCAACTCTCCGACCACCGGAATCAATCTTAGTGCCACTACTTTCCT[T/C]GTTGACGCCGACACCGGCCACCGCTTATCTTACGCCGATTTCCTTAGCCAGACTCAAAAT |
| SOT03-56290202 | CCAACGAAAAGCAGTTAACATCTGGTATGTGCCACGAAAGAAGGATGTCTTTAGTAAGCC[A/G]GATGACATCCTGACTGCTGCGGAGAAATACATAAAAGAACATGGAACCCAAGCATTTGAG |
| SOT03-61394421 | TCAACTTCTGTCATTCGGTCTTCAGGTCCATGTTCACTATCATCAAGATCGGGATCCAGG[T/C]TATTATGGATATTAATCCCATCTGCAAAAGATTGATCAATTTCCGAGTTCCACGTGACTC |
| SOT04-03548052 | ATATAGTTTGAGGTGAAAAAACATGTTAAGTGGATAAGTCATGTGTCGATACCTATTTGA[T/C]GATCACAATTTTCCTTCACCTTACATCACCTCTTGCAGGCTTTTCCTTATGTTACGGCGT |
| SOT04-11199749 | ATAGAAATTTCACATTTTTTAACTTTTAAGCAAACCAATTCAAACTAAAACTATCAAAAT[A/C]AAAAAGTAAGGCATAATAAATTCGAATCAGTACTGAATTCCACTAGCTTCAAGTAAATTA |
| SOT04-22839393 | TCAACCATCATAGAGAGAACTTTCGCTGCAACTAATCCCTTGGTAACACCCTGCAAGTCA[T/C]GTAAAGAATTCAAAACTTTTGAACAGCATTATGCAACATGATTGTGCTGCATAGTTAAAC |
| SOT04-52034868 | AAACTGTGTAATGAACATAAACTAGAGAAATTAGTACCTTTTAATTTATGACAAATAGCC[A/G]ATCGAAGTTCCATTGTACCTGCATTTGGTGTATACCTGGTATGACCTTCACGAATTGCAT |
| SOT04-58838906 | CACATCTCTAGGCTCTTTATCTGAATCCAGCTGATAAAATATATGCCTTTCTGAAGTTTT[T/C]GAGATAATTTTTTGTTATTTGTTGTTCCTGAAACTGCAGTCCTGTGAATCACTAAAAAAG |

TABLE 9-continued

SNP markers used for calculating percentage recurrent parent in the BC1 and BC2 plants. SNP marker names were based on the Chromosome's number and position on the PGSC *S. tuberosum* group Phureja DM1-3 Pseudomolecules (v4.03).

| SNP | Flanking sequence |
|---|---|
| SOT04-64087153 | GCCAGTAAGCATATTTATCTCTGTTGTGCGCGGTGCATTCATAATGCAAAAACTGCAGCT[T/G]CCACCTTTCTACAACTTGAGTTTGGTAACATCAATTTTCCTGGGAGGATAAGTATATGCC |
| SOT04-70251642 | TTTTGAACACATACATATATTTGGTTGAAATTACACGAATTGCATATATTTTTCCACAAG[A/G]GGTCCAGATAGCGACCCAGCACCCCACCCCCACCCCACAAAGCCTAATCAGCAAACACAG |
| SOT05-01105208 | TGATTTCTTCTTCATCTTCGGTGTCTGGCTCTTCGGGTAAAGGTACCTGAAATCAACTCA[T/C]CTCTAAGAACACATGCATGTGGTTAAACAAACCTCAAAAAGCAAAAGGGAAACAAAATCT |
| SOT05-07667963 | GTTAGCACAGTGATTGATGGCAATAAGATCAAAATTAATCCTTACTCCATCATCCCTGTA[T/G]CTGGTGATACTCATTTCATCATTCTTGATTCTTCTGCCAGTACTTTTTACACATTATCAT |
| SOT05-15768069 | AGGTACACTAACCAACATAGAATGTGAAGAAATATTGAAGGCAACAAACCTTCTATTTCA[T/C]AGTACATTTCATGCAATAAAATTTAATATAGTTCGGAACCAGAAAGCTGCATGTATGAAT |
| SOT05-26397339 | TGCAGGATAGGCCGTGGACCCATCCAAAATAAGTGGATAGGGTCCATGGATCCCAACCAG[T/C]AAAAGCTGGTTTGGGGTTCGGCCATAGTGGGGGTACGTTCGTAAATTCCTCTTTTATTAA |
| SOT05-43513048 | TTCTACCTCATAGCCAATGCATGTGTGACAAATGCACCGAGGATAATGGTTTCAAATTGC+T/G+AATTTGATGCGCTATATTTAACCAGAATAAGGGGATTGTTATGTGTAAAAATGAATATGA |
| SOT05-51486277 | ACTGTTTGAAGATGTTGAAATTCAACTTGAAAAAGAAAAGCAAGCTGCTCTTACGGAGGC[A/G]AGGCTGAAAGAAGTAAGTTTCTGTTGGGGTGGTTATTGACCCATTGTTGATATCTACTAA |
| SOT06-00104091 | ATCATGTTGCTCTAGCAACAGACTTATCTGATTTGATTTTATTGGTTTATAACCTTTCAG[T/C]TGGAGACTCTTCCTGAATTGATTGCTGGGGTTTGGTCTGATGACAGCAGTTTGCAACTTG |
| SOT06-03432475 | CTCTTGTCCGTGCCATTGATCTTGCAGAGTCCTCATTTGTTGACAAATAATAGATGCAGT[A/C]CTAGTGTCAGATTTTGTTTCGTCAATTTTTTTGTTTCTTGATGGGTGTAGAGAAGTTTGT |
| SOT06-13440008 | CCCAGGCTTCCCTACTCCCGATAGGACAGCTAGCCCTTTCTGCTGATCGTCGGGCTGCTA[A/G]TCTAGAGGCCTCTGTTCCAAGAATGATCCATAATGGCCTAGTTGATACTGTGACACCTTT |
| SOT06-29622294 | GCGTTTGGAAGTTTTCCCATTGTATTATCAATTGTTTCCTGCAGTAGCTTCGTATTTGAC[T/C]GAGTTCTCAGTTCATTAACAATAATTCAGATATGCTAATTCTTTACTGATACCAAGCATT |
| SOT06-38707476 | AAATGTGGATATTTTAGGCAATCTGAGTTTGTGGTGATAGTTTAAAGGCAGTGGGGCTAT[T/G]TGGATTTCATTATTGCCATGTCATCTGACTTTTCTCTCTACAAAGATTATACTACTCCTT |
| SOT06-43297148 | CAAACTACGAGGATTTTTCCATTTGATTAATTTTGCAACTCTGGTACTACTACTCTACAG[T/C]CTGTGTGGGAGGAGCAGTGAAGAGGAATTTGTGGAACAATGCATCAACACATTGGATTGT |
| SOT06-48428474 | TGCCCTTACAAGTCTTTGTTATTTCAGGTAACACAGCTCGATCTCCATCGCTACTTTCAT[T/G]CCCTTGGTGCAGGAGTGATTGAGGAAATTCGAATTCAGCGAGATAAAGGATTTGGCTTTG |
| SOT07-04466022 | TAAATAAGATAAGAACTAGTGGTTTGTGACAAATATGCTTTAGTCAAACTACCTTAATTG[T/C]AAATTTAGTGAAAGAAAAAAAATAATCTACATAGTTTGCAATACAAATTCATCAACTCTA |
| SOT07-04468977 | GATCCAATCGAGTTTAAATTCCAAAATGAAGCATTGAACTAGTTGAAAGCACATGCAAGG[A/G]AACTAACAGAATGGAAATGGGCAGGGGCAGCTCAAAAGGGGAAATAGCCCATACCAGTGC |
| SOT07-39384833 | ACGTGCTGTGGCGGGAGAGTCGTGTTTTCTAACAAGGGAACATGTCATGTTCTTCACTTG[A/G]CACAATACAAGAGTTGGGGAAGTGACATGTTGGGTCCATAATTTACATTTGAATTTTTAG |
| SOT07-49405578 | AGACTCACCAGATACAAGAGGCAAGGGCGGAGCATCAAAGCGGATCACTCATGGTTCCCA[T/C]CTGGTGAAGGGAAAGTCTAATCACGCGATGGAAGATTGTTTAGTTTGTGAGTTTAAGCAA |
| SOT07-53700808 | CTTAAATTACAATTACAATTATTTTTTTTTAAAAAATACAGCTATATATATGTCCAAATC[A/G]TTTTAAGCTTTCGGTGGTCTTTATCAGCCGCTGAATCGACGAATTACAGAAAGAAAACAA |
| SOT08-01078910 | AACTTGAAGCTTCAATCCATTAGCTTGAACCATCTTGACAAGTTCATCATATCCTTCCCA[A/G]TTATACTTCAAAGGTCCATCTTTTTCAACCAAACCCCACCAACAATCCACCATTACCCCT |
| SOT08-18393399 | GTGCCCATTCTGGTTGGGGCTCTTAGTGCTGAAAGTGAAGCCCTTTATGG[A/G]CGGTTACTCGCAAAATATGTGGATGACTCAAAGAATTTCTTCTCAGTGTC |
| SOT08-38666935 | AGGGTTGAGATGACCACCAGAAATACGGAAACCAGCAGAGATAGTCACAGCCACCACCAA[T/C]GCATGTGCCATTGCCACAAAAAATAAACTCACAAGTGGATCTCCATTTAGCTTATCTGTT |
| SOT08-43993811 | TTAGTAGCAAACTAGCTGTTTCAAGTTCTCAGTATCAGAAATCTGAACAATTGCAATACT[T/C]TAGCTGTTTTGACTGCAATCATTACCATTCTCTTGAAGCTTTACCAATTTGCGCCACAAT |

TABLE 9-continued

SNP markers used for calculating percentage recurrent parent in the BC1 and BC2 plants. SNP marker names were based on the Chromosome's number and position on the PGSC *S. tuberosum* group Phureja DM1-3 Pseudomolecules (v4.03).

| SNP | Flanking sequence |
|---|---|
| SOT08-50482569 | CTCACCTGGTGATACACCTGATCATCCTGCTGTTGGTGGTGGCTCTGCTGATGGTTATGC[T/C]TCAGAGGATTTTGTTGCTGGTTCTTCATCTAGCCGTGAAAGGAAGAAAGGTTTGATCTTT |
| SOT08-55621111 | ACCGCTAATGTACTTGGAAATACTATGAACAACAACATCAGCCCCCATTTTCACCGGCGA[T/C]AGCACCATCGGAGCAAAAGTGTTGTCCACCACCACTGTCACACCTTTTTCATGCGCTATC |
| SOT09-02470833 | TTTGCTAGTATCATAGAAAGTCTTTGATGCATAGAAATTACCATAATCGAATCTCAATCC[T/C]TTCCAACTATCAATAGAACCAACATCTGGAACATACCTATCTTTTTTTGTATCGTACTTA |
| SOT09-07835623 | ACACCCACCAACCAACTCACCCTTCACAAAAATTTGTGGAAATGTAGGCCAGTTACTATA[A/G]TTCTTCAACGTCTCCCTCAACCCGGAGTTGTACTCTTCATCAAGGACATCGATGCTTTCA |
| SOT09-20712307 | ACAATTAACTAAATGCAAACAAGACACGCCCTTGAGCAACTGCCCAGCTTAAACTGAGGG[C/A]AGAGCAGAATATAAAGGTAAAGAGAGAAAAGATCAACATAATGAGTTATGGAACAAAACT |
| SOT09-30793211 | TGTAAATATGGCGAAGACGAAATGAAGAAAAGCTCTTTGTCACTATTTGACAAACAGTAA[C/G]AAATACGAGTATTATTTACGTCTTAGCTCAGTCGGTAAATTAATTTTAAATTGATGTTTT |
| SOT09-52408174 | TTTCACCTGGAAAGATCACATTTAATGAACAATACGGTGCATTTTGCCCATGTTGCAGAT[T/C]GAAATTGTAACCAATTTGTAGGAGGTTTGTACACAAACCAAAATGCAGATTATTGGAAAC |
| SOT09-60570643 | TTTCTCGCTTTGCTTTCTCTTTGTTCTTTTTCTATCATTTGCTTATCGAGCTGCCAAAGT[T/C]CTACTTGCAGGTTGGACCTACCAGAGGTGTTATTCCTCTTGTTGATGCAGATATACAAAC |
| SOT10-11539446 | AAATATCGATGGGTGTGTGTCGGATACTTCAAAATAGTGTATTTTTGGATAATCCGGCAC[A/C]TGTGCGAGAACATATTTGGAGGGTTCGAGCAACATAGACCTCAGCTACCATCCTACACTT |
| SOT10-27379373 | ACAACAAAAGGCCCCAACTTCTCCAAACATGTCTCCACATCTCAGAGTCCAAACAATCTG[T/C]TCATTCTCCATCTCACTATCAATCATTTCCACCTCCCCTGAAACTATGATATAAACCTCA |
| SOT10-48721966 | AAAAAATGAATTCCCACTATAAAGTTGTTCCACCTACATACCTTCTCCTGATGAGAATTT[T/C]CTAGAATGCAAAGTTGCAACTATATAGCTATTTTTCAGAGCTGCGGCTAGCTTAGACAGT |
| SOT10-49584558 | CGTTGATCGTTCCGCCTTCGCTAAACCCGAATCTGTTTCCGATGCTACCCTCCGTATCCG[T/C]AAAAACTACTCCTATTTCCGTACCAATTACCTTTCTCTCCTCGCCGTTGTCCTCGCTTTC |
| SOT11-00283795 | TAACCAGTTGGAGAGAGCTTGTGAGTTGTTAGATGTTGGGCTAACTCTCAACATCTATAC[A/G]GATATTATGTCTCGAACTGCTACTCAATGGTCTTTACATTTGAAGAGCCTCTCACTTGGG |
| SOT11-00939591 | GCTCGTGTTTCTGATTTCGGGAAAAATGACACAATATTCTCCGTAAGAAC[A/G]CATCTAGGCCATCTTCTAGATGCTGGAGACTATGCCCTCGGTTATGATTT |
| SOT11-41840983 | GCTGGTGATGGAACCACAACTGCATCTGTTCTTGCTCGGGAAATCATTAAACTCGGTCTG[T/C]TGAGTGTTACATCTGGTGCAAATCCAGTGTCTTTAAAGAGGGGCATTGACAAAACTGTAC |
| SOT12-36957737 | CCGGTAGTTATGCTCTTTATGCGTAGTTCAAGCAAGTTAAGCATATTTATAAATGACCTT[C/G]TTGTCTGAAAGCTGTGTTCTTTTTAAACAGTGTGGTGCAGGAGAACTGATGAGCTTGTTG |
| SOT12-53990411 | TGATTTACTTGGTATTGTGTTCCTTCTTTTAAATATACATCTTCTCTCCCTGCATATACA[T/C]GTGAGTCAAATGTTTAATATTTTGGTAGAATATTTTGGAAGTTGCGATTTTTCCATCAAT |
| SOT12-59979506 | CTTCCTTATCCTCGATTAAGTTCAACAATAAAGAAGAAAAGCAAACCTCATCTAGCTTGA[A/C]TATCAGCTTCCTTATGAAGTAATTGATGCCATAGTCTAATTTTCGAAGCATCATTTTTTA |

TABLE 10

SNP markers as used in Examples 2, 3 and 4. All markers were generated according to the methodology as explained in Example 1. All SNPs are named according to their physical position on the DM 4.04 reference position, where the two numbers behind SOT denote the chromosome number, and the eight numbers behind the dash denote the nucleotide. The SNP is shown between brackets and 45 nucleotides of both flanks are shown with IUPAC nucleotide codes. KASP markers that were designed on the listed sequences. Stretches of continuous n-characters indicate masked regions containing variation in the germplasm that might hamper amplification via a KASP-assay.

| SNP ID | Sequence | Used for population: |
|---|---|---|
| SOT02-17705698 | CCrGAACAACATATGACTTTGAATGAGCGGCTCCACACTGAATAGAAATAAGCCTTCAACATTCAGGTATAGGGG[C/T]CAAACCTGGTGGACCTTCAAATAAGACTGCCCGGGGCCTGTTCGTCTCAAATTTGCGTCGGGTCCCACGAGCAAT | 17SC0011 |

TABLE 10-continued

SNP markers as used in Examples 2, 3 and 4. All markers were generated according to the methodology as explained in Example 1. All SNPs are named according to their physical position on the DM 4.04 reference position, where the two numbers behind SOT denote the chromosome number, and the eight numbers behind the dash denote the nucleotide. The SNP is shown between brackets and 45 nucleotides of both flanks are shown with IUPAC nucleotide codes. KASP markers that were designed on the listed sequences. Stretches of continuous n-characters indicate masked regions containing variation in the germplasm that might hamper amplification via a KASP-assay.

| SNP ID | Sequence | Used for population: |
|---|---|---|
| SOT02-17872940 | TTTATTTTATTATTTTTTGTTGTATTTGAAGGTTGATATAGCATTAGAGTGTGCAAGGTTGCAGCA TAGATTTGC[G/A]TTGCCTCCATTGGAAGTGCAAGATTTTCCCCAAGTAGGATATGTGATGTCTCA ATCAAATGATGTTATGTATCAT | 17SC0011 |
| SOT02-19914536 | AACTCAAGTATTCTGACATAsTAGTGCGCTGATTACCTGATATTCTAAGATGATATAAAGAATTCT GATCTGTAT[T/A]GGAGTTTGCACTGGACTGTATGATGTTGGTTCAATCTkGTGTTCTGTCTGTAT AATAATGTTATTGTGATGGTTC | 17SC0011 |
| SOT02-21226145 | TTCTTTATTCAACAGAGCATTTCTAGGGAATTCCTTGATATTTTCCTCTTAGCTTTTGGATGTCTG TACTTGAAA[T/A]TGAAATCCTTGTAGGCTGCAGAGCACTCTCTATGACCCTTGTGAGTTGTCTTC TAATGTTAATGATGTTAACAGT | 17SC0011 |
| SOT02-24944519 | CTATTTCwGTAAGGCTCATCATCCACAGCTCTGACACATGGAAAGTAAGGAACTTAATATTACTC GTAAATCTTT[A/T]GAGAGTATTCGGTAGCTGAACTTATCTGCATrATCTGTTTAGGTAkTTGTATC ACAAAATATTATCTTTGGGTAT | 17SC0011 |
| SOT02-25338387 | ACATCAAAGATTArGAAACAAGAATGkGCAAACTACACATATTGATGATACCATATCCAGTwCAA GGCCATGTTA[A/T]TCCCTTAATGCAGCTAGCTCAATCCnnnnnnnnnnnnnnnnnnnnnnnnnnnnnnn nnnnnnnnnnnnnnnnnnn | 17SC0011 |
| SOT02-29005162 | GCAyCCAAAGCTCTGATATTTACATGGGAGTTCAAGAGATGCAGCAACCTTCTCCAATGCAAGAC ATCGGATATT[T/A]CCAAGTTCATGCCTACATGTTGGACAGCGATTATGAACCCTAGGTTTGCAAC CAGAACATAGTGTGTGACCATTG | 17SC0011 |
| SOT02-29742666 | AATCTCATCAAGCTCACyTTAGTCAAGAATCGACTATAAAAGAACCCTTTGCAGACGCTAAAAAA GCTACGAAAA[G/T]TGAACATCTTCAAGCTGGACTGGGGAAACTATGCrTTGTGTTGGTGGCTTTT CTCAACTCGATCACTCAAAATCC | 17SC0011 |
| SOT02-32149604 | AkrTTCAAAAsTCTTCCTTTTTTTTCTTCTTAAACTCyATGCCTAGTCAAACTAAGACACTTAAATT GGGATGGA[C/T]GGAGAGTACCTTTTAGCATAATTAGTTTTGGTCTCCAGTGTTGGGGTCTGAAC CACTAGGATTGCATCTTCAAGT | 17SC0011 |
| SOT02-32812204 | GAAAACTArAATCCTCTGAAAATyATTACCTTTGAATGCTTTGTTACGAGGCACAAAGTCTCCTTC AAGCACACT[G/A]ACAAGATAGTGAAGTAGTAGCATCTTCCTTAATATCTGCAATAGGTCTTGTCA GACTATTTGATGAAGATACrAA | 17SC0011 |
| SOT02-35004833 | TCTATTGATAAAGGTATCCAGAGCATCAATCTCAAACACTGGAAGTTTACTATGTCGTCTCAACC TTCAATAGTT[C/T]CAATTACCAGAAATCATTGCAGGAACATTGACCATCTGCAAAATGATGAAAC CTGTATGCATCCCGTACAATAAT | 17SC0011 |
| SOT02-37386443 | TCTGATGAGGAAACATCCTGTTTCTGTTCAATTGAAGGCyAAGAACGATGAGGGGTTTGCGTTAA TCGACTCTAC[G/T]ATACGTGACGCCAGGGTAATTCGTAACAGyAAGGGGTTTACTGGTGTTTTTG GTGATGATTGGAATTGGCCGTTT | 17SC0011 |
| SOT02-40429447 | GAATGAAGATTTTGAAACTTCTTTGCAAGTTCTACGGGGATTTGACACAGATATATCCTCAGAAG TGAATGAGAT[C/A]AAGGTAATATGTGGAATGTGTTAAATGATGATTTCTCArCTATTTTGAACCC TCAAATTGCACTGTAGAAACTTC | 17SC0011 |
| SOT02-40500157 | CATTTCACCTGATTGAAGAAGACrTTTATAATyGATTGAGGAAAGAATAACTGAATATTGGTGGTA AAGAAGATA[C/A]AATAACAAGACAACCTCCTCCACTCCAATAAAGACAGATGGAGCTACTTCTG ATCTAGTTAAGmCAAGTTGTGAC | 17SC0011 |
| SOT02-44255433 | GAATAGkTATATTAAACACACATATATTGCTGCTAGCTCCATATTTAwAACATCATGTGCTGTTTA ATTATGATA[T/C]GATAAAGTGGTCCTGGGAGATTTTCTTTCTCCTTTTTTCwTACTTTTTTATCAG TTTCATCGACTTTATTTTTCT | 17SC0011 |
| SOT02-45679501 | TACCTTCTCTACCTGAGAyATATTAACCAyATGTATGGTAGrTGTCATCAGAGAGTTTGAwTkTTT GAATTTTTA[A/T]TGCAACTGGAATAATCGGGAAAACAnnnnnnnnnnnnnnnnnnnnnnnnnnnnnnnnn nnnnnnnnnnnnnnnnnn | 17SC0011 |
| SOT02-46079014 | TAkwGTTTCTTAATTAGTACTTCTTAACAGATAATTATCCCTAAATTAGTGTCTAATCCTCCTCAC GTAATCACA[T/C]AAGCGTGCGAATTAAAATACTTAAATGAyCTACTTCCATGGTCACACCATCCC CACCTCCACATAmCGAATTGCT | 17SC0011 |
| SOT02-47829947 | TCGGTAGAGAAGAACTCCAACATCAACCCCCATTGAGCGGAAGTACTCAGTTGCAGGCCTTAGC TTGTCCTCTAC[A/G]CTGTAACTTATGATGTTTGGACATCTGGTTAGAACCTTGCTCACACACTCA GCAGATAGACCCATTTCATAAAGA | 17SC0011 |

TABLE 10-continued

SNP markers as used in Examples 2, 3 and 4. All markers were generated according to the methodology as explained in Example 1. All SNPs are named according to their physical position on the DM 4.04 reference position, where the two numbers behind SOT denote the chromosome number, and the eight numbers behind the dash denote the nucleotide. The SNP is shown between brackets and 45 nucleotides of both flanks are shown with IUPAC nucleotide codes. KASP markers that were designed on the listed sequences. Stretches of continuous n-characters indicate masked regions containing variation in the germplasm that might hamper amplification via a KASP-assay.

| SNP ID | Sequence | Used for population: |
|---|---|---|
| SOT12-00206188 | ACCTTTGAATCATCTCACAATGCTTTTAGATCAGCTTTTCCAAGAGGATTTGCTTGGGAAGTGATCAATGTATAT[A/T]CAGGGCCACCAGTTGTTACATACAAATTTAGGCATTGGGGTTTCTTTGAAGGTCCATTTAAAGGACATGCCCCTA | 17SC0011 |
| SOT12-02478572 | TATCTGCGTwTGmCCTTCAACTrTCwAGGGATCACTTCTCCATACTCACAATTTTCTCAAGACTTCTTTTCCTTC[T/C]GCTTCGTACTACGTTGGTTCCCAACTATGrTTTGTAACATATGCCATTTACATyGCyTTCTTTTCTACTTATGCG | 18SC0011, 18SC0012 |
| SOT12-11646765 | AGCAATCCCTCGCTGAAGCAGTGGCAACATTAATTCAATTGCTGGCAAGTTCCTATCTTCCTCGTTCAAGCACGC[T/C]ACTGCACTATGGAATACCTGCTCCACAGCTTCTTTTTCCTCTTCAGTATTAAAATCAAGTTTGGTCATACACATT | 17SC0011 |
| SOT12-31545560 | nnnnnnnnnnnnnnnnnnnnnnnnnnnnnnnnnnnnnnnnnnnnnnnnnnTTAATTTCTCCTAGGTTGAACCGAT[A/C]AAAAAACCsTTGAAGTTTTATTTCGTGCACACCTAAACTCTATATTGGTTTAATTACCCTCCyCAACCTkATATT | 17SC0011 |
| SOT12-40245065 | nnnnnnnnnnnnnnnnnnnnnnnnnnnnnnnnnnnnnnnnnnnnnnnnnnATTGGGCATGGTCTAACTGGATGTC[A/G]TTGAyAACTCTTAATATATCCCACAATAwGCTGACrAGTGTGGATACAAyTCCTCTTCAGATTrTATATACTATT | 17SC0011 |
| SOT12-49301746 | TAAGTACAAGCTTTGCTGCrTTGGGTGmAwGTTyCAAyGCCTTGGTGAGTTCTTCGCGCAGTGTGTTTTTCTCTG[C/G]GAGTTTCGATACTATGTAACTTCGAAGTCCCTTGCyGCACATCGTCTTGCAGAGGGTTTCGAGCTGTGAATCCGG | 17SC0011 |
| SOT12-50632815 | TCAGCTACAArTAGCATAAGCTATATGGAGCTGGTCAAGGAArTTGCCAGCAAGGGACCTGAATCGCAGAAGAAT[G/A]TTGCGATAAGAGCTGATGAAAAGAGCTACAGTTAyCTGCAGTTGATATCATCTGCGAGGAAAATwTCAAATTTGT | 18SC0011, 18SC0012 |
| SOT12-53793483 | ATGTGAGGCAGGCATTGTATGCrTCGAAAATCTGTAGTTATGCTCAGGGGATGAATTTGCTAAGGGCAAAGAGCT[C/T]TGAGAAAGGGTGGAATTTGAATTTGGGAGArwTGGCAAGGATTTGGAAAGGTGGTTGTATTATCAGGGCAGTGTT | 17SC0011 |
| SOT12-56559959 | TCTCAAGGTTCTAGTTCTAGCACCATTCCTCrTGArATCAACAGrAATCCAGCATTTGAGGGGyGCAGTGACAAC[A/G]ATGACGATGGCTGTCAAGTGATGGAnnnnnnnnnnnnnnnnnnnnnnnnnnnnnnnnnnnnnnnnnnnnnnnnnn | 17SC0011 |
| SOT12-57125022 | nnnnnnnnnnnnnnnnnnnnnnnnnnnnnnnnnnnnnnnnnnnnnnnnnnTTACCTGAGCAGTGGCTTTCAACCC[A/G]AATGCCTTCACTGCAAyAGTGATGTTCGGATTAGCTGCCCACTTAATGACTGGTTCCATTATCAGCTCTTTCTCC | 17SC0011 |
| SOT12-57348932 | TTTTGAsCAGGTGATAAATGAGATGACTAAyGGAGGTGCTGACTACTGCTTyGAGTGTGTTGGTATGGGAACACT[C/T]GTGCAGGAAGCATATGCCTGCTGTCnnnnnnnnnnnnnnnnnnnnnnnnnnnnnnnnnnnnnnnnnnnnnnnnnn | 18SC0011, 18SC0012 |
| SOT12-57412546 | TCTTCTAAGyGGAAGGTCwTTTATAATTGTAACATCTGTTGTTAGATGTTTTATAAACCAATCAACATCAAATAT[G/A]TCAGAGAAGTCACTGCAAGAGAAAAGGAGATCATTTCAyTTTCACAGTTACAAGCAGGATTATTAGCATTTTAAA | 17SC0011 |
| SOT12-57475688 | nnnnnnnnnnnnnnnnnnnnnnnnnnnnnnnnnnnnnnnnnnnnnnnnnnGATGTATTGTGTCTCTCCTCCGAAT[A/T]ATATCCAAAAGrAAAyrCTAAsTGAAGAATAwwGCTGGAACTTGTTCCTGAAGAAAGCTGGTTGGGmTACTTGGG | 17SC0011 |
| SOT12-57602201 | nnnnnnnnnnnnnnnnnnnnnnnnnnnnnnnnnnnnnnnnnnnnnnnnnnGGGCATCCAATTTCAAAGCTTTGCA[T/G]GCAGCCATTGCrGCATTAACTTGCTCGGTTGTTCTAATTTGATCTTTTGTCCGACCCAGCATGTCATAACCACCT | 17SC0011 |
| SOT12-57716039 | TTGGGTTGTTTCCTTTTCTyrTCAGTGTGATGGTGAGTTCCGAGAGCTTAAGTGAGTCTGCTGCACCACCACCAA[T/A]GAAATATGGTGTCACAAAGCCATTATCTCTTGCTGGrCCsACTGAGGCAGATCTTCAAAGAAATGCwGAACTAGA | 17SC0011 |
| SOT12-57817238 | AATATAAGCCAAGCkCTTTCCTTTGTAATGAAGAATAAGCArCAGATACACTrAGAGATAATAACCTkCCAAGAG[T/C]ACTCCTAGACGATGCACCAAGAACAnnnnnnnnnnnnnnnnnnnnnnnnnnnnnnnnnnnnnnnnnnnnnnnnnn | 17SC0011 |
| SOT12-57902259 | GATTAGGTGyTCrTGyCCCTAGTTTCCCAAAGGkTAGTGGrGCATCAAGAACGACGACCTCCTCTAGAGACGAGG[T/C]TTCAGTTTCTGTAAGTAATGCTAGTGATATGGAGTCwGAATGGATAGAACAAGATGAACCTGGAGTGTGTATAAC | 17SC0011 |

TABLE 10-continued

SNP markers as used in Examples 2, 3 and 4. All markers were generated according to the methodology as explained in Example 1. All SNPs are named according to their physical position on the DM 4.04 reference position, where the two numbers behind SOT denote the chromosome number, and the eight numbers behind the dash denote the nucleotide. The SNP is shown between brackets and 45 nucleotides of both flanks are shown with IUPAC nucleotide codes. KASP markers that were designed on the listed sequences. Stretches of continuous n-characters indicate masked regions containing variation in the germplasm that might hamper amplification via a KASP-assay.

| SNP ID | Sequence | Used for population: |
|---|---|---|
| SOT12-58127825 | CTGCATGCTGACAGGAAkyTGGTCTTTAATCTCTCCmATCATTGAAACTTCAGACTGAAAGGAGTTATGAmAAAG[T/A]TTTCTATGGAGGAGGTGGAGCTGTAnnnnnnnnnnnnnnnnnnnnnnnnnnnnnnnnnnnnnnnnnnnnnnnnn | 17SC0011 |
| SOT12-58205669 | GTAAGATCTTCTTACGATGATGGGAACCATGAAAACAGGAAACGArnGAGTCAGGTTCAACTTACCAGAGAACTCT[G/A]GCATGGATCCTGAAGTTCGGGACGAGCTTATAGATTTGGTTCAGGCAAAGGAGGCAGGGGTTGCATATATAATGG | 17SC0011 |
| SOT12-58205669 | GTAAGATCTTCTTACGATGATGGGAACCATGAAAACAGGAAACGArnGAGTCAGGTTCAACTTACCAGAGAACTCT[G/A]GCATGGATCCTGAAGTTCGGGACGAGCTTATAGATTTGGTTCAGGCAAAGGAGGCAGGGGTTGCATATATAATGG | 17SC0011 |
| SOT12-58303052 | CTTGTTGAAAACTTAGAACCCAAACAAAAGTGGrCTTTAAGATCTCTCTTATATGCCAATTCTTCyAACTmTmTG[T/C]GCCTAGCTAGTGGCTTCCAAATAGTnnnnnnnnnnnnnnnnnnnnnnnnnnnnnnnnnnnnnnnnnnnnnnnnn | 17SC0011 |
| SOT12-58470194 | nnnnnnnnnnnnnnnnnnnnnnnnnnnnnnnnnnnnnnnnnnnnnnnnnnCTGAATCTCCAGTATAGTATGAAAC[C/T]CTTTTGGyGGTGGTkCTTGGryTCTGAATAAGGTGTTTGAAGCAGTATCTAGGAAAATTGCATCAGAAAGAGGAA | 17SC0011 |
| SOT12-58517350 | CCTTTCAAAAAAGTAAGCAAAAGGTGCAATAGAAATGGTGGCCAAAATTTGTCTATAGGATAAGTGArCATAAGG[G/A]TCCATGCCTTCATCCATTACAAGCTnnnnnnnnnnnnnnnnnnnnnnnnnnnnnnnnnnnnnnnnnnnnnnnnn | 17SC0011 |
| SOT12-58583551 | TTTGGCTCCTGTGGATGCTCTTAAGAGATATACCCAACTrAATAGTTATCCTCTTCACAAAACCAACAAACCAGG[C/T]ATCTTGTCTCTGGATATCCATTATCCTAAGGTATGGACyCCrTCTTTATGACTTTATCTGGACTATTTTTAATGA | 18SC0011, 18SC0012 |
| SOT12-58587813 | ATAATTTTGCGCTGAATCAGAGTTTATCrAGTTGCAAGTGTyAAGTCCGAyTGGAATTCCATCAAAATCCTCCCC[A/G]ACTTGTCAGGCACAGGTTAGCTTTCnnnnnnnnnnnnnnnnnnnnnnnnnnnnnnnnnnnnnnnnnnnnnnnnnn | 17SC0011 |
| SOT12-58601503 | nnnnnnnnnnnnnnnnnnnnnnnnnnnnnnnnnnnnnnnnnnnnnnnnnnTGATGAAACTGGGCTTGAATTGGGC[C/T]TGGGCyTAGGCCCAmGTGTTACAAAGrCTAACAAAyCATCAAsAAAATGGTGTGAGTATGGTAGAATTTTGACTG | 17SC0011 |
| SOT12-58601503 | nnnnnnnnnnnnnnnnnnnnnnnnnnnnnnnnnnnnnnnnnnnnnnnnnnTGATGAAACTGGGCTTGAATTGGGC[C/T]TGGGCyTAGGCCCAmGTGTTACAAAGrCTAACAAAyCATCAAsAAAATGGTGTGAGTATGGTAGAATTTTGACTG | 17SC0011 |
| SOT12-58772425 | nnnnnnnnnnnnnnnnnnnnnnnnnnnnnnnnnnnnnnnnnnnnnnnnnnCCAGAATATCATGCATGTATAACTC[A/G]AGTATyGATCmTTCGGGAACTTGAGTGTCAATTGCAAsArCAAGGGGTGACAATTTGGTTATkGCTACwAmGAAA | 17SC0011 |
| SOT12-58820928 | nnnnnnnnnnnnnnnnnnnnnnnnnnnnnnnnnnnnnnnnnnnnnnnnnnCTTCGCCGAACATGTCGATTGCGTC[G/C]ACrTCATCrACGTCCATmGCCATTGTTGATCCyTGTTCTTCCATGTCTGCTAAATAGTCTACTACCATTGGCTTC | 17SC0011 |
| SOT12-58822517 | nnnnnnnnnnnnnnnnnnnnnnnnnnnnnnnnnnnnnnnnnnnnnnnnnnGACTCTATCTAGGTGGCAAGCAGCA[G/C]CmGGATTTTGAAGGCAkkTACAGAAGCTCTCGTCrTCTTTTGGAAATGATGCTGGyAAAGGATGGTCsGGkATTA | 18SC0011, 18SC0012 |
| SOT12-58960670 | TCGTAATGTCTGGAGTATATGACTCAAGAACTGGTCTAATTCTrrTTTGGrTAGTTwTCTTGTTGGCTTCCGykA[T/C]GATGGTTTGTCCTGCAGAAGGATTGnnnnnnnnnnnnnnnnnnnnnnnnnnnnnnnnnnnnnnnnnnnnnnnnn | 17SC0011 |
| SOT12-58960670 | TCGTAATGTCTGGAGTATATGACTCAAGAACTGGTCTAATTCTrrTTTGGrTAGTTwTCTTGTTGGCTTCCGykA[T/C]GATGGTTTGTCCTGCAGAAGGATTGnnnnnnnnnnnnnnnnnnnnnnnnnnnnnnnnnnnnnnnnnnnnnnnnn | 17SC0011 |
| SOT12-58962004 | CTTGGTTCAAAyAACTTGCATGGAGwCATTCCATCTGGTGTTATTAAGTGTGACTCATTGGTACAACTTCGTCTT[G/A]ACGGTAACTGGCTACAAGGGAGTTTTCCTTCTGACTTGTGCAAACTGAGTAATCTATCTGCTCTTGAATTAGGAC | 18SC0011, 18SC0012 |
| SOT12-58964340 | CGATATCCGATTGGATTTGACAGATAAAACTACTGTTAGTCACATGCTTACAGTCTTGAAAATTGGTCTAGTmTG[T/C]ACTTGTTTGTCCCCGGCTGATCGCCnnnnnnnnnnnnnnnnnnnnnnnnnnnnnnnnnnnnnnnnnnnnnnnnnn | 17SC0011 |

TABLE 10-continued

SNP markers as used in Examples 2, 3 and 4. All markers were generated according to the methodology as explained in Example 1. All SNPs are named according to their physical position on the DM 4.04 reference position, where the two numbers behind SOT denote the chromosome number, and the eight numbers behind the dash denote the nucleotide. The SNP is shown between brackets and 45 nucleotides of both flanks are shown with IUPAC nucleotide codes. KASP markers that were designed on the listed sequences. Stretches of continuous n-characters indicate masked regions containing variation in the germplasm that might hamper amplification via a KASP-assay.

| SNP ID | Sequence | Used for population: |
|---|---|---|
| SOT12-58977155 | nnnnnnnnnnnnnnnnnnnnnnnnnnnnnnnnnnnnnnnnnnnnnnnnnnnnnnnnnnGTGACACCTTCTGTTGTTGAGA AAT[G/A]ATArGrrTTGTTCGGATGATAAGCATTATCTATTTTyAATTCTGAArTTATAyGTTCAAGTy ATCAAATGAATGA | 17SC0011 |
| SOT12-58985310 | ATGGTTGCAGGTCGAATCTGAGTACCTCCCTCTGTATAGCAACTATGGmATTGGTCTTACCACAT GGAGTCCTCT[A/C]GCTTCAGGCGTTCTGACTGGAAAATnnnnnnnnnnnnnnnnnnnnnnnnnnnnnnnnnnnn nnnnnnnnnnnnnnnnnnnnnn | 17SC0011 |
| SOT12-58990272 | GTACCAATGAyAGAATTTGGCTTCTGATGATTCCCATrCACTTCTGTATTTCACGGTAGATTGGAG mGTTCTGyG[A/G]GCAACTTGGTTGCAAGCTTGCTACAnnnnnnnnnnnnnnnnnnnnnnnnnnnnnnnnnnnn nnnnnnnnnnnnnnnnnnnnn | 17SC0011 |
| SOT12-58996133 | AAAAATAATGAAGTGAAACACAATGAGTTTTGCAACCTTTTTGTCTAGCGCCCGATTGAACTCAA CAAGAGCTTG[G/A]ACATCAGCTTCCTTTGCTAGTATTTnnnnnnnnnnnnnnnnnnnnnnnnnnnnnnnnnnnnn nnnnnnnnnnnnnnnnnnnnn | 17SC0011 |
| SOT12-58996998 | CATTAAATGATCCAATArGCAATCAGTCyrGAAAACAAyCACCTCAAAACCAAAAGTACTGAAATA CTAATyCAT[A/G]CACACAACATGTTGTGAACCAAGTAnnnnnnnnnnnnnnnnnnnnnnnnnnnnnnnnnnnnnn nnnnnnnnnnnnnnnnnnnn | 18SC0011, 18SC0012 |
| SOT12-59003185 | TTCGTTCTGTTCTTGGATCTACGCATGATGCATGCTCCTGATCTTTGATTAATTTCGGTGACATG CTCTGATTGG[C/A]TCTTTTACCCTTATTTGTTGACTTATTTGGTAATTCTTTTGCCTATAGGAGG GAAGATCAAGTCAAATTAGAAAC | 17SC0011 |
| SOT12-59011119 | ATrTTCATGCAGATTAATTATTCATTGTCATTTGTTCTAATTAAATCTTATAATAGTATCTCCACAG AACAATGA[C/T]CAAATTGATTGTTGCTGATCTGTTGCTGGGAAAAATCAACAAACCATGATTTAT GATTTTTCTTTTrACAGAGAC | 17SC0011 |
| SOT12-59016142 | ACCACCTATTCTAACArAAAAAATACTTTCGTTTrArGCTCTGACCTTCTTTTTTCAGAATTGAAGT ATGCTGGC[C/G]CGTCTACAAACTGCTTCCGAAAACTTTAGCAGACAGCACAGGArTCCAAGTCA CTCAAGGGTGTTCCGGGTCAAA | 17SC0011 |
| SOT12-59025327 | TAAATCAACTATACCGATAACTCGAGTTCGACCATTAGGTGArAAGGGCCATATTTAGAAGGATT TGAGTCGATC[A/C]AGAAGAGAGGGAGTATTGGAAAGGCATGGTTCAAAGGATTCTTCTTTTCTT TATwCTGGTCGAAACTCTATTCCT | 17SC0011 |
| SOT12-59030301 | nnnnnnnnnnnnnnnnnnnnnnnnnnnnnnnnnnnnnnnnnnnnnnnnnnnnnnnnnnTCCACGAATGTCCAACTGAAGT ACA[G/A]mGTkAAGATATGCCACTTTsGAGAATCTGCAAAAGTATTrCArGAArCATTTGTAAGGAT AATTTTATnAnnTTT | 17SC0011 |
| SOT12-59042436 | nnnnnnnnnnnnnnnnnnnnnnnnnnnnnnnnnnnnnnnnnnnnnnnnnnnnnkyTTGAAGCCGAAGTAACGTCTC AA[G/A]AATTGTTCCACTGTTTCyTCATCAGTAAGTTTGTTCTGAAGATCTCCAAATTGTGATGCA ACCAAACCATAyAAG | 17SC0011 |
| SOT12-59043512 | AGTAGGATTACGCCAGTATGACCAGTGTTGTTTCCAAAGGCAAGCTATACATTGGGTCCAAAATG GCTGTGAGTA[T/C]TTAGTATCGAAATGCAGATCTTTTGTACCAGGGCGAGGyACGCyCAGTTCAy TwATCAATGmTTTGTTCCTTGTG | 17SC0011 |
| SOT12-59043574 | ATGGCTGTGAGTAyTTAGTATCGAAATGCAGATCTTTTGTACCAGGGCGAGGyACGCyCAGTTCA yTwATCAATG[C/A]TTTGTTCCTTGTGTAAAGGTCTGATnnnnnnnnnnnnnnnnnnnnnnnnnnnnnnnnnnnn nnnnnnnnnnnnnnnnnnnn | 17SC0011 |
| SOT12-59045607 | CAAATTGTAAAAGyAGAGCAAATGATCCAAATwTACTAGCAACTCCTAAGCTCCTGCCAACTGCC CCAATGAATC[T/G]AAACAACCCTGAGGCCATCTGGCTTACTATTATGAGTAGCAAGAACTGTTT GAACAACCTGCAAAwwCArAATmm | 17SC0011 |
| SOT12-59045637 | ATwTACTAGCAACTCCTAAGCTCCTGCCAACTGCCCCAATGAATCkAAACAACCCTGAGGCCATC TGGCTTACTA[T/A]TATGAGTAGCAAGAACTGTTTGAACAACCTGCAAAwwCArAATmmCGATTA GTAATCAyrGGGAAAAGGAAATAG | 18SC0011, 18SC0012 |
| SOT12-59046301 | AAGAGCTGTTTCTTCCCTATACCGTACTTTTCAGTTGTCArAGCAGCAGGATGGCTTTTTCTCTTG TCATATGAG[A/G]CTGCAAGATCTTCCCCGAGTTTCCTCCCAACATrAAATGCTTGATATGCCTCG GAAAATTCTTTCGATGTGATAA | 17SC0011 |
| SOT12-59047597 | kCAGTTCTTTGCGGCACAAAyTCATTCATTTCATGTCCATTATAyGTCACCTTCCCACTAGCCTGA TTTCCGGGG[G/A]AAAACAAATACACAATTAGGCAAsTTACAAGATAATTCTATGTCATCwCGAGT TATACwACAATCGATAGTGTAA | 17SC0011 |

TABLE 10-continued

SNP markers as used in Examples 2, 3 and 4. All markers were generated according to the methodology as explained in Example 1. All SNPs are named according to their physical position on the DM 4.04 reference position, where the two numbers behind SOT denote the chromosome number, and the eight numbers behind the dash denote the nucleotide. The SNP is shown between brackets and 45 nucleotides of both flanks are shown with IUPAC nucleotide codes. KASP markers that were designed on the listed sequences. Stretches of continuous n-characters indicate masked regions containing variation in the germplasm that might hamper amplification via a KASP-assay.

| SNP ID | Sequence | Used for population: |
|---|---|---|
| SOT12-59047933 | TTTTCCAGCCAAAGCTAATAAGAGAGTAGTTTTGCCAGAACCAGGAGGACCTAAAAGCAAAGTC AATCTGCAAGG[C/T]TTGATGATACCGCTCATGTCATCAAGAATAGTGAGTTTCCTCTTTCGATTT GGTACrATATGGAGAGAATTCAAC | 17SC0011 |
| SOT12-59060445 | CCTCATAnTCTTATwTCAGTGCCATTCCAATCCCCCTAGAGTTGTwGAACCCATTCCTTCCCATAC TTCACTACA[C/A]CCCACTTCTTCATTATCAACACCTTCCATGTTGCAATCCCACCAGCCACCTCC ATTTGCATCTGAAAGCAGAAAA | 17SC0011 |
| SOT12-59062427 | AGGTGATACAAATGACAGAACTTAAAACTAAACTACAGTTTAGATCCTTTCTAATATTTGACATT GGTTGAAGCC[G/A]GTAACCTCGTCACCTGTTCCAATTATATACTCrAGTCwTTAGGTGTTCCAAA AGAGAAATTTAGCTCAGACCAAG | 17SC0011 |
| SOT12-59065996 | TrTGAAAATTTAATAAATCAATAyTrAAkACAGTGATTCAGATATGAAAAAGTAGAGCmATCTAAT TAnnrGAGC[T/A]GTGGTGTCAGATCTCTTTGTAAACTnnnnnnnnnnnnnnnnnnnnnnnnnnnnnnnn nnnnnnnnnnnnnnnnn | 17SC0011 |
| SOT12-59068564 | CCACCTCCwCCwCCTAAwCCACCTCCACCACCTAATCCACCwCCACCACCAAAAyGCTTCCCAAA CTTTCTwTGT[G/C]CAAATAGGAGCTTCTCATCTCCAACnnnnnnnnnnnnnnnnnnnnnnnnnnnnnnn nnnnnnnnnnnnnnnnnn | 17SC0011 |
| SOT12-59068564 | CCACCTCCTCCTCCTAATCCACCTCCACCACCTAATCCACCTCCACCACCAAAAyGCTTCCCAAAC TTTCTwTGT[G/C]CAAATAGGAGCTTCTCATCTCCAACnnnnnnnnnnnnnnnnnnnnnnnnnnnnnnnn nnnnnnnnnnnnnnnnn | 17SC0011 |
| SOT12-59068879 | CCAGTTAAAACTCAACTGyyATCTTCTTTTACTTAAATGCATGTTTGCTTTATGATTGGTCTATATA TTTAATTC[A/T]TCCAACTGCCCTCCTCCAATnCAsrGACACAGACTTACwAAGTCACAAAkACAGC ACAATTATCATAATnnGkGw | 17SC0011 |
| SOT12-59107520 | ATATATAyATrCCACTTTTTAAATGAAGAATATATTCATTyTAAATCGCAGAGTTAAAArATTTATA TkTTTTCC[C/T]TGGTGTGATTTCTGCTTTCCAAATCnnnnnnnnnnnnnnnnnnnnnnnnnnnnnnnnnnn nnnnnnnnnnnnnnn | 17SC0011 |
| SOT12-59118012 | AATATGTGCATATGTATATTTTGTTGCATATATCCTAGGCAGGAGAArGTAAATTTTACTAGTATT GGGAGCCAA[C/G]TCAAAATAATTGGGACTATTGCTACACTTGGTGGAGCCATGATTATGATGTT AGTTAGAGGCCCAGAGGTTCAAC | 17SC0011 |
| SOT12-59118012 | AATATGTGCATATGTATATTTTGTTGCATATATCCTAGGCAGGAGAAGGTAAATTTTACTAGTAT TGGGAGCCAA[C/G]TCAAAATAATTGGGACTATTGCTACACTTGGTGGAGCCATGATTATGATGT TAGTTAGAGGCCCAGAGGTTCAAC | 17SC0011 |
| SOT12-59127981 | ATCATCmACAAAACGACATTTTAACArTCAyGAAATACATTTyAGTAATTACTAmGyrTAAATTTAC mTCCArAG[C/T]TGAATTGGCATTAAGGATAATACTCnnnnnnnnnnnnnnnnnnnnnnnnnnnnnnnnnn nnnnnnnnnnnnnnnn | 18SC0011, 185C0012 |
| SOT12-59137670 | GTGTGCGAAGGTAGATTCAAGCTAAGTTTTTGCTmGTAAryGTAATGATATAArTTTGCTCGACTG TTAGAyTGA[T/C]TGATCACGAACAAAGACGAAAGTTGnnnnnnnnnnnnnnnnnnnnnnnnnnnnnnnn nnnnnnnnnnnnnnnnn | 17SC0011 |
| SOT12-59155069 | TAGTTGTACGAGTATAATGAAAGATCGAAAGAGGCTACAAAGAAGCACAGAAAATCAATGGGAT AATGTACCTTT[G/A]TTGAAACCAGTGGAGCTCTTTCACCAGGAATTTTAACATCAGGTAGATAAC TGAAATCGGAAGCGATTAwAGACA | 18SC0011, 18SC0012 |
| SOT12-59173975 | nnnnnnnnnnnnnnnnnnnnnnnnnnnnnnnnnnnnnnnnnnnnnnnnnnTGAATCAGGTACAACGCCATGT CCA[G/A]CTTCGTATyGAAGCACAGGGmAAGTATTTGCAAACGATACTCGAGAAAGCATGTAAAG TTCTTAACTACACGTCT | 18SC0011, 18SC0012 |
| SOT12-59188763 | ATGGCTGCCACTTTTGAATACTTGAGGCATCCTGGAAAGGAAGTGTAGAGGAGACATGCCCTCT ACGTTGTAACG[G/A]TTGACAAGTTGCCCATAGTAATGTATTATCTGAAAAGCCAGATCTGTTACA AGATAAGTTGTTAATACTACTGTC | 18SC0011, 18SC0012 |
| SOT12-59214797 | CGATGTGCAGCATTGmTwCAATGAGAAAAACCTTTCTTACAAyACryrTTGACTCATTGCTCCCTT TTATTTGTT[A/G]CCTGCAAAGTGTGTAGATCAGAATAATAATrTTTTTCTCATTTTGTATGTTCTT CAGGACAAGCCCAGAACTTCT | 18SC0011, 18SC0012 |
| SOT12-59225998 | GTTCAAACGyGATwGAAGATTTTTGCTTsyAGTATTACAGAAACTCGACATGATTATAGTAACAAA TGATTCATG[T/A]CGCGCATCTGTAAGAAGTGAGAGTTnnnnnnnnnnnnnnnnnnnnnnnnnnnnnnn nnnnnnnnnnnnnnnnnn | 18SC0011, 18SC0012 |

TABLE 10-continued

SNP markers as used in Examples 2, 3 and 4. All markers were generated according to the methodology as explained in Example 1. All SNPs are named according to their physical position on the DM 4.04 reference position, where the two numbers behind SOT denote the chromosome number, and the eight numbers behind the dash denote the nucleotide. The SNP is shown between brackets and 45 nucleotides of both flanks are shown with IUPAC nucleotide codes. KASP markers that were designed on the listed sequences. Stretches of continuous n-characters indicate masked regions containing variation in the germplasm that might hamper amplification via a KASP-assay.

| SNP ID | Sequence | Used for population: |
|---|---|---|
| SOT12-59230362 | ACTGTTATTTTTTkAAGCGTATGTTrTTAyAATCTTTATAGTTAGGGTTTTGTTTTGTTTGGTTGG TGGTCCCTC[T/A]ACTTTTCTCwTyTGCCATTTTTCCACCTTTCCAATTTCGAmGCAATCTATTTTT AGTGAGATGTTTyAGrTTTG | 17SC0011 |
| SOT12-59230363 | nnnnnnnnnnnnnnnnnnnnnnnnnnnnnnnnnnnnnnnnnnnnnnnnnTGTTTTGTTTGGTTGGTGGTCC CTC[T/A]ACTTTTCTCwTyTGCCATTTTTCCACCTTTCCAATTTCGAmGCAATCTATTTTTAGTGAs ATGTTTyAGrTTTGA | 17SC0011 |
| SOT12-59230363 | nnnnnnnnnnnnnnnnnnnnnnnnnnnnnnnnnnnnnnnnnnnnnnnnnTGTTTTGTTTGGTTGGTGGTCC CTC[T/A]ACTTTTCTCwTyTGCCATTTTTCCACCTTTCCAATTTCGAmGCAATCTATTTTTAGTGAs ATGTTTyAGrTTTGA | 17SC0011 |
| SOT12-59631591 | nnnnnnnnnnnnnnnnnnnnnnnnnnnnnnnnnnnnnnnnnnnnnnnnnCACTTGAGTGGGTGCAGCGGGT AAG[A/G]ATTGCTGTTGATGCTGCTAGrGGTCTyGAGTATTTGCATGAGAArGTCCAACCTTCAGT AATACACAGGGATATC | 17SC0011 |
| SOT12-60102894 | TCACATGTCTGACATTATTAATCTTsGTGTTrTAyTGArCAGAAATATTCAGCCAACTCCACTATCT GAArAAGA[T/C]CAAGTAGAGAAGGCAAGGAAATGTGnnnnnnnnnnnnnnnnnnnnnnnnnnnnnnn nnnnnnnnnnnnnnnnn | 17SC0011 |
| SOT12-60102894 | TCACATGTCTGACATTATTAATCTTsGTGTTrTAyTGArCAGAAATATTCAGCCAACTCCACTATCT GAArAAGA[T/C]CAAGTAGAGAAGGCAAGGAAATGTGnnnnnnnnnnnnnnnnnnnnnnnnnnnnnnn nnnnnnnnnnnnnnnnn | 17SC0011 |
| SOT12-60390660 | TGATCTGCyArCrATTGAGGTCsGCCGrCGAGTATTGyTTATGAAATGAyGAACAkATGTGGAAGAG AGATAATC[T/C]GGTGACCGGACAGCTGGAAGTTTTGnnnnnnnnnnnnnnnnnnnnnnnnnnnnnnn nnnnnnnnnnnnnnnnn | 17SC0011 |
| SOT12-60524226 | GCTCTTGGTTTAACrCATAGATTCCAGTCCAAATATGTCACCGTTGTCCTCTACAArCCACTGAAG AGGTGACmA[G/C]CCCGTGTTCACAATCAAATCTTTCCnnnnnnnnnnnnnnnnnnnnnnnnnnnnnn nnnnnnnnnnnnnnnnnn | 17SC0011 |
| SOT12-60708789 | TTTTTGTTTTCTACATATTATTTTTGGTTAATTATTTATACCCTmTTTAGTTTATGGGTAAATGGT AATTATAGG[G/A]CCTTCCTAGTTCCCATTTGTTCTTCATAAAAAGGGATCATTTGGTTCAAGATC AGATATTCAAGAATTmTAATAA | 17SC0011 |
| SOT12-61145775 | nnnnnnnnnnnnnnnnnnnnnnnnnnnnnnnnnnnnnnnnnnnnnnnnnTTTGTCTCATGGTTGCCACTTG GTT[C/A]TTCTTGCTTrGGTTGATGGTTGGGACAGTGATCCTrCGGATGTAGATCTTTATrACAkAG ATGAyGTAGAyTGGG | 18SC0011, 18SC0012 |

TABLE 11

SNP markers as used in Example 3. All markers were generated according to the methodology as explained in Example 1. All SNPs are named according to their physical position on the DM 4.04 reference position, where the two numbers behind SOT denote the chromosome number, and the eight numbers behind the dash denote the nucleotide. The SNP is shown between brackets and 45 nucleotides of both flanks are shown with IUPAC nucleotide codes. KASP markers that were designed on the listed sequences. Stretches of continuous n-characters indicate masked regions containing variation in the germplasm that might hamper amplification via a KASP-assay.

| | | |
|---|---|---|
| SOT12-59016142 | ACCACCTATTCTAACArAAAAAATACTTTCGTTTrArGCTCTGACCTTCTTTTTTCAGAATTGAAGT ATGCTGGC[C/G]CGTCTACAAACTGCTTCCGAAAACTTTAGCAGACAGCACAGGArTCCAAGTCA CTCAAGGGTGTTCCGGGTCAAA | 17SC0011 |
| SOT12-59016842 | nnnnnnnnnnnnnnnnnnnnnnnnnnnnnnnnnnnnnnnnnnnnnnnnnCTGATCGAACGGCTAAGGATGA GTC[C/T]ATGATATTCyCACTTTGTGGTATTTTTTTGACATCCAAAyACACCCTAAGTTCGCGTTTG ACTATAGATTTTCTC | 17SC0011 |
| SOT12-59019869 | TGrGrCArAGAAGGAAAAAACCATTGTCACACTTsATTTAGrmCAAGAGACATTTGGAGTAATGAA ACAACCTAT[A/G]TTGGAACATGATGAAAATGTCAATTTTCATAATGTTGrTGTTTTACAAGGATG TTTATCTTTGCTTAACAAAGGT | 17SC0011 |
| SOT12-59019907 | TAGrmCAAGAGACATTTGGAGTAATGAAACAACCTATrTTGGAACATGATGAAAATGTCAATTTT CATAATGTTG[A/G]TGTTTTACAAGGATGTTTATCTTTGCTTAACAAAGGTAATGGACwTTATTGT GAAATTTGGGTGATGAAGGArTA | 17SC0011 |

TABLE 11-continued

SNP markers as used in Example 3. All markers were generated according to the methodology as explained in Example 1. All SNPs are named according to their physical position on the DM 4.04 reference position, where the two numbers behind SOT denote the chromosome number, and the eight numbers behind the dash denote the nucleotide. The SNP is shown between brackets and 45 nucleotides of both flanks are shown with IUPAC nucleotide codes. KASP markers that were designed on the listed sequences. Stretches of continuous n-characters indicate masked regions containing variation in the germplasm that might hamper amplification via a KASP-assay.

| | | |
|---|---|---|
| SOT12-59022612 | nnnnnnnnnnnnnnnnnnnnnnnnnnnnnnnnnnnnnnnnnnnnnnnnnnTACCGCCATCTAGTAACAAATTT TC[T/G]TATAAyTGTGATGATCATACGTTCAATTTTCTCTCCGATAATGGATTyAGTCAGTTTCATC nTTCTCCTATATTC | 17SC0011 |
| SOT12-59024580 | GACTTCAGrCAACAGGGkACAAAGATAAGGAGGAAGATGTGGTATGAAAATATGAAGATAAAACT GGTTGTTTTT[T/G]CCATCATCTTGGTCCTGATTCTCATTAyCATTTTATCTGTCTGCCCTGGCTTC AAATGCACTTCGTGATTCAACC | 17SC0011 |
| SOT12-59025293 | GTTTTTTACATsCAGnAACATACATTAATATAGTAAATCAACTATACCGATAACTCGAGTTCGACC ATTAGGTGA[A/G]AAGGGCCATATTTAGAAGGATTTGAnnnnnnnnnnnnnnnnnnnnnnnnnnnnnnn nnnnnnnnnnnnnnnnnn | 17SC0011 |
| SOT12-59025327 | TAAATCAACTATACCGATAACTCGAGTTCGACCATTAGGTGArAAGGGCCATATTTAGAAGGATT TGAGTCGATC[A/C]AGAAGAGAGGGAGTATTGGAAAGGCATGGTTCAAAGGATTCTTCTTTTCTT TATwCTGGTCGAAACTCTATTCCT | 17SC0011 |
| SOT12-59030123 | GCTATTGAAATGTCCCAGTTCTACTTCCATCCATCCATCTCCTCTCArTTTTGCCGATGTCACAAG TTTsAAAGT[A/G]TTGGCTTGTTCTTCAGTCTCAGTATnnnnnnnnnnnnnnnnnnnnnnnnnnnnnnnn nnnnnnnnnnnnnnnnn | 17SC0011 |
| SOT12-59030235 | TTAACAAACCTAATAATTGAATTAGCATATTCAAGTTCACAkGACCTTCTTCCCAATTkGAACACC AAATAAGCA[A/G]CATAATCTGTCTTTGGTGACAACATnnnnnnnnnnnnnnnnnnnnnnnnnnnnnnnn nnnnnnnnnnnnnnnnn | 17SC0011 |
| SOT12-59030301 | nnnnnnnnnnnnnnnnnnnnnnnnnnnnnnnnnnnnnnnnnnnnnnnnnnTCCACGAATGTCCAACTGAAGT ACA[G/A]mGTkAAGATATGCCACTTTsGAGAATCTGCAAAAGTATTrCArGAArCATTTGTAAGGAT AATTTTATnAnnTTT | 17SC0011 |
| SOT12-59030880 | AGGTAGTGAAGTGTTryCGTGTTTTyyrAGAGTTTyrGCnnnTTGGTGTTTTGTCGTTGTACTAGTTG TAGTATT[G/A]TAGTTCTTGATTGTGATATCTATyATTTTATGTTGTTTATTGTGTTTTGGTTATTG CTmTATTTTGTTGTTCTTA | 17SC0011 |
| SOT12-59042250 | nnnnnnnnnnnnnnnnnnnnnnnnnnnnnnnnnnnnnnnnnnnnnnnnnnAACyGCGTCTTCCCCATTTCACG AG[G/C]wGyGGAGAGAACrTTTCACACGTTGTCTTTACTnCATCTTCAGCAGGTAAyGyCnTTTATy TCGTTTGGAAGTTr | 17SC0011 |
| SOT12-59042436 | nnnnnnnnnnnnnnnnnnnnnnnnnnnnnnnnnnnnnnnnnnnnnnnnnnkyTTGAAGCCGAAGTAACGTCTC AA[G/A]AATTGTTCCACTGTTTCyTCATCAGTAAGTTTGTTCTGAAGATCTCCAAATTGTGATGCA ACCAAACCATAyAAG | 17SC0011 |
| SOT12-59043512 | AGTAGGATTACGCCAGTATGACCAGTGTTGTTTCCAAAGGCAAGCTATACATTGGGTCCAAAATG GCTGTGAGTA[T/C]TTAGTATCGAAATGCAGATCTTTTGTACCAGGGCGAGGyACGCyCAGTTCAy TwATCAATGmTTTGTTCCTTGTG | 17SC0011 |
| SOT12-59043614 | ACCAGGGCGAGGyACGCyCAGTTCAyTwATCAATGmTTTGTTCCTTGTGTAAAGGTCTGATTTCT TGTATAAATC[T/A]GTAAAATCAACCCCGAACAGTATTTCyTGAGCyGAGGCTGTGACTTCTAACA TCCAAGTTGCTGGATTGTAGCCA | 17SC0011 |

TABLE 12

Sequences of the PSC gene and transcripts as provided herein.

| SEQ ID NO | Description | Source | Annotation | Genotype (Phenotype) | Location in application |
|---|---|---|---|---|---|
| 1 | PSC gene-region sequence incl. adjacent gene sequences in reference genome | *S. tuberosum* Group *Phureja* DM1-3 | PGSC0003 DMG400016861 | psc/psc (SI) | FIG. 7 |
| 2 | PSC gene-region sequence incl. adjacent gene sequences | *S. chacoense* "DS" (IVP07-1001/4 to Hosaka) | PSC allele | PSC/PSC (SC) | FIG. 7 |
| 3 | PSC gene-region sequence incl. adjacent gene sequences | Diploid F4 potato genotype 17SC0100-0002 (Example 4) | PSC allele | PSC/PSC (SC) | FIG. 7 |
| 4 | PSC gene-region sequence incl. adjacent gene sequences | Diploid F4 potato genotype 17SC0100-0018 (Example 4) | PSC allele | PSC/PSC (SC) | FIG. 7 |

TABLE 12-continued

Sequences of the PSC gene and transcripts as provided herein.

| SEQ ID NO | Description | Source | Annotation | Geno-type (Pheno-type) | Loca-tion in appli-cation |
|---|---|---|---|---|---|
| 5 | PSC gene-region sequence in reference genome | *S. tuberosum* Group *Phureja* DM1-3 | PGSC0003 DMT400043434 | psc/psc (SI) | FIG. 7 |
| 6 | PSC gene-region sequence | *S. chacoense* “DS” (IVP07-1001/4) | | PSC/PSC (SC) | FIG. 7 |
| 7 | PSC gene-region sequence | Diploid F4 potato genotype 17SC0100-0002 | BL_17SC0100-0002 NODE_4559_length_28844_cov_5.188734 | PSC/PSC (SC) | FIG. 7 |
| 8 | PSC gene-region sequence | Diploid F4 potato genotype 17SC0100-0018 (Example 4) | BL_17SC0100-0018 NODE_4276_length_28842_cov_5.003099 | PSC/PSC (SC) | FIG. 7 |
| 9 | protein sequence of putative F-box protein PP2-B10-like UniProt M1BEM0 | *S. tuberosum* Group *Phureja* DM1-3 | DM-PGSC0003 DMT400043434 | psc/psc (SI) | FIG. 1 no.6 |
| 10 | protein sequence F-box protein PP2-B10 | *S. chacoense* “DS” (IVP07-1001/4) | PSC-PGSC0003 DMT400043434 | PSC/PSC (SC) | FIG. 1 no.2 |
| 11 | protein sequence F-box protein PP2-B10 | Diploid breeding line D2 | FO_D2_NODE_55467_length_4836_cov | psc/psc (SI) | FIG. 1 no.3 |
| 12 | protein sequence F-box protein PP2-B10 | Diploid breeding line D8 | FO_D8_NODE_78731_length_3613_cov | psc/psc (SI) | FIG. 1 no.4 |
| 13 | protein sequence F-box protein PP2-B10 | Diploid breeding line D14 | FO_D14_NODE_41388_length_7594_cov | psc/psc (SI) | FIG. 1 no.5 |
| 14 | protein sequence F-box protein PP2-B10 | Diploid F4 potato genotype 17SC0100-0002 | BL_17SC0100-0002_NODE_4559_lengt | PSC/PSC (SC) | FIG. 1 no.1 |
| 15 | Forward_G4_S primer | Example 7 | | | Table 14 |
| 16 | Reverse_G4_S primer | Example 7 | | | Table 14 |
| 17 | PSC gene sequence | Example 8 | cloned into pBINPLUS vector | | FIG. 17 |
| 18 | PSC gene promoter | Example 8 | | | FIG. 19 |
| 19 | PSC gene coding sequence | Example 8 | | | FIG. 20 |
| 20 | PSC gene promoter | Example 8 | | | FIG. 21 |

TABLE 13

Gene expression levels of pollen-expressed genes in SC and SI pollen, compared to expression in other tissues (in the mapping intervals mentioned in the examples)

| | tissue | | | | | | | | | | | | | | | |
|---|---|---|---|---|---|---|---|---|---|---|---|---|---|---|---|---|
| | various | | | styles | | | pollen (SC) | | | pollen (SI) | | | | | | |
| | number of samples (n) | | | | | | | | | | | | | | | |
| | 388 | | | 3 | | | 5 | | | 3 | | | | | | |
| | sample type | | | | | | | | | | | | | | | |
| | SRA [various] (n = 338) | | | SRA [styles] (n = 3) | | | SC (PSC/psc) (n = 5) | | | SI (psc/psc) (n = 3) | | | | interval | | |
| geneId | max | mean | stdv | max | mean | stdv | max | mean | stdv | max | mean | stdv | HAPLO | I | II | III | IV |
| Solyc12g097050,2 | 18.1 | 0.0 | 0.9 | 0.0 | 0.0 | 0.0 | 711.0 | 479.7 | 157.1 | 424.6 | 333.3 | 144.2 | psc/(PSC) | + | | | |
| Solyc12g097070,3 | 5.3 | 0.9 | 1.2 | 4.7 | 3.7 | 1.0 | 6.3 | 5.3 | 0.9 | 12.0 | 11.0 | 0.9 | n.d. | + | | | |
| CA12g02510 | 0.0 | 0.0 | 0.0 | 0.0 | 0.0 | 0.0 | 18.0 | 10.5 | 5.8 | 25.0 | 19.4 | 4.9 | n.d. | + | | | |
| PGSC0003DMG400008637 | 0.1 | 0.0 | 0.0 | 7.5 | 3.3 | 3.8 | 536.3 | 336.0 | 178.0 | 913.3 | 611.5 | 307.0 | psc/(PSC) | + | | | |
| CA05g06620 | 0.4 | 0.0 | 0.0 | 0.8 | 0.6 | 0.2 | 103.4 | 45.7 | 38.7 | 211.5 | 178.5 | 35.5 | psc/(PSC) | + | | | |
| PGSC0003DMG400008625 | 30.9 | 1.2 | 3.9 | 0.1 | 0.1 | 0.1 | 34.8 | 7.3 | 15.4 | 1.0 | 0.8 | 0.2 | n.d. | + | | | |
| PGSC0003DMG400016876 | 0.2 | 0.0 | 0.0 | 20.5 | 8.0 | 10.9 | 1965.3 | 1452.1 | 444.4 | 1603.1 | 1207.2 | 355.5 | psc/(PSC) | + | + | | |
| PGSC0003DMG400016869 | 0.1 | 0.0 | 0.0 | 2.8 | 1.0 | 1.5 | 19.5 | 15.5 | 2.9 | 24.7 | 20.5 | 4.1 | n.d. | + | + | + | |
| PGSC0003DMG400016861 | 1.8 | 0.1 | 0.3 | 967.9 | 397.6 | 494.8 | 94.9 | 60.8 | 22.9 | 0.8 | 0.4 | 0.4 | PSC* | + | + | + | + |

TABLE 13-continued

Gene expression levels of pollen-expressed genes in SC and SI pollen, compared to expression in other tissues (in the mapping intervals mentioned in the examples)

| | tissue | | | | | | | | | | | | | | | |
|---|---|---|---|---|---|---|---|---|---|---|---|---|---|---|---|---|
| | various | | | styles | | | pollen (SC) | | | pollen (SI) | | | | | | |
| | number of samples (n) | | | | | | | | | | | | | | | |
| | 388 | | | 3 | | | 5 | | | 3 | | | | | | |
| | sample type | | | | | | | | | | | | | | | |
| | SRA [various] (n = 338) | | | SRA [styles] (n = 3) | | | SC (PSC/psc) (n = 5) | | | SI (psc/psc) (n = 3) | | | | interval | | |
| geneld | max | mean | stdv | max | mean | stdv | max | mean | stdv | max | mean | stdv | HAPLO | I | II | III | IV |
| PGSC0003DMG 403004568 | 12.4 | 0.5 | 1.3 | 0.2 | 0.1 | 0.1 | 10.6 | 8.1 | 1.4 | 14.8 | 11.9 | 4.2 | n.d. | + | | | |
| PGSC0003DMG 400004657 | 3.9 | 0.1 | 0.4 | 2.3 | 1.4 | 1.2 | 39.8 | 26.9 | 9.7 | 39.1 | 34.9 | 4.0 | psc/ (PSC) | + | | | |

Tissue indicates biological tissue for which expression was measured; number of samples (n) indicate the number of RNA-seq samples for which expression data was quantified per tissue type; SRA +various+ indicate public expression datasets downloaded from SRA, various tissues (non-pollen, non-styles); SRA +styles+ indicate public expression datasets downloaded from SRA, styles tissue; SC (PSC/psc) indicates self-compatible plants, heterozygous for PSC; SI (psc/psc) indicates self-incompatible plants, lacking PSC; Sample category geneId indicates gene accession ID reported in StringTie's expression quantifcation (on merged gene catalogues); max/mean/stdv indicate maximum, mean and standard deviation of FPKM observed in panel of samples; interval I, II, III, IV indicate location of the gene in respect to mapping intervals in this study; HAPLO indicates evidence for haplotype-specific expression for the psc and/or the PSC allele in pollen samples; psc/(PSC) means the psc (SI-plants) or the psc and PSC (SC-plants) haplotype is expressed; *indicates evidence for PSC-haplotype specific expression.

TABLE 14

Primers used in Example 7

| Primer name | sequence | SEQ ID NO |
|---|---|---|
| Forward_ G4_S | TCGTGATTTCATCCGCGATC | SEQ ID NO: 15 |
| Reverse_ G4_S | TGCCTCCATCCATTAGAACAGG | SEQ ID NO: 16 |

The invention claimed is:

1. A recombinant nucleic acid construct comprising a nucleic acid sequence encoding a protein having the amino acid sequence depicted in SEQ ID NO: 10, or a protein having a sequence having at least 98% sequence identity with SEQ ID NO: 10 and conferring self-compatibility to a potato plant when expressed in the pollen of said plant, wherein the nucleic acid sequence is complementary to an mRNA template and lacks intron sequences, said recombinant nucleic acid construct further comprising a promoter nucleic acid sequence for expression of the protein in plant pollen.

2. A vector comprising the recombinant nucleic acid construct of claim 1.

3. A potato plant protoplast, a potato plant cell, or a potato plant callus transformed with the recombinant nucleic acid construct of claim 1.

4. A transformed potato plant regenerated from the potato plant protoplast, cell, or callus of claim 3, comprising the recombinant nucleic acid construct.

5. The transformed plant of claim 4, wherein the recombinant nucleic acid construct has replaced the endogenous genomic sequences of the Potato Self Compatibility (PSC) gene of the potato plant.

6. A part of the transformed plant of claim 4, wherein said part is an isolated cell, a propagation material, or an isolated organ.

7. A food product prepared from at least one of the cell, the propagation material, and the organ of claim 6, wherein said cell, propagation material, or organ comprises the recombinant nucleic acid construct.

8. The transformed plant of claim 4, further comprising at least one allele of a *Phytophthora infestans* resistance gene of *S. tarinjense* 852-5 Rpi-tar 1.

9. The transformed plant of claim 4, wherein said plant does not comprise one or more of the genes that do not confer self-compatibility and that are present in the genomic region between genomic markers SOT12-58962004 and SOT12-59130723.

10. A potato plant comprising a recombinant nucleic acid construct comprising a nucleic acid sequence encoding a protein having the amino acid sequence depicted in SEQ ID NO:10, or a sequence having at least 98% sequence identity with said amino acid sequence and conferring self-compatibility to a potato plant when expressed in the pollen of said plant, wherein the nucleic acid sequence is complementary to an mRNA template and lacks intron sequences, said recombinant nucleic acid construct further comprising a promoter nucleic acid sequence for expression of the protein in plant pollen, and said potato plant further comprising at least one allele of each of a *Phytophthora infestans* resistance gene selected from:

*S. avilesii* 478-2 Rpi*-avl1;

*S. tarinjense* 852-5 Rpi-tar1;

*S. chacoense* 543-5 Rpi-chc1; and

*S. venturi* 283-1 Rpi-vnt1.

11. The recombinant nucleic acid construct according to claim 1, wherein said recombinant nucleic acid construct further comprises a truncated or non-truncated promoter region of the native PSC gene which is located at coordinates 53954293 to 53532708 of the Solyntus 1.0 genome assembly.

12. The recombinant nucleic acid construct according to claim 1, wherein said recombinant nucleic acid construct further comprises the nucleic acid sequence depicted in SEQ ID NO:18.

13. The potato plant protoplast, cell, or callus according to claim 3, wherein the protoplast, cell, or callus is a *S. tuberosum* Group *Tuberosum* plant protoplast, cell, or callus.

14. The transformed potato plant of claim 4, which is a *Solanum tuberosum* Group *Tuberosum* potato plant.

15. The part of the transformed plant of claim 6, wherein said part is a tuber or seed.

16. A plant part of the plant of claim 10, wherein said part comprises the recombinant nucleic acid construct.

17. The plant part of claim 16, which is a tuber or seed.

* * * * *

SEQUENCE LISTING

<160> NUMBER OF SEQ ID NOS: 233

<210> SEQ ID NO 1
<211> LENGTH: 8822
<212> TYPE: DNA
<213> ORGANISM: Solanum tuberosum

<400> SEQUENCE: 1

```
ctatattttg ttgttcttag tcctttctta taggattttg cattgccccc acccccaccc     60

cccttgttag tagctatatc tttttccatt gttttcttct tccttgtact tacatttgtt    120

gcacttgcgt tgagggtctt tcgataataa catccctagc ctccacaaag tactagtaag    180

ggctgcgtac actctaccct ccttgttttc ttcttccttg tacttacatt tgttgcactt    240

gagttgaggg tcttttgaaa ataacatctc tacctccaca aggtagtgat aaggactgcg    300

tacactctac cctccccaga ctccacttgt ggaatttcac cggatatgtt attgttattg    360

ttataaggaa aagctttggt ctcgaaactc tttaaactca atttttttct tttgcactcc    420

ctcttttctt gagtacactt cactctcaat tctttcttga gcacacactc ttttatttga    480

gtacacatac aactcaaatg accacctcaa tcgaccccac ttgtggaatt tcaccagata    540

tgttgttgtt attgttataa ggacaagctt cggtcttaaa gctcgataaa ctcatttttt    600

tcttttgcac tccctctttt cttaagtaca cttcactctc aattctttct tgagcacaca    660

ctctttattt gagtaaacat acaactcaaa tgatcacctc tatttatcgg tgttgatgga    720
```

-continued

```
aggatctagt gaatgcaata ttctagaact acaccttcca cttctttctc gaattctttt    780
agactttgca ctctagaact ctcatcctaa agttcttctt tcaatacaag tcttgaatat    840
gctagattct tctttgaaat atcttagata ttaattaagg tggtgatgac ttttaacacc    900
cctctcagca ccaacttaat ttattctttg catccatttt gagtgatcct cgagacattg    960
caatcatctt gatgtccagt aactttatga atctcttcct cctttgaact tccccactca   1020
cttttctttg aatcttattc gaaggtagta gtctccttga tctagaccac tctgctaatg   1080
ttgcatcaat atacttggtg tttgggaatt tcaatcatgt agacctcctt agtcacggtt   1140
gtggtgcttc tcggacttct tcttgcaaca ttacaggagt ttcactttga gtctaatagg   1200
aaatctcttt ggaccaccat gttgatgctt catcaaatac cagatttctt gacacatata   1260
tcctattagt gataggaagg agaaatacga agggatatag gatagacttt tcgattgagc   1320
cttcttgttg aatctataac aactctacaa taatgtaact tgataaagta ggtattaggg   1380
ctccctcgct ctaacagcta tagtgacccc cttagcagca gctgcgcagc cctcccatgg   1440
ctgctacaac cactggaaag cctcctcccg aggtagtcca gcccgcccca acatggtttt   1500
atctcgctca gtgaaggttc agtattagcg gtaatgcaag ttaaggattt gaacaaaggg   1560
agagaatttg gtagaaaaga ggagcggaac atggtaatgc gcaagaaggc aacatctaat   1620
gcttctccag gttgtgagaa gaggcacaat attagtaatg tttcaagagc cctattatgt   1680
tggaacaact ttgatgcttt attgaaggct actggaaaaa atagtaatat tatggttcca   1740
acattacata tttctaatcc ttaagtagct aattaggatt attcaagaaa atcaggatgg   1800
catgctactc aaatccaatc caacaatcaa gccactcatg gttacattga acacctcggc   1860
tcatgaggcc ccttcccaat cattggagtc acttggtcaa tatcaaggtg aatctggaca   1920
gctactattg tcaacaggga atggtgacga tttagttact ttagatgtgc aatcaatctt   1980
ttttaattca tgcacttgtc aaaggaagtt tgaggccgat aactcaacct tcttaattct   2040
tggttgttat attttaacat tatttaagca tcctcatttg taatatcatc agagtgtatt   2100
acaaactcta tggtaatcac aaaatcctag ttttttctag cttttatttt ttcttcatgc   2160
ttgttagtta gtagaggttt gttacctcat tatgactggt aaggtaaggt ccagctccct   2220
ttacttgtac ttatccctga tgaatttttt ttattatttt taatagaaag ccgctaaaaa   2280
aaataatttt aagaaattta ttttatacgt aatcaaatta aaatacgttg cataaaacat   2340
ttataagaaa gtggaatgac gtacgttgta gatcaaatta aggaaatgat aagagataaa   2400
cctggaatcg tggtgtttct tccattgcca agagtgtatg tcatcactcc ccaaaatttc   2460
aagctttctt gctgctatca taaaacattt ttttccactg tacttatcaa taaaaaaatt   2520
ctgaaaggaa aaaaaaacca ttaaacaata taaaaatgta taatattgta tttataatct   2580
aatcattaat ccaaattcac accatgtaag gaacttataa ttttataaag aaaagtagca   2640
tacataatag agttattata gataaaggta ggggaaaaaa aaaggattat aaagtaatga   2700
acaaagtcaa aataagaaaa taaaaatatc gtaatgacat ggccatatca aattgatcat   2760
tacataaaat gatactttca tcgttacata atgatgaatt tattgataag atacaataaa   2820
aattaaataa ttaacaattc aaataaacgt tgtgtttaaa ataacaatat aatacaatac   2880
gataactcac aacaacccaa aggcatatag ttcaattttt cgaataacct aaacttggtg   2940
agtgaaacag aataaaacaa gattcttttg atctttctta gtttcattaa ctatgaaaaa   3000
aataaaaaag tacaaaaaat gaaacatcaa gaaagatata gccagtgaac aatgaattga   3060
ttgaaaatta taagatatta gattttaaat tttagcaaag ataaaaaatt gggtggtcat   3120
```

-continued

```
ttcgttctac ctgcttgagc tatagaatta cctggtatag tagtcgtgat aaaagtttaa   3180
ttgaatctcc tttacttgaa attacaccga tacacatggt aaaaatatat ttttaaaaaa   3240
attatatatg aattgttgaa ttcaaagtct agtttagcaa cagaggggta caaaggttgt   3300
tttagattac gagtttaaat cctaagtgtg acactcattt tttttttaat attcttatat   3360
gaatttctaa ctcatcatta tattgtttga tacttgtgtt agtgagaggc taaaaccgat   3420
ttacaagatt aataccaatt tcatatgaat cctatacttt tatatatatc ggaacataaa   3480
tttatgtgta aaaattcatg ataaatgcaa tagatatagt agatataaat cacaacttta   3540
aagaacatca tgatttaaat gttaagtaac taaaaaattg aatccataaa tcttaaattc   3600
tgattttgcc tctggtgata ggtaccaaat acgtacctaa taaataattt aggttcacgc   3660
aaactagcac atataccacc attactaaaa tataaataaa atcattgaag gtaattaatc   3720
acatcaaaat gagattttac cagtctgccg cggtcaagga gaatgggaga atcacataga   3780
ctaaaaaaga gctccttttt ggtgttgcaa atccgaggaa gcttagatct atcaattatt   3840
ttttggtaat cggaaggcaa aaatcttccc caaatttcat cagattttgc aacaaatttg   3900
aatcctgttg atgaaattgt tgatcttact gcatctgctg gagttgttct tgaaattatt   3960
tcaaagatgc aaccttctgg caacatttca aaataattca ttggagctat agacttagaa   4020
atattcatgt caaaattctt ataaaacttt ataatcgaga aataacctaa gttttttttgt  4080
tacaagcttt atatatgatt aaataatcaa aagataaaaa agatttcaga ggtctataca   4140
ttgtcaaata tagtaataag tacatataag catatacaat tatgtttttt tttccttttt   4200
tgtcaatgag tacagataag caaaaagtca aacttattca aataacaata accattgcca   4260
caccttaatc tcaaacaagt ttcacgttgc tttaattaag tgtaccgaga ctaatattat   4320
attatataaa ataaaaataa catgtacgag aagatctatt taatttggcg tgaaatgtta   4380
tctaaagtct caaataattg gtattgctta tatgaaagta aaaaaacttc cattgtgtgc   4440
catactttcg agacaactcc tttgtgattt taggtctact tggtctcatt ttaacacctt   4500
cacactatga tttcatagtg taacaactta attaattttt tatttaatca taataaatta   4560
gtacgataca gtgtaaacat cagatgtaaa taagttaata ttcaatagag gtcaatttag   4620
aacatgacca aaccgtctca tttgttttat ttttattatg tgctcgattt attgttagct   4680
atttcaacat cgattccaat agtatttaga tctttcgaaa agcaaatagc cataacacat   4740
tattatttat atatcaagaa aacacatatg ctatattata gtactattgt gcaatttctt   4800
cttcattctg gtctaaattc aattccttga acaataaggc caccttttcc atgaagccgc   4860
gtaatctcca tcaatcgcgc ttcaacatct ccatcatctc ctgtatcgtt gataaaattt   4920
cccaattcta tttccatcca tccatcgact ctttttcgtg gacgttttac gttacgtttg   4980
cgtctcctaa cccttttttcc gactagactc acgacactag ctcgttcctc ggcatcttta  5040
tcgctcacac gattcacaaa tctaacaaat gcattagcaa tttctagtcc atcatgatcc   5100
tttgccaatt tgaacaccaa ataaacaaca tatttggttc ttttcgacaa tatttgtgtt   5160
ccaatcgtgc ctcgtatgtc tagccaactt acacccttga gatgtgccac ttccgaaaat   5220
ctacaaaata aaatgtatat atagtctcag atacatgtat ttagtgagtt taagatatat   5280
atatcatcgc caatataagt aatttttgca ccatcaaatc atcttttacc tattgtaata   5340
ggtaacatat ttcattacat attttaacga ggctcatcta tggtgacctg attgtgttaa   5400
aaaattcttt cttaccaata gtgacagagg tagaatttca accaaggat tcaaaaaata    5460
```

-continued

```
gcatatgtag aaattcgtta aaaggcattg aagtataatg ttttatacgt agtataattt   5520
ttcgacgaac ctggagtcgg gatgagaaat ccattcccaa taccatggtg tatcaactcc   5580
ccatgaaata gcaagttctc tagctgatat cataaaacat ttcttgcctg ttttcttatc   5640
aagtgaaaag ctctgttttc aaaaataaaa taaaatctta gattcacact actagcttat   5700
agtccattca aaaataaaat aaaattgaca attgttagta taatctattt aattttgcat   5760
ttttaatggt gtttgtaacc catttgccgg aaaatcttaa aagttcagtt agttgactat   5820
ctgaacttct gttttactag agagagttcg attctcagtt tttaacaaaa acaaaataaa   5880
ataagaaaaa ttcattggct gattaattaa gatttgcagc agtaagcaca ctagtggatt   5940
ttagtgcttc ctatcgacat ttcaactctg attaaaactc aaactcgaga cttcaggtca   6000
aaggttcatg acctttacgg ttatacaaca ccaacagcca ggggcggagc tagaacaccc   6060
ctataaattc taggaagtca atagttttag ttcaaactct gtatttatct ttaaaaagaa   6120
aactcctcta atatgtacca aattattaat ttcgaaccaa acaactcaaa aaacacacaa   6180
aaagaaatcc cgaacccata agcttcaacg caattataca tatattaaac taaaatgagc   6240
caaaaaaaag cttactactt cccaatttag agctacttac caatttgcct ccatccatta   6300
gaacagggaa gtcacataga ctaaagtaaa gctccttttt agacggataa atccgcgggg   6360
agacatatct cgagataata tcttcataat catctggtaa aaactttacc caaataacgt   6420
cggattcagc agcagagttg aatccccgag agatcgcgga tgaaatcacg acatctttcg   6480
gggaagtaaa ggagagaata tcacaaacac aaccttctgg tagcaatagg aaatagtcca   6540
ttattggaaa attgaatttg aagatttgtg aatttttttt tgtttatata aagcaaactg   6600
agaaaagttt attgaaaagt tgttacactc atgtctcaac ggttaagtat tgtttcgttc   6660
atttttactt ctccagtatg aatataataa gagaaaaagg tcatatgagt tagaactgat   6720
atatagctcg ttataaaaat gggctcatac atacctatat tattacacaa atagcctaga   6780
tataccettt tggcctaatg gaagtgaaaa tatttaattt tattcatttt tgtttatttt   6840
tcattatttt atctagttct cacatatgta cattttattt ccaaaaataa ataaattaaa   6900
gaattgatat ttgcttagat acaccaaaca aacaactcat gtggaggaag atattattcc   6960
actaacataa aacatgaaat gttttgagtt tgaaactttt ttttttttcc ttttttggt    7020
gaagtgaaac atgaaatgtt taggaagatt catcattggg tattcgaaat ttactggccc   7080
gactaattca agattaatat catctaaggt ccatttatca aggagcattc ccgaccaaga   7140
atttctccat tctctgaatt caaaccgaag acttcttgtt tagttaacac tggagaaatc   7200
tcattcatcg cgccacatct ttgatgagtt gtggcagttc cccaaaagca atattcacaa   7260
attcttacat tcaccatttc atcaatttct tatagttata aaactacaat aacaacatat   7320
ccaatgtctc cccacaaagt gaggtctagg gagggtagag tgtacacaga ctttacttca   7380
actttagaga tagaaagtct ttttctgata gatcctcaac tcgagaaaac taatccaaag   7440
cagttcagaa ttagacacaa caaaagtaca agaaacaaca gatagtaaca gaacagtact   7500
tcttgaatat ggtactggat taggtagaaa gaacataaaa aaaggctaat aacaatggaa   7560
tgaatttgcc actgcatttt gattcaacat taacaaatta ctatctctta cacagaacat   7620
acacttgttc aagtggaaat ctatatacag tactttcaaa atcactctca ctcgtacttg   7680
agctcgagaa aaattcctta tactaactgc gtcttcccca tttcacgagg agtggagaga   7740
acgtttcaca cgttgtcttt actacatctt cagcaggtaa cgtcttttat ctcgtttgga   7800
agttaaatgc cttaatagcg aaagcaaatg tgaagccaaa aagaacagtg tacccaacaa   7860
```

-continued tcgcgactgc aactattgga agaaaatcat gcttgaagcc gaagtaacgt ctcaagaatt 7920
gttccactgt ttcttcatca gtaagtttgt tctgaagatc tccaaattgt gatgcaacca 7980
aaccatacaa ggtccaggca acaggacaac accagtagta ccatctccac catatgggaa 8040
tacgctgttt tttcaaaatg aaaatggaaa aaaaatacag agaatatgtc atttccgagc 8100
tctaagttag ttttgatgta acaataaaat ggaagtgttt caagaactta cagttcgtgg 8160
aacgatgaat cctgagaaaa gattccatac tccgtagaag aaggagccga caatttgagc 8220
aacacttaca tttggggtaa cagcaacggt catcataccg tagaaagtga agtacaagag 8280
ggtgaaaaac aggaagaaca agtaccaaaa gaactttgct accgtccatt caaatccgat 8340
catagcatac ataattgcac cacagaaaac agattgcata aagacatatg ggatttcaat 8400
ggaaatctgc aagatagaaa aagttaagta atttagactt ttcacctaaa ttgtcgaggc 8460
acgtagtgtt aagagtggat aacatgtagt cacttatagt gggaaaagct cagtgatcaa 8520
atgtgaaatt aacgcaagat tggcttataa gaaattgaac tctatgttca cctgtccaaa 8580
ggcatagggc aaggcagaat acattccagc agctctttct ctatagaata ctgtacgttc 8640
aacggctaca acaggctgca ctgatgatga attttgtgta ccgaggaaga gaacagtagc 8700
atacaagcat cccatcgcgt taaatagatc ttgactctta ctcctgtaac cataaaagat 8760
caagttttag tgttagttga gggtattttt tagtttgtgt aattgttgtt ttttgcttcg 8820
ta 8822

<210> SEQ ID NO 2
<211> LENGTH: 8799
<212> TYPE: DNA
<213> ORGANISM: Solanum chacoense

<400> SEQUENCE: 2
ctctattttg ttgttcttag tcctttctta taggattttg cattgccccc acccccaccc 60
cccttgttat aagtaactat atctttttcc attgttttct tcttccttgt acttacattt 120
gttgcatttg agttgagggt ctttcgaaaa taacatctct acctccacga ggtagtgata 180
aggactgcgt acactctacc ctccccagac tccacttgtg gaatttcacc ggatatgttg 240
ttgttattgt tataaggaaa agctttggtc tcaaaactct ttaaactcaa tttttttct 300
tttgcactcc ctcttttctt gagtacattt cactctcaat tctttcttga gcacacactc 360
ttttatttga gtacacatac aactcaaatg accacctcaa tctatcggtg ttgatggaag 420
gatctagtga atgcaatatt ctagaactac accttccact tctttctcta attcttttag 480
actttgcact ctataactct catcctaaag ttcttctttc aatacaaatc ttgaatattc 540
tagattcttc tttgaaatat cttagatatt aattaaggtg gtgatgacct tttaacaccc 600
ctctcagcac caacttaatt tattctttgt atccattttg agtgatcctc gagacattgc 660
aatcatcttg atgtccagga actttatgaa tctcttcctc ctttgaactt ccccactcac 720
ttctctttga atcttattcg aaggtagtag tctccttgat ctagaccact ctgctaatgt 780
tgcatcaata tacttggtgt ttgggaattt caatcatgta gacctagctc cttagtcacg 840
gttgtggtgc ttctcggact tcttcttgca acatgacaag agtttcactt gagtctaata 900
gtaaatctct atagtgaccc ccttagcagc agctgcgcag ccctcccatg gctgctacaa 960
ccactggaaa gcctcctccc gaggtagtcc agcccgcccc aacatggttt tatctcgctc 1020
agtgaaggtt caatattagc agtaatgcaa gttaacaatt tgaacaaagg gagagaattt 1080

-continued

```
ggcagaaaag aggatcggaa catggtaatg cgcaagaaag caacatctaa tgcttctcca   1140
ggttgtgaga agaggcacaa tattagtaat gcttcaagag ccctattatg ttcgaacaac   1200
tttgatgctt tattgaaggc tactggaaaa aatagtaata ttatggctcc aacattacat   1260
atttctaatc ctgaagtagc taattaggat tattcaagaa aatcaggatg gcatgctact   1320
caaatccaat ccagcaatca agccactcat ggtcacattg aacacctagg ctcatgaggt   1380
cccttcccaa tctttggagt cacttggtca atatcaaggt gaatctggac aactactatt   1440
gtcaacaggg aatggtgacg atttagttac tttagatggg caatcaatct tttttaattc   1500
atgcatttgt caaaggaagt ttgaagccga taactcaacc ttcttaattc ttggttgtta   1560
tattttaaca ttatttaagc atcctcattt gtaatatcat catcgtgtgt attacaaatt   1620
ttgtggtaat cacaaaatgc tagttttttc tagcttttat tttcttcata cttgttagtt   1680
agtaaaggta tgttacctca ttatgactgg taaggtaagg ttcaacttcc tttgcttgta   1740
cttatcccta ctgagttttt tattattttt aatagaaggc tgctaaaaaa aataatttca   1800
agaaatctat tttatacgat atcaaattaa agtacgttgc ataaaacatt tataagaaag   1860
aggaatgaag tacgttgtag atcaaattaa ggaaatgata agagataaac ctggaatcgt   1920
ggtgtttctt ccattgccaa gagtgtatgt catcactacc caaaatttca agctttcttg   1980
ctgctatcat aaaacatttt ttcccactgt gcttatcgat aaaaaaactc tgaaagaaaa   2040
aaaaacatta aacaataaaa aaatgtatag tattgtattt ataatctaat tattaatcca   2100
aattcacatc aattaaggaa cttataattt tataaagaaa agtaacatac atgatagagt   2160
tattatagat aaaagtaggg gaaaaaaata aaaaaaatta taaattaatg aacaaagtca   2220
aataagaaaa taaaaatatt gtaatgacat ggccatatca aattgatcat tacataaaat   2280
gatactttca tcgttacata atgatgaatt tattggtaag atacaataaa aattaaataa   2340
ttaacaattc aaataaatat tgtatttaaa ataataatat aatacaatac gatagctcac   2400
aacaacccaa tatagttcaa ttttttgaat aacttaaact tggtgagtga aacagaataa   2460
aacatgattc ttttgatctt tctagtttca ttaactatga aaaaattaaa agatattaga   2520
tataaaattt taataaagat aaaaacactg ggtggtcatt ttttctactt gcttgagctg   2580
tagagttact tggtatacta gttgagataa atgacataaa aaaatttaat tgaaacacca   2640
atacaaacaa ggtgaaatta tttttttaaa gaaaattata tatgaatcgt tgaatctaaa   2700
attctagttt agcaacagag gggtttcaaa ggttgtttta gagtatgagt ttaaatccta   2760
agtgtgaaac tcaatatttt ttttaatatt cttatttgaa tttctaactc caccattata   2820
ttgtttaata cttgtgttag tgagaggcta aagtagatgt agaatattaa taccactttc   2880
atatgaatcc tgtactttca tatatagcgg aacataaatt tatgtgcaaa aattcatgat   2940
aaatgcaata gatagtagat atgaatcaca actttaaaga atataatgat ttaaatgtta   3000
attaaataaa aaattgaatc cataaatctt aaattctgat tttgcctcta gtgataggta   3060
ccaaatacgt acctaacaaa taatttaggt tcacacaaac tagcacatat accaccatta   3120
caaaaaataa aatgaaacat aaaaggtaat taaccacatc aaaatgagat tttaccagtc   3180
tgccgctatc aaggaggatg ggagaatcac atagactaaa aaagagctcc tttttggtgt   3240
tgaaaatccg aggaagctta gatctatcaa ttattttttg ataatcggaa ggcaaaaatc   3300
ttccccaaat ttcatcagat tttgcaacaa atttgaatcc tgttgataaa attgttgatc   3360
ttactgcatc tgctggagtt gttcttaaaa ttatttcaaa gatgcaacct tctggcaact   3420
tttcaaaata attcattgga gctatggact tagaaatatt catgtcaaaa ttcttataaa   3480
```

-continued accttataac cgagaaataa ccaaagtttt tttgttacaa gctttatata taattaaata 3540
atcaaaagat aaaaaagatt tcagaggtct atacattgtc aaatatagta ataagtacaa 3600
ataagcatat aaaattatgt tttttttcc ttttttgtca atgagtacag ataagcaaaa 3660
agtcaaactt attcaaataa caataaccat tgccacacct taatctcaaa caagtttcac 3720
gttgcttcaa ttaagtgtat cgagactaat attatattat ataaaataaa aataacatgc 3780
acgagaagat ctctatttaa tttggcgtga aatgttatct aaagtctcaa ataattggta 3840
ttgcttatat gaaagtaaaa aaacttccat tgtgtgccat actttcgaga caactccttt 3900
gtgattttag gtctacttcg tctcatttta acaccttcac actatgattt cataatgtaa 3960
caacttaatt aatttcttat ttaatcatga taaattagta cgatacagtg taaacatcgg 4020
atgcaaataa attgttatcc aatagaggtt acatgaccaa accatctcat ttgttttatt 4080
tttattatgt gctcgattta ttgttagcta tttcatcatc gattccaata gtatttagat 4140
ctttcgaaaa gcaaatagcc ataacacatt attgtttata tatcaagaaa acacataagc 4200
tatattatat tattgtacaa tttcttcttt attctggtct aaattcaatt ccttgaacaa 4260
taaggccacc ttttccatga agctgcgtaa tctccatcaa tcgcgcttca acatctccat 4320
catctcctgt atcattgata aaatttccca attctatttc catccatcca tcgactcttt 4380
ttcgtggaca tttcacatta cgtttgcgtc tcctaaccct ttttccgact agactcacga 4440
cactagctcg ttcctcggcc tctttgtcgc tcacacgatt cacaaaccta acaaatgcat 4500
tagcaatttc tagtccatca tgattctttg acaatttgaa caccaaataa acaacatatt 4560
tggttctttt cgacaatatt tgtgttccaa tcgtgcctcg tatgtctagc caacttacac 4620
ccttgagatg agccacttcc gaaaatctgc aaaataaaat gtctatattg tcttagatac 4680
acgtatttag tgagtttaag ttatatataa catcgccaat ataagtaatt tttgcaccat 4740
caaatcatct ttacctattg taataggtaa catatttcat tacacatttt agtgaggctc 4800
atctatatat atcttttagg tggcttgatt gtgtaaaaaa aaaattctca ccaatagtgg 4860
cagaggtaga atttcaacca agggattcaa aaaataacat atgtagaaat tcgttaaaag 4920
gcaatgaagt ataatttttt atacgtagta catacataaa aaaaaagaat aactttttat 4980
atgtagtata atttttcgac gaacctggag tcaggatgag aaatccattc ccaataccat 5040
ggtgtatcaa ctccccatgt aatagcaagt tctctagctg atatcataaa acatttcttg 5100
cctgttttct tatcaagtga aaaactctgt tttcaaaaat aaaataaaat cttagattca 5160
cactactagc ttatatatag tccattcaaa aataaaataa aattcacaca attattatta 5220
taatctattt aattttgcat ttttaatggt gtttgtaacc cattggccag aaaatcttag 5280
aagttcattt agttgactat ctgaacttcc gttttactat agagagttgg attcccagtt 5340
tgtaacaaaa acaaaataaa ataagaaaaa ttcattggct gattaattaa gatttgcgca 5400
gccgtaagca cactagtaga ttttagtgct tcctattaaa cacgactcaa ttcctaagat 5460
ttcaactctg attaaaactc aaactctaga cctcaggtca aaggttcatg acctttaccg 5520
ttatacaaca ccaacagtta gaggcaaagc tagaacaccc ctataaattc taggaaccca 5580
atagttttag ttcaaactct gtattttatc tttaaaaaga aaactcctct aatttgtacc 5640
aaattattaa tttcgaacca aacaactcaa aaaacacaca aaaaatcccg aacccataag 5700
cttcaaaaca attatacata tattcaacta atgagccaaa agaaaagctt gctacttccc 5760
aatttagagc tacttaccaa tttgcctcca tccattagaa cagggaagtc acatagacta 5820

-continued

```
aagtaaagct ccttttttaga cggataaatc cgcggggaga catatctcga gttgatatct   5880
tcataatcat ctggtaaaaa ctttacccaa ataacgtcgg attcagcagc agagttgaat   5940
ccccgagaga tcgcggatga aatcacgacg tctttcgggg aagtaaagga gagaatatca   6000
caaacacaat cttctggtag caataggaaa tagtccatta ttggaaaatt gaatttgaag   6060
ttttgtgaat tttttttctt tatataaagc aaactgagaa aagtttgttg aaaagttgtt   6120
acacttcata tgtctcgacg gttaagcagg ggcggctcaa cgtatttgga ggcctaaaac   6180
aaaatttaaa ttaaaggcct aaaatctttt agctgaggca attattaaat aaattgttaa   6240
cattattcta taagtaataa gttgacaaaa ctgcttataa acttcttttt ttatttaaaa   6300
gcacataaca taagtcaatc taaacaggct tgtaattcgc tttatccaac acattagttt   6360
tactattgat tcatattttt gatagagctc taacttacat agagtataaa aggggtatag   6420
aaaattacaa cgcgagagta agtgaagaga gtgtaagaag acaaaacaac gtttttcttg   6480
atttcttcta tttgattgag gttaaggaga ataaaataat atatatatga aaagtacatt   6540
tatcttaaat aattaatttt ttctataaaa aaaattaaca cataatttat tgttggtaaa   6600
aatttgaggc ccccctaaaa ttgggggcct aaggcatatg cctaattttt ataagcattg   6660
agccggcact gcggttaaat attgttttgt tcatttttac ttctccagta tgaatataat   6720
aagtgaaaag gtcatataat ttagagctga tacatacctc gttataaaaa tggctcatac   6780
atacctatac tattacacaa atagcctaga tataccctttt tggcctaatg gaagtgaaaa   6840
tatttaattt tattttattt ttaaaaaaat catttttgtt tatttttcat tatttttatc   6900
tagttctcac atatgtacat tttatttcca aaaaaaaata aaattaaaga attgatattg   6960
cttagataca ccaaacaaac aactcatgtg gaggaagata ttccaataat actaaacatg   7020
aaatgttttg agtttgaaat tttttgtctt tcctttttag tgaattaaaa catgaaatgt   7080
cttggaagat tcgaaattta ctggcccgac taatttaaga ttagcatcat ctaaggtcca   7140
tttatcaagg agcgttcccg accaagaatt tctccattct ccgaattcaa accaaagact   7200
tgttgtttag ttaacactag agaagtctca ttctcgcacc acagttgtgg cagttcccga   7260
aaagcaatat tcacaaattc ttacattcat catttcatta atttcttata gttgtaacta   7320
taagaacaac ataccatgtg tctcccccac aaagtggagt atgggaaggg tagagtgtaa   7380
gcaaacttta ctcttacctc agaggtagaa agtcttcttc cgatagatcc tcgactcgag   7440
aaaaataatc caaagcagtt cagaaaaaga cacaacaaaa gtacaagaaa caccagatag   7500
taacagaata gtacttcaac attaacaaat tactatctct tacacagaaa aatgaacttg   7560
aaattcataa aaaataataa taataacaga acataccctt gttcaagtgg taatctatat   7620
acagtacttt caaaatcaat ctcttgctcg tacttgagct cgagaaaaat tccttatact   7680
aaccgcgtct tccccatttc acgagcagtg gagagaacgt ttcacacgtt gtctttacta   7740
catcttcagc aggtaatgtc tttttatctc gtttggaagt tgaatgcctt aatagcgaaa   7800
gcaaatgtga agccaaaaag aacagtgtac ccaacaatcg cgactgcaac tattggaaga   7860
aaatcatgct tgaagccgaa gtaacgtctc aaaaattgtt ccactgtttc ctcatcagta   7920
agtttgttct gaagatctcc aaattgtgat gcaaccaaac catacaaggt ccaggcaaca   7980
ggacaacacc agtagtacca tctccaccat atgggaatac gctgtttttt aaaaatgaaa   8040
atggaaaaaa atacagagaa catgtcattt ccgagctcta agtcagtttt gatgtaacaa   8100
taaaatggaa gtgtttcaag aacttacagt tcgtggaatg atgaatcctg agaaaagatt   8160
ccatactccg tagaagaagg agccgacaat ttgagcaaca cttacatttg gggtaacagc   8220
```

aacggtcatc ataccgtaga aagtgaagta caagagggtg aaaaacagga agaacaagta 8280
ccaaaagaac tttgctaccg tccattcaaa tccgatcata gcatacataa ttgcaccaca 8340
gaaaacagat tgcataaaga catatgggat ttcaatggaa atctgcaaga tagaaaaagt 8400
taagtaattt agacttttca cctaaaattg tcgaggcacg tagtgttaag agtggataac 8460
atgtagtcac ttatagtggg aaaagttcag tgatcaaatg tgaaattaac tcgagattgg 8520
cttataagaa attgaactct atgttcacct gtccaaaggc ataaggtaag gcagaataca 8580
ttccagcagc tctttctcta tagaatactg tacgttcaac ggctacaaca ggctgcactg 8640
atgatgaatt ttgtgtaccg aggaagagaa cagtagcata caagcatccc atcgcgttaa 8700
atagatcttg actcttactc ctgtaaccaa aaaagatcaa gttttagtgt tagttgaggg 8760
tattttttag tttgtgtaat tgttgttttt tgcttcata 8799

<210> SEQ ID NO 3
<211> LENGTH: 8799
<212> TYPE: DNA
<213> ORGANISM: Artificial Sequence
<220> FEATURE:
<223> OTHER INFORMATION: Diploid F4 potato genotype 17SC0100-0002

<400> SEQUENCE: 3
ctctattttg ttgttcttag tcctttctta taggattttg cattgccccc acccccaccc 60
cccttgttat aagtaactat atctttttcc attgttttct tcttccttgt acttacattt 120
gttgcatttg agttgagggt ctttcgaaaa taacatctct acctccacga ggtagtgata 180
aggactgcgt acactctacc ctccccagac tccacttgtg gaatttcacc ggatatgttg 240
ttgttattgt tataaggaaa agctttggtc tcaaaactct ttaaactcaa tttttttct 300 tttgcactcc ctcttttctt gagtacattt cactctcaat tctttcttga gcacacactc 360
ttttatttga gtacacatac aactcaaatg accacctcaa tctatcggtg ttgatggaag 420
gatctagtga atgcaatatt ctagaactac accttccact tctttctcta attcttttag 480
actttgcact ctataactct catcctaaag ttcttctttc aatacaaatc ttgaatattc 540
tagattcttc tttgaaatat cttagatatt aattaaggtg gtgatgacct tttaacaccc 600
ctctcagcac caacttaatt tattctttgt atccattttg agtgatcctc gagacattgc 660
aatcatcttg atgtccagga actttatgaa tctcttcctc ctttgaactt ccccactcac 720
ttctctttga atcttattcg aaggtagtag tctccttgat ctagaccact ctgctaatgt 780
tgcatcaata tacttggtgt ttgggaattt caatcatgta gacctagctc cttagtcacg 840
gttgtggtgc ttctcggact tcttcttgca acatgacaag agtttcactt gagtctaata 900
gtaaatctct atagtgaccc ccttagcagc agctgcgcag ccctcccatg gctgctacaa 960
ccactggaaa gcctcctccc gaggtagtcc agcccgcccc aacatggttt tatctcgctc 1020
agtgaaggtt caatattagc agtaatgcaa gttaacaatt tgaacaaagg gagagaattt 1080
ggcagaaaag aggatcggaa catggtaatg cgcaagaaag caacatctaa tgcttctcca 1140
ggttgtgaga agaggcacaa tattagtaat gcttcaagag ccctattatg ttcgaacaac 1200
tttgatgctt tattgaaggc tactggaaaa aatagtaata ttatggctcc aacattacat 1260
atttctaatc ctgaagtagc taattaggat tattcaagaa aatcaggatg gcatgctact 1320
caaatccaat ccagcaatca agccactcat ggtcacattg aacacctagg ctcatgaggt 1380
cccttcccaa tctttggagt cacttggtca atatcaaggt gaatctggac aactactatt 1440

-continued

```
gtcaacaggg aatggtgacg atttagttac tttagatggg caatcaatct tttttaattc   1500
atgcatttgt caaaggaagt ttgaagccga taactcaacc ttcttaattc ttggttgtta   1560
tattttaaca ttatttaagc atcctcattt gtaatatcat catcgtgtgt attacaaatt   1620
ttgtggtaat cacaaaatgc tagttttttc tagcttttat tttcttcata cttgttagtt   1680
agtaaaggta tgttacctca ttatgactgg taaggtaagg ttcaacttcc tttgcttgta   1740
cttatcccta ctgagttttt tattattttt aatagaaggc tgctaaaaaa aataatttca   1800
agaaatctat tttatacgat atcaaattaa agtacgttgc ataaaacatt tataagaaag   1860
aggaatgaag tacgttgtag atcaaattaa ggaaatgata agagataaac ctggaatcgt   1920
ggtgtttctt ccattgccaa gagtgtatgt catcactacc caaaatttca agctttcttg   1980
ctgctatcat aaaacatttt ttcccactgt gcttatcgat aaaaaaactc tgaaagaaaa   2040
aaaaacatta aacaataaaa aaatgtatag tattgtattt ataatctaat tattaatcca   2100
aattcacatc aattaaggaa cttataattt tataaagaaa agtaacatac atgatagagt   2160
tattatagat aaaagtaggg gaaaaaaata aaaaaaatta taaattaatg aacaaagtca   2220
aataagaaaa taaaaatatt gtaatgacat ggccatatca aattgatcat tacataaaat   2280
gatactttca tcgttacata atgatgaatt tattggtaag atacaataaa aattaaataa   2340
ttaacaattc aaataaatat tgtatttaaa ataataatat aatacaatac gatagctcac   2400
aacaacccaa tatagttcaa ttttttgaat aacttaaact tggtgagtga aacagaataa   2460
aacatgattc ttttgatctt tctagtttca ttaactatga aaaaattaaa agatattaga   2520
tataaaattt taataaagat aaaaacactg ggtggtcatt ttttctactt gcttgagctg   2580
tagagttact tggtatacta gttgagataa atgacataaa aaaatttaat tgaaacacca   2640
atacaaacaa ggtgaaatta ttttttttaaa gaaaattata tatgaatcgt tgaatctaaa   2700
attctagttt agcaacagag gggtttcaaa ggttgtttta gagtatgagt ttaaatccta   2760
agtgtgaaac tcaatatttt ttttaatatt cttatttgaa tttctaactc caccattata   2820
ttgtttaata cttgtgttag tgagaggcta aagtagatgt agaatattaa taccactttc   2880
atatgaatcc tgtactttca tatatagcgg aacataaatt tatgtgcaaa aattcatgat   2940
aaatgcaata gatagtagat atgaatcaca actttaaaga atataatgat ttaaatgtta   3000
attaaataaa aaattgaatc cataaatctt aaattctgat tttgcctcta gtgataggta   3060
ccaaatacgt acctaacaaa taatttaggt tcacacaaac tagcacatat accaccatta   3120
caaaaaaataa aatgaaacat aaaaggtaat taaccacatc aaaatgagat tttaccagtc   3180
tgccgctatc aaggaggatg ggagaatcac atagactaaa aaagagctcc tttttggtgt   3240
tgaaaatccg aggaagctta gatctatcaa ttattttttg ataatcggaa ggcaaaaatc   3300
ttccccaaat ttcatcagat tttgcaacaa atttgaatcc tgttgataaa attgttgatc   3360
ttactgcatc tgctggagtt gttcttaaaa ttatttcaaa gatgcaacct tctggcaact   3420
tttcaaaata attcattgga gctatggact tagaaatatt catgtcaaaa ttcttataaa   3480
accttataac cgagaaataa ccaaagtttt tttgttacaa gctttatata taattaaata   3540
atcaaaagat aaaaaagatt tcagaggtct atacattgtc aaatatagta ataagtacaa   3600
ataagcatat aaaattatgt ttttttttcc ttttttgtca atgagtacag ataagcaaaa   3660
agtcaaactt attcaaataa caataaccat tgccacacct taatctcaaa caagtttcac   3720
gttgcttcaa ttaagtgtat cgagactaat attatattat ataaaataaa aataacatgc   3780
acgagaagat ctctatttaa tttggcgtga aatgttatct aaagtctcaa ataattggta   3840
```

```
ttgcttatat gaaagtaaaa aaacttccat tgtgtgccat actttcgaga caactccttt   3900
gtgattttag gtctacttcg tctcatttta acaccttcac actatgattt cataatgtaa   3960
caacttaatt aatttcttat ttaatcatga taaattagta cgatacagtg taaacatcgg   4020
atgcaaataa attgttatcc aatagaggtt acatgaccaa accatctcat ttgttttatt   4080
tttattatgt gctcgattta ttgttagcta tttcatcatc gattccaata gtatttagat   4140
ctttcgaaaa gcaaatagcc ataacacatt attgtttata tatcaagaaa acacataagc   4200
tatattatat tattgtacaa tttcttcttt attctggtct aaattcaatt ccttgaacaa   4260
taaggccacc ttttccatga agctgcgtaa tctccatcaa tcgcgcttca acatctccat   4320
catctcctgt atcattgata aaatttccca attctatttc catccatcca tcgactcttt   4380
ttcgtggaca tttcacatta cgtttgcgtc tcctaaccct ttttccgact agactcacga   4440
cactagctcg ttcctcggcc tctttgtcgc tcacacgatt cacaaaccta acaaatgcat   4500
tagcaatttc tagtccatca tgattctttg acaatttgaa caccaaataa acaacatatt   4560
tggttctttt cgacaatatt tgtgttccaa tcgtgcctcg tatgtctagc caacttacac   4620
ccttgagatg agccacttcc gaaaatctgc aaaataaaat gtctatattg tcttagatac   4680
acgtatttag tgagtttaag ttatatataa catcgccaat ataagtaatt tttgcaccat   4740
caaatcatct ttacctattg taataggtaa catatttcat tacacatttt agtgaggctc   4800
atctatatat atcttttagg tggcttgatt gtgtaaaaaa aaaattctca ccaatagtgg   4860
cagaggtaga atttcaacca agggattcaa aaaataacat atgtagaaat tcgttaaaag   4920
gcaatgaagt ataatttttt atacgtagta catacataaa aaaaaagaat aactttttat   4980
atgtagtata atttttcgac gaacctggag tcaggatgag aaatccattc ccaataccat   5040
ggtgtatcaa ctccccatgt aatagcaagt tctctagctg atatcataaa acatttcttg   5100
cctgttttct tatcaagtga aaaactctgt tttcaaaaat aaaataaaat cttagattca   5160
cactactagc ttatatatag tccattcaaa aataaaataa aattcacaca attattatta   5220
taatctattt aattttgcat ttttaatggt gtttgtaacc cattggccag aaaatcttag   5280
aagttcattt agttgactat ctgaacttcc gttttactat agagagttgg attcccagtt   5340
tgtaacaaaa acaaaataaa ataagaaaaa ttcattggct gattaattaa gatttgcgca   5400
gccgtaagca cactagtaga ttttagtgct tcctattaaa cacgactcaa ttcctaagat   5460
ttcaactctg attaaaactc aaactctaga cctcaggtca aaggttcatg acctttaccg   5520
ttatacaaca ccaacagtta gaggcaaagc tagaacaccc ctataaattc taggaaccca   5580
atagttttag ttcaaactct gtattttatc tttaaaaaga aaactcctct aatttgtacc   5640
aaattattaa tttcgaacca aacaactcaa aaaacacaca aaaaatcccg aacccataag   5700
cttcaaaaca attatacata tattcaacta atgagccaaa agaaaagctt gctacttccc   5760
aatttagagc tacttaccaa tttgcctcca tccattagaa cagggaagtc acatagacta   5820
aagtaaagct cctttttaga cggataaatc cgcggggaga catatctcga gttgatatct   5880
tcataatcat ctggtaaaaa ctttacccaa ataacgtcgg attcagcagc agagttgaat   5940
ccccgagaga tcgcggatga aatcacgacg tctttcgggg aagtaaagga gagaatatca   6000
caaacacaat cttctggtag caataggaaa tagtccatta ttggaaaatt gaatttgaag   6060
ttttgtgaat ttttttcttt tatataaagc aaactgagaa aagtttgttg aaaagttgtt   6120
acacttcata tgtctcgacg gttaagcagg ggcggctcaa cgtatttgga ggcctaaaac   6180
```

-continued

```
aaaatttaaa ttaaaggcct aaaatctttt agctgaggca attattaaat aaattgttaa   6240
cattattcta taagtaataa gttgacaaaa ctgcttataa acttcttttt ttatttaaaa   6300
gcacataaca taagtcaatc taaacaggct tgtaattcgc tttatccaac acattagttt   6360
tactattgat tcatattttt gatagagctc taacttacat agagtataaa aggggtatag   6420
aaaattacaa cgcgagagta agtgaagaga gtgtaagaag acaaaacaac gtttttcttg   6480
atttcttcta tttgattgag gttaaggaga ataaaataat atatatatga aaagtacatt   6540
tatcttaaat aattaatttt ttctataaaa aaaattaaca cataatttat tgttggtaaa   6600
aatttgaggc ccccctaaaa ttgggggcct aaggcatatg cctaattttt ataagcattg   6660
agccggcact gcggttaaat attgttttgt tcatttttac ttctccagta tgaatataat   6720
aagtgaaaag gtcatataat ttagagctga tacatacctc gttataaaaa tggctcatac   6780
atacctatac tattacacaa atagcctaga tataccottt tggcctaatg gaagtgaaaa   6840
tatttaattt tattttattt ttaaaaaaat catttttgtt tatttttcat tatttttatc   6900
tagttctcac atatgtacat tttatttcca aaaaaaaata aaattaaaga attgatattg   6960
cttagataca ccaaacaaac aactcatgtg gaggaagata ttccaataat actaaacatg   7020
aaatgttttg agtttgaaat tttttgtctt tcctttttag tgaattaaaa catgaaatgt   7080
cttggaagat tcgaaattta ctggcccgac taatttaaga ttagcatcat ctaaggtcca   7140
tttatcaagg agcgttcccg accaagaatt tctccattct ccgaattcaa accaaagact   7200
tgttgtttag ttaacactag agaagtctca ttctcgcacc acagttgtgg cagttcccga   7260
aaagcaatat tcacaaattc ttacattcat catttcatta atttcttata gttgtaacta   7320
taagaacaac ataccatgtg tctcccccac aaagtggagt atgggaaggg tagagtgtaa   7380
gcaaacttta ctcttacctc agaggtagaa agtcttcttc cgatagatcc tcgactcgag   7440
aaaaataatc caaagcagtt cagaaaaaga cacaacaaaa gtacaagaaa caccagatag   7500
taacagaata gtacttcaac attaacaaat tactatctct tacacagaaa aatgaacttg   7560
aaattcataa aaaataataa taataacaga acataccctt gttcaagtgg taatctatat   7620
acagtacttt caaaatcaat ctcttgctcg tacttgagct cgagaaaaat tccttatact   7680
aaccgcgtct tccccatttc acgagcagtg gagagaacgt ttcacacgtt gtctttacta   7740
catcttcagc aggtaatgtc tttttatctc gtttggaagt tgaatgcctt aatagcgaaa   7800
gcaaatgtga agccaaaaag aacagtgtac ccaacaatcg cgactgcaac tattggaaga   7860
aaatcatgct tgaagccgaa gtaacgtctc aaaaattgtt ccactgtttc ctcatcagta   7920
agtttgttct gaagatctcc aaattgtgat gcaaccaaac catacaaggt ccaggcaaca   7980
ggacaacacc agtagtacca tctccaccat atgggaatac gctgtttttt aaaaatgaaa   8040
atggaaaaaa atacagagaa catgtcattt ccgagctcta agtcagtttt gatgtaacaa   8100
taaaatggaa gtgtttcaag aacttacagt tcgtggaatg atgaatcctg agaaaagatt   8160
ccatactccg tagaagaagg agccgacaat ttgagcaaca cttacatttg gggtaacagc   8220
aacggtcatc ataccgtaga aagtgaagta caagagggtg aaaaacagga agaacaagta   8280
ccaaaagaac tttgctaccg tccattcaaa tccgatcata gcatacataa ttgcaccaca   8340
gaaaacagat tgcataaaga catatgggat ttcaatggaa atctgcaaga tagaaaaagt   8400
taagtaattt agacttttca cctaaaattg tcgaggcacg tagtgttaag agtggataac   8460
atgtagtcac ttatagtggg aaaagttcag tgatcaaatg tgaaattaac tcgagattgg   8520
cttataagaa attgaactct atgttcacct gtccaaaggc ataaggtaag gcagaataca   8580
```

ttccagcagc tctttctcta tagaatactg tacgttcaac ggctacaaca ggctgcactg 8640
atgatgaatt ttgtgtaccg aggaagagaa cagtagcata caagcatccc atcgcgttaa 8700
atagatcttg actcttactc ctgtaaccaa aaaagatcaa gttttagtgt tagttgaggg 8760
tattttttag tttgtgtaat tgttgttttt tgcttcata 8799

<210> SEQ ID NO 4
<211> LENGTH: 8799
<212> TYPE: DNA
<213> ORGANISM: Artificial Sequence
<220> FEATURE:
<223> OTHER INFORMATION: Diploid F4 potato genotype 17SC0100-0018

<400> SEQUENCE: 4
ctctattttg ttgttcttag tcctttctta taggattttg cattgccccc acccccaccc 60
cccttgttat aagtaactat atctttttcc attgttttct tcttccttgt acttacattt 120
gttgcatttg agttgagggt ctttcgaaaa taacatctct acctccacga ggtagtgata 180
aggactgcgt acactctacc ctccccagac tccacttgtg gaatttcacc ggatatgttg 240
ttgttattgt tataaggaaa agctttggtc tcaaaactct ttaaactcaa tttttttct 300 tttgcactcc ctcttttctt gagtacattt cactctcaat tctttcttga gcacacactc 360
ttttatttga gtacacatac aactcaaatg accacctcaa tctatcggtg ttgatggaag 420
gatctagtga atgcaatatt ctagaactac accttccact tctttctcta attcttttag 480
actttgcact ctataactct catcctaaag ttcttctttc aatacaaatc ttgaatattc 540
tagattcttc tttgaaatat cttagatatt aattaaggtg gtgatgacct tttaacaccc 600
ctctcagcac caacttaatt tattctttgt atccattttg agtgatcctc gagacattgc 660
aatcatcttg atgtccagga actttatgaa tctcttcctc ctttgaactt ccccactcac 720
ttctctttga atcttattcg aaggtagtag tctccttgat ctagaccact ctgctaatgt 780
tgcatcaata tacttggtgt ttgggaattt caatcatgta gacctagctc cttagtcacg 840
gttgtggtgc ttctcggact tcttcttgca acatgacaag agtttcactt gagtctaata 900
gtaaatctct atagtgaccc ccttagcagc agctgcgcag ccctcccatg gctgctacaa 960
ccactggaaa gcctcctccc gaggtagtcc agcccgcccc aacatggttt tatctcgctc 1020
agtgaaggtt caatattagc agtaatgcaa gttaacaatt tgaacaaagg gagagaattt 1080
ggcagaaaag aggatcggaa catggtaatg cgcaagaaag caacatctaa tgcttctcca 1140
ggttgtgaga agaggcacaa tattagtaat gcttcaagag ccctattatg ttcgaacaac 1200
tttgatgctt tattgaaggc tactggaaaa aatagtaata ttatggctcc aacattacat 1260
atttctaatc ctgaagtagc taattaggat tattcaagaa aatcaggatg gcatgctact 1320
caaatccaat ccagcaatca agccactcat ggtcacattg aacacctagg ctcatgaggt 1380
cccttcccaa tctttggagt cacttggtca atatcaaggt gaatctggac aactactatt 1440
gtcaacaggg aatggtgacg atttagttac tttagatggg caatcaatct tttttaattc 1500
atgcatttgt caaaggaagt ttgaagccga taactcaacc ttcttaattc ttggttgtta 1560
tattttaaca ttatttaagc atcctcattt gtaatatcat catcgtgtgt attacaaatt 1620
ttgtggtaat cacaaaatgc tagttttttc tagcttttat tttcttcata cttgttagtt 1680
agtaaaggta tgttacctca ttatgactgg taaggtaagg ttcaacttcc tttgcttgta 1740
cttatcccta ctgagttttt tattattttt aatagaaggc tgctaaaaaa aataatttca 1800

```
agaaatctat tttatacgat atcaaattaa agtacgttgc ataaaacatt tataagaaag   1860
aggaatgaag tacgttgtag atcaaattaa ggaaatgata agagataaac ctggaatcgt   1920
ggtgtttctt ccattgccaa gagtgtatgt catcactacc caaaatttca agctttcttg   1980
ctgctatcat aaaacatttt ttcccactgt gcttatcgat aaaaaaactc tgaaagaaaa   2040
aaaaacatta aacaataaaa aaatgtatag tattgtattt ataatctaat tattaatcca   2100
aattcacatc aattaaggaa cttataattt tataaagaaa agtaacatac atgatagagt   2160
tattatagat aaaagtaggg gaaaaaaata aaaaaaatta taaattaatg aacaaagtca   2220
aataagaaaa taaaaatatt gtaatgacat ggccatatca aattgatcat tacataaaat   2280
gatactttca tcgttacata atgatgaatt tattggtaag atacaataaa aattaaataa   2340
ttaacaattc aaataaatat tgtatttaaa ataataatat aatacaatac gatagctcac   2400
aacaacccaa tatagttcaa ttttttgaat aacttaaact tggtgagtga aacagaataa   2460
aacatgattc ttttgatctt tctagtttca ttaactatga aaaaattaaa agatattaga   2520
tataaaattt taataaagat aaaaacactg ggtggtcatt ttttctactt gcttgagctg   2580
tagagttact tggtatacta gttgagataa atgacataaa aaaatttaat tgaaacacca   2640
atacaaacaa ggtgaaatta tttttttaaa gaaaattata tatgaatcgt tgaatctaaa   2700
attctagttt agcaacagag gggtttcaaa ggttgtttta gagtatgagt ttaaatccta   2760
agtgtgaaac tcaatatttt ttttaatatt cttatttgaa tttctaactc caccattata   2820
ttgtttaata cttgtgttag tgagaggcta aagtagatgt agaatattaa taccactttc   2880
atatgaatcc tgtactttca tatatagcgg aacataaatt tatgtgcaaa aattcatgat   2940
aaatgcaata gatagtagat atgaatcaca actttaaaga atataatgat ttaaatgtta   3000
attaaataaa aaattgaatc cataaatctt aaattctgat tttgcctcta gtgataggta   3060
ccaaatacgt acctaacaaa taatttaggt tcacacaaac tagcacatat accaccatta   3120
caaaaaataa aatgaaacat aaaaggtaat taaccacatc aaaatgagat tttaccagtc   3180
tgccgctatc aaggaggatg ggagaatcac atagactaaa aaagagctcc tttttggtgt   3240
tgaaaatccg aggaagctta gatctatcaa ttattttttg ataatcggaa ggcaaaaatc   3300
ttccccaaat ttcatcagat tttgcaacaa atttgaatcc tgttgataaa attgttgatc   3360
ttactgcatc tgctggagtt gttcttaaaa ttatttcaaa gatgcaacct tctggcaact   3420
tttcaaaata attcattgga gctatggact tagaaatatt catgtcaaaa ttcttataaa   3480
accttataac cgagaaataa ccaaagtttt tttgttacaa gctttatata taattaaata   3540
atcaaaagat aaaaaagatt tcagaggtct atacattgtc aaatatagta ataagtacaa   3600
ataagcatat aaaattatgt tttttttttcc tttttgtca atgagtacag ataagcaaaa   3660
agtcaaactt attcaaataa caataaccat tgccacacct taatctcaaa caagtttcac   3720
gttgcttcaa ttaagtgtat cgagactaat attatattat ataaaataaa aataacatgc   3780
acgagaagat ctctatttaa tttggcgtga aatgttatct aaagtctcaa ataattggta   3840
ttgcttatat gaaagtaaaa aaacttccat tgtgtgccat actttcgaga caactccttt   3900
gtgattttag gtctacttcg tctcatttta acaccttcac actatgattt cataatgtaa   3960
caacttaatt aatttcttat ttaatcatga taaattagta cgatacagtg taaacatcgg   4020
atgcaaataa attgttatcc aatagaggtt acatgaccaa accatctcat ttgttttatt   4080
tttattatgt gctcgattta ttgttagcta tttcatcatc gattccaata gtatttagat   4140
ctttcgaaaa gcaaatagcc ataacacatt attgtttata tatcaagaaa acacataagc   4200
```

tatattatat tattgtacaa tttcttcttt attctggtct aaattcaatt ccttgaacaa 4260
taaggccacc ttttccatga agctgcgtaa tctccatcaa tcgcgcttca acatctccat 4320
catctcctgt atcattgata aaatttccca attctatttc catccatcca tcgactcttt 4380
ttcgtggaca tttcacatta cgtttgcgtc tcctaaccct ttttccgact agactcacga 4440
cactagctcg ttcctcggcc tctttgtcgc tcacacgatt cacaaaccta acaaatgcat 4500
tagcaatttc tagtccatca tgattctttg acaatttgaa caccaaataa acaacatatt 4560
tggttctttt cgacaatatt tgtgttccaa tcgtgcctcg tatgtctagc caacttacac 4620
ccttgagatg agccacttcc gaaaatctgc aaaataaaat gtctatattg tcttagatac 4680
acgtatttag tgagtttaag ttatatataa catcgccaat ataagtaatt tttgcaccat 4740
caaatcatct ttacctattg taataggtaa catatttcat tacacatttt agtgaggctc 4800
atctatatat atcttttagg tggcttgatt gtgtaaaaaa aaaattctca ccaatagtgg 4860
cagaggtaga atttcaacca agggattcaa aaaataacat atgtagaaat tcgttaaaag 4920
gcaatgaagt ataatttttt atacgtagta catacataaa aaaaaagaat aactttttat 4980
atgtagtata atttttcgac gaacctggag tcaggatgag aaatccattc ccaataccat 5040
ggtgtatcaa ctccccatgt aatagcaagt tctctagctg atatcataaa acatttcttg 5100
cctgttttct tatcaagtga aaaactctgt tttcaaaaat aaaataaaat cttagattca 5160
cactactagc ttatatatag tccattcaaa aataaaataa aattcacaca attattatta 5220
taatctattt aattttgcat ttttaatggt gtttgtaacc cattggccag aaaatcttag 5280
aagttcattt agttgactat ctgaacttcc gttttactat agagagttgg attcccagtt 5340
tgtaacaaaa acaaaataaa ataagaaaaa ttcattggct gattaattaa gatttgcgca 5400
gccgtaagca cactagtaga ttttagtgct tcctattaaa cacgactcaa ttcctaagat 5460
ttcaactctg attaaaactc aaactctaga cctcaggtca aaggttcatg acctttaccg 5520
ttatacaaca ccaacagtta gaggcaaagc tagaacaccc ctataaattc taggaaccca 5580
atagttttag ttcaaactct gtattttatc tttaaaaaga aaactcctct aatttgtacc 5640
aaattattaa tttcgaacca aacaactcaa aaaacacaca aaaaatcccg aacccataag 5700
cttcaaaaca attatacata tattcaacta atgagccaaa agaaaagctt gctacttccc 5760
aatttagagc tacttaccaa tttgcctcca tccattagaa cagggaagtc acatagacta 5820
aagtaaagct cctttttaga cggataaatc cgcggggaga catatctcga gttgatatct 5880
tcataatcat ctggtaaaaa ctttacccaa ataacgtcgg attcagcagc agagttgaat 5940
ccccgagaga tcgcggatga aatcacgacg tctttcgggg aagtaaagga gagaatatca 6000
caaacacaat cttctggtag caataggaaa tagtccatta ttggaaaatt gaatttgaag 6060
ttttgtgaat ttttttcttt tatataaagc aaactgagaa aagtttgttg aaaagttgtt 6120
acacttcata tgtctcgacg gttaagcagg ggcggctcaa cgtatttgga ggcctaaaac 6180
aaaatttaaa ttaaaggcct aaaatctttt agctgaggca attattaaat aaattgttaa 6240
cattattcta taagtaataa gttgacaaaa ctgcttataa acttcttttt ttatttaaaa 6300
gcacataaca taagtcaatc taaacaggct tgtaattcgc tttatccaac acattagttt 6360
tactattgat tcatattttt gatagagctc taacttacat agagtataaa aggggtatag 6420
aaaattacaa cgcgagagta agtgaagaga gtgtaagaag acaaaacaac gtttttcttg 6480
atttcttcta tttgattgag gttaaggaga ataaaataat atatatatga aaagtacatt 6540

-continued

```
tatcttaaat aattaatttt ttctataaaa aaaattaaca cataatttat tgttggtaaa   6600
aatttgaggc ccccctaaaa ttgggggcct aaggcatatg cctaattttt ataagcattg   6660
agccggcact gcggttaaat attgttttgt tcatttttac ttctccagta tgaatataat   6720
aagtgaaaag gtcatataat ttagagctga tacatacctc gttataaaaa tggctcatac   6780
atacctatac tattacacaa atagcctaga tataccettt tggcctaatg gaagtgaaaa   6840
tatttaattt tattttattt ttaaaaaaat catttttgtt tatttttcat tatttttatc   6900
tagttctcac atatgtacat tttatttcca aaaaaaaata aaattaaaga attgatattg   6960
cttagataca ccaaacaaac aactcatgtg gaggaagata ttccaataat actaaacatg   7020
aaatgttttg agtttgaaat tttttgtctt tcctttttag tgaattaaaa catgaaatgt   7080
cttggaagat tcgaaattta ctggcccgac taatttaaga ttagcatcat ctaaggtcca   7140
tttatcaagg agcgttcccg accaagaatt tctccattct ccgaattcaa accaaagact   7200
tgttgtttag ttaacactag agaagtctca ttctcgcacc acagttgtgg cagttcccga   7260
aaagcaatat tcacaaattc ttacattcat catttcatta atttcttata gttgtaacta   7320
taagaacaac ataccatgtg tctcccccac aaagtggagt atgggaaggg tagagtgtaa   7380
gcaaacttta ctcttacctc agaggtagaa agtcttcttc cgatagatcc tcgactcgag   7440
aaaaataatc caaagcagtt cagaaaaaga cacaacaaaa gtacaagaaa caccagatag   7500
taacagaata gtacttcaac attaacaaat tactatctct tacacagaaa aatgaacttg   7560
aaattcataa aaaataataa taataacaga acataccctt gttcaagtgg taatctatat   7620
acagtacttt caaaatcaat ctcttgctcg tacttgagct cgagaaaaat tccttatact   7680
aaccgcgtct tccccatttc acgagcagtg gagagaacgt ttcacacgtt gtctttacta   7740
catcttcagc aggtaatgtc tttttatctc gtttggaagt tgaatgcctt aatagcgaaa   7800
gcaaatgtga agccaaaaag aacagtgtac ccaacaatcg cgactgcaac tattggaaga   7860
aaatcatgct tgaagccgaa gtaacgtctc aaaaattgtt ccactgtttc ctcatcagta   7920
agtttgttct gaagatctcc aaattgtgat gcaaccaaac catacaaggt ccaggcaaca   7980
ggacaacacc agtagtacca tctccaccat atgggaatac gctgtttttt aaaaatgaaa   8040
atggaaaaaa atacagagaa catgtcattt ccgagctcta agtcagtttt gatgtaacaa   8100
taaaatggaa gtgtttcaag aacttacagt tcgtggaatg atgaatcctg agaaaagatt   8160
ccatactccg tagaagaagg agccgacaat ttgagcaaca cttacatttg gggtaacagc   8220
aacggtcatc ataccgtaga aagtgaagta caagagggtg aaaaacagga agaacaagta   8280
ccaaaagaac tttgctaccg tccattcaaa tccgatcata gcatacataa ttgcaccaca   8340
gaaaacagat tgcataaaga catatgggat ttcaatggaa atctgcaaga tagaaaaagt   8400
taagtaattt agacttttca cctaaaattg tcgaggcacg tagtgttaag agtggataac   8460
atgtagtcac ttatagtggg aaaagttcag tgatcaaatg tgaaattaac tcgagattgg   8520
cttataagaa attgaactct atgttcacct gtccaaaggc ataaggtaag gcagaataca   8580
ttccagcagc tctttctcta tagaatactg tacgttcaac ggctacaaca ggctgcactg   8640
atgatgaatt ttgtgtaccg aggaagagaa cagtagcata caagcatccc atcgcgttaa   8700
atagatcttg actcttactc ctgtaaccaa aaaagatcaa gttttagtgt tagttgaggg   8760
tattttttag tttgtgtaat tgttgttttt tgcttcata                          8799
```

<210> SEQ ID NO 5
<211> LENGTH: 7786

<212> TYPE: DNA
<213> ORGANISM: Solanum tuberosum

<400> SEQUENCE: 5

```
ctatatttg ttgttcttag tcctttctta taggattttg cattgccccc acccccaccc     60
cccttgttag tagctatatc tttttccatt gttttcttct tccttgtact tacatttgtt    120
gcacttgcgt tgagggtctt tcgataataa catccctagc ctccacaaag tactagtaag    180
ggctgcgtac actctaccct ccttgttttc ttcttccttg tacttacatt tgttgcactt    240
gagttgaggg tcttttgaaa ataacatctc tacctccaca aggtagtgat aaggactgcg    300
tacactctac cctccccaga ctccacttgt ggaatttcac cggatatgtt attgttattg    360
ttataaggaa aagctttggt ctcgaaactc tttaaactca atttttttct tttgcactcc    420
ctcttttctt gagtacactt cactctcaat tctttcttga gcacacactc ttttatttga    480
gtacacatac aactcaaatg accacctcaa tcgaccccac ttgtggaatt tcaccagata    540
tgttgttgtt attgttataa ggacaagctt cggtcttaaa gctcgataaa ctcatttttt    600
tcttttgcac tccctctttt cttaagtaca cttcactctc aattctttct tgagcacaca    660
ctctttattt gagtaaacat acaactcaaa tgatcacctc tatttatcgg tgttgatgga    720
aggatctagt gaatgcaata ttctagaact acaccttcca cttctttctc gaattctttt    780
agactttgca ctctagaact ctcatcctaa agttcttctt tcaatacaag tcttgaatat    840
gctagattct tctttgaaat atcttagata ttaattaagg tggtgatgac ttttaacacc    900
cctctcagca ccaacttaat ttattctttg catccatttt gagtgatcct cgagacattg    960
caatcatctt gatgtccagt aactttatga atctcttcct cctttgaact tccccactca   1020
cttttctttg aatcttattc gaaggtagta gtctccttga tctagaccac tctgctaatg   1080
ttgcatcaat atacttggtg tttgggaatt tcaatcatgt agacctcctt agtcacggtt   1140
gtggtgcttc tcggacttct tcttgcaaca ttacaggagt ttcactttga gtctaatagg   1200
aaatctcttt ggaccaccat gttgatgctt catcaaatac cagatttctt gacacatata   1260
tcctattagt gataggaagg agaaatacga agggatatag gatagacttt tcgattgagc   1320
cttcttgttg aatctataac aactctacaa taatgtaact tgataaagta ggtattaggg   1380
ctccctcgct ctaacagcta tagtgacccc cttagcagca gctgcgcagc cctcccatgg   1440
ctgctacaac cactggaaag cctcctcccg aggtagtcca gcccgcccca acatggtttt   1500
atctcgctca gtgaaggttc agtattagcg gtaatgcaag ttaaggattt gaacaaaggg   1560
agagaatttg gtagaaaaga ggagcggaac atggtaatgc gcaagaaggc aacatctaat   1620
gcttctccag gttgtgagaa gaggcacaat attagtaatg tttcaagagc cctattatgt   1680
tggaacaact ttgatgcttt attgaaggct actggaaaaa atagtaatat tatggttcca   1740
acattacata tttctaatcc ttaagtagct aattaggatt attcaagaaa atcaggatgg   1800
catgctactc aaatccaatc caacaatcaa gccactcatg gttacattga acacctcggc   1860
tcatgaggcc ccttcccaat cattggagtc acttggtcaa tatcaaggtg aatctggaca   1920
gctactattg tcaacaggga atggtgacga tttagttact ttagatgtgc aatcaatctt   1980
ttttaattca tgcacttgtc aaaggaagtt tgaggccgat aactcaacct tcttaattct   2040
tggttgttat attttaacat tatttaagca tcctcatttg taatatcatc agagtgtatt   2100
acaaactcta tggtaatcac aaaatcctag ttttttctag cttttatttt ttcttcatgc   2160
ttgttagtta gtagaggttt gttacctcat tatgactggt aaggtaaggt ccagctccct   2220
```

-continued

```
ttacttgtac ttatccctga tgaatttttt ttattatttt taatagaaag ccgctaaaaa   2280
aaataatttt aagaaattta ttttatacgt aatcaaatta aaatacgttg cataaaacat   2340
ttataagaaa gtggaatgac gtacgttgta gatcaaatta aggaaatgat aagagataaa   2400
cctggaatcg tggtgtttct tccattgcca agagtgtatg tcatcactcc ccaaaatttc   2460
aagctttctt gctgctatca taaaacattt ttttccactg tacttatcaa taaaaaaatt   2520
ctgaaaggaa aaaaaaacca ttaaacaata taaaaatgta taatattgta tttataatct   2580
aatcattaat ccaaattcac accatgtaag gaacttataa ttttataaag aaaagtagca   2640
tacataatag agttattata gataaaggta ggggaaaaaa aaaggattat aaagtaatga   2700
acaaagtcaa aataagaaaa taaaaatatc gtaatgacat ggccatatca aattgatcat   2760
tacataaaat gatactttca tcgttacata atgatgaatt tattgataag atacaataaa   2820
aattaaataa ttaacaattc aaataaacgt tgtgtttaaa ataacaatat aatacaatac   2880
gataactcac aacaacccaa aggcatatag ttcaattttt cgaataacct aaacttggtg   2940
agtgaaacag aataaaacaa gattcttttg atctttctta gtttcattaa ctatgaaaaa   3000
aataaaaaag tacaaaaaat gaaacatcaa gaaagatata gccagtgaac aatgaattga   3060
ttgaaaatta taagatatta gattttaaat tttagcaaag ataaaaaatt gggtggtcat   3120
ttcgttctac ctgcttgagc tatagaatta cctggtatag tagtcgtgat aaaagtttaa   3180
ttgaatctcc tttacttgaa attacaccga tacacatggt aaaaatatat ttttaaaaaa   3240
attatatatg aattgttgaa ttcaaagtct agtttagcaa cagaggggta caaaggttgt   3300
tttagattac gagtttaaat cctaagtgtg acactcattt ttttttaat attcttatat   3360
gaatttctaa ctcatcatta tattgtttga tacttgtgtt agtgagaggc taaaaccgat   3420
ttacaagatt aataccaatt tcatatgaat cctatacttt tatatatatc ggaacataaa   3480
tttatgtgta aaaattcatg ataaatgcaa tagatatagt agatataaat cacaacttta   3540
aagaacatca tgatttaaat gttaagtaac taaaaaattg aatccataaa tcttaaattc   3600
tgattttgcc tctggtgata ggtaccaaat acgtacctaa taaataattt aggttcacgc   3660
aaactagcac atataccacc attactaaaa tataaataaa atcattgaag gtaattaatc   3720
acatcaaaat gagattttac cagtctgccg cggtcaagga gaatgggaga atcacataga   3780
ctaaaaaaga gctccttttt ggtgttgcaa atccgaggaa gcttagatct atcaattatt   3840
ttttggtaat cggaaggcaa aaatcttccc caaatttcat cagattttgc aacaaatttg   3900
aatcctgttg atgaaattgt tgatcttact gcatctgctg gagttgttct tgaaattatt   3960
tcaaagatgc aaccttctgg caacatttca aaataattca ttggagctat agacttagaa   4020
atattcatgt caaaattctt ataaaacttt ataatcgaga aataacctaa gttttttttgt   4080
tacaagcttt atatatgatt aaataatcaa aagataaaaa agatttcaga ggtctataca   4140
ttgtcaaata tagtaataag tacatataag catatacaat tatgtttttt tttcctttttt   4200
tgtcaatgag tacagataag caaaaagtca aacttattca aataacaata accattgcca   4260
caccttaatc tcaaacaagt ttcacgttgc tttaattaag tgtaccgaga ctaatattat   4320
attatataaa ataaaaataa catgtacgag aagatctatt taatttggcg tgaaatgtta   4380
tctaaagtct caaataattg gtattgctta tatgaaagta aaaaaacttc cattgtgtgc   4440
catactttcg agacaactcc tttgtgattt taggtctact tggtctcatt ttaacacctt   4500
cacactatga tttcatagtg taacaactta attaattttt tatttaatca taataaatta   4560
gtacgataca gtgtaaacat cagatgtaaa taagttaata ttcaatagag gtcaatttag   4620
```

-continued

```
aacatgacca aaccgtctca tttgttttat ttttattatg tgctcgattt attgttagct   4680
atttcaacat cgattccaat agtatttaga tctttcgaaa agcaaatagc cataacacat   4740
tattatttat atatcaagaa aacacatatg ctatattata gtactattgt gcaatttctt   4800
cttcattctg gtctaaattc aattccttga acaataaggc caccttttcc atgaagccgc   4860
gtaatctcca tcaatcgcgc ttcaacatct ccatcatctc ctgtatcgtt gataaaattt   4920
cccaattcta tttccatcca tccatcgact ctttttcgtg gacgttttac gttacgtttg   4980
cgtctcctaa cccttttttcc gactagactc acgacactag ctcgttcctc ggcatcttta   5040
tcgctcacac gattcacaaa tctaacaaat gcattagcaa tttctagtcc atcatgatcc   5100
tttgccaatt tgaacaccaa ataaacaaca tatttggttc ttttcgacaa tatttgtgtt   5160
ccaatcgtgc ctcgtatgtc tagccaactt acacccttga gatgtgccac ttccgaaaat   5220
ctacaaaata aaatgtatat atagtctcag atacatgtat ttagtgagtt taagatatat   5280
atatcatcgc caatataagt aatttttgca ccatcaaatc atcttttacc tattgtaata   5340
ggtaacatat ttcattacat attttaacga ggctcatcta tggtgacctg attgtgttaa   5400
aaaattcttt cttaccaata gtgacagagg tagaatttca accaagggat tcaaaaaata   5460
gcatatgtag aaattcgtta aaaggcattg aagtataatg ttttatacgt agtataattt   5520
ttcgacgaac ctggagtcgg gatgagaaat ccattcccaa taccatggtg tatcaactcc   5580
ccatgaaata gcaagttctc tagctgatat cataaaacat ttcttgcctg ttttcttatc   5640
aagtgaaaag ctctgttttc aaaaataaaa taaaatctta gattcacact actagcttat   5700
agtccattca aaaataaaat aaaattgaca attgttagta taatctattt aattttgcat   5760
ttttaatggt gtttgtaacc catttgccgg aaaatcttaa aagttcagtt agttgactat   5820
ctgaacttct gttttactag agagagttcg attctcagtt tttaacaaaa acaaaataaa   5880
ataagaaaaa ttcattggct gattaattaa gatttgcagc agtaagcaca ctagtggatt   5940
ttagtgcttc ctatcgacat ttcaactctg attaaaactc aaactcgaga cttcaggtca   6000
aaggttcatg acctttacgg ttatacaaca ccaacagcca ggggcggagc tagaacaccc   6060
ctataaattc taggaagtca atagttttag ttcaaactct gtatttatct ttaaaaagaa   6120
aactcctcta atatgtacca aattattaat ttcgaaccaa acaactcaaa aaacacacaa   6180
aaagaaatcc cgaacccata agcttcaacg caattataca tatattaaac taaaatgagc   6240
caaaaaaaag cttactactt cccaatttag agctacttac caatttgcct ccatccatta   6300
gaacagggaa gtcacataga ctaaagtaaa gctccttttt agacggataa atccgcgggg   6360
agacatatct cgagataata tcttcataat catctggtaa aaactttacc caaataacgt   6420
cggattcagc agcagagttg aatccccgag agatcgcgga tgaaatcacg acatctttcg   6480
gggaagtaaa ggagagaata tcacaaacac aaccttctgg tagcaatagg aaatagtcca   6540
ttattggaaa attgaatttg aagatttgtg aatttttttt tgtttatata aagcaaactg   6600
agaaaagttt attgaaaagt tgttacactc atgtctcaac ggttaagtat tgtttcgttc   6660
atttttactt ctccagtatg aatataataa gagaaaaagg tcatatgagt tagaactgat   6720
atatagctcg ttataaaaat gggctcatac atacctatat tattacacaa atagcctaga   6780
tatacccttt tggcctaatg gaagtgaaaa tatttaattt tattcatttt tgtttatttt   6840
tcattatttt atctagttct cacatatgta cattttattt ccaaaaaataa ataaattaaa   6900
gaattgatat ttgcttagat acaccaaaca aacaactcat gtggaggaag atattattcc   6960
```

-continued

```
actaacataa aacatgaaat gttttgagtt tgaaactttt tttttttcc ttttttggt   7020
gaagtgaaac atgaaatgtt taggaagatt catcattggg tattcgaaat ttactggccc   7080
gactaattca agattaatat catctaaggt ccatttatca aggagcattc ccgaccaaga   7140
atttctccat tctctgaatt caaaccgaag acttcttgtt tagttaacac tggagaaatc   7200
tcattcatcg cgccacatct ttgatgagtt gtggcagttc cccaaaagca atattcacaa   7260
attcttacat tcaccatttc atcaatttct tatagttata aaactacaat aacaacatat   7320
ccaatgtctc cccacaaagt gaggtctagg gagggtagag tgtacacaga ctttacttca   7380
actttagaga tagaaagtct ttttctgata gatcctcaac tcgagaaaac taatccaaag   7440
cagttcagaa ttagacacaa caaaagtaca agaaacaaca gatagtaaca gaacagtact   7500
tcttgaatat ggtactggat taggtagaaa gaacataaaa aaaggctaat aacaatggaa   7560
tgaatttgcc actgcatttt gattcaacat taacaaatta ctatctctta cacagaacat   7620
acacttgttc aagtggaaat ctatatacag tactttcaaa atcactctca ctcgtacttg   7680
agctcgagaa aaattcctta tactaactgc gtcttcccca tttcacgagg agtggagaga   7740
acgtttcaca cgttgtcttt actacatctt cagcaggtaa cgtctt                 7786
```

<210> SEQ ID NO 6
<211> LENGTH: 7763
<212> TYPE: DNA
<213> ORGANISM: Solanum chacoense

<400> SEQUENCE: 6

```
ctctattttg ttgttcttag tcctttctta taggattttg cattgccccc acccccaccc     60
cccttgttat aagtaactat atctttttcc attgttttct tcttccttgt acttacattt    120
gttgcatttg agttgagggt ctttcgaaaa taacatctct acctccacga ggtagtgata    180
aggactgcgt acactctacc ctccccagac tccacttgtg gaatttcacc ggatatgttg    240
ttgttattgt tataaggaaa agctttggtc tcaaaactct ttaaactcaa ttttttttct    300
tttgcactcc ctcttttctt gagtacattt cactctcaat tctttcttga gcacacactc    360
ttttatttga gtacacatac aactcaaatg accacctcaa tctatcggtg ttgatggaag    420
gatctagtga atgcaatatt ctagaactac accttccact tctttctcta attcttttag    480
actttgcact ctataactct catcctaaag ttcttctttc aatacaaatc ttgaatattc    540
tagattcttc tttgaaatat cttagatatt aattaaggtg gtgatgacct tttaacaccc    600
ctctcagcac caacttaatt tattctttgt atccattttg agtgatcctc gagacattgc    660
aatcatcttg atgtccagga actttatgaa tctcttcctc ctttgaactt ccccactcac    720
ttctctttga atcttattcg aaggtagtag tctccttgat ctagaccact ctgctaatgt    780
tgcatcaata tacttggtgt ttgggaattt caatcatgta gacctagctc cttagtcacg    840
gttgtggtgc ttctcggact tcttcttgca acatgacaag agtttcactt gagtctaata    900
gtaaatctct atagtgaccc ccttagcagc agctgcgcag ccctcccatg gctgctacaa    960
ccactggaaa gcctcctccc gaggtagtcc agcccgcccc aacatggttt tatctcgctc   1020
agtgaaggtt caatattagc agtaatgcaa gttaacaatt tgaacaaagg gagagaattt   1080
ggcagaaaag aggatcggaa catggtaatg cgcaagaaag caacatctaa tgcttctcca   1140
ggttgtgaga agaggcacaa tattagtaat gcttcaagag ccctattatg ttcgaacaac   1200
tttgatgctt tattgaaggc tactggaaaa aatagtaata ttatggctcc aacattacat   1260
atttctaatc ctgaagtagc taattaggat tattcaagaa aatcaggatg gcatgctact   1320
```

```
caaatccaat ccagcaatca agccactcat ggtcacattg aacacctagg ctcatgaggt   1380
cccttcccaa tctttggagt cacttggtca atatcaaggt gaatctggac aactactatt   1440
gtcaacaggg aatggtgacg atttagttac tttagatggg caatcaatct tttttaattc   1500
atgcatttgt caaaggaagt ttgaagccga taactcaacc ttcttaattc ttggttgtta   1560
tattttaaca ttatttaagc atcctcattt gtaatatcat catcgtgtgt attacaaatt   1620
ttgtggtaat cacaaaatgc tagttttttc tagcttttat tttcttcata cttgttagtt   1680
agtaaaggta tgttacctca ttatgactgg taaggtaagg ttcaacttcc tttgcttgta   1740
cttatcccta ctgagttttt tattattttt aatagaaggc tgctaaaaaa aataatttca   1800
agaaatctat tttatacgat atcaaattaa agtacgttgc ataaaacatt tataagaaag   1860
aggaatgaag tacgttgtag atcaaattaa ggaaatgata agagataaac ctggaatcgt   1920
ggtgtttctt ccattgccaa gagtgtatgt catcactacc caaaatttca agctttcttg   1980
ctgctatcat aaaacatttt ttcccactgt gcttatcgat aaaaaaactc tgaaagaaaa   2040
aaaaacatta aacaataaaa aaatgtatag tattgtattt ataatctaat tattaatcca   2100
aattcacatc aattaaggaa cttataattt tataaagaaa agtaacatac atgatagagt   2160
tattatagat aaaagtaggg gaaaaaaata aaaaaaatta taaattaatg aacaaagtca   2220
aataagaaaa taaaaatatt gtaatgacat ggccatatca aattgatcat tacataaaat   2280
gatactttca tcgttacata atgatgaatt tattggtaag atacaataaa aattaaataa   2340
ttaacaattc aaataaatat tgtatttaaa ataataatat aatacaatac gatagctcac   2400
aacaacccaa tatagttcaa ttttttgaat aacttaaact tggtgagtga aacagaataa   2460
aacatgattc ttttgatctt tctagtttca ttaactatga aaaaattaaa agatattaga   2520
tataaaattt taataaagat aaaaacactg ggtggtcatt ttttctactt gcttgagctg   2580
tagagttact tggtatacta gttgagataa atgacataaa aaaatttaat tgaaacacca   2640
atacaaacaa ggtgaaatta tttttttaaa gaaaattata tatgaatcgt tgaatctaaa   2700
attctagttt agcaacagag gggtttcaaa ggttgtttta gagtatgagt ttaaatccta   2760
agtgtgaaac tcaatatttt ttttaatatt cttatttgaa tttctaactc caccattata   2820
ttgtttaata cttgtgttag tgagaggcta aagtagatgt agaatattaa taccactttc   2880
atatgaatcc tgtactttca tatatagcgg aacataaatt tatgtgcaaa aattcatgat   2940
aaatgcaata gatagtagat atgaatcaca actttaaaga atataatgat ttaaatgtta   3000
attaaataaa aaattgaatc cataaatctt aaattctgat tttgcctcta gtgataggta   3060
ccaaatacgt acctaacaaa taatttaggt tcacacaaac tagcacatat accaccatta   3120
caaaaaaataa aatgaaacat aaaaggtaat taaccacatc aaaatgagat tttaccagtc   3180
tgccgctatc aaggaggatg ggagaatcac atagactaaa aaagagctcc tttttggtgt   3240
tgaaaatccg aggaagctta gatctatcaa ttattttttg ataatcggaa ggcaaaaatc   3300
ttccccaaat ttcatcagat tttgcaacaa atttgaatcc tgttgataaa attgttgatc   3360
ttactgcatc tgctggagtt gttcttaaaa ttatttcaaa gatgcaacct tctggcaact   3420
tttcaaaata attcattgga gctatggact tagaaatatt catgtcaaaa ttcttataaa   3480
accttataac cgagaaataa ccaaagtttt tttgttacaa gctttatata taattaaata   3540
atcaaaagat aaaaaagatt tcagaggtct atacattgtc aaatatagta ataagtacaa   3600
ataagcatat aaaattatgt ttttttttcc ttttttgtca atgagtacag ataagcaaaa   3660
```

-continued

```
agtcaaactt attcaaataa caataaccat tgccacacct taatctcaaa caagtttcac   3720
gttgcttcaa ttaagtgtat cgagactaat attatattat ataaaataaa aataacatgc   3780
acgagaagat ctctatttaa tttggcgtga aatgttatct aaagtctcaa ataattggta   3840
ttgcttatat gaaagtaaaa aaacttccat tgtgtgccat actttcgaga caactccttt   3900
gtgattttag gtctacttcg tctcatttta acaccttcac actatgattt cataatgtaa   3960
caacttaatt aatttcttat ttaatcatga taaattagta cgatacagtg taaacatcgg   4020
atgcaaataa attgttatcc aatagaggtt acatgaccaa accatctcat ttgttttatt   4080
tttattatgt gctcgattta ttgttagcta tttcatcatc gattccaata gtatttagat   4140
ctttcgaaaa gcaaatagcc ataacacatt attgtttata tatcaagaaa acacataagc   4200
tatattatat tattgtacaa tttcttcttt attctggtct aaattcaatt ccttgaacaa   4260
taaggccacc ttttccatga agctgcgtaa tctccatcaa tcgcgcttca acatctccat   4320
catctcctgt atcattgata aaatttccca attctatttc catccatcca tcgactcttt   4380
ttcgtggaca tttcacatta cgtttgcgtc tcctaaccct ttttccgact agactcacga   4440
cactagctcg ttcctcggcc tctttgtcgc tcacacgatt cacaaaccta acaaatgcat   4500
tagcaatttc tagtccatca tgattctttg acaatttgaa caccaaataa acaacatatt   4560
tggttctttt cgacaatatt tgtgttccaa tcgtgcctcg tatgtctagc caacttacac   4620
ccttgagatg agccacttcc gaaaatctgc aaaataaaat gtctatattg tcttagatac   4680
acgtatttag tgagtttaag ttatatataa catcgccaat ataagtaatt tttgcaccat   4740
caaatcatct ttacctattg taataggtaa catatttcat tacacatttt agtgaggctc   4800
atctatatat atcttttagg tggcttgatt gtgtaaaaaa aaaattctca ccaatagtgg   4860
cagaggtaga atttcaacca agggattcaa aaaataacat atgtagaaat tcgttaaaag   4920
gcaatgaagt ataatttttt atacgtagta catacataaa aaaaaagaat aactttttat   4980
atgtagtata atttttcgac gaacctggag tcaggatgag aaatccattc ccaataccat   5040
ggtgtatcaa ctccccatgt aatagcaagt tctctagctg atatcataaa acatttcttg   5100
cctgttttct tatcaagtga aaaactctgt tttcaaaaat aaaataaaat cttagattca   5160
cactactagc ttatatatag tccattcaaa aataaaataa aattcacaca attattatta   5220
taatctattt aattttgcat ttttaatggt gtttgtaacc cattggccag aaaatcttag   5280
aagttcattt agttgactat ctgaacttcc gttttactat agagagttgg attcccagtt   5340
tgtaacaaaa acaaaataaa ataagaaaaa ttcattggct gattaattaa gatttgcgca   5400
gccgtaagca cactagtaga ttttagtgct tcctattaaa cacgactcaa ttcctaagat   5460
ttcaactctg attaaaactc aaactctaga cctcaggtca aaggttcatg acctttaccg   5520
ttatacaaca ccaacagtta gaggcaaagc tagaacaccc ctataaattc taggaaccca   5580
atagttttag ttcaaactct gtattttatc tttaaaaaga aaactcctct aatttgtacc   5640
aaattattaa tttcgaacca aacaactcaa aaaacacaca aaaaatcccg aacccataag   5700
cttcaaaaca attatacata tattcaacta atgagccaaa agaaaagctt gctacttccc   5760
aatttagagc tacttaccaa tttgcctcca tccattagaa cagggaagtc acatagacta   5820
aagtaaagct ccttttttaga cggataaatc cgcggggaga catatctcga gttgatatct   5880
tcataatcat ctggtaaaaa ctttacccaa ataacgtcgg attcagcagc agagttgaat   5940
ccccgagaga tcgcggatga aatcacgacg tctttcgggg aagtaaagga gagaatatca   6000
caaacacaat cttctggtag caataggaaa tagtccatta ttggaaaatt gaatttgaag   6060
```

```
ttttgtgaat tttttttctt tatataaagc aaactgagaa aagtttgttg aaaagttgtt   6120
acacttcata tgtctcgacg gttaagcagg ggcggctcaa cgtatttgga ggcctaaaac   6180
aaaatttaaa ttaaaggcct aaaatctttt agctgaggca attattaaat aaattgttaa   6240
cattattcta taagtaataa gttgacaaaa ctgcttataa acttcttttt ttatttaaaa   6300
gcacataaca taagtcaatc taaacaggct tgtaattcgc tttatccaac acattagttt   6360
tactattgat tcatattttt gatagagctc taacttacat agagtataaa aggggtatag   6420
aaaattacaa cgcgagagta agtgaagaga gtgtaagaag acaaaacaac gtttttcttg   6480
atttcttcta tttgattgag gttaaggaga ataaaataat atatatatga aaagtacatt   6540
tatcttaaat aattaatttt ttctataaaa aaaattaaca cataatttat tgttggtaaa   6600
aatttgaggc ccccctaaaa ttgggggcct aaggcatatg cctaattttt ataagcattg   6660
agccggcact gcggttaaat attgttttgt tcatttttac ttctccagta tgaatataat   6720
aagtgaaaag gtcatataat ttagagctga tacatacctc gttataaaaa tggctcatac   6780
atacctatac tattacacaa atagcctaga tatacccttt tggcctaatg gaagtgaaaa   6840
tatttaattt tattttattt ttaaaaaaat catttttgtt tatttttcat tatttttatc   6900
tagttctcac atatgtacat tttatttcca aaaaaaaata aaattaaaga attgatattg   6960
cttagataca ccaaacaaac aactcatgtg gaggaagata ttccaataat actaaacatg   7020
aaatgttttg agtttgaaat tttttgtctt tcctttttag tgaattaaaa catgaaatgt   7080
cttggaagat tcgaaattta ctggcccgac taatttaaga ttagcatcat ctaaggtcca   7140
tttatcaagg agcgttcccg accaagaatt tctccattct ccgaattcaa accaaagact   7200
tgttgtttag ttaacactag agaagtctca ttctcgcacc acagttgtgg cagttcccga   7260
aaagcaatat tcacaaattc ttacattcat catttcatta atttcttata gttgtaacta   7320
taagaacaac ataccatgtg tctcccccac aaagtggagt atgggaaggg tagagtgtaa   7380
gcaaacttta ctcttacctc agaggtagaa agtcttcttc cgatagatcc tcgactcgag   7440
aaaaaataatc caaagcagtt cagaaaaaga cacaacaaaa gtacaagaaa caccagatag   7500
taacagaata gtacttcaac attaacaaat tactatctct tacacagaaa aatgaacttg   7560
aaattcataa aaaataataa taataacaga acataccctt gttcaagtgg taatctatat   7620
acagtacttt caaaatcaat ctcttgctcg tacttgagct cgagaaaaat tccttatact   7680
aaccgcgtct tccccatttc acgagcagtg gagagaacgt ttcacacgtt gtctttacta   7740
catcttcagc aggtaatgtc ttt                                           7763
```

```
<210> SEQ ID NO 7
<211> LENGTH: 7763
<212> TYPE: DNA
<213> ORGANISM: Artificial Sequence
<220> FEATURE:
<223> OTHER INFORMATION: Diploid F4 potato genotype 17SC0100-0002

<400> SEQUENCE: 7
```

```
ctctattttg ttgttcttag tcctttctta taggattttg cattgccccc acccccaccc     60
cccttgttat aagtaactat atctttttcc attgttttct tcttccttgt acttacattt    120
gttgcatttg agttgagggt ctttcgaaaa taacatctct acctccacga ggtagtgata    180
aggactgcgt acactctacc ctccccagac tccacttgtg gaatttcacc ggatatgttg    240
ttgttattgt tataaggaaa agctttggtc tcaaaactct ttaaactcaa ttttttttct    300
```

-continued

```
tttgcactcc ctcttttctt gagtacattt cactctcaat tctttcttga gcacacactc    360
ttttatttga gtacacatac aactcaaatg accacctcaa tctatcggtg ttgatggaag    420
gatctagtga atgcaatatt ctagaactac accttccact tctttctcta attcttttag    480
actttgcact ctataactct catcctaaag ttcttctttc aatacaaatc ttgaatattc    540
tagattcttc tttgaaatat cttagatatt aattaaggtg gtgatgacct tttaacaccc    600
ctctcagcac caacttaatt tattctttgt atccattttg agtgatcctc gagacattgc    660
aatcatcttg atgtccagga actttatgaa tctcttcctc ctttgaactt ccccactcac    720
ttctctttga atcttattcg aaggtagtag tctccttgat ctagaccact ctgctaatgt    780
tgcatcaata tacttggtgt ttgggaattt caatcatgta gacctagctc cttagtcacg    840
gttgtggtgc ttctcggact tcttcttgca acatgacaag agtttcactt gagtctaata    900
gtaaatctct atagtgaccc ccttagcagc agctgcgcag ccctcccatg gctgctacaa    960
ccactggaaa gcctcctccc gaggtagtcc agcccgcccc aacatggttt tatctcgctc   1020
agtgaaggtt caatattagc agtaatgcaa gttaacaatt tgaacaaagg gagagaattt   1080
ggcagaaaag aggatcggaa catggtaatg cgcaagaaag caacatctaa tgcttctcca   1140
ggttgtgaga agaggcacaa tattagtaat gcttcaagag ccctattatg ttcgaacaac   1200
tttgatgctt tattgaaggc tactggaaaa aatagtaata ttatggctcc aacattacat   1260
atttctaatc ctgaagtagc taattaggat tattcaagaa aatcaggatg gcatgctact   1320
caaatccaat ccagcaatca agccactcat ggtcacattg aacacctagg ctcatgaggt   1380
cccttcccaa tctttggagt cacttggtca atatcaaggt gaatctggac aactactatt   1440
gtcaacaggg aatggtgacg atttagttac tttagatggg caatcaatct tttttaattc   1500
atgcatttgt caaaggaagt ttgaagccga taactcaacc ttcttaattc ttggttgtta   1560
tattttaaca ttatttaagc atcctcattt gtaatatcat catcgtgtgt attacaaatt   1620
ttgtggtaat cacaaaatgc tagttttttc tagcttttat tttcttcata cttgttagtt   1680
agtaaaggta tgttacctca ttatgactgg taaggtaagg ttcaacttcc tttgcttgta   1740
cttatcccta ctgagttttt tattattttt aatagaaggc tgctaaaaaa aataatttca   1800
agaaatctat tttatacgat atcaaattaa agtacgttgc ataaaacatt tataagaaag   1860
aggaatgaag tacgttgtag atcaaattaa ggaaatgata agagataaac ctggaatcgt   1920
ggtgtttctt ccattgccaa gagtgtatgt catcactacc caaaatttca agctttcttg   1980
ctgctatcat aaaacatttt ttcccactgt gcttatcgat aaaaaaactc tgaaagaaaa   2040
aaaaacatta aacaataaaa aaatgtatag tattgtattt ataatctaat tattaatcca   2100
aattcacatc aattaaggaa cttataattt tataaagaaa agtaacatac atgatagagt   2160
tattatagat aaaagtaggg gaaaaaaata aaaaaaatta taaattaatg aacaaagtca   2220
aataagaaaa taaaaatatt gtaatgacat ggccatatca aattgatcat tacataaaat   2280
gatactttca tcgttacata atgatgaatt tattggtaag atacaataaa aattaaataa   2340
ttaacaattc aaataaatat tgtatttaaa ataataatat aatacaatac gatagctcac   2400
aacaacccaa tatagttcaa ttttttgaat aacttaaact tggtgagtga aacagaataa   2460
aacatgattc ttttgatctt tctagtttca ttaactatga aaaaattaaa agatattaga   2520
tataaaattt taataaagat aaaaacactg ggtggtcatt ttttctactt gcttgagctg   2580
tagagttact tggtatacta gttgagataa atgacataaa aaaatttaat tgaaacacca   2640
atacaaacaa ggtgaaatta ttttttaaa gaaaattata tatgaatcgt tgaatctaaa   2700
```

```
attctagttt agcaacagag gggtttcaaa ggttgtttta gagtatgagt ttaaatccta   2760
agtgtgaaac tcaatatttt ttttaatatt cttatttgaa tttctaactc caccattata   2820
ttgtttaata cttgtgttag tgagaggcta aagtagatgt agaatattaa taccactttc   2880
atatgaatcc tgtactttca tatatagcgg aacataaatt tatgtgcaaa aattcatgat   2940
aaatgcaata gatagtagat atgaatcaca actttaaaga atataatgat ttaaatgtta   3000
attaaataaa aaattgaatc cataaatctt aaattctgat tttgcctcta gtgataggta   3060
ccaaatacgt acctaacaaa taatttaggt tcacacaaac tagcacatat accaccatta   3120
caaaaaataa aatgaaacat aaaaggtaat taaccacatc aaaatgagat tttaccagtc   3180
tgccgctatc aaggaggatg ggagaatcac atagactaaa aaagagctcc tttttggtgt   3240
tgaaaatccg aggaagctta gatctatcaa ttatttttg ataatcggaa ggcaaaaatc    3300
ttccccaaat ttcatcagat tttgcaacaa atttgaatcc tgttgataaa attgttgatc   3360
ttactgcatc tgctggagtt gttcttaaaa ttatttcaaa gatgcaacct tctggcaact   3420
tttcaaaata attcattgga gctatggact tagaaatatt catgtcaaaa ttcttataaa   3480
accttataac cgagaaataa ccaaagtttt tttgttacaa gctttatata taattaaata   3540
atcaaaagat aaaaaagatt tcagaggtct atacattgtc aaatatagta ataagtacaa   3600
ataagcatat aaaattatgt tttttttcc tttttgtca atgagtacag ataagcaaaa     3660
agtcaaactt attcaaataa caataaccat tgccacacct taatctcaaa caagtttcac   3720
gttgcttcaa ttaagtgtat cgagactaat attatattat ataaaataaa aataacatgc   3780
acgagaagat ctctatttaa tttggcgtga aatgttatct aaagtctcaa ataattggta   3840
ttgcttatat gaaagtaaaa aaacttccat tgtgtgccat actttcgaga caactccttt   3900
gtgattttag gtctacttcg tctcatttta acaccttcac actatgattt cataatgtaa   3960
caacttaatt aatttcttat ttaatcatga taaattagta cgatacagtg taaacatcgg   4020
atgcaaataa attgttatcc aatagaggtt acatgaccaa accatctcat ttgttttatt   4080
tttattatgt gctcgattta ttgttagcta tttcatcatc gattccaata gtatttagat   4140
ctttcgaaaa gcaaatagcc ataacacatt attgtttata tatcaagaaa acacataagc   4200
tatattatat tattgtacaa tttcttcttt attctggtct aaattcaatt ccttgaacaa   4260
taaggccacc ttttccatga agctgcgtaa tctccatcaa tcgcgcttca acatctccat   4320
catctcctgt atcattgata aaatttccca attctatttc catccatcca tcgactcttt   4380
ttcgtggaca tttcacatta cgtttgcgtc tcctaaccct ttttccgact agactcacga   4440
cactagctcg ttcctcggcc tctttgtcgc tcacacgatt cacaaaccta acaaatgcat   4500
tagcaatttc tagtccatca tgattctttg acaatttgaa caccaaataa acaacatatt   4560
tggttctttt cgacaatatt tgtgttccaa tcgtgcctcg tatgtctagc caacttacac   4620
ccttgagatg agccacttcc gaaaatctgc aaaataaaat gtctatattg tcttagatac   4680
acgtatttag tgagtttaag ttatatataa catcgccaat ataagtaatt tttgcaccat   4740
caaatcatct ttacctattg taataggtaa catatttcat tacacatttt agtgaggctc   4800
atctatatat atcttttagg tggcttgatt gtgtaaaaaa aaaattctca ccaatagtgg   4860
cagaggtaga atttcaacca agggattcaa aaaataacat atgtagaaat tcgttaaaag   4920
gcaatgaagt ataatttttt atacgtagta catacataaa aaaaaagaat aactttttat   4980
atgtagtata atttttcgac gaacctggag tcaggatgag aaatccattc ccaataccat   5040
```

```
ggtgtatcaa ctccccatgt aatagcaagt tctctagctg atatcataaa acatttcttg   5100
cctgttttct tatcaagtga aaaactctgt tttcaaaaat aaaataaaat cttagattca   5160
cactactagc ttatatatag tccattcaaa aataaaataa aattcacaca attattatta   5220
taatctattt aattttgcat ttttaatggt gtttgtaacc cattggccag aaaatcttag   5280
aagttcattt agttgactat ctgaacttcc gttttactat agagagttgg attcccagtt   5340
tgtaacaaaa acaaaataaa ataagaaaaa ttcattggct gattaattaa gatttgcgca   5400
gccgtaagca cactagtaga ttttagtgct tcctattaaa cacgactcaa ttcctaagat   5460
ttcaactctg attaaaactc aaactctaga cctcaggtca aaggttcatg acctttaccg   5520
ttatacaaca ccaacagtta gaggcaaagc tagaacaccc ctataaattc taggaaccca   5580
atagttttag ttcaaactct gtattttatc tttaaaaaga aaactcctct aatttgtacc   5640
aaattattaa tttcgaacca aacaactcaa aaaacacaca aaaaatcccg aacccataag   5700
cttcaaaaca attatacata tattcaacta atgagccaaa agaaaagctt gctacttccc   5760
aatttagagc tacttaccaa tttgcctcca tccattagaa cagggaagtc acatagacta   5820
aagtaaagct ccttttaga cggataaatc cgcggggaga catatctcga gttgatatct   5880
tcataatcat ctggtaaaaa ctttacccaa ataacgtcgg attcagcagc agagttgaat   5940
ccccgagaga tcgcggatga aatcacgacg tctttcgggg aagtaaagga gagaatatca   6000
caaacacaat cttctggtag caataggaaa tagtccatta ttggaaaatt gaatttgaag   6060
ttttgtgaat ttttttcttt tatataaagc aaactgagaa aagtttgttg aaaagttgtt   6120
acacttcata tgtctcgacg gttaagcagg ggcggctcaa cgtatttgga ggcctaaaac   6180
aaaatttaaa ttaaaggcct aaaatctttt agctgaggca attattaaat aaattgttaa   6240
cattattcta taagtaataa gttgacaaaa ctgcttataa acttcttttt ttatttaaaa   6300
gcacataaca taagtcaatc taaacaggct tgtaattcgc tttatccaac acattagttt   6360
tactattgat tcatattttt gatagagctc taacttacat agagtataaa aggggtatag   6420
aaaattacaa cgcgagagta agtgaagaga gtgtaagaag acaaaacaac gtttttcttg   6480
atttcttcta tttgattgag gttaaggaga ataaaataat atatatatga aaagtacatt   6540
tatcttaaat aattaatttt ttctataaaa aaaattaaca cataatttat tgttggtaaa   6600
aatttgaggc ccccctaaaa ttgggggcct aaggcatatg cctaattttt ataagcattg   6660
agccggcact gcggttaaat attgttttgt tcatttttac ttctccagta tgaatataat   6720
aagtgaaaag gtcatataat ttagagctga tacatacctc gttataaaaa tggctcatac   6780
atacctatac tattacacaa atagcctaga tatacccttt tggcctaatg gaagtgaaaa   6840
tatttaattt tattttattt ttaaaaaaat catttttgtt tatttttcat tatttttatc   6900
tagttctcac atatgtacat tttatttcca aaaaaaaata aaattaaaga attgatattg   6960
cttagataca ccaaacaaac aactcatgtg gaggaagata ttccaataat actaaacatg   7020
aaatgttttg agtttgaaat tttttgtctt tcctttttag tgaattaaaa catgaaatgt   7080
cttggaagat tcgaaattta ctggcccgac taatttaaga ttagcatcat ctaaggtcca   7140
tttatcaagg agcgttcccg accaagaatt tctccattct ccgaattcaa accaaagact   7200
tgttgtttag ttaacactag agaagtctca ttctcgcacc acagttgtgg cagttcccga   7260
aaagcaatat tcacaaattc ttacattcat catttcatta atttcttata gttgtaacta   7320
taagaacaac ataccatgtg tctcccccac aaagtggagt atgggaaggg tagagtgtaa   7380
gcaaacttta ctcttacctc agaggtagaa agtcttcttc cgatagatcc tcgactcgag   7440
```

aaaaataatc caaagcagtt cagaaaaaga cacaacaaaa gtacaagaaa caccagatag 7500
taacagaata gtacttcaac attaacaaat tactatctct tacacagaaa aatgaacttg 7560
aaattcataa aaaataataa taataacaga acataccctt gttcaagtgg taatctatat 7620
acagtacttt caaaatcaat ctcttgctcg tacttgagct cgagaaaaat tccttatact 7680
aaccgcgtct tccccatttc acgagcagtg gagagaacgt ttcacacgtt gtctttacta 7740
catcttcagc aggtaatgtc ttt 7763

<210> SEQ ID NO 8
<211> LENGTH: 7763
<212> TYPE: DNA
<213> ORGANISM: Artificial Sequence
<220> FEATURE:
<223> OTHER INFORMATION: Diploid F4 potato genotype 17SC0100-0018

<400> SEQUENCE: 8
ctctattttg ttgttcttag tcctttctta taggattttg cattgccccc acccccaccc 60
cccttgttat aagtaactat atctttttcc attgttttct tcttccttgt acttacattt 120
gttgcatttg agttgagggt ctttcgaaaa taacatctct acctccacga ggtagtgata 180
aggactgcgt acactctacc ctccccagac tccacttgtg gaatttcacc ggatatgttg 240
ttgttattgt tataaggaaa agctttggtc tcaaaactct ttaaactcaa ttttttttct 300
tttgcactcc ctcttttctt gagtacattt cactctcaat tctttcttga gcacacactc 360
ttttatttga gtacacatac aactcaaatg accacctcaa tctatcggtg ttgatggaag 420
gatctagtga atgcaatatt ctagaactac accttccact tctttctcta attcttttag 480
actttgcact ctataactct catcctaaag ttcttctttc aatacaaatc ttgaatattc 540
tagattcttc tttgaaatat cttagatatt aattaaggtg gtgatgacct tttaacaccc 600
ctctcagcac caacttaatt tattctttgt atccattttg agtgatcctc gagacattgc 660
aatcatcttg atgtccagga actttatgaa tctcttcctc ctttgaactt ccccactcac 720
ttctctttga atcttattcg aaggtagtag tctccttgat ctagaccact ctgctaatgt 780
tgcatcaata tacttggtgt ttgggaattt caatcatgta gacctagctc cttagtcacg 840
gttgtggtgc ttctcggact tcttcttgca acatgacaag agtttcactt gagtctaata 900
gtaaatctct atagtgaccc ccttagcagc agctgcgcag ccctcccatg gctgctacaa 960
ccactggaaa gcctcctccc gaggtagtcc agcccgcccc aacatggttt tatctcgctc 1020
agtgaaggtt caatattagc agtaatgcaa gttaacaatt tgaacaaagg gagagaattt 1080
ggcagaaaag aggatcggaa catggtaatg cgcaagaaag caacatctaa tgcttctcca 1140
ggttgtgaga agaggcacaa tattagtaat gcttcaagag ccctattatg ttcgaacaac 1200
tttgatgctt tattgaaggc tactggaaaa aatagtaata ttatggctcc aacattacat 1260
atttctaatc ctgaagtagc taattaggat tattcaagaa aatcaggatg gcatgctact 1320
caaatccaat ccagcaatca agccactcat ggtcacattg aacacctagg ctcatgaggt 1380
cccttcccaa tctttggagt cacttggtca atatcaaggt gaatctggac aactactatt 1440
gtcaacaggg aatggtgacg atttagttac tttagatggg caatcaatct tttttaattc 1500
atgcatttgt caaaggaagt ttgaagccga taactcaacc ttcttaattc ttggttgtta 1560
tattttaaca ttatttaagc atcctcattt gtaatatcat catcgtgtgt attacaaatt 1620
ttgtggtaat cacaaaatgc tagtttttttc tagcttttat tttcttcata cttgttagtt 1680

-continued

```
agtaaaggta tgttacctca ttatgactgg taaggtaagg ttcaacttcc tttgcttgta   1740
cttatcccta ctgagttttt tattattttt aatagaaggc tgctaaaaaa aataatttca   1800
agaaatctat tttatacgat atcaaattaa agtacgttgc ataaaacatt tataagaaag   1860
aggaatgaag tacgttgtag atcaaattaa ggaaatgata agagataaac ctggaatcgt   1920
ggtgtttctt ccattgccaa gagtgtatgt catcactacc caaaatttca agctttcttg   1980
ctgctatcat aaaacatttt ttcccactgt gcttatcgat aaaaaaactc tgaaagaaaa   2040
aaaaacatta aacaataaaa aaatgtatag tattgtattt ataatctaat tattaatcca   2100
aattcacatc aattaaggaa cttataattt tataaagaaa agtaacatac atgatagagt   2160
tattatagat aaaagtaggg gaaaaaaata aaaaaaatta taaattaatg aacaaagtca   2220
aataagaaaa taaaaatatt gtaatgacat ggccatatca aattgatcat tacataaaat   2280
gatactttca tcgttacata atgatgaatt tattggtaag atacaataaa aattaaataa   2340
ttaacaattc aaataaatat tgtatttaaa ataataatat aatacaatac gatagctcac   2400
aacaacccaa tatagttcaa ttttttgaat aacttaaact tggtgagtga aacagaataa   2460
aacatgattc ttttgatctt tctagtttca ttaactatga aaaaattaaa agatattaga   2520
tataaaattt taataaagat aaaaacactg ggtggtcatt ttttctactt gcttgagctg   2580
tagagttact tggtatacta gttgagataa atgacataaa aaaatttaat tgaaacacca   2640
atacaaacaa ggtgaaatta ttttttttaaa gaaaattata tatgaatcgt tgaatctaaa   2700
attctagttt agcaacagag gggtttcaaa ggttgtttta gagtatgagt ttaaatccta   2760
agtgtgaaac tcaatatttt ttttaatatt cttatttgaa tttctaactc caccattata   2820
ttgtttaata cttgtgttag tgagaggcta aagtagatgt agaatattaa taccactttc   2880
atatgaatcc tgtactttca tatatagcgg aacataaatt tatgtgcaaa aattcatgat   2940
aaatgcaata gatagtagat atgaatcaca actttaaaga atataatgat ttaaatgtta   3000
attaaataaa aaattgaatc cataaatctt aaattctgat tttgcctcta gtgataggta   3060
ccaaatacgt acctaacaaa taatttaggt tcacacaaac tagcacatat accaccatta   3120
caaaaaaataa aatgaaacat aaaaggtaat taaccacatc aaaatgagat tttaccagtc   3180
tgccgctatc aaggaggatg ggagaatcac atagactaaa aaagagctcc tttttggtgt   3240
tgaaaatccg aggaagctta gatctatcaa ttattttttg ataatcggaa ggcaaaaatc   3300
ttccccaaat ttcatcagat tttgcaacaa atttgaatcc tgttgataaa attgttgatc   3360
ttactgcatc tgctggagtt gttcttaaaa ttatttcaaa gatgcaacct tctggcaact   3420
tttcaaaata attcattgga gctatggact tagaaatatt catgtcaaaa ttcttataaa   3480
accttataac cgagaaataa ccaaagtttt tttgttacaa gctttatata taattaaata   3540
atcaaaagat aaaaaagatt tcagaggtct atacattgtc aaatatagta ataagtacaa   3600
ataagcatat aaaattatgt tttttttttcc tttttgtca atgagtacag ataagcaaaa   3660
agtcaaactt attcaaataa caataaccat tgccacacct taatctcaaa caagtttcac   3720
gttgcttcaa ttaagtgtat cgagactaat attatattat ataaaataaa aataacatgc   3780
acgagaagat ctctatttaa tttggcgtga aatgttatct aaagtctcaa ataattggta   3840
ttgcttatat gaaagtaaaa aaacttccat tgtgtgccat actttcgaga caactccttt   3900
gtgattttag gtctacttcg tctcatttta acaccttcac actatgattt cataatgtaa   3960
caacttaatt aatttcttat ttaatcatga taaattagta cgatacagtg taaacatcgg   4020
atgcaaataa attgttatcc aatagaggtt acatgaccaa accatctcat ttgttttatt   4080
```

```
tttattatgt gctcgattta ttgttagcta tttcatcatc gattccaata gtatttagat   4140
ctttcgaaaa gcaaatagcc ataacacatt attgtttata tatcaagaaa acacataagc   4200
tatattatat tattgtacaa tttcttcttt attctggtct aaattcaatt ccttgaacaa   4260
taaggccacc ttttccatga agctgcgtaa tctccatcaa tcgcgcttca acatctccat   4320
catctcctgt atcattgata aaatttccca attctatttc catccatcca tcgactcttt   4380
ttcgtggaca tttcacatta cgtttgcgtc tcctaaccct ttttccgact agactcacga   4440
cactagctcg ttcctcggcc tctttgtcgc tcacacgatt cacaaaccta acaaatgcat   4500
tagcaatttc tagtccatca tgattctttg acaatttgaa caccaaataa acaacatatt   4560
tggttctttt cgacaatatt tgtgttccaa tcgtgcctcg tatgtctagc caacttacac   4620
ccttgagatg agccacttcc gaaaatctgc aaaataaaat gtctatattg tcttagatac   4680
acgtatttag tgagtttaag ttatatataa catcgccaat ataagtaatt tttgcaccat   4740
caaatcatct ttacctattg taataggtaa catatttcat tacacatttt agtgaggctc   4800
atctatatat atcttttagg tggcttgatt gtgtaaaaaa aaaattctca ccaatagtgg   4860
cagaggtaga atttcaacca agggattcaa aaaataacat atgtagaaat tcgttaaaag   4920
gcaatgaagt ataatttttt atacgtagta catacataaa aaaaaagaat aactttttat   4980
atgtagtata atttttcgac gaacctggag tcaggatgag aaatccattc ccaataccat   5040
ggtgtatcaa ctccccatgt aatagcaagt tctctagctg atatcataaa acatttcttg   5100
cctgttttct tatcaagtga aaaactctgt tttcaaaaat aaaataaaat cttagattca   5160
cactactagc ttatatatag tccattcaaa aataaaataa aattcacaca attattatta   5220
taatctattt aattttgcat ttttaatggt gtttgtaacc cattggccag aaaatcttag   5280
aagttcattt agttgactat ctgaacttcc gttttactat agagagttgg attcccagtt   5340
tgtaacaaaa acaaaataaa ataagaaaaa ttcattggct gattaattaa gatttgcgca   5400
gccgtaagca cactagtaga ttttagtgct tcctattaaa cacgactcaa ttcctaagat   5460
ttcaactctg attaaaactc aaactctaga cctcaggtca aaggttcatg acctttaccg   5520
ttatacaaca ccaacagtta gaggcaaagc tagaacaccc ctataaattc taggaaccca   5580
atagttttag ttcaaactct gtattttatc tttaaaaaga aaactcctct aatttgtacc   5640
aaattattaa tttcgaacca aacaactcaa aaaacacaca aaaaatcccg aacccataag   5700
cttcaaaaca attatacata tattcaacta atgagccaaa agaaaagctt gctacttccc   5760
aatttagagc tacttaccaa tttgcctcca tccattagaa cagggaagtc acatagacta   5820
aagtaaagct cctttttaga cggataaatc cgcggggaga catatctcga gttgatatct   5880
tcataatcat ctggtaaaaa ctttacccaa ataacgtcgg attcagcagc agagttgaat   5940
ccccgagaga tcgcggatga aatcacgacg tctttcgggg aagtaaagga gagaatatca   6000
caaacacaat cttctggtag caataggaaa tagtccatta ttggaaaatt gaatttgaag   6060
ttttgtgaat ttttttcttt tatataaagc aaactgagaa aagtttgttg aaaagttgtt   6120
acacttcata tgtctcgacg gttaagcagg ggcggctcaa cgtatttgga ggcctaaaac   6180
aaaatttaaa ttaaaggcct aaaatctttt agctgaggca attattaaat aaattgttaa   6240
cattattcta taagtaataa gttgacaaaa ctgcttataa acttcttttt ttatttaaaa   6300
gcacataaca taagtcaatc taaacaggct tgtaattcgc tttatccaac acattagttt   6360
tactattgat tcatattttt gatagagctc taacttacat agagtataaa aggggtatag   6420
```

-continued

```
aaaattacaa cgcgagagta agtgaagaga gtgtaagaag acaaaacaac gtttttcttg   6480
atttcttcta tttgattgag gttaaggaga ataaaataat atatatatga aaagtacatt   6540
tatcttaaat aattaatttt ttctataaaa aaaattaaca cataatttat tgttggtaaa   6600
aatttgaggc ccccctaaaa ttgggggcct aaggcatatg cctaattttt ataagcattg   6660
agccggcact gcggttaaat attgttttgt tcatttttac ttctccagta tgaatataat   6720
aagtgaaaag gtcatataat ttagagctga tacatacctc gttataaaaa tggctcatac   6780
atacctatac tattacacaa atagcctaga tataccettt tggcctaatg gaagtgaaaa   6840
tatttaattt tattttattt ttaaaaaaat catttttgtt tatttttcat tatttttatc   6900
tagttctcac atatgtacat tttatttcca aaaaaaaata aaattaaaga attgatattg   6960
cttagataca ccaaacaaac aactcatgtg gaggaagata ttccaataat actaaacatg   7020
aaatgttttg agtttgaaat tttttgtctt tcctttttag tgaattaaaa catgaaatgt   7080
cttggaagat tcgaaattta ctggcccgac taatttaaga ttagcatcat ctaaggtcca   7140
tttatcaagg agcgttcccg accaagaatt tctccattct ccgaattcaa accaaagact   7200
tgttgtttag ttaacactag agaagtctca ttctcgcacc acagttgtgg cagttcccga   7260
aaagcaatat tcacaaattc ttacattcat catttcatta atttcttata gttgtaacta   7320
taagaacaac ataccatgtg tctcccccac aaagtggagt atgggaaggg tagagtgtaa   7380
gcaaacttta ctcttacctc agaggtagaa agtcttcttc cgatagatcc tcgactcgag   7440
aaaaataatc caaagcagtt cagaaaaaga cacaacaaaa gtacaagaaa caccagatag   7500
taacagaata gtacttcaac attaacaaat tactatctct tacacagaaa aatgaacttg   7560
aaattcataa aaaataataa taataacaga acataccctt gttcaagtgg taatctatat   7620
acagtacttt caaaatcaat ctcttgctcg tacttgagct cgagaaaaat tccttatact   7680
aaccgcgtct tccccatttc acgagcagtg gagagaacgt ttcacacgtt gtctttacta   7740
catcttcagc aggtaatgtc ttt                                           7763
```

```
<210> SEQ ID NO 9
<211> LENGTH: 266
<212> TYPE: PRT
<213> ORGANISM: Solanum tuberosum

<400> SEQUENCE: 9

Met Asp Tyr Phe Leu Leu Leu Pro Glu Gly Cys Val Cys Asp Ile Leu
1               5                   10                  15

Ser Phe Thr Ser Pro Lys Asp Val Val Ile Ser Ser Ala Ile Ser Arg
            20                  25                  30

Gly Phe Asn Ser Ala Ala Glu Ser Asp Val Ile Trp Val Lys Phe Leu
        35                  40                  45

Pro Asp Asp Tyr Glu Asp Ile Ile Ser Arg Tyr Val Ser Pro Arg Ile
    50                  55                  60

Tyr Pro Ser Lys Lys Glu Leu Tyr Phe Ser Leu Cys Asp Phe Pro Val
65                  70                  75                  80

Leu Met Asp Gly Gly Lys Leu Ser Phe Ser Leu Asp Lys Lys Thr Gly
                85                  90                  95

Lys Lys Cys Phe Met Ile Ser Ala Arg Glu Leu Ala Ile Ser Trp Gly
            100                 105                 110

Val Asp Thr Pro Trp Tyr Trp Glu Trp Ile Ser His Pro Asp Ser Arg
        115                 120                 125

Phe Ser Glu Val Ala His Leu Lys Gly Val Ser Trp Leu Asp Ile Arg
```

```
    130                 135                 140

Gly Thr Ile Gly Thr Gln Ile Leu Ser Lys Arg Thr Lys Tyr Val Val
145                 150                 155                 160

Tyr Leu Val Phe Lys Leu Ala Lys Asp His Asp Gly Leu Glu Ile Ala
                165                 170                 175

Asn Ala Phe Val Arg Phe Val Asn Arg Val Ser Asp Lys Asp Ala Glu
            180                 185                 190

Glu Arg Ala Ser Val Val Ser Leu Val Gly Lys Arg Val Arg Arg Arg
        195                 200                 205

Lys Arg Asn Val Lys Arg Pro Arg Lys Arg Val Asp Gly Trp Met Glu
    210                 215                 220

Ile Glu Leu Gly Asn Phe Ile Asn Asp Thr Gly Asp Asp Gly Asp Val
225                 230                 235                 240

Glu Ala Arg Leu Met Glu Ile Thr Arg Leu His Gly Lys Gly Gly Leu
                245                 250                 255

Ile Val Gln Gly Ile Glu Phe Arg Pro Glu
            260                 265


<210> SEQ ID NO 10
<211> LENGTH: 266
<212> TYPE: PRT
<213> ORGANISM: Solanum chacoense

<400> SEQUENCE: 10

Met Asp Tyr Phe Leu Leu Leu Pro Glu Asp Cys Val Cys Asp Ile Leu
1               5                   10                  15

Ser Phe Thr Ser Pro Lys Asp Val Val Ile Ser Ser Ala Ile Ser Arg
            20                  25                  30

Gly Phe Asn Ser Ala Ala Glu Ser Asp Val Ile Trp Val Lys Phe Leu
        35                  40                  45

Pro Asp Asp Tyr Glu Asp Ile Asn Ser Arg Tyr Val Ser Pro Arg Ile
    50                  55                  60

Tyr Pro Ser Lys Lys Glu Leu Tyr Phe Ser Leu Cys Asp Phe Pro Val
65                  70                  75                  80

Leu Met Asp Gly Gly Lys Leu Ser Phe Ser Leu Asp Lys Lys Thr Gly
                85                  90                  95

Lys Lys Cys Phe Met Ile Ser Ala Arg Glu Leu Ala Ile Thr Trp Gly
            100                 105                 110

Val Asp Thr Pro Trp Tyr Trp Glu Trp Ile Ser His Pro Asp Ser Arg
        115                 120                 125

Phe Ser Glu Val Ala His Leu Lys Gly Val Ser Trp Leu Asp Ile Arg
    130                 135                 140

Gly Thr Ile Gly Thr Gln Ile Leu Ser Lys Arg Thr Lys Tyr Val Val
145                 150                 155                 160

Tyr Leu Val Phe Lys Leu Ser Lys Asn His Asp Gly Leu Glu Ile Ala
                165                 170                 175

Asn Ala Phe Val Arg Phe Val Asn Arg Val Ser Asp Lys Glu Ala Glu
            180                 185                 190

Glu Arg Ala Ser Val Val Ser Leu Val Gly Lys Arg Val Arg Arg Arg
        195                 200                 205

Lys Arg Asn Val Lys Cys Pro Arg Lys Arg Val Asp Gly Trp Met Glu
    210                 215                 220

Ile Glu Leu Gly Asn Phe Ile Asn Asp Thr Gly Asp Asp Gly Asp Val
225                 230                 235                 240
```

```
Glu Ala Arg Leu Met Glu Ile Thr Gln Leu His Gly Lys Gly Gly Leu
                245                 250                 255

Ile Val Gln Gly Ile Glu Phe Arg Pro Glu
            260                 265


<210> SEQ ID NO 11
<211> LENGTH: 266
<212> TYPE: PRT
<213> ORGANISM: Artificial Sequence
<220> FEATURE:
<223> OTHER INFORMATION: Diploid breeding line D2

<400> SEQUENCE: 11

Met Asp Tyr Phe Leu Leu Leu Pro Glu Gly Cys Val Cys Asp Ile Leu
1               5                   10                  15

Ser Phe Thr Ser Pro Lys Asp Val Val Ile Ser Ser Ala Ile Ser Arg
            20                  25                  30

Gly Phe Asn Ser Val Ala Glu Ser Asp Val Ile Trp Val Lys Leu Leu
        35                  40                  45

Pro Asp Asp Tyr Glu Asp Ile Ile Ser Arg Tyr Val Ser Pro Arg Ile
    50                  55                  60

Tyr Pro Ser Lys Lys Glu Leu Tyr Phe Ser Leu Cys Asp Phe Pro Val
65                  70                  75                  80

Leu Met Asp Gly Gly Lys Leu Ser Phe Ser Leu Asp Lys Lys Thr Gly
                85                  90                  95

Lys Lys Cys Phe Met Ile Ser Ala Arg Glu Leu Ala Ile Ser Trp Gly
            100                 105                 110

Val Asp Thr Pro Trp Tyr Trp Glu Trp Ile Ser His Pro Asp Ser Arg
        115                 120                 125

Phe Ser Glu Val Ala His Leu Lys Gly Val Ser Trp Leu Asp Ile Arg
    130                 135                 140

Gly Thr Ile Gly Thr Gln Ile Leu Ser Lys Arg Ser Lys Tyr Val Val
145                 150                 155                 160

Tyr Leu Val Phe Lys Leu Ala Lys Asp His Asp Gly Leu Glu Ile Ala
                165                 170                 175

Asn Ala Phe Val Arg Phe Val Asn Arg Val Ser Asp Lys Glu Ala Glu
            180                 185                 190

Glu Arg Ala Ser Val Val Ser Leu Val Gly Lys Arg Val Arg Arg Arg
        195                 200                 205

Lys Arg Asn Val Lys Arg Pro Arg Lys Arg Val Asp Gly Trp Met Glu
    210                 215                 220

Ile Glu Leu Gly Asn Phe Ile Asn Asp Thr Arg Asp Asp Gly Asp Val
225                 230                 235                 240

Glu Ala Arg Leu Met Glu Ile Thr Arg Leu His Gly Lys Gly Gly Leu
                245                 250                 255

Ile Val Gln Gly Ile Glu Phe Arg Pro Glu
            260                 265


<210> SEQ ID NO 12
<211> LENGTH: 266
<212> TYPE: PRT
<213> ORGANISM: Artificial Sequence
<220> FEATURE:
<223> OTHER INFORMATION: Diploid breeding line D8

<400> SEQUENCE: 12

Met Asp Tyr Phe Leu Leu Leu Pro Glu Gly Cys Val Cys Asp Ile Leu
1               5                   10                  15
```

```
Ser Phe Thr Ser Pro Lys Asp Val Val Ile Ser Ser Ala Ile Ser Arg
            20                  25                  30

Gly Phe Asn Ser Ala Ala Glu Ser Asp Val Ile Trp Val Lys Phe Leu
        35                  40                  45

Pro Asp Asp Tyr Glu Asp Ile Ile Ser Arg Tyr Val Ser Pro Arg Ile
    50                  55                  60

Tyr Pro Ser Lys Arg Glu Leu Tyr Phe Ser Leu Cys Asp Phe Pro Val
65                  70                  75                  80

Leu Met Asp Gly Gly Lys Leu Ser Phe Ser Leu Asp Lys Lys Thr Gly
                85                  90                  95

Asn Lys Cys Phe Met Ile Ser Ala Arg Glu Leu Ala Ile Ser Trp Gly
            100                 105                 110

Val Asp Thr Pro Trp Tyr Trp Glu Trp Ile Ser His Pro Asp Ser Arg
        115                 120                 125

Phe Ser Glu Val Ala His Leu Lys Gly Val Ser Trp Leu Asp Ile Arg
    130                 135                 140

Gly Thr Ile Gly Thr Gln Ile Leu Ser Lys Arg Thr Lys Tyr Val Val
145                 150                 155                 160

Tyr Leu Val Phe Lys Leu Ala Lys Asp His Asp Gly Leu Glu Ile Ala
                165                 170                 175

Asn Ala Phe Val Arg Phe Val Asn Arg Val Ser Asp Lys Glu Ala Glu
            180                 185                 190

Glu Arg Ala Ser Val Val Ser Leu Val Gly Lys Arg Val Arg Arg Arg
        195                 200                 205

Lys Arg Asn Val Lys Arg Pro Arg Lys Arg Val Asp Gly Trp Met Glu
    210                 215                 220

Ile Glu Leu Gly Asn Phe Ile Asn Asp Thr Gly Asp Asp Gly Asp Val
225                 230                 235                 240

Glu Ala Arg Leu Met Glu Ile Thr Arg Leu His Gly Lys Gly Gly Leu
                245                 250                 255

Ile Val Gln Gly Ile Glu Phe Arg Pro Glu
            260                 265
```

<210> SEQ ID NO 13
<211> LENGTH: 266
<212> TYPE: PRT
<213> ORGANISM: Artificial Sequence
<220> FEATURE:
<223> OTHER INFORMATION: Diploid breeding line D14

<400> SEQUENCE: 13

```
Met Asp Tyr Phe Leu Leu Leu Pro Glu Gly Cys Val Cys Asp Ile Leu
1               5                   10                  15

Ser Phe Thr Ser Pro Lys Asp Val Val Ile Ser Ser Ala Ile Ser Arg
            20                  25                  30

Gly Phe Asn Ser Ala Ala Glu Ser Asp Phe Ile Trp Val Lys Phe Leu
        35                  40                  45

Pro Asp Asp Tyr Glu Asp Ile Ile Ser Arg Tyr Val Ser Pro Arg Ile
    50                  55                  60

Tyr Pro Ser Lys Lys Glu Leu Tyr Phe Ser Leu Cys Asp Phe Pro Val
65                  70                  75                  80

Leu Met Asp Gly Gly Lys Leu Ser Phe Ser Leu Asp Lys Lys Thr Gly
                85                  90                  95

Lys Lys Cys Phe Met Ile Ser Ala Arg Glu Leu Ala Ile Ser Trp Gly
            100                 105                 110
```

Val Asp Thr Pro Trp Tyr Trp Glu Trp Ile Ser His Pro Asp Ser Arg
        115                 120                 125

Phe Ser Glu Val Ala His Leu Lys Gly Val Ser Trp Leu Asp Ile Arg
    130                 135                 140

Gly Lys Ile Gly Thr Gln Ile Leu Ser Lys Arg Thr Lys Tyr Val Val
145                 150                 155                 160

Tyr Leu Val Phe Lys Leu Ala Lys Asp His Asp Gly Leu Glu Ile Ala
                165                 170                 175

Asn Ala Phe Val Arg Phe Val Asn Arg Val Ser Asp Lys Glu Ala Glu
            180                 185                 190

Glu Arg Ala Ser Val Val Ser Leu Val Gly Lys Arg Val Arg Arg Arg
        195                 200                 205

Lys Arg Asn Val Lys Arg Pro Arg Lys Arg Val Asp Gly Trp Met Glu
    210                 215                 220

Ile Glu Leu Gly Asn Phe Ile Asn Asp Thr Gly Asp Asp Gly Asp Val
225                 230                 235                 240

Glu Ala Arg Leu Met Glu Ile Thr Arg Leu His Gly Lys Gly Gly Leu
                245                 250                 255

Ile Val Gln Gly Ile Glu Phe Arg Pro Glu
            260                 265

<210> SEQ ID NO 14
<211> LENGTH: 266
<212> TYPE: PRT
<213> ORGANISM: Artificial Sequence
<220> FEATURE:
<223> OTHER INFORMATION: Diploid F4 potato genotype 17SC0100-0002

<400> SEQUENCE: 14

Met Asp Tyr Phe Leu Leu Leu Pro Glu Asp Cys Val Cys Asp Ile Leu
1               5                   10                  15

Ser Phe Thr Ser Pro Lys Asp Val Val Ile Ser Ser Ala Ile Ser Arg
            20                  25                  30

Gly Phe Asn Ser Ala Ala Glu Ser Asp Val Ile Trp Val Lys Phe Leu
        35                  40                  45

Pro Asp Asp Tyr Glu Asp Ile Asn Ser Arg Tyr Val Ser Pro Arg Ile
    50                  55                  60

Tyr Pro Ser Lys Lys Glu Leu Tyr Phe Ser Leu Cys Asp Phe Pro Val
65                  70                  75                  80

Leu Met Asp Gly Gly Lys Leu Ser Phe Ser Leu Asp Lys Lys Thr Gly
                85                  90                  95

Lys Lys Cys Phe Met Ile Ser Ala Arg Glu Leu Ala Ile Thr Trp Gly
            100                 105                 110

Val Asp Thr Pro Trp Tyr Trp Glu Trp Ile Ser His Pro Asp Ser Arg
        115                 120                 125

Phe Ser Glu Val Ala His Leu Lys Gly Val Ser Trp Leu Asp Ile Arg
    130                 135                 140

Gly Thr Ile Gly Thr Gln Ile Leu Ser Lys Arg Thr Lys Tyr Val Val
145                 150                 155                 160

Tyr Leu Val Phe Lys Leu Ser Lys Asn His Asp Gly Leu Glu Ile Ala
                165                 170                 175

Asn Ala Phe Val Arg Phe Val Asn Arg Val Ser Asp Lys Glu Ala Glu
            180                 185                 190

Glu Arg Ala Ser Val Val Ser Leu Val Gly Lys Arg Val Arg Arg Arg
        195                 200                 205

```
Lys Arg Asn Val Lys Cys Pro Arg Lys Arg Val Asp Gly Trp Met Glu
    210                 215                 220

Ile Glu Leu Gly Asn Phe Ile Asn Asp Thr Gly Asp Asp Gly Asp Val
225                 230                 235                 240

Glu Ala Arg Leu Met Glu Ile Thr Gln Leu His Gly Lys Gly Gly Leu
                245                 250                 255

Ile Val Gln Gly Ile Glu Phe Arg Pro Glu
            260                 265
```

<210> SEQ ID NO 15
<211> LENGTH: 20
<212> TYPE: DNA
<213> ORGANISM: Artificial Sequence
<220> FEATURE:
<223> OTHER INFORMATION: forward primer

<400> SEQUENCE: 15

```
tcgtgatttc atccgcgatc                                                 20
```

<210> SEQ ID NO 16
<211> LENGTH: 22
<212> TYPE: DNA
<213> ORGANISM: Artificial Sequence
<220> FEATURE:
<223> OTHER INFORMATION: reverse primer

<400> SEQUENCE: 16

```
tgcctccatc cattagaaca gg                                              22
```

<210> SEQ ID NO 17
<211> LENGTH: 3104
<212> TYPE: DNA
<213> ORGANISM: Artificial Sequence
<220> FEATURE:
<223> OTHER INFORMATION: PSC gene sequence cloned into pBINPLUS vector

<400> SEQUENCE: 17

```
caagggtatg ttctgttatt attattattt tttatgaatt tcaagttcat ttttctgtgt     60

aagagatagt aatttgttaa tgttgaagta ctattctgtt actatctggt gtttcttgta    120

cttttgttgt gtcttttttct gaactgcttt ggattatttt tctcgagtcg aggatctatc    180

ggaagaagac tttctacctc tgaggtaaga gtaaagtttg cttacactct acccttccca    240

tactccactt tgtgggggag acacatggta tgttgttctt atagttacaa ctataagaaa    300

ttaatgaaat gatgaatgta agaatttgtg aatattgctt ttcgggaact gccacaactg    360

tggtgcgaga atgagacttc tctagtgtta actaaacaac aagtctttgg tttgaattcg    420

gagaatggag aaattcttgg tcgggaacgc tccttgataa atggacctta gatgatgcta    480

atcttaaatt agtcgggcca gtaaatttcg aatcttccaa gacatttcat gttttaattc    540

actaaaaagg aaagacaaaa aatttcaaac tcaaaacatt tcatgtttag tattattgga    600

atatcttcct ccacatgagt tgtttgtttg gtgtatctaa gcaatatcaa ttctttaatt    660

ttattttttt ttggaaataa aatgtacata tgtgagaact agataaaaat aatgaaaaat    720

aaacaaaaat gatttttttta aaaataaaat aaaattaaat attttcactt ccattaggcc    780

aaaagggtat atctaggcta tttgtgtaat agtataggta tgtatgagcc atttttataa    840

cgaggtatgt atcagctcta aattatatga ccttttcact tattatattc atactggaga    900

agtaaaaatg aacaaaacaa tatttaaccg cagtgccggc tcaatgctta taaaaattag    960
```

-continued

```
gcatatgcct taggcccccca attttagggg ggcctcaaat ttttaccaac aataaattat   1020
gtgttaattt tttttataga aaaaattaat tatttaagat aaatgtactt ttcatatata   1080
tattatttta ttctccttaa cctcaatcaa atagaagaaa tcaagaaaaa cgttgttttg   1140
tcttcttaca ctctcttcac ttactctcgc gttgtaattt tctatacccc ttttatactc   1200
tatgtaagtt agagctctat caaaaatatg aatcaatagt aaaactaatg tgttggataa   1260
agcgaattac aagcctgttt agattgactt atgttatgtg cttttaaata aaaaaagaag   1320
tttataagca gttttgtcaa cttattactt atagaataat gttaacaatt tatttaataa   1380
ttgcctcagc taaaagattt taggccttta atttaaattt tgttttaggc ctccaaatac   1440
gttgagccgc ccctgcttaa ccgtcgagac atatgaagtg taacaacttt tcaacaaact   1500
tttctcagtt tgctttatat aaagaaaaaa aattcacaaa acttcaaatt caattttcca   1560
ataatggact atttcctatt gctaccagaa gattgtgttt gtgatattct ctcctttact   1620
tccccgaaag acgtcgtgat ttcatccgcg atctctcggg gattcaactc tgctgctgaa   1680
tccgacgtta tttgggtaaa gtttttacca gatgattatg aagatatcaa ctcgagatat   1740
gtctccccgc ggatttatcc gtctaaaaag gagctttact ttagtctatg tgacttccct   1800
gttctaatgg atggaggcaa attgagtttt tcacttgata agaaaacagg caagaaatgt   1860
tttatgatat cagctagaga acttgctatt acatggggag ttgatacacc atggtattgg   1920
gaatggattt ctcatcctga ctccagattt tcggaagtgg ctcatctcaa gggtgtaagt   1980
tggctagaca tacgaggcac gattggaaca caaatattgt cgaaaagaac caaatatgtt   2040
gtttatttgg tgttcaaatt gtcaaagaat catgatggac tagaaattgc taatgcattt   2100
gttaggtttg tgaatcgtgt gagcgacaaa gaggccgagg aacgagctag tgtcgtgagt   2160
ctagtcggaa aaagggttag gagacgcaaa cgtaatgtga aatgtccacg aaaaagagtc   2220
gatggatgga tggaaataga attgggaaat tttatcaatg atacaggaga tgatggagat   2280
gttgaagcgc gattgatgga gattacgcag cttcatggaa aaggtggcct tattgttcaa   2340
ggaattgaat ttagaccaga ataaagaaga aattgtacaa taatataata tagcttatgt   2400
gttttcttga tatataaaca ataatgtgtt atggctattt gcttttcgaa agatctaaat   2460
actattggaa tcgatgatga aatagctaac aataaatcga gcacataata aaaataaaac   2520
aaatgagatg gtttggtcat gtaacctcta ttggataaca atttatttgc atccgatgtt   2580
tacactgtat cgtactaatt tatcatgatt aaataagaaa ttaattaagt tgttacatta   2640
tgaaatcata gtgtgaaggt gttaaaatga gacgaagtag acctaaaatc acaaaggagt   2700
tgtctcgaaa gtatggcaca caatggaagt ttttttactt tcatataagc aataccaatt   2760
atttgagact ttagataaca tttcacgcca aattaaatag agatcttctc gtgcatgtta   2820
tttttatttt atataatata atattagtct cgatacactt aattgaagca acgtgaaact   2880
tgtttgagat taaggtgtgg caatggttat tgttatttga ataagtttga ctttttgctt   2940
atctgtactc attgacaaaa aaggaaaaaa aaacataatt ttatatgctt atttgtactt   3000
attactatat ttgacaatgt atagacctct gaaatctttt ttatcttttg attatttaat   3060
tatatataaa gcttgtaaca aaaaaacttt ggttatttct cggt                    3104
```

<210> SEQ ID NO 18
<211> LENGTH: 1563
<212> TYPE: DNA
<213> ORGANISM: Artificial Sequence
<220> FEATURE:
<223> OTHER INFORMATION: PSC gene promoter

<400> SEQUENCE: 18
caagggtatg ttctgttatt attattattt tttatgaatt tcaagttcat ttttctgtgt 60
aagagatagt aatttgttaa tgttgaagta ctattctgtt actatctggt gtttcttgta 120
cttttgttgt gtctttttct gaactgcttt ggattatttt tctcgagtcg aggatctatc 180
ggaagaagac tttctacctc tgaggtaaga gtaaagtttg cttacactct acccttccca 240
tactccactt tgtgggggag acacatggta tgttgttctt atagttacaa ctataagaaa 300
ttaatgaaat gatgaatgta agaatttgtg aatattgctt ttcgggaact gccacaactg 360
tggtgcgaga atgagacttc tctagtgtta actaaacaac aagtctttgg tttgaattcg 420
gagaatggag aaattcttgg tcgggaacgc tccttgataa atggacctta gatgatgcta 480
atcttaaatt agtcgggcca gtaaatttcg aatcttccaa gacatttcat gttttaattc 540
actaaaaagg aaagacaaaa aatttcaaac tcaaaacatt tcatgtttag tattattgga 600
atatcttcct ccacatgagt tgtttgtttg gtgtatctaa gcaatatcaa ttctttaatt 660
ttattttttt ttggaaataa aatgtacata tgtgagaact agataaaaat aatgaaaaat 720
aaacaaaaat gatttttttta aaaataaaat aaaattaaat attttcactt ccattaggcc 780
aaaagggtat atctaggcta tttgtgtaat agtataggta tgtatgagcc atttttataa 840
cgaggtatgt atcagctcta aattatatga ccttttcact tattatattc atactggaga 900
agtaaaaatg aacaaaacaa tatttaaccg cagtgccggc tcaatgctta taaaaattag 960
gcatatgcct taggccccca attttagggg ggcctcaaat ttttaccaac aataaattat 1020
gtgttaattt tttttataga aaaaattaat tatttaagat aaatgtactt ttcatatata 1080
tattatttta ttctccttaa cctcaatcaa atagaagaaa tcaagaaaaa cgttgttttg 1140
tcttcttaca ctctcttcac ttactctcgc gttgtaattt tctataccccc ttttatactc 1200 tatgtaagtt agagctctat caaaaatatg aatcaatagt aaaactaatg tgttggataa 1260
agcgaattac aagcctgttt agattgactt atgttatgtg cttttaaata aaaaaagaag 1320
tttataagca gttttgtcaa cttattactt atagaataat gttaacaatt tatttaataa 1380
ttgcctcagc taaaagattt taggccttta atttaaattt tgttttaggc ctccaaatac 1440
gttgagccgc ccctgcttaa ccgtcgagac atatgaagtg taacaacttt tcaacaaact 1500
tttctcagtt tgctttatat aaagaaaaaa aattcacaaa acttcaaatt caattttcca 1560
ata 1563

<210> SEQ ID NO 19
<211> LENGTH: 801
<212> TYPE: DNA
<213> ORGANISM: Artificial Sequence
<220> FEATURE:
<223> OTHER INFORMATION: PSC gene coding sequence

<400> SEQUENCE: 19
atggactatt tcctattgct accagaagat tgtgtttgtg atattctctc ctttacttcc 60
ccgaaagacg tcgtgatttc atccgcgatc tctcggggat tcaactctgc tgctgaatcc 120
gacgttattt gggtaaagtt tttaccagat gattatgaag atatcaactc gagatatgtc 180
tccccgcgga tttatccgtc taaaaaggag ctttacttta gtctatgtga cttccctgtt 240
ctaatggatg gaggcaaatt gagtttttca cttgataaga aaacaggcaa gaaatgtttt 300
atgatatcag ctagagaact tgctattaca tggggagttg atacaccatg gtattgggaa 360

```
tggatttctc atcctgactc cagattttcg gaagtggctc atctcaaggg tgtaagttgg    420

ctagacatac gaggcacgat tggaacacaa atattgtcga aaagaaccaa atatgttgtt    480

tatttggtgt tcaaattgtc aaagaatcat gatggactag aaattgctaa tgcatttgtt    540

aggtttgtga atcgtgtgag cgacaaagag gccgaggaac gagctagtgt cgtgagtcta    600

gtcggaaaaa gggttaggag acgcaaacgt aatgtgaaat gtccacgaaa aagagtcgat    660

ggatggatgg aaatagaatt gggaaatttt atcaatgata caggagatga tggagatgtt    720

gaagcgcgat tgatggagat tacgcagctt catggaaaag gtggccttat tgttcaagga    780

attgaattta gaccagaata a                                              801


<210> SEQ ID NO 20
<211> LENGTH: 500
<212> TYPE: DNA
<213> ORGANISM: Artificial Sequence
<220> FEATURE:
<223> OTHER INFORMATION: PSC gene promoter

<400> SEQUENCE: 20

tgtacttttc atatatatat tattttattc tccttaacct caatcaaata gaagaaatca     60

agaaaaacgt tgttttgtct tcttacactc tcttcactta ctctcgcgtt gtaattttct    120

atacccettt tatactctat gtaagttaga gctctatcaa aaatatgaat caatagtaaa    180

actaatgtgt tggataaagc gaattacaag cctgtttaga ttgacttatg ttatgtgctt    240

ttaaataaaa aaagaagttt ataagcagtt ttgtcaactt attacttata gaataatgtt    300

aacaatttat ttaataattg cctcagctaa aagattttag gcctttaatt taaattttgt    360

tttaggcctc caaatacgtt gagccgcccc tgcttaaccg tcgagacata tgaagtgtaa    420

caacttttca acaaactttt ctcagtttgc tttatataaa gaaaaaaaat tcacaaaact    480

tcaaattcaa ttttccaata                                                500


<210> SEQ ID NO 21
<211> LENGTH: 168
<212> TYPE: DNA
<213> ORGANISM: Artificial Sequence
<220> FEATURE:
<223> OTHER INFORMATION: PSC ref seq

<400> SEQUENCE: 21

attgttttct tcttccttgt acttacattt gttgcacttg cgttgagggt ctttcgataa     60

taacatccct agcctccaca aagtactagt aagggctgcg tacactctac cctccttgtt    120

ttcttcttcc ttgtacttac atttgttgca cttgagttga gggtcttt                 168


<210> SEQ ID NO 22
<211> LENGTH: 54
<212> TYPE: DNA
<213> ORGANISM: Artificial Sequence
<220> FEATURE:
<223> OTHER INFORMATION: PSC alteration

<400> SEQUENCE: 22

attgttttct tcttccttgt acttacattt gttgcacttg agttgagggt cttt           54


<210> SEQ ID NO 23
<211> LENGTH: 193
<212> TYPE: DNA
<213> ORGANISM: Artificial Sequence
<220> FEATURE:
<223> OTHER INFORMATION: PSC ref sequence
```

<400> SEQUENCE: 23
cgaccccact tgtggaattt caccagatat gttgttgtta ttgttataag gacaagcttc 60
ggtcttaaag ctcgataaac tcattttttt cttttgcact ccctcttttc ttaagtacac 120
ttcactctca attctttctt gagcacacac tctttatttg agtaaacata caactcaaat 180
gatcacctct att 193

<210> SEQ ID NO 24
<211> LENGTH: 194
<212> TYPE: DNA
<213> ORGANISM: Artificial Sequence
<220> FEATURE:
<223> OTHER INFORMATION: PSC ref sequence

<400> SEQUENCE: 24
tctttggacc accatgttga tgcttcatca aataccagat ttcttgacac atatatccta 60
ttagtgatag gaaggagaaa tacgaaggga tataggatag acttttcgat tgagccttct 120
tgttgaatct ataacaactc tacaataatg taacttgata aagtaggtat tagggctccc 180
tcgctctaac agct 194

<210> SEQ ID NO 25
<211> LENGTH: 71
<212> TYPE: DNA
<213> ORGANISM: Artificial Sequence
<220> FEATURE:
<223> OTHER INFORMATION: PSC ref sequence

<400> SEQUENCE: 25
aaaaaataaa aaagtacaaa aaatgaaaca tcaagaaaga tatagccagt gaacaatgaa 60
ttgattgaaa a 71

<210> SEQ ID NO 26
<211> LENGTH: 13
<212> TYPE: DNA
<213> ORGANISM: Artificial Sequence
<220> FEATURE:
<223> OTHER INFORMATION: PSC alteration

<400> SEQUENCE: 26
tatatatctt tta 13

<210> SEQ ID NO 27
<211> LENGTH: 45
<212> TYPE: DNA
<213> ORGANISM: Artificial Sequence
<220> FEATURE:
<223> OTHER INFORMATION: PSC alteration

<400> SEQUENCE: 27
cgtagtacat acataaaaaa aaagaataac tttttatatg tagta 45

<210> SEQ ID NO 28
<211> LENGTH: 13
<212> TYPE: DNA
<213> ORGANISM: Artificial Sequence
<220> FEATURE:
<223> OTHER INFORMATION: PSC alteration

<400> SEQUENCE: 28
ctcaattcct aag 13

<210> SEQ ID NO 29
<211> LENGTH: 534
<212> TYPE: DNA
<213> ORGANISM: Artificial Sequence
<220> FEATURE:
<223> OTHER INFORMATION: PSC alteration

<400> SEQUENCE: 29
gcaggggcgg ctcaacgtat ttggaggcct aaaacaaaat ttaaattaaa ggcctaaaat 60
cttttagctg aggcaattat taaataaatt gttaacatta ttctataagt aataagttga 120
caaaactgct tataaacttc tttttttatt taaaagcaca taacataagt caatctaaac 180
aggcttgtaa ttcgctttat ccaacacatt agttttacta ttgattcata tttttgatag 240
agctctaact tacatagagt ataaaagggg tatagaaaat tacaacgcga gagtaagtga 300
agagagtgta agaagacaaa acaacgtttt tcttgatttc ttctatttga ttgaggttaa 360
ggagaataaa ataatatata tatgaaaagt acatttatct taaataatta atttttteta 420 taaaaaaaat taacacataa tttattgttg gtaaaaattt gaggcccccc taaaattggg 480
ggcctaaggc atatgcctaa tttttataag cattgagccg gcactgcggt taaa 534

<210> SEQ ID NO 30
<211> LENGTH: 18
<212> TYPE: DNA
<213> ORGANISM: Artificial Sequence
<220> FEATURE:
<223> OTHER INFORMATION: PSC alteration'

<400> SEQUENCE: 30
ttttattttt aaaaaaat 18

<210> SEQ ID NO 31
<211> LENGTH: 19
<212> TYPE: DNA
<213> ORGANISM: Artificial Sequence
<220> FEATURE:
<223> OTHER INFORMATION: PSC ref sequence

<400> SEQUENCE: 31
gattcatcat tgggtattc 19

<210> SEQ ID NO 32
<211> LENGTH: 12
<212> TYPE: DNA
<213> ORGANISM: Artificial Sequence
<220> FEATURE:
<223> OTHER INFORMATION: PSC ref sequence

<400> SEQUENCE: 32
catctttgat ga 12

<210> SEQ ID NO 33
<211> LENGTH: 49
<212> TYPE: DNA
<213> ORGANISM: Artificial Sequence
<220> FEATURE:
<223> OTHER INFORMATION: PSC alteration

<400> SEQUENCE: 33
cacagaaaaa tgaacttgaa attcataaaa aataataata ataacagaa 49

<210> SEQ ID NO 34
<211> LENGTH: 151

-continued

```
<212> TYPE: DNA
<213> ORGANISM: Artificial Sequence
<220> FEATURE:
<223> OTHER INFORMATION: SOT09-46180085
<220> FEATURE:
<221> NAME/KEY: misc_feature
<222> LOCATION: (76)..(76)
<223> OTHER INFORMATION: n is a or g

<400> SEQUENCE: 34

gcctgcagga attgaagcta agtatattat gcggactcca cgagactggg acaggttcat       60

gagatttatg gagcgntatg ctaattcaaa tggcttgcaa tttgttaaaa gttgagatta      120

tattgtatgt tttcttttgc ctcgccaatt t                                     151

<210> SEQ ID NO 35
<211> LENGTH: 151
<212> TYPE: DNA
<213> ORGANISM: Artificial Sequence
<220> FEATURE:
<223> OTHER INFORMATION: SOT09-49453657
<220> FEATURE:
<221> NAME/KEY: misc_feature
<222> LOCATION: (76)..(76)
<223> OTHER INFORMATION: n is a or g

<400> SEQUENCE: 35

gctaagacga cgccagctaa ggttgcaaag acagctacca gaacgactcc aagtcggaaa       60

gctgcaccaa aggcancacc tgccaaaaag gagccggcta agaaggcacc tgcgaagaac      120

gtgaagtcgc cggtgaagaa ggctacccca a                                     151

<210> SEQ ID NO 36
<211> LENGTH: 151
<212> TYPE: DNA
<213> ORGANISM: Artificial Sequence
<220> FEATURE:
<223> OTHER INFORMATION: SOT09-50367159
<220> FEATURE:
<221> NAME/KEY: misc_feature
<222> LOCATION: (76)..(76)
<223> OTHER INFORMATION: n is a or c

<400> SEQUENCE: 36

tttcttatct cctgttttac aaccataacc acaagaacca caataatgat tctctgaaga       60

atttcttggt attttntcaa ccttcaaacc aagattttca cacccttttc gtattacttg      120

attctgaagt ccttcctcag agcaattctc t                                     151

<210> SEQ ID NO 37
<211> LENGTH: 151
<212> TYPE: DNA
<213> ORGANISM: Artificial Sequence
<220> FEATURE:
<223> OTHER INFORMATION: SOT09-50367228
<220> FEATURE:
<221> NAME/KEY: misc_feature
<222> LOCATION: (76)..(76)
<223> OTHER INFORMATION: n is a or g

<400> SEQUENCE: 37

tgcagtacat ccagtcaaga taacggcgcc tgcattaaca gcatcgacaa gccaagtgga       60

atcagtccct ttcttntctc ctgttttaca accataacca caagaaccac aataatgatt      120

ctctgaagaa tttcttggta ttttatcaac c                                     151

<210> SEQ ID NO 38
```

<211> LENGTH: 151
<212> TYPE: DNA
<213> ORGANISM: Artificial Sequence
<220> FEATURE:
<223> OTHER INFORMATION: SOT09-52799014
<220> FEATURE:
<221> NAME/KEY: misc_feature
<222> LOCATION: (76)..(76)
<223> OTHER INFORMATION: n is a or g

<400> SEQUENCE: 38
aagtactgtc tccggcttac cggaagcaaa acccttgcgc acaaaaggcc caacatcttc 60
accgttgcag atggcngcgg ataagaggac ttggtcaaat ttgtcggcgg agtctccgtt 120
ttctaccgcc ggaacaactt tccggcgcat c 151

<210> SEQ ID NO 39
<211> LENGTH: 151
<212> TYPE: DNA
<213> ORGANISM: Artificial Sequence
<220> FEATURE:
<223> OTHER INFORMATION: SOT09-54060817
<220> FEATURE:
<221> NAME/KEY: misc_feature
<222> LOCATION: (76)..(76)
<223> OTHER INFORMATION: n is t or c

<400> SEQUENCE: 39
accttttcaa aatttgctca accaaacact ctgaaacaac aaatctgctt ttattcaatg 60
catccacaac agcatngggt gatttgaaat taaacctcag tactttgctg atcttatcaa 120
catcgttttc cgtcaaatca cttgccaaac t 151

<210> SEQ ID NO 40
<211> LENGTH: 151
<212> TYPE: DNA
<213> ORGANISM: Artificial Sequence
<220> FEATURE:
<223> OTHER INFORMATION: SOT09-54548387
<220> FEATURE:
<221> NAME/KEY: misc_feature
<222> LOCATION: (76)..(76)
<223> OTHER INFORMATION: n is t or c

<400> SEQUENCE: 40
agaggatcta gcaaagtctt gttctagctc ggaccttgac aagaaacaat ctgaatctcg 60
tatcctgaaa cttctngttt ctatttatcg ttggtgtact gagaaggatc caaacgaccg 120
tcccacagca gagaacctct acaacctctt a 151

<210> SEQ ID NO 41
<211> LENGTH: 151
<212> TYPE: DNA
<213> ORGANISM: Artificial Sequence
<220> FEATURE:
<223> OTHER INFORMATION: SOT10-46118085
<220> FEATURE:
<221> NAME/KEY: misc_feature
<222> LOCATION: (76)..(76)
<223> OTHER INFORMATION: n is a or g

<400> SEQUENCE: 41
cctctcatta aaactcgaat aactatagtt aaatctgcct ctatatagtg atttatagtt 60
tcaacaggaa gtagtnacaa aagttggcct aaggaaaaaa ggaggatccc aagcataaga 120
gaagttgaca gtattctttc ctggtatgat a 151

<210> SEQ ID NO 42
<211> LENGTH: 151
<212> TYPE: DNA
<213> ORGANISM: Artificial Sequence
<220> FEATURE:
<223> OTHER INFORMATION: SOT10-47116772
<220> FEATURE:
<221> NAME/KEY: misc_feature
<222> LOCATION: (76)..(76)
<223> OTHER INFORMATION: n is t or c

<400> SEQUENCE: 42
agttctccct gcaatatact atctaacaat gatgctcgaa ccaatgaagg atcagcactg 60
gaacttgttg aagaantggt tttcatagac ttggaaattg aactcccaga cccactcgac 120
ctctcaggtt ggttgtctgc cctctggtat g 151

<210> SEQ ID NO 43
<211> LENGTH: 151
<212> TYPE: DNA
<213> ORGANISM: Artificial Sequence
<220> FEATURE:
<223> OTHER INFORMATION: SOT10-50782097
<220> FEATURE:
<221> NAME/KEY: misc_feature
<222> LOCATION: (76)..(76)
<223> OTHER INFORMATION: n is g or c

<400> SEQUENCE: 43
aataatatta ttattattat gatctcttcc tatctgatga ttttgtggtt caaatccatc 60
accaaacatg aatccntcgt tatttgcatc gataccaaaa cgtcgtgctg catttctggg 120
gaaagactcc gatgataaac ccccaattcc a 151

<210> SEQ ID NO 44
<211> LENGTH: 151
<212> TYPE: DNA
<213> ORGANISM: Artificial Sequence
<220> FEATURE:
<223> OTHER INFORMATION: SOT10-52167709
<220> FEATURE:
<221> NAME/KEY: misc_feature
<222> LOCATION: (76)..(76)
<223> OTHER INFORMATION: n is t or c

<400> SEQUENCE: 44
aagggaggtc agagttcagc tgataccggg caaatgcctt ggtaatttct cctccagcaa 60
tactggcact tcgaanggac atttgatcat ttttgagttc cttctctgac atgctttggg 120
tttcccaagg tttagcaccc atccatcgat c 151

<210> SEQ ID NO 45
<211> LENGTH: 151
<212> TYPE: DNA
<213> ORGANISM: Artificial Sequence
<220> FEATURE:
<223> OTHER INFORMATION: SOT10-54199691
<220> FEATURE:
<221> NAME/KEY: misc_feature
<222> LOCATION: (76)..(76)
<223> OTHER INFORMATION: n is t or c

<400> SEQUENCE: 45
actgagatct tcctgtggat tttctcatga tgcaaaagat tataggaaag aagttacaag 60
tgcttcaaac aaaacnggtc ctcctttgaa ttgtagcaac atcaaccata aatcaaatgt 120
tattggttct agtcctggcc aacaccgaca t 151

<210> SEQ ID NO 46
<211> LENGTH: 151
<212> TYPE: DNA
<213> ORGANISM: Artificial Sequence
<220> FEATURE:
<223> OTHER INFORMATION: SOT10-55698400
<220> FEATURE:
<221> NAME/KEY: misc_feature
<222> LOCATION: (76)..(76)
<223> OTHER INFORMATION: n is t or c

<400> SEQUENCE: 46
tgaatctggt tttcttcgat cagaaagact attacaagat gaaagcattt caggaggtct 60
ccacaagctg tctcanaacc cccatgaacg gtatgttaag tcagcaaacc atagtccccg 120
ctcttctcca cgattttcca ttaagccatt c 151

<210> SEQ ID NO 47
<211> LENGTH: 151
<212> TYPE: DNA
<213> ORGANISM: Artificial Sequence
<220> FEATURE:
<223> OTHER INFORMATION: SOT10-56448463
<220> FEATURE:
<221> NAME/KEY: misc_feature
<222> LOCATION: (76)..(76)
<223> OTHER INFORMATION: n is a or c

<400> SEQUENCE: 47
ggctttgcgt gttcgtgaca aggactcaca aactctaatg cccggaacag ctaaatctgg 60
tgcagagtac ttcgcnacta ggtcatatca cggccttgac attcatcctg aaaataattt 120
ctccgagccg tttttgattg gtaaaagtgg g 151

<210> SEQ ID NO 48
<211> LENGTH: 151
<212> TYPE: DNA
<213> ORGANISM: Artificial Sequence
<220> FEATURE:
<223> OTHER INFORMATION: SOT10-58620886
<220> FEATURE:
<221> NAME/KEY: misc_feature
<222> LOCATION: (76)..(76)
<223> OTHER INFORMATION: n is t or c

<400> SEQUENCE: 48
atactcccat gattggactg aatgtccatt tgtccatcca ggtgaaaatg ctcgaagaag 60
agatccaaga aagtancact acagctgtgt accttgccct gagttccgca agggagcttg 120
cagacgaggg gacatgtgtg aatatgctca t 151

<210> SEQ ID NO 49
<211> LENGTH: 152
<212> TYPE: DNA
<213> ORGANISM: Artificial Sequence
<220> FEATURE:
<223> OTHER INFORMATION: SOT11-00597066
<220> FEATURE:
<221> NAME/KEY: misc_feature
<222> LOCATION: (76)..(76)
<223> OTHER INFORMATION: n is a or g

<400> SEQUENCE: 49
ctaatacatc gacgacttat tgtaggttca aaatgcaaag cttgagatca tctattctga 60
agtatgtgcg ggttagaggt cccattgcaa gtatcattat ctcaagctga aggccggagt 120
gcgttaaata tactcaattt gcaaatacgc ac 152

<210> SEQ ID NO 50
<211> LENGTH: 151
<212> TYPE: DNA
<213> ORGANISM: Artificial Sequence
<220> FEATURE:
<223> OTHER INFORMATION: SOT11-00761409
<220> FEATURE:
<221> NAME/KEY: misc_feature
<222> LOCATION: (76)..(76)
<223> OTHER INFORMATION: n is a or g

<400> SEQUENCE: 50
atgtggcaac tgggaacact caaatttgga caaaaatgct ccaccaaact ttgtcaaatc 60
agtgaatggc atctcngcgt gaacagcaat agtgttgcca ggaatgctcc tttcatctgg 120
accagactga gccaaaaata actgtaaggc a 151

<210> SEQ ID NO 51
<211> LENGTH: 151
<212> TYPE: DNA
<213> ORGANISM: Artificial Sequence
<220> FEATURE:
<223> OTHER INFORMATION: SOT11-01776687
<220> FEATURE:
<221> NAME/KEY: misc_feature
<222> LOCATION: (76)..(76)
<223> OTHER INFORMATION: n is g or t

<400> SEQUENCE: 51
gaaaagcttt tcaactacat cgttccagtt agttcttgca tcggtggaat ggcttgtact 60
tgtggatgca tcttcnataa gagaagccgt ctctgttact cctcgcgctg attcttcctc 120
tttatgtact gatagttcct catctgtgtc t 151

<210> SEQ ID NO 52
<211> LENGTH: 151
<212> TYPE: DNA
<213> ORGANISM: Artificial Sequence
<220> FEATURE:
<223> OTHER INFORMATION: SOT11-01859231
<220> FEATURE:
<221> NAME/KEY: misc_feature
<222> LOCATION: (76)..(76)
<223> OTHER INFORMATION: n is a or g

<400> SEQUENCE: 52
tcgggtgaaa agtggagttg gaattaccta tgagtttact gaagacgaac tggataatat 60
ggcgttatca gagcgnatgc agctatactc taagagaagg gctccttcat tcaagatagg 120
tagagttgta gagtgctcaa gcaaaatagc t 151

<210> SEQ ID NO 53
<211> LENGTH: 151
<212> TYPE: DNA
<213> ORGANISM: Artificial Sequence
<220> FEATURE:
<223> OTHER INFORMATION: SOT11-02259927
<220> FEATURE:
<221> NAME/KEY: misc_feature
<222> LOCATION: (76)..(76)
<223> OTHER INFORMATION: n is t or c

<400> SEQUENCE: 53
tgtcgacgag tacgagaccg gtgttaacgt cgccggagag aagcagcgat tcatcttcct 60
ccaccggaat ctcacncttc agtaagtcaa tcgccgcctc ttgcgccacc gttcccatca 120
ctgatttttt tatttgtctt ctccttcttt c 151

<210> SEQ ID NO 54
<211> LENGTH: 151
<212> TYPE: DNA
<213> ORGANISM: Artificial Sequence
<220> FEATURE:
<223> OTHER INFORMATION: SOT11-03155246
<220> FEATURE:
<221> NAME/KEY: misc_feature
<222> LOCATION: (76)..(76)
<223> OTHER INFORMATION: n is c or t

<400> SEQUENCE: 54
ttaatcttct ttcccatgtt ttacttgtcc gccttttaag aatctcatga accagtaagc 60
agaagatttc agatgncggg ttagcccatt cttgaagtcc acatatgtca gaccgaagcg 120
ttttgtataa ccaagattcc attcaaagtt a 151

<210> SEQ ID NO 55
<211> LENGTH: 121
<212> TYPE: DNA
<213> ORGANISM: Artificial Sequence
<220> FEATURE:
<223> OTHER INFORMATION: SOT01-02505120
<220> FEATURE:
<221> NAME/KEY: misc_feature
<222> LOCATION: (61)..(61)
<223> OTHER INFORMATION: n is t or c

<400> SEQUENCE: 55
agcataatga agtttcgcca aatgcataca cgccattgaa tacgcatctc tccatatagg 60
nacaaccgaa tgccatggac ctgaatgtaa ctgttcccac gccatctcct tcgccgcctc 120
c 121

<210> SEQ ID NO 56
<211> LENGTH: 121
<212> TYPE: DNA
<213> ORGANISM: Artificial Sequence
<220> FEATURE:
<223> OTHER INFORMATION: SOT01-10559698
<220> FEATURE:
<221> NAME/KEY: misc_feature
<222> LOCATION: (61)..(61)
<223> OTHER INFORMATION: n is a or g

<400> SEQUENCE: 56
ggggtggtcc tttctttttc actgttctca taatttcaag cagcataact ttcaatgtgt 60
ntaagtttga gactgaggca tggaattctt caattagctt gaaggacttc aagattatat 120
t 121

<210> SEQ ID NO 57
<211> LENGTH: 121
<212> TYPE: DNA
<213> ORGANISM: Artificial Sequence
<220> FEATURE:
<223> OTHER INFORMATION: SOT01-23932807
<220> FEATURE:
<221> NAME/KEY: misc_feature
<222> LOCATION: (61)..(61)
<223> OTHER INFORMATION: n is a or g

<400> SEQUENCE: 57
tgtcacaaag gcgtgtatca cattgctgaa ccctcgagcc cacgaaggga catttgagtc 60
nacgggcatc ctcatcctca aactggttgt cttgttcttg ctccttgcag ttcttatgaa 120
c 121

<210> SEQ ID NO 58
<211> LENGTH: 121
<212> TYPE: DNA
<213> ORGANISM: Artificial Sequence
<220> FEATURE:
<223> OTHER INFORMATION: SOT01-46271058
<220> FEATURE:
<221> NAME/KEY: misc_feature
<222> LOCATION: (61)..(61)
<223> OTHER INFORMATION: n is a or g

<400> SEQUENCE: 58
tccctgaatt ctctcactaa gtcaatgatg accgatcttg ctcgaatttt caagtctctg 60
nacgcagatg attcggttcg ggtcattata ctcaccggat cgggtcgatc gttctgctcc 120
g 121

<210> SEQ ID NO 59
<211> LENGTH: 121
<212> TYPE: DNA
<213> ORGANISM: Artificial Sequence
<220> FEATURE:
<223> OTHER INFORMATION: SOT01-61269756
<220> FEATURE:
<221> NAME/KEY: misc_feature
<222> LOCATION: (61)..(61)
<223> OTHER INFORMATION: n is a or c

<400> SEQUENCE: 59
gcttgcagac aaagttgcag cagctggctt ctatgtagta gtccctgatt tccttcgtgg 60
ngatccccgt atacctaatg atgagaagcc tttagaagta tggataatag atcatggacc 120
g 121

<210> SEQ ID NO 60
<211> LENGTH: 121
<212> TYPE: DNA
<213> ORGANISM: Artificial Sequence
<220> FEATURE:
<223> OTHER INFORMATION: SOT01-80162442
<220> FEATURE:
<221> NAME/KEY: misc_feature
<222> LOCATION: (61)..(61)
<223> OTHER INFORMATION: n is t or c

<400> SEQUENCE: 60
acctggcagt tctgatggac cttcagaatc atcatctggg aagggacctg atggagatga 60
ngtaattgat gctgatttca ccgacagcaa gtgaacatag aggagcaatt ttgaggctat 120
a 121

<210> SEQ ID NO 61
<211> LENGTH: 121
<212> TYPE: DNA
<213> ORGANISM: Artificial Sequence
<220> FEATURE:
<223> OTHER INFORMATION: SOT01-84986138
<220> FEATURE:
<221> NAME/KEY: misc_feature
<222> LOCATION: (61)..(61)
<223> OTHER INFORMATION: n is a or g

<400> SEQUENCE: 61
atttctccgt gccataagta aagaaaaatt ccagtaattg tcaagaaacc caattcttta 60
natcaagaat cacatacatg cttaaatatt tcaagaaacg cataaatcca cgctaagaat 120
t 121

<210> SEQ ID NO 62
<211> LENGTH: 121
<212> TYPE: DNA
<213> ORGANISM: Artificial Sequence
<220> FEATURE:
<223> OTHER INFORMATION: SOT02-05170759
<220> FEATURE:
<221> NAME/KEY: misc_feature
<222> LOCATION: (61)..(61)
<223> OTHER INFORMATION: n is t or c

<400> SEQUENCE: 62
cctatatctt aaattactta gattgggtac atgaatcatc taaaatctaa atctaatgct 60
naataatttg tattttaatg taaattaaaa gtttcctgaa gtctgggggc tcctttaaaa 120
g 121

<210> SEQ ID NO 63
<211> LENGTH: 121
<212> TYPE: DNA
<213> ORGANISM: Artificial Sequence
<220> FEATURE:
<223> OTHER INFORMATION: SOT02-17760016
<220> FEATURE:
<221> NAME/KEY: misc_feature
<222> LOCATION: (61)..(61)
<223> OTHER INFORMATION: n is a or g

<400> SEQUENCE: 63
gatgaggcat catctacaca gtgtctgaag ttgtttggta aaaccgtatt agtcactgat 60
ncttatatgc cttcttcaac ttctggccaa atatcactga cagatgagaa tgatgagcca 120
g 121

<210> SEQ ID NO 64
<211> LENGTH: 121
<212> TYPE: DNA
<213> ORGANISM: Artificial Sequence
<220> FEATURE:
<223> OTHER INFORMATION: SOT02-24387762
<220> FEATURE:
<221> NAME/KEY: misc_feature
<222> LOCATION: (61)..(61)
<223> OTHER INFORMATION: n is a or g

<400> SEQUENCE: 64
ttggatgaca cgaagcaagg aaaactaaat agtagcaaac aagagaagtt tacctgaaga 60
ngtggaataa cactgcaggg aaactgaaga aaatatatgg gactagaagt ccagtcagca 120
t 121

<210> SEQ ID NO 65
<211> LENGTH: 121
<212> TYPE: DNA
<213> ORGANISM: Artificial Sequence
<220> FEATURE:
<223> OTHER INFORMATION: SOT02-31350493
<220> FEATURE:
<221> NAME/KEY: misc_feature
<222> LOCATION: (61)..(61)
<223> OTHER INFORMATION: n is t or c

<400> SEQUENCE: 65
ggagcttaca acttctgagg ttgacagcct caaggctcgt cctcgcattg acttctcctc 60

-continued nattttcggc actgtgagtt aacaatgctt cttgaactaa tttcttattt ttttttccct 120
t 121

<210> SEQ ID NO 66
<211> LENGTH: 121
<212> TYPE: DNA
<213> ORGANISM: Artificial Sequence
<220> FEATURE:
<223> OTHER INFORMATION: SOT02-41359775
<220> FEATURE:
<221> NAME/KEY: misc_feature
<222> LOCATION: (61)..(61)
<223> OTHER INFORMATION: n is a or g

<400> SEQUENCE: 66
tggctttggc cttgaccgaa tttgaggcct tgtgtggctt cataagtctt gaggtacttc 60
ntaagttgtg ctagatttca agaaattcca atagagttaa gcaacttgtt ttactggatc 120
a 121

<210> SEQ ID NO 67
<211> LENGTH: 121
<212> TYPE: DNA
<213> ORGANISM: Artificial Sequence
<220> FEATURE:
<223> OTHER INFORMATION: SOT02-44565469
<220> FEATURE:
<221> NAME/KEY: misc_feature
<222> LOCATION: (61)..(61)
<223> OTHER INFORMATION: n is a or g

<400> SEQUENCE: 67
aacaaatcag gaaatgaaaa tgccgtgctg gtaggcagtg cattgacttc aagtacgccc 60
ntgcttactg aattgaatga tgtcttcaaa ggcgagtcac aacttggtta tgaatttgac 120
g 121

<210> SEQ ID NO 68
<211> LENGTH: 121
<212> TYPE: DNA
<213> ORGANISM: Artificial Sequence
<220> FEATURE:
<223> OTHER INFORMATION: SOT02-45091129
<220> FEATURE:
<221> NAME/KEY: misc_feature
<222> LOCATION: (61)..(61)
<223> OTHER INFORMATION: n is t or c

<400> SEQUENCE: 68
gatttgttaa attctctgct ttgttgtata tgtaaaaaga gttcttcctt gtagaccacg 60
ntgcagtcaa tacgtacaat ttttctcagg aagaagtaaa gaaacagatc ctccagtgtg 120
a 121

<210> SEQ ID NO 69
<211> LENGTH: 121
<212> TYPE: DNA
<213> ORGANISM: Artificial Sequence
<220> FEATURE:
<223> OTHER INFORMATION: SOT02-45105742
<220> FEATURE:
<221> NAME/KEY: misc_feature
<222> LOCATION: (61)..(61)
<223> OTHER INFORMATION: n is t or c

<400> SEQUENCE: 69
taattccaaa atgtatagca ttaagtagca agaacattta aagattgaac ccatcaaact 60
naaattctaa attctcttga ttccactttc caggaaccct ttatggtcct ccagctgtcg 120
a 121

<210> SEQ ID NO 70
<211> LENGTH: 121
<212> TYPE: DNA
<213> ORGANISM: Artificial Sequence
<220> FEATURE:
<223> OTHER INFORMATION: SOT02-46731334
<220> FEATURE:
<221> NAME/KEY: misc_feature
<222> LOCATION: (61)..(61)
<223> OTHER INFORMATION: n is t or c

<400> SEQUENCE: 70
tggtataaca gcaagcaaat tgtcccatcc tccacgaaca ccaccacagt gcctctctat 60
nagctccttc aatgaaatac tcatttcctc ttcaactgtg cagggcttgt taacatggcc 120
t 121

<210> SEQ ID NO 71
<211> LENGTH: 121
<212> TYPE: DNA
<213> ORGANISM: Artificial Sequence
<220> FEATURE:
<223> OTHER INFORMATION: SOT02-46774414
<220> FEATURE:
<221> NAME/KEY: misc_feature
<222> LOCATION: (61)..(61)
<223> OTHER INFORMATION: n is a or g

<400> SEQUENCE: 71
agcgtcacgt tcagctttgt tgaaaggagt ggaggagacg aggacggagg cgtcgcagcc 60
nccgacgaag cagtcgtgga agaagaggcg gagggtggcg gcggcggtag taggtgaagt 120
g 121

<210> SEQ ID NO 72
<211> LENGTH: 121
<212> TYPE: DNA
<213> ORGANISM: Artificial Sequence
<220> FEATURE:
<223> OTHER INFORMATION: SOT03-50790774
<220> FEATURE:
<221> NAME/KEY: misc_feature
<222> LOCATION: (61)..(61)
<223> OTHER INFORMATION: n is t or c

<400> SEQUENCE: 72
cgccctctct ctcctcaact ctccgaccac cggaatcaat cttagtgcca ctactttcct 60
ngttgacgcc gacaccggcc accgcttatc ttacgccgat ttccttagcc agactcaaaa 120
t 121

<210> SEQ ID NO 73
<211> LENGTH: 121
<212> TYPE: DNA
<213> ORGANISM: Artificial Sequence
<220> FEATURE:
<223> OTHER INFORMATION: SOT03-56290202
<220> FEATURE:
<221> NAME/KEY: misc_feature
<222> LOCATION: (61)..(61)
<223> OTHER INFORMATION: n is a or g

<400> SEQUENCE: 73
ccaacgaaaa gcagttaaca tctggtatgt gccacgaaag aaggatgtct ttagtaagcc 60
ngatgacatc ctgactgctg cggagaaata cataaaagaa catggaaccc aagcatttga 120
g 121

<210> SEQ ID NO 74
<211> LENGTH: 121
<212> TYPE: DNA
<213> ORGANISM: Artificial Sequence
<220> FEATURE:
<223> OTHER INFORMATION: SOT03-61394421
<220> FEATURE:
<221> NAME/KEY: misc_feature
<222> LOCATION: (61)..(61)
<223> OTHER INFORMATION: n is t or c

<400> SEQUENCE: 74
tcaacttctg tcattcggtc ttcaggtcca tgttcactat catcaagatc gggatccagg 60
ntattatgga tattaatccc atctgcaaaa gattgatcaa tttccgagtt ccacgtgact 120
c 121

<210> SEQ ID NO 75
<211> LENGTH: 121
<212> TYPE: DNA
<213> ORGANISM: Artificial Sequence
<220> FEATURE:
<223> OTHER INFORMATION: SOT04-03548052
<220> FEATURE:
<221> NAME/KEY: misc_feature
<222> LOCATION: (61)..(61)
<223> OTHER INFORMATION: n is t or c

<400> SEQUENCE: 75
atatagtttg aggtgaaaaa acatgttaag tggataagtc atgtgtcgat acctatttga 60
ngatcacaat tttccttcac cttacatcac ctcttgcagg cttttcctta tgttacggcg 120
t 121

<210> SEQ ID NO 76
<211> LENGTH: 121
<212> TYPE: DNA
<213> ORGANISM: Artificial Sequence
<220> FEATURE:
<223> OTHER INFORMATION: SOT04-11199749
<220> FEATURE:
<221> NAME/KEY: misc_feature
<222> LOCATION: (61)..(61)
<223> OTHER INFORMATION: n is a or c

<400> SEQUENCE: 76
atagaaattt cacatttttt aacttttaag caaaccaatt caaactaaaa ctatcaaaat 60
naaaaagtaa ggcataataa attcgaatca gtactgaatt ccactagctt caagtaaatt 120
a 121

<210> SEQ ID NO 77
<211> LENGTH: 121
<212> TYPE: DNA
<213> ORGANISM: Artificial Sequence
<220> FEATURE:
<223> OTHER INFORMATION: SOT04-22839393
<220> FEATURE:
<221> NAME/KEY: misc_feature
<222> LOCATION: (61)..(61)
<223> OTHER INFORMATION: n is t or c

<400> SEQUENCE: 77
tcaaccatca tagagagaac tttcgctgca actaatccct tggtaacacc ctgcaagtca 60
ngtaaagaat tcaaaacttt tgaacagcat tatgcaacat gattgtgctg catagttaaa 120
c 121

<210> SEQ ID NO 78
<211> LENGTH: 121
<212> TYPE: DNA
<213> ORGANISM: Artificial Sequence
<220> FEATURE:
<223> OTHER INFORMATION: SOT04-52034868
<220> FEATURE:
<221> NAME/KEY: misc_feature
<222> LOCATION: (61)..(61)
<223> OTHER INFORMATION: n is a or g

<400> SEQUENCE: 78
aaactgtgta atgaacataa actagagaaa ttagtacctt ttaatttatg acaaatagcc 60
natcgaagtt ccattgtacc tgcatttggt gtatacctgg tatgaccttc acgaattgca 120
t 121

<210> SEQ ID NO 79
<211> LENGTH: 121
<212> TYPE: DNA
<213> ORGANISM: Artificial Sequence
<220> FEATURE:
<223> OTHER INFORMATION: SOT04-58838906
<220> FEATURE:
<221> NAME/KEY: misc_feature
<222> LOCATION: (61)..(61)
<223> OTHER INFORMATION: n is t or c

<400> SEQUENCE: 79
cacatctcta ggctctttat ctgaatccag ctgataaaat atatgccttt ctgaagtttt 60
ngagataatt ttttgttatt tgttgttcct gaaactgcag tcctgtgaat cactaaaaaa 120
g 121

<210> SEQ ID NO 80
<211> LENGTH: 121
<212> TYPE: DNA
<213> ORGANISM: Artificial Sequence
<220> FEATURE:
<223> OTHER INFORMATION: SOT04-64087153
<220> FEATURE:
<221> NAME/KEY: misc_feature
<222> LOCATION: (61)..(61)
<223> OTHER INFORMATION: n is t or g

<400> SEQUENCE: 80
gccagtaagc atatttatct ctgttgtgcg cggtgcattc ataatgcaaa aactgcagct 60
nccacctttc tacaacttga gtttggtaac atcaattttc ctgggaggat aagtatatgc 120
c 121

<210> SEQ ID NO 81
<211> LENGTH: 121
<212> TYPE: DNA
<213> ORGANISM: Artificial Sequence
<220> FEATURE:
<223> OTHER INFORMATION: SOT04-70251642
<220> FEATURE:
<221> NAME/KEY: misc_feature
<222> LOCATION: (61)..(61)
<223> OTHER INFORMATION: n is a or g

<400> SEQUENCE: 81
ttttgaacac atacatatat ttggttgaaa ttacacgaat tgcatatatt tttccacaag 60
nggtccagat agcgacccag caccccaccc ccaccccaca aagcctaatc agcaaacaca 120
g 121

<210> SEQ ID NO 82
<211> LENGTH: 121
<212> TYPE: DNA
<213> ORGANISM: Artificial Sequence
<220> FEATURE:
<223> OTHER INFORMATION: SOT05-01105208
<220> FEATURE:
<221> NAME/KEY: misc_feature
<222> LOCATION: (61)..(61)
<223> OTHER INFORMATION: n is t or c

<400> SEQUENCE: 82
tgatttcttc ttcatcttcg gtgtctggct cttcgggtaa aggtacctga aatcaactca 60
nctctaagaa cacatgcatg tggttaaaca aacctcaaaa agcaaaaggg aaacaaaatc 120
t 121

<210> SEQ ID NO 83
<211> LENGTH: 121
<212> TYPE: DNA
<213> ORGANISM: Artificial Sequence
<220> FEATURE:
<223> OTHER INFORMATION: SOT05-07667963
<220> FEATURE:
<221> NAME/KEY: misc_feature
<222> LOCATION: (61)..(61)
<223> OTHER INFORMATION: n is t or g

<400> SEQUENCE: 83
gttagcacag tgattgatgg caataagatc aaaattaatc cttactccat catccctgta 60
nctggtgata ctcatttcat cattcttgat tcttctgcca gtacttttta cacattatca 120
t 121

<210> SEQ ID NO 84
<211> LENGTH: 121
<212> TYPE: DNA
<213> ORGANISM: Artificial Sequence
<220> FEATURE:
<223> OTHER INFORMATION: SOT05-15768069
<220> FEATURE:
<221> NAME/KEY: misc_feature
<222> LOCATION: (61)..(61)
<223> OTHER INFORMATION: n is t or c

<400> SEQUENCE: 84
aggtacacta accaacatag aatgtgaaga aatattgaag gcaacaaacc ttctatttca 60
nagtacattt catgcaataa aatttaatat agttcggaac cagaaagctg catgtatgaa 120
t 121

<210> SEQ ID NO 85
<211> LENGTH: 121
<212> TYPE: DNA
<213> ORGANISM: Artificial Sequence
<220> FEATURE:
<223> OTHER INFORMATION: SOT05-26397339
<220> FEATURE:
<221> NAME/KEY: misc_feature
<222> LOCATION: (61)..(61)

<223> OTHER INFORMATION: n is t or c

<400> SEQUENCE: 85
tgcaggatag gccgtggacc catccaaaat aagtggatag ggtccatgga tcccaaccag 60
naaaagctgg tttggggttc ggccatagtg ggggtacgtt cgtaaattcc tcttttatta 120
a 121

<210> SEQ ID NO 86
<211> LENGTH: 121
<212> TYPE: DNA
<213> ORGANISM: Artificial Sequence
<220> FEATURE:
<223> OTHER INFORMATION: SOT05-43513048
<220> FEATURE:
<221> NAME/KEY: misc_feature
<222> LOCATION: (61)..(61)
<223> OTHER INFORMATION: n is t or g

<400> SEQUENCE: 86
ttctacctca tagccaatgc atgtgtgaca aatgcaccga ggataatggt ttcaaattgc 60
naatttgatg cgctatattt aaccagaata aggggattgt tatgtgtaaa aatgaatatg 120
a 121

<210> SEQ ID NO 87
<211> LENGTH: 121
<212> TYPE: DNA
<213> ORGANISM: Artificial Sequence
<220> FEATURE:
<223> OTHER INFORMATION: SOT05-51486277
<220> FEATURE:
<221> NAME/KEY: misc_feature
<222> LOCATION: (61)..(61)
<223> OTHER INFORMATION: n is a or g

<400> SEQUENCE: 87
actgtttgaa gatgttgaaa ttcaacttga aaaagaaaag caagctgctc ttacggaggc 60
naggctgaaa gaagtaagtt tctgttgggg tggttattga cccattgttg atatctacta 120
a 121

<210> SEQ ID NO 88
<211> LENGTH: 121
<212> TYPE: DNA
<213> ORGANISM: Artificial Sequence
<220> FEATURE:
<223> OTHER INFORMATION: SOT06-00104091
<220> FEATURE:
<221> NAME/KEY: misc_feature
<222> LOCATION: (61)..(61)
<223> OTHER INFORMATION: n is t or c

<400> SEQUENCE: 88
atcatgttgc tctagcaaca gacttatctg atttgatttt attggtttat aacctttcag 60
ntggagactc ttcctgaatt gattgctggg gtttggtctg atgacagcag tttgcaactt 120
g 121

<210> SEQ ID NO 89
<211> LENGTH: 121
<212> TYPE: DNA
<213> ORGANISM: Artificial Sequence
<220> FEATURE:
<223> OTHER INFORMATION: SOT06-03432475
<220> FEATURE:
<221> NAME/KEY: misc_feature
<222> LOCATION: (61)..(61)
<223> OTHER INFORMATION: n is a or c

<400> SEQUENCE: 89
ctcttgtccg tgccattgat cttgcagagt cctcatttgt tgacaaataa tagatgcagt 60
nctagtgtca gattttgttt cgtcaatttt tttgtttctt gatgggtgta gagaagtttg 120
t 121

<210> SEQ ID NO 90
<211> LENGTH: 121
<212> TYPE: DNA
<213> ORGANISM: Artificial Sequence
<220> FEATURE:
<223> OTHER INFORMATION: SOT06-13440008
<220> FEATURE:
<221> NAME/KEY: misc_feature
<222> LOCATION: (61)..(61)
<223> OTHER INFORMATION: n is a or g

<400> SEQUENCE: 90
cccaggcttc cctactcccg ataggacagc tagccctttc tgctgatcgt cgggctgcta 60
ntctagaggc ctctgttcca agaatgatcc ataatggcct agttgatact gtgacacctt 120
t 121

<210> SEQ ID NO 91
<211> LENGTH: 121
<212> TYPE: DNA
<213> ORGANISM: Artificial Sequence
<220> FEATURE:
<223> OTHER INFORMATION: SOT06-29622294
<220> FEATURE:
<221> NAME/KEY: misc_feature
<222> LOCATION: (61)..(61)
<223> OTHER INFORMATION: n is t or c

<400> SEQUENCE: 91
gcgtttggaa gttttcccat tgtattatca attgtttcct gcagtagctt cgtatttgac 60
ngagttctca gttcattaac aataattcag atatgctaat tctttactga taccaagcat 120
t 121

<210> SEQ ID NO 92
<211> LENGTH: 121
<212> TYPE: DNA
<213> ORGANISM: Artificial Sequence
<220> FEATURE:
<223> OTHER INFORMATION: SOT06-38707476
<220> FEATURE:
<221> NAME/KEY: misc_feature
<222> LOCATION: (61)..(61)
<223> OTHER INFORMATION: n is t or g

<400> SEQUENCE: 92
aaatgtggat attttaggca atctgagttt gtggtgatag tttaaaggca gtggggctat 60
ntggatttca ttattgccat gtcatctgac ttttctctct acaaagatta tactactcct 120
t 121

<210> SEQ ID NO 93
<211> LENGTH: 121
<212> TYPE: DNA
<213> ORGANISM: Artificial Sequence
<220> FEATURE:
<223> OTHER INFORMATION: SOT06-43297148
<220> FEATURE:

<221> NAME/KEY: misc_feature
<222> LOCATION: (61)..(61)
<223> OTHER INFORMATION: n is t or c

<400> SEQUENCE: 93
caaactacga ggatttttcc atttgattaa ttttgcaact ctggtactac tactctacag 60
nctgtgtggg aggagcagtg aagaggaatt tgtggaacaa tgcatcaaca cattggattg 120
t 121

<210> SEQ ID NO 94
<211> LENGTH: 121
<212> TYPE: DNA
<213> ORGANISM: Artificial Sequence
<220> FEATURE:
<223> OTHER INFORMATION: SOT06-48428474
<220> FEATURE:
<221> NAME/KEY: misc_feature
<222> LOCATION: (61)..(61)
<223> OTHER INFORMATION: n is t or g

<400> SEQUENCE: 94
tgcccttaca agtctttgtt atttcaggta acacagctcg atctccatcg ctactttcat 60
ncccttggtg caggagtgat tgaggaaatt cgaattcagc gagataaagg atttggcttt 120
g 121

<210> SEQ ID NO 95
<211> LENGTH: 121
<212> TYPE: DNA
<213> ORGANISM: Artificial Sequence
<220> FEATURE:
<223> OTHER INFORMATION: SOT07-04466022
<220> FEATURE:
<221> NAME/KEY: misc_feature
<222> LOCATION: (61)..(61)
<223> OTHER INFORMATION: n is t or c

<400> SEQUENCE: 95
taaataagat aagaactagt ggtttgtgac aaatatgctt tagtcaaact accttaattg 60
naaatttagt gaaagaaaaa aaataatcta catagtttgc aatacaaatt catcaactct 120
a 121

<210> SEQ ID NO 96
<211> LENGTH: 121
<212> TYPE: DNA
<213> ORGANISM: Artificial Sequence
<220> FEATURE:
<223> OTHER INFORMATION: SOT07-04468977
<220> FEATURE:
<221> NAME/KEY: misc_feature
<222> LOCATION: (61)..(61)
<223> OTHER INFORMATION: n is a or g

<400> SEQUENCE: 96
gatccaatcg agtttaaatt ccaaaatgaa gcattgaact agttgaaagc acatgcaagg 60
naactaacag aatggaaatg ggcaggggca gctcaaaagg ggaaatagcc cataccagtg 120
c 121

<210> SEQ ID NO 97
<211> LENGTH: 121
<212> TYPE: DNA
<213> ORGANISM: Artificial Sequence
<220> FEATURE:
<223> OTHER INFORMATION: SOT07-39384833

<220> FEATURE:
<221> NAME/KEY: misc_feature
<222> LOCATION: (61)..(61)
<223> OTHER INFORMATION: n is a or g

<400> SEQUENCE: 97
acgtgctgtg gcgggagagt cgtgttttct aacaagggaa catgtcatgt tcttcacttg 60
ncacaataca agagttgggg aagtgacatg ttgggtccat aatttacatt tgaattttta 120
g 121

<210> SEQ ID NO 98
<211> LENGTH: 121
<212> TYPE: DNA
<213> ORGANISM: Artificial Sequence
<220> FEATURE:
<223> OTHER INFORMATION: SOT07-49405578
<220> FEATURE:
<221> NAME/KEY: misc_feature
<222> LOCATION: (61)..(61)
<223> OTHER INFORMATION: n is t or c

<400> SEQUENCE: 98
agactcacca gatacaagag gcaagggcgg agcatcaaag cggatcactc atggttccca 60
nctggtgaag ggaaagtcta atcacgcgat ggaagattgt ttagtttgtg agtttaagca 120
a 121

<210> SEQ ID NO 99
<211> LENGTH: 121
<212> TYPE: DNA
<213> ORGANISM: Artificial Sequence
<220> FEATURE:
<223> OTHER INFORMATION: SOT07-53700808
<220> FEATURE:
<221> NAME/KEY: misc_feature
<222> LOCATION: (61)..(61)
<223> OTHER INFORMATION: n is a or g

<400> SEQUENCE: 99
cttaaattac aattacaatt attttttttt aaaaaataca gctatatata tgtccaaatc 60
nttttaagct ttcggtggtc tttatcagcc gctgaatcga cgaattacag aaagaaaaca 120
a 121

<210> SEQ ID NO 100
<211> LENGTH: 121
<212> TYPE: DNA
<213> ORGANISM: Artificial Sequence
<220> FEATURE:
<223> OTHER INFORMATION: SOT08-01078910
<220> FEATURE:
<221> NAME/KEY: misc_feature
<222> LOCATION: (61)..(61)
<223> OTHER INFORMATION: n is a or g

<400> SEQUENCE: 100
aacttgaagc ttcaatccat tagcttgaac catcttgaca agttcatcat atccttccca 60
nttatacttc aaaggtccat ctttttcaac caaaccccac caacaatcca ccattacccc 120
t 121

<210> SEQ ID NO 101
<211> LENGTH: 101
<212> TYPE: DNA
<213> ORGANISM: Artificial Sequence
<220> FEATURE:

```
<223> OTHER INFORMATION: SOT08-18393399
<220> FEATURE:
<221> NAME/KEY: misc_feature
<222> LOCATION: (51)..(51)
<223> OTHER INFORMATION: n is a or g

<400> SEQUENCE: 101

gtgcccattc tggttggggc tcttagtgct gaaagtgaag ccctttatgg ncggttactc      60

gcaaaatatg tggatgactc aaagaatttc ttctcagtgt c                         101


<210> SEQ ID NO 102
<211> LENGTH: 121
<212> TYPE: DNA
<213> ORGANISM: Artificial Sequence
<220> FEATURE:
<223> OTHER INFORMATION: SOT08-38666935
<220> FEATURE:
<221> NAME/KEY: misc_feature
<222> LOCATION: (61)..(61)
<223> OTHER INFORMATION: n is t or c

<400> SEQUENCE: 102

agggttgaga tgaccaccag aaatacggaa accagcagag atagtcacag ccaccaccaa      60

ngcatgtgcc attgccacaa aaaataaact cacaagtgga tctccattta gcttatctgt     120

t                                                                     121


<210> SEQ ID NO 103
<211> LENGTH: 121
<212> TYPE: DNA
<213> ORGANISM: Artificial Sequence
<220> FEATURE:
<223> OTHER INFORMATION: SOT08-43993811
<220> FEATURE:
<221> NAME/KEY: misc_feature
<222> LOCATION: (61)..(61)
<223> OTHER INFORMATION: n is t or c

<400> SEQUENCE: 103

ttagtagcaa actagctgtt tcaagttctc agtatcagaa atctgaacaa ttgcaatact      60

ntagctgttt tgactgcaat cattaccatt ctcttgaagc tttaccaatt tgcgccacaa     120

t                                                                     121


<210> SEQ ID NO 104
<211> LENGTH: 121
<212> TYPE: DNA
<213> ORGANISM: Artificial Sequence
<220> FEATURE:
<223> OTHER INFORMATION: SOT08-50482569
<220> FEATURE:
<221> NAME/KEY: misc_feature
<222> LOCATION: (61)..(61)
<223> OTHER INFORMATION: n is t or c

<400> SEQUENCE: 104

ctcacctggt gatacacctg atcatcctgc tgttggtggt ggctctgctg atggttatgc      60

ntcagaggat tttgttgctg gttcttcatc tagccgtgaa aggaagaaag gtttgatctt     120

t                                                                     121


<210> SEQ ID NO 105
<211> LENGTH: 121
<212> TYPE: DNA
<213> ORGANISM: Artificial Sequence
<220> FEATURE:
<223> OTHER INFORMATION: SOT08-55621111
```

<220> FEATURE:
<221> NAME/KEY: misc_feature
<222> LOCATION: (61)..(61)
<223> OTHER INFORMATION: n is t or c

<400> SEQUENCE: 105
accgctaatg tacttggaaa tactatgaac aacaacatca gcccccattt tcaccggcga 60
nagcaccatc ggagcaaaag tgttgtccac caccactgtc acaccttttt catgcgctat 120
c 121

<210> SEQ ID NO 106
<211> LENGTH: 121
<212> TYPE: DNA
<213> ORGANISM: Artificial Sequence
<220> FEATURE:
<223> OTHER INFORMATION: SOT09-02470833
<220> FEATURE:
<221> NAME/KEY: misc_feature
<222> LOCATION: (61)..(61)
<223> OTHER INFORMATION: n is t or c

<400> SEQUENCE: 106
tttgctagta tcatagaaag tctttgatgc atagaaatta ccataatcga atctcaatcc 60
nttccaacta tcaatagaac caacatctgg aacataccta tctttttttg tatcgtactt 120
a 121

<210> SEQ ID NO 107
<211> LENGTH: 121
<212> TYPE: DNA
<213> ORGANISM: Artificial Sequence
<220> FEATURE:
<223> OTHER INFORMATION: SOT09-07835623
<220> FEATURE:
<221> NAME/KEY: misc_feature
<222> LOCATION: (61)..(61)
<223> OTHER INFORMATION: n is a or g

<400> SEQUENCE: 107
acacccacca accaactcac ccttcacaaa aatttgtgga aatgtaggcc agttactata 60
nttcttcaac gtctccctca acccggagtt gtactcttca tcaaggacat cgatgctttc 120
a 121

<210> SEQ ID NO 108
<211> LENGTH: 121
<212> TYPE: DNA
<213> ORGANISM: Artificial Sequence
<220> FEATURE:
<223> OTHER INFORMATION: SOT09-20712307
<220> FEATURE:
<221> NAME/KEY: misc_feature
<222> LOCATION: (61)..(61)
<223> OTHER INFORMATION: n is c or a

<400> SEQUENCE: 108
acaattaact aaatgcaaac aagacacgcc cttgagcaac tgcccagctt aaactgaggg 60
nagagcagaa tataaaggta aagagagaaa agatcaacat aatgagttat ggaacaaaac 120
t 121

<210> SEQ ID NO 109
<211> LENGTH: 121
<212> TYPE: DNA
<213> ORGANISM: Artificial Sequence
<220> FEATURE:

<223> OTHER INFORMATION: SOT09-30793211
<220> FEATURE:
<221> NAME/KEY: misc_feature
<222> LOCATION: (61)..(61)
<223> OTHER INFORMATION: n is c or g

<400> SEQUENCE: 109
tgtaaatatg gcgaagacga aatgaagaaa agctctttgt cactatttga caaacagtaa 60
naaatacgag tattatttac gtcttagctc agtcggtaaa ttaattttaa attgatgttt 120
t 121

<210> SEQ ID NO 110
<211> LENGTH: 121
<212> TYPE: DNA
<213> ORGANISM: Artificial Sequence
<220> FEATURE:
<223> OTHER INFORMATION: SOT09-52408174
<220> FEATURE:
<221> NAME/KEY: misc_feature
<222> LOCATION: (61)..(61)
<223> OTHER INFORMATION: n is t or c

<400> SEQUENCE: 110
tttcacctgg aaagatcaca tttaatgaac aatacggtgc attttgccca tgttgcagat 60
ngaaattgta accaatttgt aggaggtttg tacacaaacc aaaatgcaga ttattggaaa 120
c 121

<210> SEQ ID NO 111
<211> LENGTH: 121
<212> TYPE: DNA
<213> ORGANISM: Artificial Sequence
<220> FEATURE:
<223> OTHER INFORMATION: SOT09-60570643
<220> FEATURE:
<221> NAME/KEY: misc_feature
<222> LOCATION: (61)..(61)
<223> OTHER INFORMATION: n is t or c

<400> SEQUENCE: 111
tttctcgctt tgctttctct ttgttctttt tctatcattt gcttatcgag ctgccaaagt 60
nctacttgca ggttggacct accagaggtg ttattcctct tgttgatgca gatatacaaa 120
c 121

<210> SEQ ID NO 112
<211> LENGTH: 121
<212> TYPE: DNA
<213> ORGANISM: Artificial Sequence
<220> FEATURE:
<223> OTHER INFORMATION: SOT10-11539446
<220> FEATURE:
<221> NAME/KEY: misc_feature
<222> LOCATION: (61)..(61)
<223> OTHER INFORMATION: n is a or c

<400> SEQUENCE: 112
aaatatcgat gggtgtgtgt cggatacttc aaaatagtgt atttttggat aatccggcac 60
ntgtgcgaga acatatttgg agggttcgag caacatagac ctcagctacc atcctacact 120
t 121

<210> SEQ ID NO 113
<211> LENGTH: 121
<212> TYPE: DNA
<213> ORGANISM: Artificial Sequence
<220> FEATURE:
<223> OTHER INFORMATION: SOT10-27379373
<220> FEATURE:
<221> NAME/KEY: misc_feature
<222> LOCATION: (61)..(61)
<223> OTHER INFORMATION: n is t or c

<400> SEQUENCE: 113
acaacaaaag gccccaactt ctccaaacat gtctccacat ctcagagtcc aaacaatctg 60
ntcattctcc atctcactat caatcatttc cacctcccct gaaactatga tataaacctc 120
a 121

<210> SEQ ID NO 114
<211> LENGTH: 121
<212> TYPE: DNA
<213> ORGANISM: Artificial Sequence
<220> FEATURE:
<223> OTHER INFORMATION: SOT10-48721966
<220> FEATURE:
<221> NAME/KEY: misc_feature
<222> LOCATION: (61)..(61)
<223> OTHER INFORMATION: n is t or c

<400> SEQUENCE: 114
aaaaaatgaa ttcccactat aaagttgttc cacctacata ccttctcctg atgagaattt 60
nctagaatgc aaagttgcaa ctatatagct atttttcaga gctgcggcta gcttagacag 120
t 121

<210> SEQ ID NO 115
<211> LENGTH: 121
<212> TYPE: DNA
<213> ORGANISM: Artificial Sequence
<220> FEATURE:
<223> OTHER INFORMATION: SOT10-49584558
<220> FEATURE:
<221> NAME/KEY: misc_feature
<222> LOCATION: (61)..(61)
<223> OTHER INFORMATION: n is t or c

<400> SEQUENCE: 115
cgttgatcgt tccgccttcg ctaaacccga atctgtttcc gatgctaccc tccgtatccg 60
naaaaactac tcctatttcc gtaccaatta cctttctctc ctcgccgttg tcctcgcttt 120
c 121

<210> SEQ ID NO 116
<211> LENGTH: 121
<212> TYPE: DNA
<213> ORGANISM: Artificial Sequence
<220> FEATURE:
<223> OTHER INFORMATION: SOT11-00283795
<220> FEATURE:
<221> NAME/KEY: misc_feature
<222> LOCATION: (61)..(61)
<223> OTHER INFORMATION: n is a or g

<400> SEQUENCE: 116
taaccagttg gagagagctt gtgagttgtt agatgttggg ctaactctca acatctatac 60
ngatattatg tctcgaactg ctactcaatg gtctttacat ttgaagagcc tctcacttgg 120
g 121

<210> SEQ ID NO 117
<211> LENGTH: 101
<212> TYPE: DNA

<213> ORGANISM: Artificial Sequence
<220> FEATURE:
<223> OTHER INFORMATION: SOT11-00939591
<220> FEATURE:
<221> NAME/KEY: misc_feature
<222> LOCATION: (51)..(51)
<223> OTHER INFORMATION: n is a or g

<400> SEQUENCE: 117
gctcgtgttt ctgatttcgg gaaaaatgac acaatattct ccgtaagaac ncatctaggc 60
catcttctag atgctggaga ctatgccctc ggttatgatt t 101

<210> SEQ ID NO 118
<211> LENGTH: 121
<212> TYPE: DNA
<213> ORGANISM: Artificial Sequence
<220> FEATURE:
<223> OTHER INFORMATION: SOT11-41840983
<220> FEATURE:
<221> NAME/KEY: misc_feature
<222> LOCATION: (61)..(61)
<223> OTHER INFORMATION: n is t or c

<400> SEQUENCE: 118
gctggtgatg gaaccacaac tgcatctgtt cttgctcggg aaatcattaa actcggtctg 60
ntgagtgtta catctggtgc aaatccagtg tctttaaaga ggggcattga caaaactgta 120
c 121

<210> SEQ ID NO 119
<211> LENGTH: 121
<212> TYPE: DNA
<213> ORGANISM: Artificial Sequence
<220> FEATURE:
<223> OTHER INFORMATION: SOT12-36957737
<220> FEATURE:
<221> NAME/KEY: misc_feature
<222> LOCATION: (61)..(61)
<223> OTHER INFORMATION: n is c or g

<400> SEQUENCE: 119
ccggtagtta tgctctttat gcgtagttca agcaagttaa gcatatttat aaatgacctt 60
nttgtctgaa agctgtgttc tttttaaaca gtgtggtgca ggagaactga tgagcttgtt 120
g 121

<210> SEQ ID NO 120
<211> LENGTH: 121
<212> TYPE: DNA
<213> ORGANISM: Artificial Sequence
<220> FEATURE:
<223> OTHER INFORMATION: SOT12-53990411
<220> FEATURE:
<221> NAME/KEY: misc_feature
<222> LOCATION: (61)..(61)
<223> OTHER INFORMATION: n is t or c

<400> SEQUENCE: 120
tgatttactt ggtattgtgt tccttctttt aaatatacat cttctctccc tgcatataca 60
ngtgagtcaa atgtttaata ttttggtaga atattttgga agttgcgatt tttccatcaa 120
t 121

<210> SEQ ID NO 121
<211> LENGTH: 121
<212> TYPE: DNA
<213> ORGANISM: Artificial Sequence
<220> FEATURE:
<223> OTHER INFORMATION: SOT12-59979506
<220> FEATURE:
<221> NAME/KEY: misc_feature
<222> LOCATION: (61)..(61)
<223> OTHER INFORMATION: n is a or c

<400> SEQUENCE: 121
cttccttatc ctcgattaag ttcaacaata aagaagaaaa gcaaacctca tctagcttga 60
ntatcagctt ccttatgaag taattgatgc catagtctaa ttttcgaagc atcatttttt 120
a 121

<210> SEQ ID NO 122
<211> LENGTH: 151
<212> TYPE: DNA
<213> ORGANISM: Artificial Sequence
<220> FEATURE:
<223> OTHER INFORMATION: SOT02-17705698
<220> FEATURE:
<221> NAME/KEY: misc_feature
<222> LOCATION: (76)..(76)
<223> OTHER INFORMATION: n is c or t

<400> SEQUENCE: 122
ccrgaacaac atatgacttt gaatgagcgg ctccacactg aatagaaata agccttcaac 60
attcaggtat aggggncaaa cctggtggac cttcaaataa gactgcccgg ggcctgttcg 120
tctcaaattt gcgtcgggtc ccacgagcaa t 151

<210> SEQ ID NO 123
<211> LENGTH: 151
<212> TYPE: DNA
<213> ORGANISM: Artificial Sequence
<220> FEATURE:
<223> OTHER INFORMATION: SOT02-17872940
<220> FEATURE:
<221> NAME/KEY: misc_feature
<222> LOCATION: (76)..(76)
<223> OTHER INFORMATION: n is a or g

<400> SEQUENCE: 123
tttattttat tattttttgt tgtatttgaa ggttgatata gcattagagt gtgcaaggtt 60
gcagcataga tttgcnttgc ctccattgga agtgcaagat tttccccaag taggatatgt 120
gatgtctcaa tcaaatgatg ttatgtatca t 151

<210> SEQ ID NO 124
<211> LENGTH: 151
<212> TYPE: DNA
<213> ORGANISM: Artificial Sequence
<220> FEATURE:
<223> OTHER INFORMATION: SOT02-19914536
<220> FEATURE:
<221> NAME/KEY: misc_feature
<222> LOCATION: (76)..(76)
<223> OTHER INFORMATION: n is t or a

<400> SEQUENCE: 124
aactcaagta ttctgacata stagtgcgct gattacctga tattctaaga tgatataaag 60
aattctgatc tgtatnggag tttgcactgg actgtatgat gttggttcaa tctkgtgttc 120
tgtctgtata ataatgttat tgtgatggtt c 151

<210> SEQ ID NO 125
<211> LENGTH: 151
<212> TYPE: DNA

<213> ORGANISM: Artificial Sequence
<220> FEATURE:
<223> OTHER INFORMATION: SOT02-21226145
<220> FEATURE:
<221> NAME/KEY: misc_feature
<222> LOCATION: (76)..(76)
<223> OTHER INFORMATION: n is t or a

<400> SEQUENCE: 125
ttctttattc aacagagcat ttctagggaa ttccttgata ttttcctctt agcttttgga 60
tgtctgtact tgaaantgaa atccttgtag gctgcagagc actctctatg acccttgtga 120
gttgtcttct aatgttaatg atgttaacag t 151

<210> SEQ ID NO 126
<211> LENGTH: 151
<212> TYPE: DNA
<213> ORGANISM: Artificial Sequence
<220> FEATURE:
<223> OTHER INFORMATION: SOT02-24944519
<220> FEATURE:
<221> NAME/KEY: misc_feature
<222> LOCATION: (76)..(76)
<223> OTHER INFORMATION: n ia a or t

<400> SEQUENCE: 126
ctatttcwgt aaggctcatc atccacagct ctgacacatg gaaagtaagg aacttaatat 60
tactcgtaaa tctttngaga gtattcggta gctgaactta tctgcatrat ctgtttaggt 120
akttgtatca caaaatatta tctttgggta t 151

<210> SEQ ID NO 127
<211> LENGTH: 151
<212> TYPE: DNA
<213> ORGANISM: Artificial Sequence
<220> FEATURE:
<223> OTHER INFORMATION: SOT02-25338387
<220> FEATURE:
<221> NAME/KEY: misc_feature
<222> LOCATION: (76)..(76)
<223> OTHER INFORMATION: n is a or t
<220> FEATURE:
<221> NAME/KEY: misc_feature
<222> LOCATION: (102)..(151)
<223> OTHER INFORMATION: n is any nucleotide

<400> SEQUENCE: 127
acatcaaaga ttargaaaca agaatgkgca aactacacat attgatgata ccatatccag 60
twcaaggcca tgttantccc ttaatgcagc tagctcaatc cnnnnnnnnn nnnnnnnnnn 120
nnnnnnnnnn nnnnnnnnnn nnnnnnnnnn n 151

<210> SEQ ID NO 128
<211> LENGTH: 151
<212> TYPE: DNA
<213> ORGANISM: Artificial Sequence
<220> FEATURE:
<223> OTHER INFORMATION: SOT02-29005162
<220> FEATURE:
<221> NAME/KEY: misc_feature
<222> LOCATION: (76)..(76)
<223> OTHER INFORMATION: n is t or a

<400> SEQUENCE: 128
gcayccaaag ctctgatatt tacatgggag ttcaagagat gcagcaacct tctccaatgc 60
aagacatcgg atattnccaa gttcatgcct acatgttgga cagcgattat gaaccctagg 120
tttgcaacca gaacatagtg tgtgaccatt g 151

<210> SEQ ID NO 129
<211> LENGTH: 151
<212> TYPE: DNA
<213> ORGANISM: Artificial Sequence
<220> FEATURE:
<223> OTHER INFORMATION: SOT02-29742666
<220> FEATURE:
<221> NAME/KEY: misc_feature
<222> LOCATION: (76)..(76)
<223> OTHER INFORMATION: n is g or t

<400> SEQUENCE: 129
aatctcatca agctcacytt agtcaagaat cgactataaa agaacccttt gcagacgcta 60
aaaaagctac gaaaantgaa catcttcaag ctggactggg gaaactatgc rttgtgttgg 120
tggcttttct caactcgatc actcaaaatc c 151

<210> SEQ ID NO 130
<211> LENGTH: 151
<212> TYPE: DNA
<213> ORGANISM: Artificial Sequence
<220> FEATURE:
<223> OTHER INFORMATION: SOT02-32149604
<220> FEATURE:
<221> NAME/KEY: misc_feature
<222> LOCATION: (76)..(76)
<223> OTHER INFORMATION: n is c or t

<400> SEQUENCE: 130
akrttcaaaa stcttccttt tttttcttct taaactcyat gcctagtcaa actaagacac 60
ttaaattggg atgganggag agtacctttt agcataatta gttttggtct ccagtgttgg 120
ggtctgaacc actaggattg catcttcaag t 151

<210> SEQ ID NO 131
<211> LENGTH: 151
<212> TYPE: DNA
<213> ORGANISM: Artificial Sequence
<220> FEATURE:
<223> OTHER INFORMATION: SOT02-32812204
<220> FEATURE:
<221> NAME/KEY: misc_feature
<222> LOCATION: (76)..(76)
<223> OTHER INFORMATION: n is g or a

<400> SEQUENCE: 131
gaaaactara atcctctgaa aatyattacc tttgaatgct ttgttacgag gcacaaagtc 60
tccttcaagc acactnacaa gatagtgaag tagtagcatc ttccttaata tctgcaatag 120
gtcttgtcag actatttgat gaagatacra a 151

<210> SEQ ID NO 132
<211> LENGTH: 151
<212> TYPE: DNA
<213> ORGANISM: Artificial Sequence
<220> FEATURE:
<223> OTHER INFORMATION: SOT02-35004833
<220> FEATURE:
<221> NAME/KEY: misc_feature
<222> LOCATION: (76)..(76)
<223> OTHER INFORMATION: n is c or t

<400> SEQUENCE: 132
tctattgata aaggtatcca gagcatcaat ctcaaacact ggaagtttac tatgtcgtct 60
caaccttcaa tagttncaat taccagaaat cattgcagga acattgacca tctgcaaaat 120
gatgaaacct gtatgcatcc cgtacaataa t 151

<210> SEQ ID NO 133
<211> LENGTH: 151
<212> TYPE: DNA
<213> ORGANISM: Artificial Sequence
<220> FEATURE:
<223> OTHER INFORMATION: SOT02-37386443
<220> FEATURE:
<221> NAME/KEY: misc_feature
<222> LOCATION: (76)..(76)
<223> OTHER INFORMATION: n is g or t

<400> SEQUENCE: 133
tctgatgagg aaacatcctg tttctgttca attgaaggcy aagaacgatg aggggtttgc 60
gttaatcgac tctacnatac gtgacgccag ggtaattcgt aacagyaagg ggtttactgg 120
tgtttttggt gatgattgga attggccgtt t 151

<210> SEQ ID NO 134
<211> LENGTH: 151
<212> TYPE: DNA
<213> ORGANISM: Artificial Sequence
<220> FEATURE:
<223> OTHER INFORMATION: SOT02-40429447
<220> FEATURE:
<221> NAME/KEY: misc_feature
<222> LOCATION: (76)..(76)
<223> OTHER INFORMATION: n is c or a

<400> SEQUENCE: 134
gaatgaagat tttgaaactt ctttgcaagt tctacgggga tttgacacag atatatcctc 60
agaagtgaat gagatnaagg taatatgtgg aatgtgttaa atgatgattt ctcarctatt 120
ttgaaccctc aaattgcact gtagaaactt c 151

<210> SEQ ID NO 135
<211> LENGTH: 151
<212> TYPE: DNA
<213> ORGANISM: Artificial Sequence
<220> FEATURE:
<223> OTHER INFORMATION: SOT02-40500157
<220> FEATURE:
<221> NAME/KEY: misc_feature
<222> LOCATION: (76)..(76)
<223> OTHER INFORMATION: n is c or a

<400> SEQUENCE: 135
catttcacct gattgaagaa gacrtttata atygattgag gaaagaataa ctgaatattg 60
gtggtaaaga agatanaata acaagacaac ctcctccact ccaataaaga cagatggagc 120
tacttctgat ctagttaagm caagttgtga c 151

<210> SEQ ID NO 136
<211> LENGTH: 151
<212> TYPE: DNA
<213> ORGANISM: Artificial Sequence
<220> FEATURE:
<223> OTHER INFORMATION: SOT02-44255433
<220> FEATURE:
<221> NAME/KEY: misc_feature
<222> LOCATION: (76)..(76)
<223> OTHER INFORMATION: n is t or c

<400> SEQUENCE: 136
gaatagktat attaaacaca catatattgc tgctagctcc atatttawaa catcatgtgc 60
tgtttaatta tgatangata aagtggtcct gggagatttt ctttctcctt ttttcwtact 120
tttttatcag tttcatcgac tttatttttc t 151

<210> SEQ ID NO 137
<211> LENGTH: 151
<212> TYPE: DNA
<213> ORGANISM: Artificial Sequence
<220> FEATURE:
<223> OTHER INFORMATION: SOT02-45679501
<220> FEATURE:
<221> NAME/KEY: misc_feature
<222> LOCATION: (76)..(76)
<223> OTHER INFORMATION: n is a or t
<220> FEATURE:
<221> NAME/KEY: misc_feature
<222> LOCATION: (102)..(151)
<223> OTHER INFORMATION: n is any nucleotide

<400> SEQUENCE: 137
taccttctct acctgagaya tattaaccay atgtatggta grtgtcatca gagagtttga 60
wtktttgaat ttttantgca actggaataa tcgggaaaac annnnnnnnn nnnnnnnnnn 120
nnnnnnnnnn nnnnnnnnnn nnnnnnnnnn n 151

<210> SEQ ID NO 138
<211> LENGTH: 151
<212> TYPE: DNA
<213> ORGANISM: Artificial Sequence
<220> FEATURE:
<223> OTHER INFORMATION: SOT02-46079014
<220> FEATURE:
<221> NAME/KEY: misc_feature
<222> LOCATION: (76)..(76)
<223> OTHER INFORMATION: n is t or c

<400> SEQUENCE: 138
takwgtttct taattagtac ttcttaacag ataattatcc ctaaattagt gtctaatcct 60
cctcacgtaa tcacanaagc gtgcgaatta aaatacttaa atgayctact tccatggtca 120
caccatcccc acctccacat amcgaattgc t 151

<210> SEQ ID NO 139
<211> LENGTH: 151
<212> TYPE: DNA
<213> ORGANISM: Artificial Sequence
<220> FEATURE:
<223> OTHER INFORMATION: SOT02-47829947
<220> FEATURE:
<221> NAME/KEY: misc_feature
<222> LOCATION: (76)..(76)
<223> OTHER INFORMATION: n is a or g

<400> SEQUENCE: 139
tcggtagaga agaactccaa catcaacccc cattgagcgg aagtactcag ttgcaggcct 60
tagcttgtcc tctacnctgt aacttatgat gtttggacat ctggttagaa ccttgctcac 120
acactcagca gatagaccca tttcataaag a 151

<210> SEQ ID NO 140
<211> LENGTH: 151
<212> TYPE: DNA
<213> ORGANISM: Artificial Sequence
<220> FEATURE:
<223> OTHER INFORMATION: SOT12-00206188
<220> FEATURE:
<221> NAME/KEY: misc_feature
<222> LOCATION: (76)..(76)
<223> OTHER INFORMATION: n is a or t

<400> SEQUENCE: 140
acctttgaat catctcacaa tgcttttaga tcagcttttc caagaggatt tgcttgggaa 60
gtgatcaatg tatatncagg gccaccagtt gttacataca aatttaggca ttggggtttc 120
tttgaaggtc catttaaagg acatgcccct a 151

<210> SEQ ID NO 141
<211> LENGTH: 151
<212> TYPE: DNA
<213> ORGANISM: Artificial Sequence
<220> FEATURE:
<223> OTHER INFORMATION: SOT12-02478572
<220> FEATURE:
<221> NAME/KEY: misc_feature
<222> LOCATION: (76)..(76)
<223> OTHER INFORMATION: n is t or c

<400> SEQUENCE: 141
tatctgcgtw tgmccttcaa ctrtcwaggg atcacttctc catactcaca attttctcaa 60
gacttctttt ccttcngctt cgtactacgt tggttcccaa ctatgrtttg taacatatgc 120
catttacaty gcyttctttt ctacttatgc g 151

<210> SEQ ID NO 142
<211> LENGTH: 151
<212> TYPE: DNA
<213> ORGANISM: Artificial Sequence
<220> FEATURE:
<223> OTHER INFORMATION: SOT12-11646765
<220> FEATURE:
<221> NAME/KEY: misc_feature
<222> LOCATION: (76)..(76)
<223> OTHER INFORMATION: n is t or c

<400> SEQUENCE: 142
agcaatccct cgctgaagca gtggcaacat taattcaatt gctggcaagt tcctatcttc 60
ctcgttcaag cacgcnactg cactatggaa tacctgctcc acagcttctt tttcctcttc 120
agtattaaaa tcaagtttgg tcatacacat t 151

<210> SEQ ID NO 143
<211> LENGTH: 151
<212> TYPE: DNA
<213> ORGANISM: Artificial Sequence
<220> FEATURE:
<223> OTHER INFORMATION: SOT12-31545560
<220> FEATURE:
<221> NAME/KEY: misc_feature
<222> LOCATION: (1)..(50)
<223> OTHER INFORMATION: n is any nucleotide
<220> FEATURE:
<221> NAME/KEY: misc_feature
<222> LOCATION: (76)..(76)
<223> OTHER INFORMATION: n is a or c

<400> SEQUENCE: 143
nnnnnnnnnn nnnnnnnnnn nnnnnnnnnn nnnnnnnnnn nnnnnnnnnn ttaatttctc 60
ctaggttgaa ccgatnaaaa aaccsttgaa gttttatttc gtgcacacct aaactctata 120
ttggtttaat taccctccyc aacctkatat t 151

<210> SEQ ID NO 144
<211> LENGTH: 151
<212> TYPE: DNA
<213> ORGANISM: Artificial Sequence
<220> FEATURE:
<223> OTHER INFORMATION: SOT12-40245065

<220> FEATURE:
<221> NAME/KEY: misc_feature
<222> LOCATION: (1)..(50)
<223> OTHER INFORMATION: n is any nucleotide
<220> FEATURE:
<221> NAME/KEY: misc_feature
<222> LOCATION: (76)..(76)
<223> OTHER INFORMATION: n is a or g

<400> SEQUENCE: 144
nnnnnnnnnn nnnnnnnnnn nnnnnnnnnn nnnnnnnnnn nnnnnnnnnn attgggcatg 60
gtctaactgg atgtcnttga yaactcttaa tatatcccac aatawgctga cragtgtgga 120
tacaaytcct cttcagattr tatatactat t 151

<210> SEQ ID NO 145
<211> LENGTH: 151
<212> TYPE: DNA
<213> ORGANISM: Artificial Sequence
<220> FEATURE:
<223> OTHER INFORMATION: SOT12-49301746
<220> FEATURE:
<221> NAME/KEY: misc_feature
<222> LOCATION: (76)..(76)
<223> OTHER INFORMATION: n is c or g

<400> SEQUENCE: 145
taagtacaag ctttgctgcr ttgggtgmaw gttycaaygc cttggtgagt tcttcgcgca 60
gtgtgttttt ctctgngagt ttcgatacta tgtaacttcg aagtcccttg cygcacatcg 120
tcttgcagag ggtttcgagc tgtgaatccg g 151

<210> SEQ ID NO 146
<211> LENGTH: 151
<212> TYPE: DNA
<213> ORGANISM: Artificial Sequence
<220> FEATURE:
<223> OTHER INFORMATION: SOT12-50632815
<220> FEATURE:
<221> NAME/KEY: misc_feature
<222> LOCATION: (76)..(76)
<223> OTHER INFORMATION: n is g or a

<400> SEQUENCE: 146
tcagctacaa rtagcataag ctatatggag ctggtcaagg aarttgccag caagggacct 60
gaatcgcaga agaatnttgc gataagagct gatgaaaaga gctacagtta yctgcagttg 120
atatcatctg cgaggaaaat wtcaaatttg t 151

<210> SEQ ID NO 147
<211> LENGTH: 151
<212> TYPE: DNA
<213> ORGANISM: Artificial Sequence
<220> FEATURE:
<223> OTHER INFORMATION: SOT12-53793483
<220> FEATURE:
<221> NAME/KEY: misc_feature
<222> LOCATION: (76)..(76)
<223> OTHER INFORMATION: n is c or t

<400> SEQUENCE: 147
atgtgaggca ggcattgtat gcrtcgaaaa tctgtagtta tgctcagggg atgaatttgc 60
taagggcaaa gagctntgag aaagggtgga atttgaattt gggagarwtg gcaaggattt 120
ggaaaggtgg ttgtattatc agggcagtgt t 151

<210> SEQ ID NO 148

<211> LENGTH: 151
<212> TYPE: DNA
<213> ORGANISM: Artificial Sequence
<220> FEATURE:
<223> OTHER INFORMATION: SOT12-56559959
<220> FEATURE:
<221> NAME/KEY: misc_feature
<222> LOCATION: (76)..(76)
<223> OTHER INFORMATION: n is a or g
<220> FEATURE:
<221> NAME/KEY: misc_feature
<222> LOCATION: (102)..(151)
<223> OTHER INFORMATION: n is any nucleotide

<400> SEQUENCE: 148
tctcaaggtt ctagttctag caccattcct crtgaratca acagraatcc agcatttgag 60
gggygcagtg acaacnatga cgatggctgt caagtgatgg annnnnnnnn nnnnnnnnnn 120
nnnnnnnnnn nnnnnnnnnn nnnnnnnnnn n 151

<210> SEQ ID NO 149
<211> LENGTH: 151
<212> TYPE: DNA
<213> ORGANISM: Artificial Sequence
<220> FEATURE:
<223> OTHER INFORMATION: SOT12-57125022
<220> FEATURE:
<221> NAME/KEY: misc_feature
<222> LOCATION: (1)..(50)
<223> OTHER INFORMATION: n is any nucleotide
<220> FEATURE:
<221> NAME/KEY: misc_feature
<222> LOCATION: (76)..(76)
<223> OTHER INFORMATION: n is a or g

<400> SEQUENCE: 149
nnnnnnnnnn nnnnnnnnnn nnnnnnnnnn nnnnnnnnnn nnnnnnnnnn ttacctgagc 60
agtggctttc aacccnaatg ccttcactgc aayagtgatg ttcggattag ctgcccactt 120
aatgactggt tccattatca gctctttctc c 151

<210> SEQ ID NO 150
<211> LENGTH: 151
<212> TYPE: DNA
<213> ORGANISM: Artificial Sequence
<220> FEATURE:
<223> OTHER INFORMATION: SOT12-57348932
<220> FEATURE:
<221> NAME/KEY: misc_feature
<222> LOCATION: (76)..(76)
<223> OTHER INFORMATION: n is c or t
<220> FEATURE:
<221> NAME/KEY: misc_feature
<222> LOCATION: (102)..(151)
<223> OTHER INFORMATION: n is any nucleotide

<400> SEQUENCE: 150
ttttgascag gtgataaatg agatgactaa yggaggtgct gactactgct tygagtgtgt 60
tggtatggga acactngtgc aggaagcata tgcctgctgt cnnnnnnnnn nnnnnnnnnn 120
nnnnnnnnnn nnnnnnnnnn nnnnnnnnnn n 151

<210> SEQ ID NO 151
<211> LENGTH: 151
<212> TYPE: DNA
<213> ORGANISM: Artificial Sequence
<220> FEATURE:
<223> OTHER INFORMATION: SOT12-57412546
<220> FEATURE:
<221> NAME/KEY: misc_feature
<222> LOCATION: (76)..(76)
<223> OTHER INFORMATION: n is g or a

<400> SEQUENCE: 151
tcttctaagy ggaaggtcwt ttataattgt aacatctgtt gttagatgtt ttataaacca 60
atcaacatca aatatntcag agaagtcact gcaagagaaa aggagatcat ttcaytttca 120
cagttacaag caggattatt agcattttaa a 151

<210> SEQ ID NO 152
<211> LENGTH: 151
<212> TYPE: DNA
<213> ORGANISM: Artificial Sequence
<220> FEATURE:
<223> OTHER INFORMATION: SOT12-57475688
<220> FEATURE:
<221> NAME/KEY: misc_feature
<222> LOCATION: (1)..(50)
<223> OTHER INFORMATION: n is any nucleotide
<220> FEATURE:
<221> NAME/KEY: misc_feature
<222> LOCATION: (76)..(76)
<223> OTHER INFORMATION: n is a or t

<400> SEQUENCE: 152
nnnnnnnnnn nnnnnnnnnn nnnnnnnnnn nnnnnnnnnn nnnnnnnnnn gatgtattgt 60
gtctctcctc cgaatnatat ccaaaagraa ayrctaastg aagaatawwg ctggaacttg 120
ttcctgaaga aagctggttg ggmtacttgg g 151

<210> SEQ ID NO 153
<211> LENGTH: 151
<212> TYPE: DNA
<213> ORGANISM: Artificial Sequence
<220> FEATURE:
<223> OTHER INFORMATION: SOT12-57602201
<220> FEATURE:
<221> NAME/KEY: misc_feature
<222> LOCATION: (1)..(50)
<223> OTHER INFORMATION: n is any nucleotide
<220> FEATURE:
<221> NAME/KEY: misc_feature
<222> LOCATION: (76)..(76)
<223> OTHER INFORMATION: n is t or g

<400> SEQUENCE: 153
nnnnnnnnnn nnnnnnnnnn nnnnnnnnnn nnnnnnnnnn nnnnnnnnnn gggcatccaa 60
tttcaaagct ttgcangcag ccattgcrgc attaacttgc tcggttgttc taatttgatc 120
ttttgtccga cccagcatgt cataaccacc t 151

<210> SEQ ID NO 154
<211> LENGTH: 151
<212> TYPE: DNA
<213> ORGANISM: Artificial Sequence
<220> FEATURE:
<223> OTHER INFORMATION: SOT12-57716039
<220> FEATURE:
<221> NAME/KEY: misc_feature
<222> LOCATION: (76)..(76)
<223> OTHER INFORMATION: n is t or a

<400> SEQUENCE: 154
ttgggttgtt tccttttcty rtcagtgtga tggtgagttc cgagagctta agtgagtctg 60
ctgcaccacc accaangaaa tatggtgtca caaagccatt atctcttgct ggrccsactg 120
aggcagatct tcaaagaaat gcwgaactag a 151

-continued

<210> SEQ ID NO 155
<211> LENGTH: 151
<212> TYPE: DNA
<213> ORGANISM: Artificial Sequence
<220> FEATURE:
<223> OTHER INFORMATION: SOT12-57817238
<220> FEATURE:
<221> NAME/KEY: misc_feature
<222> LOCATION: (76)..(76)
<223> OTHER INFORMATION: n is t or c
<220> FEATURE:
<221> NAME/KEY: misc_feature
<222> LOCATION: (102)..(151)
<223> OTHER INFORMATION: n is any nucleotide

<400> SEQUENCE: 155
aatataagcc aagckctttc ctttgtaatg aagaataagc arcagataca ctragagata 60
ataacctkcc aagagnactc ctagacgatg caccaagaac annnnnnnnn nnnnnnnnnn 120
nnnnnnnnnn nnnnnnnnnn nnnnnnnnnn n 151

<210> SEQ ID NO 156
<211> LENGTH: 151
<212> TYPE: DNA
<213> ORGANISM: Artificial Sequence
<220> FEATURE:
<223> OTHER INFORMATION: SOT12-57902259
<220> FEATURE:
<221> NAME/KEY: misc_feature
<222> LOCATION: (76)..(76)
<223> OTHER INFORMATION: n is t or c

<400> SEQUENCE: 156
gattaggtgy tcrtgyccct agtttcccaa aggktagtgg rgcatcaaga acgacgacct 60
cctctagaga cgaggnttca gtttctgtaa gtaatgctag tgatatggag tcwgaatgga 120
tagaacaaga tgaacctgga gtgtgtataa c 151

<210> SEQ ID NO 157
<211> LENGTH: 151
<212> TYPE: DNA
<213> ORGANISM: Artificial Sequence
<220> FEATURE:
<223> OTHER INFORMATION: SOT12-58127825
<220> FEATURE:
<221> NAME/KEY: misc_feature
<222> LOCATION: (76)..(76)
<223> OTHER INFORMATION: n is t or a
<220> FEATURE:
<221> NAME/KEY: misc_feature
<222> LOCATION: (102)..(151)
<223> OTHER INFORMATION: n is any nucleotide

<400> SEQUENCE: 157
ctgcatgctg acaggaakyt ggtctttaat ctctccmatc attgaaactt cagactgaaa 60
ggagttatga maaagntttc tatggaggag gtggagctgt annnnnnnnn nnnnnnnnnn 120
nnnnnnnnnn nnnnnnnnnn nnnnnnnnnn n 151

<210> SEQ ID NO 158
<211> LENGTH: 151
<212> TYPE: DNA
<213> ORGANISM: Artificial Sequence
<220> FEATURE:
<223> OTHER INFORMATION: SOT12-58205669
<220> FEATURE:
<221> NAME/KEY: misc_feature
<222> LOCATION: (76)..(76)
<223> OTHER INFORMATION: n is g or a

<400> SEQUENCE: 158
gtaagatctt cttacgatga tgggaaccat gaaaacagga aacgamgagt caggttcaac 60
ttaccagaga actctngcat ggatcctgaa gttcgggacg agcttataga tttggttcag 120
gcaaaggagg caggggttgc atatataatg g 151

<210> SEQ ID NO 159
<211> LENGTH: 151
<212> TYPE: DNA
<213> ORGANISM: Artificial Sequence
<220> FEATURE:
<223> OTHER INFORMATION: SOT12-58205669
<220> FEATURE:
<221> NAME/KEY: misc_feature
<222> LOCATION: (76)..(76)
<223> OTHER INFORMATION: n is g or a

<400> SEQUENCE: 159
gtaagatctt cttacgatga tgggaaccat gaaaacagga aacgamgagt caggttcaac 60
ttaccagaga actctngcat ggatcctgaa gttcgggacg agcttataga tttggttcag 120
gcaaaggagg caggggttgc atatataatg g 151

<210> SEQ ID NO 160
<211> LENGTH: 151
<212> TYPE: DNA
<213> ORGANISM: Artificial Sequence
<220> FEATURE:
<223> OTHER INFORMATION: SOT12-58303052
<220> FEATURE:
<221> NAME/KEY: misc_feature
<222> LOCATION: (76)..(76)
<223> OTHER INFORMATION: n is t or c
<220> FEATURE:
<221> NAME/KEY: misc_feature
<222> LOCATION: (102)..(151)
<223> OTHER INFORMATION: n is any nucleotide

<400> SEQUENCE: 160
cttgttgaaa acttagaacc caaacaaaag tggrctttaa gatctctctt atatgccaat 60
tcttcyaact mtmtgngcct agctagtggc ttccaaatag tnnnnnnnnn nnnnnnnnnn 120
nnnnnnnnnn nnnnnnnnnn nnnnnnnnnn n 151

<210> SEQ ID NO 161
<211> LENGTH: 151
<212> TYPE: DNA
<213> ORGANISM: Artificial Sequence
<220> FEATURE:
<223> OTHER INFORMATION: SOT12-58470194
<220> FEATURE:
<221> NAME/KEY: misc_feature
<222> LOCATION: (1)..(50)
<223> OTHER INFORMATION: n is any nucleotide
<220> FEATURE:
<221> NAME/KEY: misc_feature
<222> LOCATION: (76)..(76)
<223> OTHER INFORMATION: n is c or t

<400> SEQUENCE: 161
nnnnnnnnnn nnnnnnnnnn nnnnnnnnnn nnnnnnnnnn nnnnnnnnnn ctgaatctcc 60
agtatagtat gaaacncttt tggyggtggt kcttggrytc tgaataaggt gtttgaagca 120
gtatctagga aaattgcatc agaaagagga a 151

<210> SEQ ID NO 162

<211> LENGTH: 151
<212> TYPE: DNA
<213> ORGANISM: Artificial Sequence
<220> FEATURE:
<223> OTHER INFORMATION: SOT12-58517350
<220> FEATURE:
<221> NAME/KEY: misc_feature
<222> LOCATION: (76)..(76)
<223> OTHER INFORMATION: n is g or a
<220> FEATURE:
<221> NAME/KEY: misc_feature
<222> LOCATION: (102)..(151)
<223> OTHER INFORMATION: n is any nucleotide

<400> SEQUENCE: 162
cctttcaaaa aagtaagcaa aaggtgcaat agaaatggtg gccaaaattt gtctatagga 60
taagtgarca taaggntcca tgccttcatc cattacaagc tnnnnnnnnn nnnnnnnnnn 120
nnnnnnnnnn nnnnnnnnnn nnnnnnnnnn n 151

<210> SEQ ID NO 163
<211> LENGTH: 151
<212> TYPE: DNA
<213> ORGANISM: Artificial Sequence
<220> FEATURE:
<223> OTHER INFORMATION: SOT12-58583551
<220> FEATURE:
<221> NAME/KEY: misc_feature
<222> LOCATION: (76)..(76)
<223> OTHER INFORMATION: n is c or t

<400> SEQUENCE: 163
tttggctcct gtggatgctc ttaagagata tacccaactr aatagttatc ctcttcacaa 60
aaccaacaaa ccaggnatct tgtctctgga tatccattat cctaaggtat ggacyccrtc 120
tttatgactt tatctggact atttttaatg a 151

<210> SEQ ID NO 164
<211> LENGTH: 151
<212> TYPE: DNA
<213> ORGANISM: Artificial Sequence
<220> FEATURE:
<223> OTHER INFORMATION: SOT12-58587813
<220> FEATURE:
<221> NAME/KEY: misc_feature
<222> LOCATION: (76)..(76)
<223> OTHER INFORMATION: n is a or g
<220> FEATURE:
<221> NAME/KEY: misc_feature
<222> LOCATION: (102)..(151)
<223> OTHER INFORMATION: n is any nucleotide

<400> SEQUENCE: 164
ataattttgc gctgaatcag agtttatcra gttgcaagtg tyaagtccga ytggaattcc 60
atcaaaatcc tccccnactt gtcaggcaca ggttagcttt cnnnnnnnnn nnnnnnnnnn 120
nnnnnnnnnn nnnnnnnnnn nnnnnnnnnn n 151

<210> SEQ ID NO 165
<211> LENGTH: 151
<212> TYPE: DNA
<213> ORGANISM: Artificial Sequence
<220> FEATURE:
<223> OTHER INFORMATION: SOT12-58601503
<220> FEATURE:
<221> NAME/KEY: misc_feature
<222> LOCATION: (1)..(50)
<223> OTHER INFORMATION: n is any nucleotide
<220> FEATURE:
<221> NAME/KEY: misc_feature
<222> LOCATION: (76)..(76)
<223> OTHER INFORMATION: n is c or t

<400> SEQUENCE: 165
nnnnnnnnnn nnnnnnnnnn nnnnnnnnnn nnnnnnnnnn nnnnnnnnnn tgatgaaact 60
gggcttgaat tgggcntggg cytaggccca mgtgttacaa agrctaacaa aycatcaasa 120
aaatggtgtg agtatggtag aattttgact g 151

<210> SEQ ID NO 166
<211> LENGTH: 151
<212> TYPE: DNA
<213> ORGANISM: Artificial Sequence
<220> FEATURE:
<223> OTHER INFORMATION: SOT12-58601503
<220> FEATURE:
<221> NAME/KEY: misc_feature
<222> LOCATION: (1)..(50)
<223> OTHER INFORMATION: n is any nucleotide
<220> FEATURE:
<221> NAME/KEY: misc_feature
<222> LOCATION: (76)..(76)
<223> OTHER INFORMATION: n is c or t

<400> SEQUENCE: 166
nnnnnnnnnn nnnnnnnnnn nnnnnnnnnn nnnnnnnnnn nnnnnnnnnn tgatgaaact 60
gggcttgaat tgggcntggg cytaggccca mgtgttacaa agrctaacaa aycatcaasa 120
aaatggtgtg agtatggtag aattttgact g 151

<210> SEQ ID NO 167
<211> LENGTH: 151
<212> TYPE: DNA
<213> ORGANISM: Artificial Sequence
<220> FEATURE:
<223> OTHER INFORMATION: SOT12-58772425
<220> FEATURE:
<221> NAME/KEY: misc_feature
<222> LOCATION: (1)..(50)
<223> OTHER INFORMATION: n is any nucleotide
<220> FEATURE:
<221> NAME/KEY: misc_feature
<222> LOCATION: (76)..(76)
<223> OTHER INFORMATION: n is a or g

<400> SEQUENCE: 167
nnnnnnnnnn nnnnnnnnnn nnnnnnnnnn nnnnnnnnnn nnnnnnnnnn ccagaatatc 60
atgcatgtat aactcnagta tygatcmttc gggaacttga gtgtcaattg caasarcaag 120
gggtgacaat ttggttatkg ctacwamgaa a 151

<210> SEQ ID NO 168
<211> LENGTH: 151
<212> TYPE: DNA
<213> ORGANISM: Artificial Sequence
<220> FEATURE:
<223> OTHER INFORMATION: SOT12-58820928
<220> FEATURE:
<221> NAME/KEY: misc_feature
<222> LOCATION: (1)..(50)
<223> OTHER INFORMATION: n is any nucleotide
<220> FEATURE:
<221> NAME/KEY: misc_feature
<222> LOCATION: (76)..(76)
<223> OTHER INFORMATION: n is g or c

<400> SEQUENCE: 168
nnnnnnnnnn nnnnnnnnnn nnnnnnnnnn nnnnnnnnnn nnnnnnnnnn cttcgccgaa 60
catgtcgatt gcgtcnacrt catcracgtc catmgccatt gttgatccyt gttcttccat 120
gtctgctaaa tagtctacta ccattggctt c 151

<210> SEQ ID NO 169
<211> LENGTH: 151
<212> TYPE: DNA
<213> ORGANISM: Artificial Sequence
<220> FEATURE:
<223> OTHER INFORMATION: SOT12-58822517
<220> FEATURE:
<221> NAME/KEY: misc_feature
<222> LOCATION: (1)..(50)
<223> OTHER INFORMATION: n is any nucleotide
<220> FEATURE:
<221> NAME/KEY: misc_feature
<222> LOCATION: (76)..(76)
<223> OTHER INFORMATION: n is g or c

<400> SEQUENCE: 169
nnnnnnnnnn nnnnnnnnnn nnnnnnnnnn nnnnnnnnnn nnnnnnnnnn gactctatct 60
aggtggcaag cagcancmgg attttgaagg cakktacaga agctctcgtc rtcttttgga 120
aatgatgctg gyaaaggatg gtcsggkatt a 151

<210> SEQ ID NO 170
<211> LENGTH: 151
<212> TYPE: DNA
<213> ORGANISM: Artificial Sequence
<220> FEATURE:
<223> OTHER INFORMATION: SOT12-58960670
<220> FEATURE:
<221> NAME/KEY: misc_feature
<222> LOCATION: (76)..(76)
<223> OTHER INFORMATION: n is t or c
<220> FEATURE:
<221> NAME/KEY: misc_feature
<222> LOCATION: (102)..(151)
<223> OTHER INFORMATION: n is any nucleotide

<400> SEQUENCE: 170
tcgtaatgtc tggagtatat gactcaagaa ctggtctaat tctrrtttgg rtagttwtct 60
tgttggcttc cgykangatg gtttgtcctg cagaaggatt gnnnnnnnnn nnnnnnnnnn 120
nnnnnnnnnn nnnnnnnnnn nnnnnnnnnn n 151

<210> SEQ ID NO 171
<211> LENGTH: 151
<212> TYPE: DNA
<213> ORGANISM: Artificial Sequence
<220> FEATURE:
<223> OTHER INFORMATION: SOT12-58960670
<220> FEATURE:
<221> NAME/KEY: misc_feature
<222> LOCATION: (76)..(76)
<223> OTHER INFORMATION: n is t or c
<220> FEATURE:
<221> NAME/KEY: misc_feature
<222> LOCATION: (102)..(151)
<223> OTHER INFORMATION: n is any nucleotide

<400> SEQUENCE: 171
tcgtaatgtc tggagtatat gactcaagaa ctggtctaat tctrrtttgg rtagttwtct 60
tgttggcttc cgykangatg gtttgtcctg cagaaggatt gnnnnnnnnn nnnnnnnnnn 120
nnnnnnnnnn nnnnnnnnnn nnnnnnnnnn n 151

<210> SEQ ID NO 172
<211> LENGTH: 151

<212> TYPE: DNA
<213> ORGANISM: Artificial Sequence
<220> FEATURE:
<223> OTHER INFORMATION: SOT12-58962004
<220> FEATURE:
<221> NAME/KEY: misc_feature
<222> LOCATION: (76)..(76)
<223> OTHER INFORMATION: n is g or a

<400> SEQUENCE: 172
cttggttcaa ayaacttgca tggagwcatt ccatctggtg ttattaagtg tgactcattg 60
gtacaacttc gtcttnacgg taactggcta caagggagtt ttccttctga cttgtgcaaa 120
ctgagtaatc tatctgctct tgaattagga c 151

<210> SEQ ID NO 173
<211> LENGTH: 151
<212> TYPE: DNA
<213> ORGANISM: Artificial Sequence
<220> FEATURE:
<223> OTHER INFORMATION: SOT12-58964340
<220> FEATURE:
<221> NAME/KEY: misc_feature
<222> LOCATION: (76)..(76)
<223> OTHER INFORMATION: n is t or c
<220> FEATURE:
<221> NAME/KEY: misc_feature
<222> LOCATION: (102)..(151)
<223> OTHER INFORMATION: n is any nucleotide

<400> SEQUENCE: 173
cgatatccga ttggatttga cagataaaac tactgttagt cacatgctta cagtcttgaa 60
aattggtcta gtmtgnactt gtttgtcccc ggctgatcgc cnnnnnnnnn nnnnnnnnnn 120
nnnnnnnnnn nnnnnnnnnn nnnnnnnnnn n 151

<210> SEQ ID NO 174
<211> LENGTH: 151
<212> TYPE: DNA
<213> ORGANISM: Artificial Sequence
<220> FEATURE:
<223> OTHER INFORMATION: SOT12-58977155
<220> FEATURE:
<221> NAME/KEY: misc_feature
<222> LOCATION: (1)..(50)
<223> OTHER INFORMATION: n is any nucleotide
<220> FEATURE:
<221> NAME/KEY: misc_feature
<222> LOCATION: (76)..(76)
<223> OTHER INFORMATION: n is g or a

<400> SEQUENCE: 174
nnnnnnnnnn nnnnnnnnnn nnnnnnnnnn nnnnnnnnnn nnnnnnnnnn gtgacacctt 60
ctgttgttga gaaatnatar grrttgttcg gatgataagc attatctatt ttyaattctg 120
aarttatayg ttcaagtyat caaatgaatg a 151

<210> SEQ ID NO 175
<211> LENGTH: 151
<212> TYPE: DNA
<213> ORGANISM: Artificial Sequence
<220> FEATURE:
<223> OTHER INFORMATION: SOT12-58985310
<220> FEATURE:
<221> NAME/KEY: misc_feature
<222> LOCATION: (76)..(76)
<223> OTHER INFORMATION: n is a or c
<220> FEATURE:
<221> NAME/KEY: misc_feature
<222> LOCATION: (102)..(151)

<223> OTHER INFORMATION: n is any nucleotide

<400> SEQUENCE: 175
atggttgcag gtcgaatctg agtacctccc tctgtatagc aactatggma ttggtcttac 60
cacatggagt cctctngctt caggcgttct gactggaaaa tnnnnnnnnn nnnnnnnnnn 120
nnnnnnnnnn nnnnnnnnnn nnnnnnnnnn n 151

<210> SEQ ID NO 176
<211> LENGTH: 151
<212> TYPE: DNA
<213> ORGANISM: Artificial Sequence
<220> FEATURE:
<223> OTHER INFORMATION: SOT12-58990272
<220> FEATURE:
<221> NAME/KEY: misc_feature
<222> LOCATION: (76)..(76)
<223> OTHER INFORMATION: n is a or g
<220> FEATURE:
<221> NAME/KEY: misc_feature
<222> LOCATION: (102)..(151)
<223> OTHER INFORMATION: n is any nucleotide

<400> SEQUENCE: 176
gtaccaatga yagaatttgg cttctgatga ttcccatrca cttctgtatt tcacggtaga 60
ttggagmgtt ctgygngcaa cttggttgca agcttgctac annnnnnnnn nnnnnnnnnn 120
nnnnnnnnnn nnnnnnnnnn nnnnnnnnnn n 151

<210> SEQ ID NO 177
<211> LENGTH: 151
<212> TYPE: DNA
<213> ORGANISM: Artificial Sequence
<220> FEATURE:
<223> OTHER INFORMATION: SOT12-58996133
<220> FEATURE:
<221> NAME/KEY: misc_feature
<222> LOCATION: (76)..(76)
<223> OTHER INFORMATION: n is g or a
<220> FEATURE:
<221> NAME/KEY: misc_feature
<222> LOCATION: (102)..(151)
<223> OTHER INFORMATION: n is any nucleotide

<400> SEQUENCE: 177
aaaaataatg aagtgaaaca caatgagttt tgcaaccttt ttgtctagcg cccgattgaa 60
ctcaacaaga gcttgnacat cagcttcctt tgctagtatt tnnnnnnnnn nnnnnnnnnn 120
nnnnnnnnnn nnnnnnnnnn nnnnnnnnnn n 151

<210> SEQ ID NO 178
<211> LENGTH: 151
<212> TYPE: DNA
<213> ORGANISM: Artificial Sequence
<220> FEATURE:
<223> OTHER INFORMATION: SOT12-58996998
<220> FEATURE:
<221> NAME/KEY: misc_feature
<222> LOCATION: (76)..(76)
<223> OTHER INFORMATION: n is a or g
<220> FEATURE:
<221> NAME/KEY: misc_feature
<222> LOCATION: (102)..(151)
<223> OTHER INFORMATION: n is a or g

<400> SEQUENCE: 178
cattaaatga tccaatargc aatcagtcyr gaaaacaayc acctcaaaac caaaagtact 60
gaaatactaa tycatncaca caacatgttg tgaaccaagt annnnnnnnn nnnnnnnnnn 120
nnnnnnnnnn nnnnnnnnnn nnnnnnnnnn n 151

<210> SEQ ID NO 179
<211> LENGTH: 151
<212> TYPE: DNA
<213> ORGANISM: Artificial Sequence
<220> FEATURE:
<223> OTHER INFORMATION: SOT12-59003185
<220> FEATURE:
<221> NAME/KEY: misc_feature
<222> LOCATION: (76)..(76)
<223> OTHER INFORMATION: n is c or a

<400> SEQUENCE: 179
ttcgttctgt tcttggatct acgcatgatg catgctcctg atctttgatt aatttcggtg 60
acatgctctg attggntctt ttacccttat ttgttgactt atttggtaat tcttttgcct 120
ataggaggga agatcaagtc aaattagaaa c 151

<210> SEQ ID NO 180
<211> LENGTH: 151
<212> TYPE: DNA
<213> ORGANISM: Artificial Sequence
<220> FEATURE:
<223> OTHER INFORMATION: SOT12-59011119
<220> FEATURE:
<221> NAME/KEY: misc_feature
<222> LOCATION: (76)..(76)
<223> OTHER INFORMATION: n is c or t

<400> SEQUENCE: 180
atrttcatgc agattaatta ttcattgtca tttgttctaa ttaaatctta taatagtatc 60
tccacagaac aatgancaaa ttgattgttg ctgatctgtt gctgggaaaa atcaacaaac 120
catgatttat gatttttctt ttracagaga c 151

<210> SEQ ID NO 181
<211> LENGTH: 151
<212> TYPE: DNA
<213> ORGANISM: Artificial Sequence
<220> FEATURE:
<223> OTHER INFORMATION: SOT12-59016142
<220> FEATURE:
<221> NAME/KEY: misc_feature
<222> LOCATION: (76)..(76)
<223> OTHER INFORMATION: n is c or g

<400> SEQUENCE: 181
accacctatt ctaacaraaa aaatactttc gtttrargct ctgaccttct tttttcagaa 60
ttgaagtatg ctggcncgtc tacaaactgc ttccgaaaac tttagcagac agcacaggar 120
tccaagtcac tcaagggtgt tccgggtcaa a 151

<210> SEQ ID NO 182
<211> LENGTH: 151
<212> TYPE: DNA
<213> ORGANISM: Artificial Sequence
<220> FEATURE:
<223> OTHER INFORMATION: SOT12-59025327
<220> FEATURE:
<221> NAME/KEY: misc_feature
<222> LOCATION: (76)..(76)
<223> OTHER INFORMATION: n is a or c

<400> SEQUENCE: 182
taaatcaact ataccgataa ctcgagttcg accattaggt garaagggcc atatttagaa 60

-continued

```
ggatttgagt cgatcnagaa gagagggagt attggaaagg catggttcaa aggattcttc    120

ttttctttat wctggtcgaa actctattcc t                                   151


<210> SEQ ID NO 183
<211> LENGTH: 151
<212> TYPE: DNA
<213> ORGANISM: Artificial Sequence
<220> FEATURE:
<223> OTHER INFORMATION: SOT12-59030301
<220> FEATURE:
<221> NAME/KEY: misc_feature
<222> LOCATION: (1)..(50)
<223> OTHER INFORMATION: n is any nucleotide
<220> FEATURE:
<221> NAME/KEY: misc_feature
<222> LOCATION: (76)..(76)
<223> OTHER INFORMATION: n is g or a
<220> FEATURE:
<221> NAME/KEY: misc_feature
<222> LOCATION: (145)..(145)
<223> OTHER INFORMATION: n is any nucleotide
<220> FEATURE:
<221> NAME/KEY: misc_feature
<222> LOCATION: (147)..(148)
<223> OTHER INFORMATION: n is any nucleotide

<400> SEQUENCE: 183

nnnnnnnnnn nnnnnnnnnn nnnnnnnnnn nnnnnnnnnn nnnnnnnnnn tccacgaatg     60

tccaactgaa gtacanmgtk aagatatgcc actttsgaga atctgcaaaa gtattrcarg    120

aarcatttgt aaggataatt ttatnanntt t                                   151


<210> SEQ ID NO 184
<211> LENGTH: 151
<212> TYPE: DNA
<213> ORGANISM: Artificial Sequence
<220> FEATURE:
<223> OTHER INFORMATION: SOT12-59042436
<220> FEATURE:
<221> NAME/KEY: misc_feature
<222> LOCATION: (1)..(50)
<223> OTHER INFORMATION: n is any nucleotide
<220> FEATURE:
<221> NAME/KEY: misc_feature
<222> LOCATION: (76)..(76)
<223> OTHER INFORMATION: n is g or a

<400> SEQUENCE: 184

nnnnnnnnnn nnnnnnnnnn nnnnnnnnnn nnnnnnnnnn nnnnnnnnnn kyttgaagcc     60

gaagtaacgt ctcaanaatt gttccactgt ttcytcatca gtaagtttgt tctgaagatc    120

tccaaattgt gatgcaacca aaccatayaa g                                   151


<210> SEQ ID NO 185
<211> LENGTH: 151
<212> TYPE: DNA
<213> ORGANISM: Artificial Sequence
<220> FEATURE:
<223> OTHER INFORMATION: SOT12-59043512
<220> FEATURE:
<221> NAME/KEY: misc_feature
<222> LOCATION: (76)..(76)
<223> OTHER INFORMATION: n is t or c

<400> SEQUENCE: 185

agtaggatta cgccagtatg accagtgttg tttccaaagg caagctatac attgggtcca     60

aaatggctgt gagtanttag tatcgaaatg cagatctttt gtaccagggc gaggyacgcy    120

cagttcaytw atcaatgmtt tgttccttgt g                                   151
```

<210> SEQ ID NO 186
<211> LENGTH: 151
<212> TYPE: DNA
<213> ORGANISM: Artificial Sequence
<220> FEATURE:
<223> OTHER INFORMATION: SOT12-59043574
<220> FEATURE:
<221> NAME/KEY: misc_feature
<222> LOCATION: (76)..(76)
<223> OTHER INFORMATION: n is t or c
<220> FEATURE:
<221> NAME/KEY: misc_feature
<222> LOCATION: (102)..(151)
<223> OTHER INFORMATION: n is any nucleotide

<400> SEQUENCE: 186
atggctgtga gtayttagta tcgaaatgca gatcttttgt accagggcga ggyacgcyca 60
gttcaytwat caatgntttg ttccttgtgt aaaggtctga tnnnnnnnnn nnnnnnnnnn 120
nnnnnnnnnn nnnnnnnnnn nnnnnnnnnn n 151

<210> SEQ ID NO 187
<211> LENGTH: 151
<212> TYPE: DNA
<213> ORGANISM: Artificial Sequence
<220> FEATURE:
<223> OTHER INFORMATION: SOT12-59045607
<220> FEATURE:
<221> NAME/KEY: misc_feature
<222> LOCATION: (76)..(76)
<223> OTHER INFORMATION: n is t or g

<400> SEQUENCE: 187
caaattgtaa aagyagagca aatgatccaa atwtactagc aactcctaag ctcctgccaa 60
ctgccccaat gaatcnaaac aaccctgagg ccatctggct tactattatg agtagcaaga 120
actgtttgaa caacctgcaa awwcaraatm m 151

<210> SEQ ID NO 188
<211> LENGTH: 151
<212> TYPE: DNA
<213> ORGANISM: Artificial Sequence
<220> FEATURE:
<223> OTHER INFORMATION: SOT12-59045637
<220> FEATURE:
<221> NAME/KEY: misc_feature
<222> LOCATION: (76)..(76)
<223> OTHER INFORMATION: n is t or a

<400> SEQUENCE: 188
atwtactagc aactcctaag ctcctgccaa ctgccccaat gaatckaaac aaccctgagg 60
ccatctggct tactantatg agtagcaaga actgtttgaa caacctgcaa awwcaraatm 120
mcgattagta atcayrggga aaaggaaata g 151

<210> SEQ ID NO 189
<211> LENGTH: 151
<212> TYPE: DNA
<213> ORGANISM: Artificial Sequence
<220> FEATURE:
<223> OTHER INFORMATION: SOT12-59046301
<220> FEATURE:
<221> NAME/KEY: misc_feature
<222> LOCATION: (76)..(76)
<223> OTHER INFORMATION: n is a or g

<400> SEQUENCE: 189

-continued aagagctgtt tcttccctat accgtacttt tcagttgtca ragcagcagg atggcttttt 60
ctcttgtcat atgagnctgc aagatcttcc ccgagtttcc tcccaacatr aaatgcttga 120
tatgcctcgg aaaattcttt cgatgtgata a 151

<210> SEQ ID NO 190
<211> LENGTH: 151
<212> TYPE: DNA
<213> ORGANISM: Artificial Sequence
<220> FEATURE:
<223> OTHER INFORMATION: SOT12-59047597
<220> FEATURE:
<221> NAME/KEY: misc_feature
<222> LOCATION: (76)..(76)
<223> OTHER INFORMATION: n is g or a

<400> SEQUENCE: 190
kcagttcttt gcggcacaaa ytcattcatt tcatgtccat tataygtcac cttcccacta 60
gcctgatttc cggggnaaaa caaatacaca attaggcaas ttacaagata attctatgtc 120
atcwcgagtt atacwacaat cgatagtgta a 151

<210> SEQ ID NO 191
<211> LENGTH: 151
<212> TYPE: DNA
<213> ORGANISM: Artificial Sequence
<220> FEATURE:
<223> OTHER INFORMATION: SOT12-59047933
<220> FEATURE:
<221> NAME/KEY: misc_feature
<222> LOCATION: (76)..(76)
<223> OTHER INFORMATION: n is c or t

<400> SEQUENCE: 191
ttttccagcc aaagctaata agagagtagt tttgccagaa ccaggaggac ctaaaagcaa 60
agtcaatctg caaggnttga tgataccgct catgtcatca agaatagtga gtttcctctt 120
tcgatttggt acratatgga gagaattcaa c 151

<210> SEQ ID NO 192
<211> LENGTH: 152
<212> TYPE: DNA
<213> ORGANISM: Artificial Sequence
<220> FEATURE:
<223> OTHER INFORMATION: SOT12-59060445
<220> FEATURE:
<221> NAME/KEY: misc_feature
<222> LOCATION: (8)..(8)
<223> OTHER INFORMATION: n is any nucleotide
<220> FEATURE:
<221> NAME/KEY: misc_feature
<222> LOCATION: (76)..(76)
<223> OTHER INFORMATION: n is c or a

<400> SEQUENCE: 192
cctcatantc ttatwtcagt gccattccaa tccccctaga gttgtwgaac ccattccttc 60
ccatacttca ctacacaccc acttcttcat tatcaacacc ttccatgttg caatcccacc 120
agccacctcc atttgcatct gaaagcagaa aa 152

<210> SEQ ID NO 193
<211> LENGTH: 151
<212> TYPE: DNA
<213> ORGANISM: Artificial Sequence
<220> FEATURE:
<223> OTHER INFORMATION: SOT12-59062427
<220> FEATURE:
<221> NAME/KEY: misc_feature
<222> LOCATION: (76)..(76)
<223> OTHER INFORMATION: n is g or a

<400> SEQUENCE: 193
aggtgataca aatgacagaa cttaaaacta aactacagtt tagatccttt ctaatatttg 60
acattggttg aagccngtaa cctcgtcacc tgttccaatt atatactcra gtcwttaggt 120
gttccaaaag agaaatttag ctcagaccaa g 151

<210> SEQ ID NO 194
<211> LENGTH: 151
<212> TYPE: DNA
<213> ORGANISM: Artificial Sequence
<220> FEATURE:
<223> OTHER INFORMATION: SOT12-59065996
<220> FEATURE:
<221> NAME/KEY: misc_feature
<222> LOCATION: (69)..(70)
<223> OTHER INFORMATION: n is any nucleotide
<220> FEATURE:
<221> NAME/KEY: misc_feature
<222> LOCATION: (76)..(76)
<223> OTHER INFORMATION: n is t or a
<220> FEATURE:
<221> NAME/KEY: misc_feature
<222> LOCATION: (102)..(151)
<223> OTHER INFORMATION: n is any nucleotide

<400> SEQUENCE: 194
trtgaaaatt taataaatca ataytraaka cagtgattca gatatgaaaa agtagagcma 60
tctaattann rgagcngtgg tgtcagatct ctttgtaaac tnnnnnnnnn nnnnnnnnnn 120
nnnnnnnnnn nnnnnnnnnn nnnnnnnnnn n 151

<210> SEQ ID NO 195
<211> LENGTH: 151
<212> TYPE: DNA
<213> ORGANISM: Artificial Sequence
<220> FEATURE:
<223> OTHER INFORMATION: SOT12-59068564
<220> FEATURE:
<221> NAME/KEY: misc_feature
<222> LOCATION: (76)..(76)
<223> OTHER INFORMATION: n is g or c
<220> FEATURE:
<221> NAME/KEY: misc_feature
<222> LOCATION: (102)..(151)
<223> OTHER INFORMATION: n is any nucleotide

<400> SEQUENCE: 195
ccacctccwc cwcctaawcc acctccacca cctaatccac cwccaccacc aaaaygcttc 60
ccaaactttc twtgtncaaa taggagcttc tcatctccaa cnnnnnnnnn nnnnnnnnnn 120
nnnnnnnnnn nnnnnnnnnn nnnnnnnnnn n 151

<210> SEQ ID NO 196
<211> LENGTH: 151
<212> TYPE: DNA
<213> ORGANISM: Artificial Sequence
<220> FEATURE:
<223> OTHER INFORMATION: SOT12-59068564
<220> FEATURE:
<221> NAME/KEY: misc_feature
<222> LOCATION: (76)..(76)
<223> OTHER INFORMATION: n is g or c
<220> FEATURE:
<221> NAME/KEY: misc_feature
<222> LOCATION: (102)..(151)
<223> OTHER INFORMATION: n is any nucleotide

<400> SEQUENCE: 196
ccacctcctc ctcctaatcc acctccacca cctaatccac ctccaccacc aaaaygcttc 60
ccaaactttc twtgtncaaa taggagcttc tcatctccaa cnnnnnnnnn nnnnnnnnnn 120
nnnnnnnnnn nnnnnnnnnn nnnnnnnnnn n 151

<210> SEQ ID NO 197
<211> LENGTH: 151
<212> TYPE: DNA
<213> ORGANISM: Artificial Sequence
<220> FEATURE:
<223> OTHER INFORMATION: SOT12-59068879
<220> FEATURE:
<221> NAME/KEY: misc_feature
<222> LOCATION: (76)..(76)
<223> OTHER INFORMATION: n is a or t
<220> FEATURE:
<221> NAME/KEY: misc_feature
<222> LOCATION: (97)..(97)
<223> OTHER INFORMATION: n is a, c, g, or t
<220> FEATURE:
<221> NAME/KEY: misc_feature
<222> LOCATION: (146)..(147)
<223> OTHER INFORMATION: n is any nucleotide

<400> SEQUENCE: 197
ccagttaaaa ctcaactgyy atcttctttt acttaaatgc atgtttgctt tatgattggt 60
ctatatattt aattcntcca actgccctcc tccaatncas rgacacagac ttacwaagtc 120
acaaakacag cacaattatc ataatnngkg w 151

<210> SEQ ID NO 198
<211> LENGTH: 151
<212> TYPE: DNA
<213> ORGANISM: Artificial Sequence
<220> FEATURE:
<223> OTHER INFORMATION: SOT12-59107520
<220> FEATURE:
<221> NAME/KEY: misc_feature
<222> LOCATION: (76)..(76)
<223> OTHER INFORMATION: n is c or t
<220> FEATURE:
<221> NAME/KEY: misc_feature
<222> LOCATION: (102)..(151)
<223> OTHER INFORMATION: n is any nucleotide

<400> SEQUENCE: 198
atatatayat rccacttttt aaatgaagaa tatattcatt ytaaatcgca gagttaaaar 60
atttatatkt tttccntggt gtgatttctg ctttccaaat cnnnnnnnnn nnnnnnnnnn 120
nnnnnnnnnn nnnnnnnnnn nnnnnnnnnn n 151

<210> SEQ ID NO 199
<211> LENGTH: 151
<212> TYPE: DNA
<213> ORGANISM: Artificial Sequence
<220> FEATURE:
<223> OTHER INFORMATION: SOT12-59118012
<220> FEATURE:
<221> NAME/KEY: misc_feature
<222> LOCATION: (76)..(76)
<223> OTHER INFORMATION: n is c or g

<400> SEQUENCE: 199
aatatgtgca tatgtatatt ttgttgcata tatcctaggc aggagaargt aaattttact 60
agtattggga gccaantcaa aataattggg actattgcta cacttggtgg agccatgatt 120
atgatgttag ttagaggccc agaggttcaa c 151

<210> SEQ ID NO 200
<211> LENGTH: 151
<212> TYPE: DNA
<213> ORGANISM: Artificial Sequence
<220> FEATURE:
<223> OTHER INFORMATION: SOT12-59118012
<220> FEATURE:
<221> NAME/KEY: misc_feature
<222> LOCATION: (76)..(76)
<223> OTHER INFORMATION: n is c or g

<400> SEQUENCE: 200
aatatgtgca tatgtatatt ttgttgcata tatcctaggc aggagaaggt aaattttact 60
agtattggga gccaantcaa aataattggg actattgcta cacttggtgg agccatgatt 120
atgatgttag ttagaggccc agaggttcaa c 151

<210> SEQ ID NO 201
<211> LENGTH: 151
<212> TYPE: DNA
<213> ORGANISM: Artificial Sequence
<220> FEATURE:
<223> OTHER INFORMATION: SOT12-59127981
<220> FEATURE:
<221> NAME/KEY: misc_feature
<222> LOCATION: (76)..(76)
<223> OTHER INFORMATION: n is c or t
<220> FEATURE:
<221> NAME/KEY: misc_feature
<222> LOCATION: (102)..(151)
<223> OTHER INFORMATION: n is any nucleotide

<400> SEQUENCE: 201
atcatcmaca aaacgacatt ttaacartca ygaaatacat ttyagtaatt actamgyrta 60
aatttacmtc caragntgaa ttggcattaa ggataatact cnnnnnnnnn nnnnnnnnnn 120
nnnnnnnnnn nnnnnnnnnn nnnnnnnnnn n 151

<210> SEQ ID NO 202
<211> LENGTH: 151
<212> TYPE: DNA
<213> ORGANISM: Artificial Sequence
<220> FEATURE:
<223> OTHER INFORMATION: SOT12-59137670
<220> FEATURE:
<221> NAME/KEY: misc_feature
<222> LOCATION: (76)..(76)
<223> OTHER INFORMATION: n is t or c
<220> FEATURE:
<221> NAME/KEY: misc_feature
<222> LOCATION: (102)..(151)
<223> OTHER INFORMATION: n is any nucleotide

<400> SEQUENCE: 202
gtgtgcgaag gtagattcaa gctaagtttt tgctmgtaar ygtaatgata taartttgct 60
cgactgttag aytgantgat cacgaacaaa gacgaaagtt gnnnnnnnnn nnnnnnnnnn 120
nnnnnnnnnn nnnnnnnnnn nnnnnnnnnn n 151

<210> SEQ ID NO 203
<211> LENGTH: 151
<212> TYPE: DNA
<213> ORGANISM: Artificial Sequence
<220> FEATURE:
<223> OTHER INFORMATION: SOT12-59155069
<220> FEATURE:
<221> NAME/KEY: misc_feature
<222> LOCATION: (76)..(76)

<223> OTHER INFORMATION: n is g or a

<400> SEQUENCE: 203
tagttgtacg agtataatga aagatcgaaa gaggctacaa agaagcacag aaaatcaatg          60
ggataatgta cctttnttga aaccagtgga gctctttcac caggaatttt aacatcaggt          120
agataactga aatcggaagc gattawagac a                                          151

<210> SEQ ID NO 204
<211> LENGTH: 151
<212> TYPE: DNA
<213> ORGANISM: Artificial Sequence
<220> FEATURE:
<223> OTHER INFORMATION: SOT12-59173975
<220> FEATURE:
<221> NAME/KEY: misc_feature
<222> LOCATION: (1)..(50)
<223> OTHER INFORMATION: n is any nucleotide
<220> FEATURE:
<221> NAME/KEY: misc_feature
<222> LOCATION: (76)..(76)
<223> OTHER INFORMATION: n is g or a

<400> SEQUENCE: 204
nnnnnnnnnn nnnnnnnnnn nnnnnnnnnn nnnnnnnnnn nnnnnnnnnn tgaatcaggt          60
acaacgccat gtccancttc gtatygaagc acagggmaag tatttgcaaa cgatactcga          120
gaaagcatgt aaagttctta actacacgtc t                                          151

<210> SEQ ID NO 205
<211> LENGTH: 151
<212> TYPE: DNA
<213> ORGANISM: Artificial Sequence
<220> FEATURE:
<223> OTHER INFORMATION: SOT12-59188763
<220> FEATURE:
<221> NAME/KEY: misc_feature
<222> LOCATION: (76)..(76)
<223> OTHER INFORMATION: n is g or a

<400> SEQUENCE: 205
atggctgcca cttttgaata cttgaggcat cctggaaagg aagtgtagag gagacatgcc          60
ctctacgttg taacgnttga caagttgccc atagtaatgt attatctgaa aagccagatc          120
tgttacaaga taagttgtta atactactgt c                                          151

<210> SEQ ID NO 206
<211> LENGTH: 151
<212> TYPE: DNA
<213> ORGANISM: Artificial Sequence
<220> FEATURE:
<223> OTHER INFORMATION: SOT12-59214797
<220> FEATURE:
<221> NAME/KEY: misc_feature
<222> LOCATION: (76)..(76)
<223> OTHER INFORMATION: n is a or g

<400> SEQUENCE: 206
cgatgtgcag cattgmtwca atgagaaaaa cctttcttac aayacryrtt gactcattgc          60
tcccttttat ttgttncctg caaagtgtgt agatcagaat aataatrttt ttctcatttt          120
gtatgttctt caggacaagc ccagaacttc t                                          151

<210> SEQ ID NO 207
<211> LENGTH: 151
<212> TYPE: DNA
<213> ORGANISM: Artificial Sequence
<220> FEATURE:
<223> OTHER INFORMATION: SOT12-59225998
<220> FEATURE:
<221> NAME/KEY: misc_feature
<222> LOCATION: (76)..(76)
<223> OTHER INFORMATION: n is t or a
<220> FEATURE:
<221> NAME/KEY: misc_feature
<222> LOCATION: (102)..(151)
<223> OTHER INFORMATION: n is any nucleotide

<400> SEQUENCE: 207
gttcaaacgy gatwgaagat ttttgcttsy agtattacag aaactcgaca tgattatagt 60
aacaaatgat tcatgncgcg catctgtaag aagtgagagt tnnnnnnnnn nnnnnnnnnn 120
nnnnnnnnnn nnnnnnnnnn nnnnnnnnnn n 151

<210> SEQ ID NO 208
<211> LENGTH: 151
<212> TYPE: DNA
<213> ORGANISM: Artificial Sequence
<220> FEATURE:
<223> OTHER INFORMATION: SOT12-59230362
<220> FEATURE:
<221> NAME/KEY: misc_feature
<222> LOCATION: (77)..(77)
<223> OTHER INFORMATION: n is t or a

<400> SEQUENCE: 208
actgttattt tttkaagcgt atgttrttay aatctttata gttagggttt ttgttttgtt 60
tggttggtgg tccctcnact tttctcwtyt gccatttttc cacctttcca atttcgamgc 120
aatctatttt tagtgagatg tttyagrttt g 151

<210> SEQ ID NO 209
<211> LENGTH: 151
<212> TYPE: DNA
<213> ORGANISM: Artificial Sequence
<220> FEATURE:
<223> OTHER INFORMATION: SOT12-59230363
<220> FEATURE:
<221> NAME/KEY: misc_feature
<222> LOCATION: (1)..(50)
<223> OTHER INFORMATION: n is any nucleotide
<220> FEATURE:
<221> NAME/KEY: misc_feature
<222> LOCATION: (76)..(76)
<223> OTHER INFORMATION: n is t or a

<400> SEQUENCE: 209
nnnnnnnnnn nnnnnnnnnn nnnnnnnnnn nnnnnnnnnn nnnnnnnnnn tgttttgttt 60
ggttggtggt ccctcnactt ttctcwtytg ccatttttcc acctttccaa tttcgamgca 120
atctattttt agtgasatgt ttyagrtttg a 151

<210> SEQ ID NO 210
<211> LENGTH: 151
<212> TYPE: DNA
<213> ORGANISM: Artificial Sequence
<220> FEATURE:
<223> OTHER INFORMATION: SOT12-59230363
<220> FEATURE:
<221> NAME/KEY: misc_feature
<222> LOCATION: (1)..(50)
<223> OTHER INFORMATION: n is any nucleotide
<220> FEATURE:
<221> NAME/KEY: misc_feature
<222> LOCATION: (76)..(76)
<223> OTHER INFORMATION: n is t or a

<400> SEQUENCE: 210
nnnnnnnnnn nnnnnnnnnn nnnnnnnnnn nnnnnnnnnn nnnnnnnnnn tgttttgttt 60
ggttggtggt ccctcnactt ttctcwtytg ccatttttcc acctttccaa tttcgamgca 120
atctattttt agtgasatgt ttyagrtttg a 151

<210> SEQ ID NO 211
<211> LENGTH: 151
<212> TYPE: DNA
<213> ORGANISM: Artificial Sequence
<220> FEATURE:
<223> OTHER INFORMATION: SOT12-59631591
<220> FEATURE:
<221> NAME/KEY: misc_feature
<222> LOCATION: (1)..(50)
<223> OTHER INFORMATION: n is any nucleotide
<220> FEATURE:
<221> NAME/KEY: misc_feature
<222> LOCATION: (76)..(76)
<223> OTHER INFORMATION: n is t or c
<220> FEATURE:
<221> NAME/KEY: misc_feature
<222> LOCATION: (102)..(151)
<223> OTHER INFORMATION: n is any nucleotide

<400> SEQUENCE: 211
nnnnnnnnnn nnnnnnnnnn nnnnnnnnnn nnnnnnnnnn nnnnnnnnnn cacttgagtg 60
ggtgcagcgg gtaagnattg ctgttgatgc tgctagrggt ctygagtatt tgcatgagaa 120
rgtccaacct tcagtaatac acagggatat c 151

<210> SEQ ID NO 212
<211> LENGTH: 151
<212> TYPE: DNA
<213> ORGANISM: Artificial Sequence
<220> FEATURE:
<223> OTHER INFORMATION: SOT12-60102894
<220> FEATURE:
<221> NAME/KEY: misc_feature
<222> LOCATION: (76)..(76)
<223> OTHER INFORMATION: n is t or c
<220> FEATURE:
<221> NAME/KEY: misc_feature
<222> LOCATION: (102)..(151)
<223> OTHER INFORMATION: n is any nucleotide

<400> SEQUENCE: 212
tcacatgtct gacattatta atcttsgtgt trtaytgarc agaaatattc agccaactcc 60
actatctgaa raagancaag tagagaaggc aaggaaatgt gnnnnnnnnn nnnnnnnnnn 120
nnnnnnnnnn nnnnnnnnnn nnnnnnnnnn n 151

<210> SEQ ID NO 213
<211> LENGTH: 151
<212> TYPE: DNA
<213> ORGANISM: Artificial Sequence
<220> FEATURE:
<223> OTHER INFORMATION: SOT12-60102894
<220> FEATURE:
<221> NAME/KEY: misc_feature
<222> LOCATION: (76)..(76)
<223> OTHER INFORMATION: n is t or c
<220> FEATURE:
<221> NAME/KEY: misc_feature
<222> LOCATION: (102)..(151)
<223> OTHER INFORMATION: n is any nucleotide

<400> SEQUENCE: 213
tcacatgtct gacattatta atcttsgtgt trtaytgarc agaaatattc agccaactcc 60
actatctgaa raagancaag tagagaaggc aaggaaatgt gnnnnnnnnn nnnnnnnnnn 120
nnnnnnnnnn nnnnnnnnnn nnnnnnnnnn n 151

<210> SEQ ID NO 214
<211> LENGTH: 151
<212> TYPE: DNA
<213> ORGANISM: Artificial Sequence
<220> FEATURE:
<223> OTHER INFORMATION: SOT12-60390660
<220> FEATURE:
<221> NAME/KEY: misc_feature
<222> LOCATION: (76)..(76)
<223> OTHER INFORMATION: n is t or c
<220> FEATURE:
<221> NAME/KEY: misc_feature
<222> LOCATION: (102)..(151)
<223> OTHER INFORMATION: n is any nucleotide

<400> SEQUENCE: 214
tgatctgcya rcrattgagg tcsgccgrcg agtattgytt atgaaatgay gaacakatgt 60
ggaagagaga taatcnggtg accggacagc tggaagtttt gnnnnnnnnn nnnnnnnnnn 120
nnnnnnnnnn nnnnnnnnnn nnnnnnnnnn n 151

<210> SEQ ID NO 215
<211> LENGTH: 151
<212> TYPE: DNA
<213> ORGANISM: Artificial Sequence
<220> FEATURE:
<223> OTHER INFORMATION: SOT12-60524226
<220> FEATURE:
<221> NAME/KEY: misc_feature
<222> LOCATION: (76)..(76)
<223> OTHER INFORMATION: n is g or c
<220> FEATURE:
<221> NAME/KEY: misc_feature
<222> LOCATION: (102)..(151)
<223> OTHER INFORMATION: n is any nucleotide

<400> SEQUENCE: 215
gctcttggtt taacrcatag attccagtcc aaatatgtca ccgttgtcct ctacaarcca 60
ctgaagaggt gacmancccg tgttcacaat caaatctttc cnnnnnnnnn nnnnnnnnnn 120
nnnnnnnnnn nnnnnnnnnn nnnnnnnnnn n 151

<210> SEQ ID NO 216
<211> LENGTH: 151
<212> TYPE: DNA
<213> ORGANISM: Artificial Sequence
<220> FEATURE:
<223> OTHER INFORMATION: SOT12-60708789
<220> FEATURE:
<221> NAME/KEY: misc_feature
<222> LOCATION: (76)..(76)
<223> OTHER INFORMATION: n is g or a

<400> SEQUENCE: 216
tttttgtttt ctacatatta tttttggtta attatttata ccctmtttag tttatgggta 60
aatggtaatt ataggncctt cctagttccc atttgttctt cataaaaagg gatcatttgg 120
ttcaagatca gatattcaag aattmtaata a 151

<210> SEQ ID NO 217
<211> LENGTH: 151
<212> TYPE: DNA
<213> ORGANISM: Artificial Sequence
<220> FEATURE:

<223> OTHER INFORMATION: SOT12-61145775
<220> FEATURE:
<221> NAME/KEY: misc_feature
<222> LOCATION: (1)..(50)
<223> OTHER INFORMATION: n is a, c, g, or t
<220> FEATURE:
<221> NAME/KEY: misc_feature
<222> LOCATION: (76)..(76)
<223> OTHER INFORMATION: n is c or a
<220> FEATURE:
<221> NAME/KEY: misc_feature
<222> LOCATION: (102)..(151)
<223> OTHER INFORMATION: n is any nucleotide

<400> SEQUENCE: 217
nnnnnnnnnn nnnnnnnnnn nnnnnnnnnn nnnnnnnnnn nnnnnnnnnn tttgtctcat 60
ggttgccact tggttnttct tgcttrggtt gatggttggg acagtgatcc trcggatgta 120
gatctttatr acakagatga ygtagaytgg g 151

<210> SEQ ID NO 218
<211> LENGTH: 151
<212> TYPE: DNA
<213> ORGANISM: Artificial Sequence
<220> FEATURE:
<223> OTHER INFORMATION: SOT12-59016142
<220> FEATURE:
<221> NAME/KEY: misc_feature
<222> LOCATION: (76)..(76)
<223> OTHER INFORMATION: n is c or g

<400> SEQUENCE: 218
accacctatt ctaacaraaa aaatactttc gtttrargct ctgaccttct tttttcagaa 60
ttgaagtatg ctggcncgtc tacaaactgc ttccgaaaac tttagcagac agcacaggar 120
tccaagtcac tcaagggtgt tccgggtcaa a 151

<210> SEQ ID NO 219
<211> LENGTH: 152
<212> TYPE: DNA
<213> ORGANISM: Artificial Sequence
<220> FEATURE:
<223> OTHER INFORMATION: SOT12-59016842
<220> FEATURE:
<221> NAME/KEY: misc_feature
<222> LOCATION: (1)..(50)
<223> OTHER INFORMATION: n is any nucleotide
<220> FEATURE:
<221> NAME/KEY: misc_feature
<222> LOCATION: (76)..(76)
<223> OTHER INFORMATION: n is c or t

<400> SEQUENCE: 219
nnnnnnnnnn nnnnnnnnnn nnnnnnnnnn nnnnnnnnnn nnnnnnnnnn ctgatcgaac 60
ggctaaggat gagtcctatg atattcycac tttgtggtat ttttttgaca tccaaayaca 120
ccctaagttc gcgtttgact atagattttc tc 152

<210> SEQ ID NO 220
<211> LENGTH: 151
<212> TYPE: DNA
<213> ORGANISM: Artificial Sequence
<220> FEATURE:
<223> OTHER INFORMATION: SOT12-59019869
<220> FEATURE:
<221> NAME/KEY: misc_feature
<222> LOCATION: (76)..(76)
<223> OTHER INFORMATION: n is a or g

<400> SEQUENCE: 220
tgrgrcarag aaggaaaaaa ccattgtcac acttsattta grmcaagaga catttggagt 60
aatgaaacaa cctatnttgg aacatgatga aaatgtcaat tttcataatg ttgrtgtttt 120
acaaggatgt ttatctttgc ttaacaaagg t 151

<210> SEQ ID NO 221
<211> LENGTH: 151
<212> TYPE: DNA
<213> ORGANISM: Artificial Sequence
<220> FEATURE:
<223> OTHER INFORMATION: SOT12-59019907
<220> FEATURE:
<221> NAME/KEY: misc_feature
<222> LOCATION: (76)..(76)
<223> OTHER INFORMATION: n is a or g

<400> SEQUENCE: 221
tagrmcaaga gacatttgga gtaatgaaac aacctatrtt ggaacatgat gaaaatgtca 60
attttcataa tgttgntgtt ttacaaggat gtttatcttt gcttaacaaa ggtaatggac 120
wttattgtga aatttgggtg atgaaggart a 151

<210> SEQ ID NO 222
<211> LENGTH: 151
<212> TYPE: DNA
<213> ORGANISM: Artificial Sequence
<220> FEATURE:
<223> OTHER INFORMATION: SOT12-59022612
<220> FEATURE:
<221> NAME/KEY: misc_feature
<222> LOCATION: (1)..(50)
<223> OTHER INFORMATION: n is any nucleotide
<220> FEATURE:
<221> NAME/KEY: misc_feature
<222> LOCATION: (76)..(76)
<223> OTHER INFORMATION: n is t or g
<220> FEATURE:
<221> NAME/KEY: misc_feature
<222> LOCATION: (138)..(138)
<223> OTHER INFORMATION: n is a, c, g, or t

<400> SEQUENCE: 222
nnnnnnnnnn nnnnnnnnnn nnnnnnnnnn nnnnnnnnnn nnnnnnnnnn taccgccatc 60
tagtaacaaa ttttcntata aytgtgatga tcatacgttc aattttctct ccgataatgg 120
attyagtcag tttcatcntt ctcctatatt c 151

<210> SEQ ID NO 223
<211> LENGTH: 151
<212> TYPE: DNA
<213> ORGANISM: Artificial Sequence
<220> FEATURE:
<223> OTHER INFORMATION: SOT12-59024580
<220> FEATURE:
<221> NAME/KEY: misc_feature
<222> LOCATION: (76)..(76)
<223> OTHER INFORMATION: n is t or g

<400> SEQUENCE: 223
gacttcagrc aacagggkac aaagataagg aggaagatgt ggtatgaaaa tatgaagata 60
aaactggttg tttttnccat catcttggtc ctgattctca ttaycatttt atctgtctgc 120
cctggcttca aatgcacttc gtgattcaac c 151

<210> SEQ ID NO 224
<211> LENGTH: 151
<212> TYPE: DNA

<213> ORGANISM: Artificial Sequence
<220> FEATURE:
<223> OTHER INFORMATION: SOT12-59025293
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (76)..(76)
<223> OTHER INFORMATION: n is a or g
<220> FEATURE:
<221> NAME/KEY: misc_feature
<222> LOCATION: (102)..(151)
<223> OTHER INFORMATION: n is any nucleotide

<400> SEQUENCE: 224 gtttttaca tscagnaaca tacattaata tagtaaatca actataccga taactcgagt 60
tcgaccatta ggtganaagg gccatattta gaaggatttg annnnnnnnn nnnnnnnnnn 120
nnnnnnnnnn nnnnnnnnnn nnnnnnnnnn n 151

<210> SEQ ID NO 225
<211> LENGTH: 151
<212> TYPE: DNA
<213> ORGANISM: Artificial Sequence
<220> FEATURE:
<223> OTHER INFORMATION: SOT12-59025327
<220> FEATURE:
<221> NAME/KEY: misc_feature
<222> LOCATION: (76)..(76)
<223> OTHER INFORMATION: n is a or c

<400> SEQUENCE: 225
taaatcaact ataccgataa ctcgagttcg accattaggt garaagggcc atatttagaa 60
ggatttgagt cgatcnagaa gagagggagt attggaaagg catggttcaa aggattcttc 120
ttttctttat wctggtcgaa actctattcc t 151

<210> SEQ ID NO 226
<211> LENGTH: 151
<212> TYPE: DNA
<213> ORGANISM: Artificial Sequence
<220> FEATURE:
<223> OTHER INFORMATION: SOT12-59030123
<220> FEATURE:
<221> NAME/KEY: misc_feature
<222> LOCATION: (76)..(76)
<223> OTHER INFORMATION: n is a or g
<220> FEATURE:
<221> NAME/KEY: misc_feature
<222> LOCATION: (102)..(151)
<223> OTHER INFORMATION: n is any nucleotide

<400> SEQUENCE: 226
gctattgaaa tgtcccagtt ctacttccat ccatccatct cctctcartt ttgccgatgt 60
cacaagttts aaagtnttgg cttgttcttc agtctcagta tnnnnnnnnn nnnnnnnnnn 120
nnnnnnnnnn nnnnnnnnnn nnnnnnnnnn n 151

<210> SEQ ID NO 227
<211> LENGTH: 151
<212> TYPE: DNA
<213> ORGANISM: Artificial Sequence
<220> FEATURE:
<223> OTHER INFORMATION: SOT12-59030235
<220> FEATURE:
<221> NAME/KEY: misc_feature
<222> LOCATION: (76)..(76)
<223> OTHER INFORMATION: n is a or g
<220> FEATURE:
<221> NAME/KEY: misc_feature
<222> LOCATION: (102)..(151)
<223> OTHER INFORMATION: n is any nucleotide

<400> SEQUENCE: 227
ttaacaaacc taataattga attagcatat tcaagttcac akgaccttct tcccaattkg 60
aacaccaaat aagcancata atctgtcttt ggtgacaaca tnnnnnnnnn nnnnnnnnnn 120
nnnnnnnnnn nnnnnnnnnn nnnnnnnnnn n 151

<210> SEQ ID NO 228
<211> LENGTH: 151
<212> TYPE: DNA
<213> ORGANISM: Artificial Sequence
<220> FEATURE:
<223> OTHER INFORMATION: SOT12-59030301
<220> FEATURE:
<221> NAME/KEY: misc_feature
<222> LOCATION: (1)..(50)
<223> OTHER INFORMATION: n is any nucleotide
<220> FEATURE:
<221> NAME/KEY: misc_feature
<222> LOCATION: (76)..(76)
<223> OTHER INFORMATION: n is g or a
<220> FEATURE:
<221> NAME/KEY: misc_feature
<222> LOCATION: (145)..(145)
<223> OTHER INFORMATION: n is any nucleotide
<220> FEATURE:
<221> NAME/KEY: misc_feature
<222> LOCATION: (147)..(148)
<223> OTHER INFORMATION: n is any nucleotide

<400> SEQUENCE: 228
nnnnnnnnnn nnnnnnnnnn nnnnnnnnnn nnnnnnnnnn nnnnnnnnnn tccacgaatg 60
tccaactgaa gtacanmgtk aagatatgcc actttsgaga atctgcaaaa gtattrcarg 120
aarcatttgt aaggataatt ttatnanntt t 151

<210> SEQ ID NO 229
<211> LENGTH: 151
<212> TYPE: DNA
<213> ORGANISM: Artificial Sequence
<220> FEATURE:
<223> OTHER INFORMATION: SOT12-59030880
<220> FEATURE:
<221> NAME/KEY: misc_feature
<222> LOCATION: (40)..(42)
<223> OTHER INFORMATION: n is a, c, g, or t
<220> FEATURE:
<221> NAME/KEY: misc_feature
<222> LOCATION: (76)..(76)
<223> OTHER INFORMATION: n is g or a

<400> SEQUENCE: 229
aggtagtgaa gtgttrycgt gttttyyrag agtttyrgcn nnttggtgtt ttgtcgttgt 60
actagttgta gtattntagt tcttgattgt gatatctaty attttatgtt gtttattgtg 120
ttttggttat tgctmtattt tgttgttctt a 151

<210> SEQ ID NO 230
<211> LENGTH: 151
<212> TYPE: DNA
<213> ORGANISM: Artificial Sequence
<220> FEATURE:
<223> OTHER INFORMATION: SOT12-59042250
<220> FEATURE:
<221> NAME/KEY: misc_feature
<222> LOCATION: (1)..(50)

<223> OTHER INFORMATION: n is any nucleotide
<220> FEATURE:
<221> NAME/KEY: misc_feature
<222> LOCATION: (76)..(76)
<223> OTHER INFORMATION: n is g or c
<220> FEATURE:
<221> NAME/KEY: misc_feature
<222> LOCATION: (110)..(110)
<223> OTHER INFORMATION: n is any nucleotide
<220> FEATURE:
<221> NAME/KEY: misc_feature
<222> LOCATION: (131)..(131)
<223> OTHER INFORMATION: n is any nucleotide

<400> SEQUENCE: 230
nnnnnnnnnn nnnnnnnnnn nnnnnnnnnn nnnnnnnnnn nnnnnnnnnn aacygcgtct 60
tccccatttc acgagnwgyg gagagaacrt ttcacacgtt gtctttactn catcttcagc 120
aggtaaygyc ntttatytcg tttggaagtt r 151

<210> SEQ ID NO 231
<211> LENGTH: 151
<212> TYPE: DNA
<213> ORGANISM: Artificial Sequence
<220> FEATURE:
<223> OTHER INFORMATION: SOT12-59042436
<220> FEATURE:
<221> NAME/KEY: misc_feature
<222> LOCATION: (1)..(50)
<223> OTHER INFORMATION: n is any nucleotide
<220> FEATURE:
<221> NAME/KEY: misc_feature
<222> LOCATION: (76)..(76)
<223> OTHER INFORMATION: n is g or a

<400> SEQUENCE: 231
nnnnnnnnnn nnnnnnnnnn nnnnnnnnnn nnnnnnnnnn nnnnnnnnnn kyttgaagcc 60
gaagtaacgt ctcaanaatt gttccactgt ttcytcatca gtaagtttgt tctgaagatc 120
tccaaattgt gatgcaacca aaccatayaa g 151

<210> SEQ ID NO 232
<211> LENGTH: 151
<212> TYPE: DNA
<213> ORGANISM: Artificial Sequence
<220> FEATURE:
<223> OTHER INFORMATION: SOT12-59043512
<220> FEATURE:
<221> NAME/KEY: misc_feature
<222> LOCATION: (76)..(76)
<223> OTHER INFORMATION: n is t or c

<400> SEQUENCE: 232
agtaggatta cgccagtatg accagtgttg tttccaaagg caagctatac attgggtcca 60
aaatggctgt gagtanttag tatcgaaatg cagatctttt gtaccagggc gaggyacgcy 120
cagttcaytw atcaatgmtt tgttccttgt g 151

<210> SEQ ID NO 233
<211> LENGTH: 151
<212> TYPE: DNA
<213> ORGANISM: Artificial Sequence
<220> FEATURE:
<223> OTHER INFORMATION: SOT12-59043614
<220> FEATURE:
<221> NAME/KEY: misc_feature
<222> LOCATION: (76)..(76)
<223> OTHER INFORMATION: n is t or a

<400> SEQUENCE: 233

-continued

```
accagggcga ggyacgcyca gttcaytwat caatgmtttg ttccttgtgt aaaggtctga     60

tttcttgtat aaatcngtaa aatcaacccc gaacagtatt tcytgagcyg aggctgtgac    120

ttctaacatc caagttgctg gattgtagcc a                                   151
```